US012807990B2

(12) United States Patent
Francais et al.

(10) Patent No.: US 12,807,990 B2
(45) **Date of Patent: *Nov. 24, 2026**

(54) METHODS OF SEQUENCING USING 3' BLOCKED NUCLEOTIDES

(71) Applicant: Illumina, Inc., San Diego, CA (US)

(72) Inventors: Antoine Francais, Cambridge (GB); Elena Cressina, Cambridge (GB); Adam Culley, Cambridge (GB); Angelica Mariani, Cambridge (GB); Xiaolin Wu, Cambridge (GB); Xiaohai Liu, Cambridge (GB); Kathryn Hattingh, Cambridge (GB)

(73) Assignee: ILLUMINA, INC., San Diego, CA (US)

( * ) Notice: Subject to any disclaimer, the term of this patent is extended or adjusted under 35 U.S.C. 154(b) by 395 days.

This patent is subject to a terminal disclaimer.

(21) Appl. No.: 18/392,975

(22) Filed: Dec. 21, 2023

(65) Prior Publication Data

US 2024/0182963 A1 Jun. 6, 2024

Related U.S. Application Data

(63) Continuation-in-part of application No. 18/488,801, filed on Oct. 17, 2023, now Pat. No. 12,227,802, which is a continuation of application No. 17/708,498, filed on Mar. 30, 2022, now Pat. No. 11,827,931, which is a continuation of application No. 16/724,088, filed on Dec. 20, 2019, now Pat. No. 11,293,061.

(60) Provisional application No. 63/477,302, filed on Dec. 27, 2022, provisional application No. 62/784,970, filed on Dec. 26, 2018, provisional application No. 62/784,994, filed on Dec. 26, 2018.

(51) Int. Cl.

| | |
|---|---|
| ***C12Q 1/68*** | (2018.01) |
| ***C07H 19/06*** | (2006.01) |
| ***C07H 19/16*** | (2006.01) |
| ***C07H 21/00*** | (2006.01) |
| ***C12Q 1/6869*** | (2018.01) |

(52) U.S. Cl.

CPC ........... *C12Q 1/6869* (2013.01); *C07H 19/06* (2013.01); *C07H 19/16* (2013.01); *C07H 21/00* (2013.01)

(58) Field of Classification Search

CPC ...... C12Q 1/6869; C07H 19/06; C07H 19/16; C07H 21/00

See application file for complete search history.

(56) References Cited

U.S. PATENT DOCUMENTS

| | | | |
|---|---|---|---|
| 4,772,691 | A | 9/1988 | Herman |
| 4,804,748 | A | 2/1989 | Seela |
| 5,242,796 | A | 9/1993 | Prober et al. |
| 5,302,509 | A | 4/1994 | Cheeseman |
| 5,429,807 | A | 7/1995 | Matson et al. |
| 5,436,327 | A | 7/1995 | Southern et al. |
| 5,547,839 | A | 8/1996 | Dower et al. |
| 5,561,071 | A | 10/1996 | Hollenberg et al. |
| 5,583,211 | A | 12/1996 | Coassin et al. |
| 5,658,734 | A | 8/1997 | Brock et al. |
| 5,837,858 | A | 11/1998 | Brennan |
| 5,874,219 | A | 2/1999 | Rava et al. |
| 5,919,523 | A | 7/1999 | Sundberg et al. |
| 6,136,269 | A | 10/2000 | Winkler et al. |
| 6,172,218 | B1 | 1/2001 | Brenner |
| 6,210,891 | B1 | 4/2001 | Nyren et al. |
| 6,232,465 | B1 | 5/2001 | Hiatt |
| 6,258,568 | B1 | 7/2001 | Nyren |
| 6,274,320 | B1 | 8/2001 | Rothberg et al. |
| 6,287,768 | B1 | 9/2001 | Chenchik et al. |
| 6,287,776 | B1 | 9/2001 | Hefti |
| 6,288,220 | B1 | 9/2001 | Kambara et al. |
| 6,291,193 | B1 | 9/2001 | Khodadoust |
| 6,297,006 | B1 | 10/2001 | Drmanac et al. |
| 6,306,597 | B1 | 10/2001 | Macevicz |
| 6,335,155 | B1 | 1/2002 | Wells et al. |
| 6,346,413 | B1 | 2/2002 | Fodor et al. |
| 6,355,431 | B1 | 3/2002 | Chee et al. |
| 6,416,949 | B1 | 7/2002 | Dower et al. |
| 6,432,360 | B1 | 8/2002 | Church |
| 6,465,178 | B2 | 10/2002 | Chappa et al. |
| 6,482,591 | B2 | 11/2002 | Lockhart et al. |
| 6,514,751 | B2 | 2/2003 | Johann et al. |
| 6,524,793 | B1 | 2/2003 | Chandler et al. |

(Continued)

FOREIGN PATENT DOCUMENTS

| | | |
|---|---|---|
| CN | 105315318 | 2/2016 |
| EP | 0 104 857 | 4/1984 |

(Continued)

OTHER PUBLICATIONS

Beckman Coulter CEQ(TM) 2000 DNA Analysis System User's Guide, 606913-AC, dated Jun. 2000.

(Continued)

*Primary Examiner* — Jezia Riley

(74) *Attorney, Agent, or Firm* — KNOBBE, MARTENS, OLSON & BEAR, LLP

(57) ABSTRACT

Embodiments of the present disclosure relate to nucleotide and nucleoside molecules with 3' acetal, thiocarbamate or allyl blocking groups. Also provided herein are methods to prepare such nucleotide and nucleoside molecules, and the uses of fully functionalized nucleotides containing the 3'-OH blocking group for sequencing applications.

24 Claims, 11 Drawing Sheets

(56) References Cited

U.S. PATENT DOCUMENTS

| | | | |
|---|---|---|---|
| 6,610,482 | B1 | 8/2003 | Fodor et al. |
| 6,664,079 | B2 | 12/2003 | Ju et al. |
| 6,969,488 | B2 | 11/2005 | Bridgham et al. |
| 7,001,792 | B2 | 2/2006 | Sauer et al. |
| 7,057,026 | B2 | 6/2006 | Barnes et al. |
| 7,078,499 | B2 | 7/2006 | Odedra et al. |
| 7,211,414 | B2 | 5/2007 | Hardin et al. |
| 7,270,951 | B1 | 9/2007 | Stemple et al. |
| 7,315,019 | B2 | 1/2008 | Turner et al. |
| 7,329,492 | B2 | 2/2008 | Hardin et al. |
| 7,405,281 | B2 | 7/2008 | Xu et al. |
| 7,785,796 | B2 | 8/2010 | Balasubramanian et al. |
| 8,754,244 | B1 | 6/2014 | Romano et al. |
| 8,951,781 | B2 | 2/2015 | Williamson et al. |
| 9,222,132 | B2 | 12/2015 | Drmanac |
| 9,605,301 | B2 | 3/2017 | Gordon et al. |
| 11,293,061 | B2 | 4/2022 | Francais et al. |
| 11,787,831 | B2 | 10/2023 | Francais et al. |
| 11,827,931 | B2 | 11/2023 | Francais et al. |
| 12,227,802 | B2 | 2/2025 | Francais et al. |
| 12,286,453 | B2 | 4/2025 | Francais et al. |
| 2002/0102578 | A1 | 8/2002 | Dickinson et al. |
| 2007/0166705 | A1 | 7/2007 | Milton et al. |
| 2008/0108082 | A1 | 5/2008 | Rank et al. |
| 2009/0026082 | A1 | 1/2009 | Rothberg et al. |
| 2009/0088327 | A1 | 4/2009 | Rigatti et al. |
| 2009/0118128 | A1 | 5/2009 | Liu et al. |
| 2009/0127589 | A1 | 5/2009 | Rothberg et al. |
| 2010/0111768 | A1 | 5/2010 | Banerjee et al. |
| 2010/0137143 | A1 | 6/2010 | Rothberg et al. |
| 2010/0282617 | A1 | 11/2010 | Rothberg et al. |
| 2013/0079232 | A1 | 3/2013 | Kain et al. |
| 2014/0079923 | A1 | 3/2014 | George et al. |
| 2016/0040225 | A1 | 2/2016 | Wu et al. |
| 2018/0094140 | A1 | 4/2018 | Romanov |
| 2018/0201981 | A1 | 7/2018 | Romanov |
| 2019/0352327 | A1 | 11/2019 | Wu et al. |
| 2020/0131484 | A1 | 4/2020 | Golynskiy et al. |
| 2020/0181587 | A1 | 6/2020 | Klausing et al. |
| 2020/0190569 | A1 | 6/2020 | Gatti-Lafanconi et al. |
| 2020/0216891 | A1 | 7/2020 | Francais et al. |
| 2020/0277529 | A1 | 9/2020 | Romanov et al. |
| 2020/0277670 | A1 | 9/2020 | Romanov et al. |
| 2021/0187470 | A1 | 6/2021 | Yang et al. |
| 2021/0188832 | A1 | 6/2021 | Romanov et al. |
| 2021/0403500 | A1 | 12/2021 | Francais et al. |
| 2022/0033900 | A1 | 2/2022 | Romanov et al. |
| 2022/0195517 | A1 | 6/2022 | Cressina et al. |
| 2022/0213542 | A1 | 7/2022 | Ju |
| 2022/0380389 | A1 | 12/2022 | Callingham et al. |
| 2022/0396832 | A1 | 12/2022 | Mariani et al. |
| 2023/0313292 | A1 | 10/2023 | Callingham et al. |
| 2023/0314322 | A1 | 10/2023 | Callingham et al. |
| 2023/0383342 | A1 | 11/2023 | Wu et al. |
| 2023/0416279 | A1 | 12/2023 | Callingham et al. |
| 2024/0209015 | A1 | 6/2024 | Francais et al. |
| 2024/0218443 | A1 | 7/2024 | Mariani et al. |
| 2024/0271206 | A1 | 8/2024 | Francais et al. |
| 2025/0146066 | A1 | 5/2025 | Francais et al. |
| 2025/0236635 | A1 | 7/2025 | Francais et al. |

FOREIGN PATENT DOCUMENTS

| | | | |
|---|---|---|---|
| EP | 0 742 287 | 11/1996 | |
| EP | 0 799 897 | 10/1997 | |
| JP | 59-036696 | 2/1984 | |
| JP | 2017-518750 | 7/2017 | |
| JP | 2018-008186 | 1/2018 | |
| JP | 2018-509177 | 4/2018 | |
| RU | 2563808 C2 | 9/2015 | |
| WO | WO 91/06678 | 5/1991 | |
| WO | WO 93/17126 | 9/1993 | |
| WO | WO 95/11995 | 5/1995 | |
| WO | WO 95/35505 | 12/1995 | |
| WO | WO 96/27025 | 9/1996 | |
| WO | WO 98/33939 | 8/1998 | |
| WO | WO 98/44151 | 10/1998 | |
| WO | WO 98/44152 | 10/1998 | |
| WO | WO 98/53300 | 11/1998 | |
| WO | WO 00/06770 | 2/2000 | |
| WO | WO 00/18957 | 4/2000 | |
| WO | WO 00/31148 | 6/2000 | |
| WO | WO 00/53805 | 9/2000 | |
| WO | WO 00/63437 | 10/2000 | |
| WO | WO 01/01143 | 1/2001 | |
| WO | WO 01/57248 | 8/2001 | |
| WO | WO 02/012566 | 2/2002 | |
| WO | WO 02/029003 | 4/2002 | |
| WO | WO 03/014392 | 2/2003 | |
| WO | WO 2004/018493 | 3/2004 | |
| WO | WO 2004/018497 | 3/2004 | |
| WO | WO-2004018493 A1 * | 3/2004 | ............ C07H 19/10 |
| WO | WO 2005/024010 | 3/2005 | |
| WO | WO 2005/047301 | 5/2005 | |
| WO | WO 2005/065814 | 7/2005 | |
| WO | WO 06/120433 | 11/2006 | |
| WO | WO 2007/010251 | 1/2007 | |
| WO | WO 2007/020457 | 2/2007 | |
| WO | WO 2007/123744 | 11/2007 | |
| WO | WO 08/069973 | 6/2008 | |
| WO | WO 2009/054922 | 4/2009 | |
| WO | WO 2012/162429 | 11/2012 | |
| WO | WO 2013/041117 | 3/2013 | |
| WO | WO 14/039225 | 3/2014 | |
| WO | WO 2014/135221 | 9/2014 | |
| WO | WO 2014/139596 | 9/2014 | |
| WO | WO 2016/189287 | 12/2016 | |
| WO | WO 2017/051201 | 3/2017 | |
| WO | WO 2017/079498 | 5/2017 | |
| WO | WO 2018/060482 | 4/2018 | |
| WO | WO 2018/129214 | 7/2018 | |
| WO | WO 2018/138685 | 8/2018 | |
| WO | WO 19/183272 | 9/2019 | |
| WO | WO 19/222264 | 11/2019 | |
| WO | WO 2020/097607 | 5/2020 | |
| WO | WO 2020/126593 | 6/2020 | |
| WO | WO 00/53812 | 9/2020 | |
| WO | WO 22/243480 | 11/2022 | |
| WO | WO 24/145154 | 7/2024 | |

OTHER PUBLICATIONS

Bentley et al., Nov. 6, 2008, Accurate whole human genome sequencing using reversible terminator chemistry, Nature, 456:53-59 and supplementary information.

Bi et al., 2006, Design and synthesis of a chemically cleavable fluorescent nucleotide, 3'-O-allyl-dGTP-allyl-Bodipy-FL-510, as a reversible terminator for DNA sequencing by synthesis, JACS, 128:2542-2543.

Boss et al., "Cleavage of Allyl Ethers with Pd/C", Angew. Chem. Int. Ed. Engl., 15:558-559 (1976).

Burns et al., 1991, Selective reduction of disulfides by Tris(2-carboxyethyl)phosphine, J. Org. Chem., 56:2648-2650.

Canard et al., 1994, DNA Polymerase Fluorescent Substrates with Reversible 3'-Tags, Gene, 148:1-6.

Cockroft et al., Jan. 23, 2008, A single-molecule nanopore device detects DNA polymerase activity with single-nucleotide resolution, J. Am. Chem. Soc. 130:818-820.

Deamer, 2000, Nanopores and nucleic acids: prospects for ultrarapid sequencing. Trends Biotechnol. 18:147-151.

Deamer, 2002, Characterization of nucleic acids by nanopore analysis, Acc. Chem. Res. 35:817-825.

Faucher et al., 2003, Tris(2-Carboxyethyl)phosphine (TCEP) for the Reduction of Sulfoxides, Sulfonylchlorides, N-Oxides, and Azides, Synthetic Communications, 33(22):3503-3511.

Genet et al., 1994, Practical palladium-mediated deprotective method of allyloxycarbonyl in aqueous media, Tetrahedron, 50(2):497-503.

Gigg et al., "The Allyl Ether as a Protecting Group in Carbohydrate Chemistry Part II", J. Chem. Soc. (C), 1903-1911 (1968).

Goodwin et al., Jul. 2016, Coming of age: ten years of next-generation sequencing technologies, Nat Rev Genet. 17(6):333-351.

(56) References Cited

OTHER PUBLICATIONS

Greene & Wuts, 1999, Protective Groups in Organic Synthesis, Third Edition, John Wiley & Sons, New York.
Guillier et al., 2000, Linkers and cleavage strategies in solid-phase organic synthesis and combinatorial chemistry, Chem. Rev. 100:2092-2157.
Guo et al., Apr. 20, 2010, An integrated system for DNA sequencing by synthesis using novel nucleotide analogues, Acc Chem Res., 43(4):551-563.
Guo et al., Jul. 8, 2008, PNAS, Four-color DNA sequencing with 3'-0-modified nucleotide reversible terminators and chemically cleavable fluorescent dideoxynucleotides, 105(27):9145-9150.
Healy, 2007, Nanopore-based single-molecule DNA analysis. Nanomed, 2:459-481.
Heidmann et al., 1980, Festphasensynthese von oligonucleotides, 11. Verwendugn eines neuartigen hydrophilen perlpolymerists als trager, Makromol. Chem and Physics, 181(12):2495-2506.
Hovinen et al., 1994, Synthesis of 3'-0-(ω-Aminoalkoxymethyl)thymidine 5'-Triphosphates, terminator of DNA synthesis that enable 3'-labelling, J. Chem. Soc. Perkin Trans, pp. 211-217.
Jacobs et al., Jan. 1994, Combinatorial chemistry—application of light-directed chemical synthesis, Trends Biotech. 12:19-26.
Ju et al., 2006, Four-color DNA sequencing by synthesis using cleavable fluorescent nucleotide reversible terminators, PNAS USA, 103:19635-40.
Kamal et al., Jul. 28, 1999, A Mild and Rapid Regeneration of Alcohols from their Allylic Ethers by Chlorotrimethylsilane/Sodium Iodide, Tetrahedron Letters 40:371-372.
Korlach et al., 2008, Selective aluminum passivation for targeted immobilization of single DNA polymerase molecules in zero-mode waveguide nano structures. Proc. Natl. Acad. Sci. USA 105:1176-1181.
Krainer et al., 1993, A new method for the detritylation of alcohols bearing other reducible and acid-hydrolyzable functionalities, Tetrahedron Letters, 34(11):1713-1716.
Levene et al., Jan. 31, 2003, Zero-mode waveguides for single-molecule analysis at high concentrations. Science 299:682-686.
Li et al., 2003, DNA molecules and configurations in a solid-state nanopore microscope, Nat. Mater. 2:611-615.
Loubinoux et al., 1988, Protection of Phenols by the Azidomethylene Group Application to the Synthesis of Unstable Phenols, TETRAHEDRON 44:6055-6064.
Lundquist et al., May 1, 2008, Parallel confocal detection of single molecules in real time, Opt. Lett. 33:1026-1028.
Margulies et al., Sep. 15, 2005, Genome sequencing in microfabricated high-density picolitre reactors, Nature, 437:376-380.
Matsumoto et al., 1968, A Revised Structure of Pederin, 60 Tetrahedron Letters, 60:6297-6300.
Meinwald, 1977, An Approach to the Synthesis of Pederin, Pure and Appl. Chem., vol. 49, Pergamon Press, pp. 1275-1290.
Metzker et al., 1994, Termination of DNA synthesis by novel 3'-modified-deoxyribonucleoside 5'-triphosphates, Nucleic Acids Research, 22(20):4259-4267.
Metzker et al., 2005, Emerging technologies in DNA sequencing, Genome Research, 15:1767-1776.
Metzker, Jan. 2010, Sequencing technologies—the next generation, Nature Reviews Genetics, 11:31-46.
Mukaiyama et al. 1996, Catalytic stereoselective synthesis of pyrimidine 2-deoxyribonucleosides, Chemistry Letters, 56(2):99-100.
Wuts, 2007, Preface to the Fourth Edition, in Greene's Protective Groups in Organic Synthesis, Greene & Wuts (Eds.), Hoboken, NJ: John Wiley & Sons.
Prestat et al. 2000, Synthesis of 3'-$O^2$-(azaheterocycle)-thymidines, Nucleosides, Nucleotides & Nucleic Acids 19(4):735-748.
Prober et al., Oct. 16, 1987, A System for Rapid DNA Sequencing with Fluorescent Chain-Terminating Dideoxynucleotides, Science, 238:336-341.
Qian et al., 1998, Unexpected Enzymatic Fucosylation of the Hindered Tertiary Alcohol of 3-C-Methyl-N-Acetyllactosamine Produces a Novel Analogue of the LeX-Trisaccharide, Journal of the American Chemical Society, 120:2184-2185.
Qian et al., 1999, Chemoenzymatic synthesis of α-(1→3)-Gal(NAc) terminating glycosides of complex tertiary sugar alcohols, J. Am. Chem. Soc. 121:12063-12072.
Qian, 2006, Enzymatic and Chemical Synthesis of Oligosaccharide Analogs, Thesis, University of Alberta.
Ronaghi et al., 1996, Real-time DNA sequencing using detection of pyrophosphate release, Analytical Biochemistry, 242(1):84-89.
Ronaghi et al., Jul. 17, 1998, A sequencing method based on real-time pyrophosphate. Science 281(5375):363-365.
Ronaghi, 2001, Pyrosequencing sheds light on DNA sequencing, Genome Res. 11(1):3-11.
Ruby et al., 1990, Affinity Chromatography with Biotinylated RNAs, Methods in Enzymology, 181:97-121.
Scheit, 1980, Nucleotide analogs: Synthesis and biological function. New York: John Wiley & Sons (TOC).
Serafinowski et al., 2000, New method for the preparation of some 2'- and 3'-Trifluoromehyl-2',3'-dideoxyuridine derivatives, Tetrahedron 56(2):333-339.
Shendure et al., Sep. 9, 2005, Accurate multiplex polony sequencing of an evolved bacterial genome, Science, 309:1728-1732.
Soni et al., 2007, Progress toward ultrafast DNA sequencing using solid-state nanopores, Clin. Chem. 53:1996-2001.
Stimpson et al., 1995, Real-time detection of DNA hybridization and melting on oligonucleotide arrays by using optical wave guides, Proc. Natl. Acad. Sci. 92:6379-6383.
Ulhman et al., Jun. 1990, Antisense oligonucleotides: a new therapeutic principle, Chemical Reviews, 90(4):543-584.
Veeneman et al., 1991, An efficient approach to the synthesis of thymidine derivatives containing phosphate-isosteric methylene acetal linkages, Tetrahedron, 47(8):1547-1562.
Welch et al., "Syntheses of Nucleosides Designed for Combinatorial DNA Sequencing", Chem. Eur. J., 5:951-960 (1999).
Wincott et al., 1994, 2'-(Trimethylsilyl)ethoxymethyl protection of the 2'-Hydroxyl group in oligoribonucleotide synthesis, Tetrahedron Letters, 35(37):6827-6830.
Wu et al., Oct. 16, 2007, 3'-O-modified nucleotides as reversible terminators for pyrosequencing, PNAS, 104(42):16462-16467.
Yamashita et al., 1987, Studies on antitumor agents. VII. Antitumor activities of O-alkoxyalkyl derivatives of 2'-deoxy-5-trifluoromethyluridine, Chemical and Pharmaceutical Bulletin, 35(6):2373-2381.
Young, A Strategy for the Synthesis of Sulfated Peptides, A dissertation submitted in partial fulfillment of the requirements for the degree of Doctor of Philosophy (Chemistry) at the University of Wisconsin—Madison (2001).
Zavgorodny et al., 1991, 1-Alkylthioalkylation of Nucleoside Hydroxyl Functions and its Synthetic Applications, Tetrahedron Letters, 32(51):7593-7596.
Zavgorodny et al., 2000, S,X-Acetals in Nucleoside Chemistry III. Synthesis of 2' and 3'-O-Azidomethyl Derivatives of Ribonucleosides, Nucleosides, Nucleotides & Nucleic Acids, 19(10-12):1977-1991.
Drmanac et al., Feb. 20, 2020, CoolMPS™: advanced massively parallel sequencing using antibodies specific to each natural nucleobase, https://www.biorxiv.org/content/10.1101/2020.02.19.953307v1, 19 pp.
Silicycle, UltraPure Silica Gels, 2014, Application Note: Scavenging of Pd(dt-bpf)CI2, 8 pp.

* cited by examiner

METHODS OF SEQUENCING USING 3' BLOCKED NUCLEOTIDES

BACKGROUND

Field

The present disclosure generally relates to nucleotides, nucleosides, or oligonucleotides comprising 3'-hydroxy protecting groups and their use in polynucleotide sequencing methods. Methods of preparing the 3'-hydroxy protected nucleotides, nucleosides, or oligonucleotides are also disclosed.

Description of the Related Art

Advances in the study of molecules have been led, in part, by improvement in technologies used to characterize the molecules or their biological reactions. In particular, the study of the nucleic acids DNA and RNA has benefited from developing technologies used for sequence analysis and the study of hybridization events.

An example of the technologies that have improved the study of nucleic acids is the development of fabricated arrays of immobilized nucleic acids. These arrays consist typically of a high-density matrix of polynucleotides immobilized onto a solid support material. See, e.g., Fodor et al., *Trends Biotech.* 12: 19-26, 1994, which describes ways of assembling the nucleic acids using a chemically sensitized glass surface protected by a mask, but exposed at defined areas to allow attachment of suitably modified nucleotide phosphoramidites. Fabricated arrays can also be manufactured by the technique of "spotting" known polynucleotides onto a solid support at predetermined positions (e.g., Stimpson et al., *Proc. Natl. Acad. Sci.* 92: 6379-6383, 1995).

One way of determining the nucleotide sequence of a nucleic acid bound to an array is called "sequencing by synthesis" or "SBS." This technique for determining the sequence of DNA ideally requires the controlled (i.e., one at a time) incorporation of the correct complementary nucleotide opposite the nucleic acid being sequenced. This allows for accurate sequencing by adding nucleotides in multiple cycles as each nucleotide residue is sequenced one at a time, thus preventing an uncontrolled series of incorporations from occurring. The incorporated nucleotide is read using an appropriate label attached thereto before removal of the label moiety and the subsequent next round of sequencing.

In order to ensure that only a single incorporation occurs, a structural modification ("protecting group" or "blocking group") is included in each labeled nucleotide that is added to the growing chain to ensure that only one nucleotide is incorporated. After the nucleotide with the protecting group has been added, the protecting group is then removed, under reaction conditions which do not interfere with the integrity of the DNA being sequenced. The sequencing cycle can then continue with the incorporation of the next protected, labeled nucleotide. To be useful in DNA sequencing, nucleotides, which are usually nucleotide triphosphates, generally require a 3' hydroxy blocking group so as to prevent the polymerase used to incorporate it into a polynucleotide chain from continuing to replicate once the base on the nucleotide is added.

Reversible protecting groups have been described previously. For example, Metzker et al., (*Nucleic Acids Research,* 22 (20): 4259-4267, 1994) discloses the synthesis and use of eight 3'-modified 2-deoxyribonucleoside 5'-triphosphates (3'-modified dNTPs) and testing in two DNA template assays for incorporation activity. WO 2002/029003 describes a sequencing method which may include the use of an allyl protecting group to cap the 3'-OH group on a growing strand of DNA in a polymerase reaction. In addition, the development of a number of reversible protecting groups and methods of deprotecting them under DNA compatible conditions was previously reported in International Application Publication Nos. WO 2004/018497 and WO 2014/139596, each of which is hereby incorporated by reference in its entirety. Although the use of 3'allyl blocked nucleotides has been reported over 20 years ago, SBS using such nucleotides was never successfully applied in the commercial setting for long DNA reads, due to various factors including the low efficiency of the 3'blocking group cleavage chemistry, as well as the rapid loss of signal intensity during sequencing. For example, Ju et al. reported four-color DNA sequencing by synthesis using 3' allyl blocked nucleotides and only 25 cycles of SBS were reported with substantial loss of fluorescent intensity only after five cycles. See Ju et al., PNAS, 2006, 103(52):19635-19640. As such, there remain a need to improve the sequencing conditions (e.g., the cleavage condition of the 3' allyl blocking group) and the sequencing metrics of SBS using nucleotides with 3' allyl blocking group.

SUMMARY

Some embodiments of the present disclosure relate to a nucleotide or nucleoside comprising a ribose or deoxyribose having a removable 3'-OH protecting or blocking group forming a structure

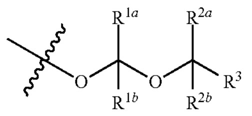

covalently attached to the 3'-carbon atom, wherein:

each $R^{1a}$ and $R^{1b}$ is independently H, $C_1$-$C_6$ alkyl, $C_1$-$C_6$ haloalkyl, $C_1$-$C_6$ alkoxy, $C_1$-$C_6$ haloalkoxy, cyano, halogen, optionally substituted phenyl, or optionally substituted aralkyl;

each $R^{2a}$ and $R^{2b}$ is independently H, $C_1$-$C_6$ alkyl, $C_1$-$C_6$ haloalkyl, cyano, or halogen;

alternatively, $R^{1a}$ and $R^{2a}$ together with the atoms to which they are attached form an optionally substituted five to eight membered heterocyclyl group;

$R^3$ is H, optionally substituted $C_2$-$C_6$ alkenyl, optionally substituted $C_3$-$C_7$ cycloalkenyl, optionally substituted $C_2$-$C_6$ alkynyl, or optionally substituted ($C_1$-$C_6$ alkylene)$Si(R^4)_3$; and each $R^4$ is independently H, $C_1$-$C_6$ alkyl, or optionally substituted $C_6$-$C_{10}$ aryl. In some embodiments, when each $R^{1a}$ and $R^{1b}$ is H or $C_1$-$C_6$ alkyl, both $R^{2a}$ and $R^{2b}$ are H, then $R^3$ is substituted $C_2$-$C_6$ alkenyl, optionally substituted $C_3$-$C_7$ cycloalkenyl, optionally substituted $C_2$-$C_6$ alkynyl, or optionally substituted ($C_1$-$C_6$ alkylene)$Si(R^4)_3$. In some embodiments, when each $R^{1a}$, $R^{1b}$, $R^{2a}$ and $R^{2b}$ is H, then $R^3$ is not H.

Some embodiments of the present disclosure relate to a nucleoside or nucleotide comprising a ribose or deoxyribose having a removable 3'-OH blocking group forming a structure

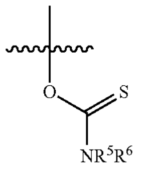

covalently attached to the 3'-carbon atom, wherein:

each of $R^5$ and $R^6$ is independently H, $C_1$-$C_6$ alkyl, $C_2$-$C_6$ alkenyl, $C_2$-$C_6$ alkynyl, $C_1$-$C_6$ haloalkyl, $C_2$-$C_8$ alkoxyalkyl, optionally substituted $-(CH_2)_m$-phenyl, optionally substituted $-(CH_2)_n$-(5 or 6 membered heteroaryl), optionally substituted $-(CH_2)_k-C_3$-$C_7$ carbocyclyl, or optionally substituted $-(CH_2)_p$-(3 to 7 membered heterocyclyl);

each of $-(CH_2)_m-$, $-(CH_2)_n-$, $-(CH_2)_k-$, and $-(CH_2)_p-$ is optionally substituted; and each of m, n, k, and p is independently 0, 1, 2, 3, or 4.

Some embodiments of the present disclosure relate to an oligonucleotide or polynucleotide comprising a 3'-OH blocked nucleotide molecule described herein.

Some embodiments of the present disclosure relate to a method of preparing a growing polynucleotide complementary to a target single-stranded polynucleotide in a sequencing reaction, comprising incorporating a nucleotide molecule described herein into the growing complementary polynucleotide, wherein the incorporation of the nucleotide prevents the introduction of any subsequent nucleotide into the growing complementary polynucleotide. In some embodiments, the incorporation of the nucleotide is accomplished by a polymerase, a terminal deoxynucleotidyl transferase (TdT), or a reverse transcriptase. In one embodiment, the incorporation is accomplished by a polymerase (e.g., a DNA polymerase).

Some further embodiments of the present disclosure relate to a method for determining the sequence of a target single-stranded polynucleotide, comprising:

(a) incorporating a nucleotide comprising a 3'-OH blocking group and a detectable label as described herein into a copy polynucleotide strand complementary to at least a portion of the target polynucleotide strand;

(b) detecting the identity of the nucleotide incorporated into the copy polynucleotide strand; and (c) chemically removing the label and the 3'-OH blocking group from the nucleotide incorporated into the copy polynucleotide strand.

In some embodiments, the sequencing method further comprises (d) washing the chemically removed label and the 3' blocking group away from the copy polynucleotide strand. In some embodiment, such washing step also removes the unincorporated nucleotides. In some such embodiments, the 3' blocking group and the detectable label of the incorporated nucleotide are removed prior to introducing the next complementary nucleotide. In some further embodiments, the 3' blocking group and the detectable label are removed in a single step of chemical reaction. In some embodiments, the sequential incorporation described herein is performed at least 50 times, at least 100 times, at least 150 times, at least 200 times, or at least 250 times.

Some further embodiments of the present disclosure relate to kits comprising a plurality of nucleotide or nucleoside molecules described herein, and packaging materials therefor. The nucleotides, nucleosides, oligonucleotides, or kits that are set forth herein may be used to detect, measure, or identify a biological system (including, for example, processes or components thereof). Exemplary techniques that can employ the nucleotides, oligonucleotides, or kits include sequencing, expression analysis, hybridization analysis, genetic analysis, RNA analysis, cellular assay (e.g., cell binding or cell function analysis), or protein assay (e.g., protein binding assay or protein activity assay). The use may be on an automated instrument for carrying out a particular technique, such as an automated sequencing instrument. The sequencing instrument may contain two or more lasers operating at different wavelengths to distinguish between different detectable labels.

Additional aspect of the present disclosure relates to a method of determining the sequence of a plurality of different target polynucleotides in parallel, the method comprising:

(a) contacting a solid support with a solution comprising sequencing primers under hybridization conditions, wherein:

(i) the solid support comprises at least 5,000,000 spatially distinguishable sites/$cm^2$ that comprise multiple copies of target polynucleotides;

(ii) the solid support comprises a plurality of different target polynucleotides; and (iii) the sequencing primers are complementary to at least a portion of the different target polynucleotides;

(b) contacting the solid support with an aqueous solution comprising DNA polymerase and nucleotides A, G, C and T or U under conditions suitable for DNA polymerase-mediated primer extension, wherein each nucleotide comprises a 2' deoxyribose moiety with a 3' allyl blocking group

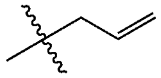 [SMILES: *CC=C]

attached to the 3' oxygen atom;

(c) imaging the solid support to determine the identity of incorporated nucleotides;

(d) contacting the solid support with an aqueous deblocking solution comprising a palladium catalyst and tris(hydroxyalkyl)phosphine under conditions suitable to chemically remove 3' allyl blocking groups from incorporated nucleotides to expose a 3'-OH group for further nucleotide incorporation on the solid support;

(e) contacting said solid support with an aqueous wash solution; and (f) repeating steps (b)-(e) to determine target polynucleotide sequences.

Additional aspect of the present disclosure relates to a method of determining the sequence of a plurality of different target polynucleotides in parallel, the method comprising:

(a) contacting a solid support with a solution comprising sequencing primers under hybridization conditions, wherein:

(i) the solid support comprises at least 5,000,000 spatially distinguishable sites/$cm^2$ that comprise multiple copies of target polynucleotides;

(ii) the solid support comprises a plurality of different target polynucleotides; and (iii) the sequencing primers are complementary to at least a portion of the different target polynucleotides;

(b) contacting the solid support with an aqueous solution comprising DNA polymerase and nucleotides A, G, C, and T or U under conditions suitable for DNA polymerase-mediated primer extension, wherein:

(i) each of at least three types of nucleotides independently comprises a base that is attached to a detectable label via a cleavable linker, and the cleavable linker comprises a moiety selected from the group consisting of:

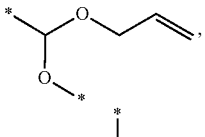

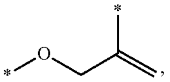

, and

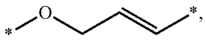

and * indicates where the moiety is connected to the remainder of the nucleotide;

(ii) each nucleotide comprises a 2' deoxyribose moiety with a 3' allyl group

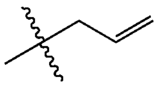 [SMILES: *CC=C]

attached to the 3' oxygen atom; and (iii) the DNA polymerase is an altered archaeal DNA polymerase;

(c) contacting the solid support with a solution comprising one or more radical scavengers and imaging the solid support to determine the identity of incorporated nucleotides;

(d) contacting the solid support with an aqueous deblocking solution comprising a palladium catalyst and tris(hydroxyalkyl)phosphine under conditions suitable to chemically remove (i) 3' allyl blocking groups from incorporated nucleotides to expose a 3'-OH group for further nucleotide incorporation on the solid support, and (ii) detectable labels attached via cleavable linkers;

(e) contacting said solid support with an aqueous wash solution comprising a palladium scavenger; and (f) repeating steps (b)-(e) to determine target polynucleotide sequences.

Additional aspect of the present disclosure relates to a method of determining the sequence of a plurality of different target polynucleotides in parallel, the method comprising:

(a) contacting a solid support with a solution comprising sequencing primers under hybridization conditions, wherein:

(i) the solid support comprises at least 5,000,000 spatially distinguishable sites/cm2 that comprise multiple copies of target polynucleotides;

(ii) the solid support comprises a plurality of different target polynucleotides; and (iii) the sequencing primers are complementary to at least a portion of the different target polynucleotides;

(b) contacting the solid support with an aqueous solution comprising DNA polymerase and nucleotides A, G, C, and T or U under conditions suitable for DNA polymerase-mediated primer extension, wherein:

(i) at least one of the nucleotides comprise a base that is attached to a detectable label via a cleavable linker; and (ii) the nucleotides each comprises a 2' deoxyribose moiety with a 3' allyl blocking group

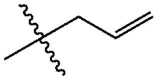 [SMILES: *CC=C]

attached to the 3' oxygen atom;

(c) contacting the solid support with a solution comprising one or more radical scavengers and imaging the solid support to determine the identity of incorporated nucleotides;

(d) contacting the solid support with an aqueous deblocking solution comprising a palladium catalyst and tris(hydroxyalkyl)phosphine under conditions suitable to chemically remove (i) 3' allyl groups from incorporated nucleotides to expose a 3'-OH group for further nucleotide incorporation on the solid support, and (ii) detectable labels attached via cleavable linkers;

(e) contacting said solid support with an aqueous wash solution; and (f) repeating steps (b)-(e) to determine target polynucleotide sequences.

Another aspect of the present disclosure relates to a method of determining the sequence of a plurality of different target polynucleotides in parallel, the method comprising:

(a) contacting a solid support with a solution comprising sequencing primers under hybridization conditions, wherein:

(i) the solid support comprises at least 5,000,000 spatially distinguishable sites/$cm^2$ that comprise multiple copies of target polynucleotides;

(ii) the solid support comprises a plurality of different target polynucleotides; and (iii) the sequencing primers are complementary to at least a portion of the different target polynucleotides;

(b) contacting the solid support with an aqueous incorporation mixture comprising DNA polymerase and one or more of four types of nucleotides A, G, C, and T or U under conditions suitable for DNA polymerase-mediated primer extension, wherein:

(i) the nucleotides each comprises a 2' deoxyribose moiety with a 3' allyl blocking group

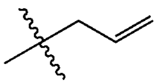 [SMILES: *CC=C]

attached to the 3' oxygen atom;

(ii) at least one type of nucleotide is unlabeled; and (iii) the first type of unlabeled nucleotides comprises a first functional moiety;

(c) contacting the extended copy polynucleotides with an aqueous labeling mixture comprising a first labeling reagent, wherein the first labeling reagent comprises one or more first detectable labels and a first binding moiety that is capable of specific binding to the first functional moiety of the first type of unlabeled nucleotide;

(d) imaging the solid support and performing one or more fluorescent measurements to determine the identity of incorporated nucleotides;

(e) contacting the solid support with an aqueous deblocking solution comprising a palladium catalyst and tris(hydroxyalkyl)phosphine under conditions suitable to chemically remove (i) 3' allyl groups from incorporated nucleotides to expose a 3'-OH group for further nucleotide incorporation on the solid support;

(f) contacting said solid support with an aqueous wash solution; and (g) repeating steps (b)-(f) to determine target polynucleotide sequences.

A further aspect of the present disclosure relates to a sequencing kit comprising:

(a) an incorporation mixture comprising DNA polymerase and nucleotides A, G, C, and T or U, wherein:

(i) the nucleotides comprise a 2' deoxyribose moiety with a 3' allyl group

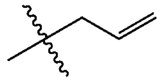

attached to the 3' carbon atom; and (ii) the DNA polymerase is an altered archaeal DNA polymerase;

(b) an aqueous deblocking solution comprising a palladium catalyst, tris(hydroxyalkyl)phosphine, and one or more buffer reagents that is suitable to chemically remove (i) 3' allyl groups from incorporated nucleotides to expose a 3'-OH group for further nucleotide incorporation on the solid support, and (ii) detectable labels attached via cleavable linkers; and (c) an aqueous wash solution comprising a Pd(II) scavenger;

wherein said kit is configured for performing at least about 100 cycles of sequencing-by-synthesis.

DETAILED DESCRIPTION

Figure 1:
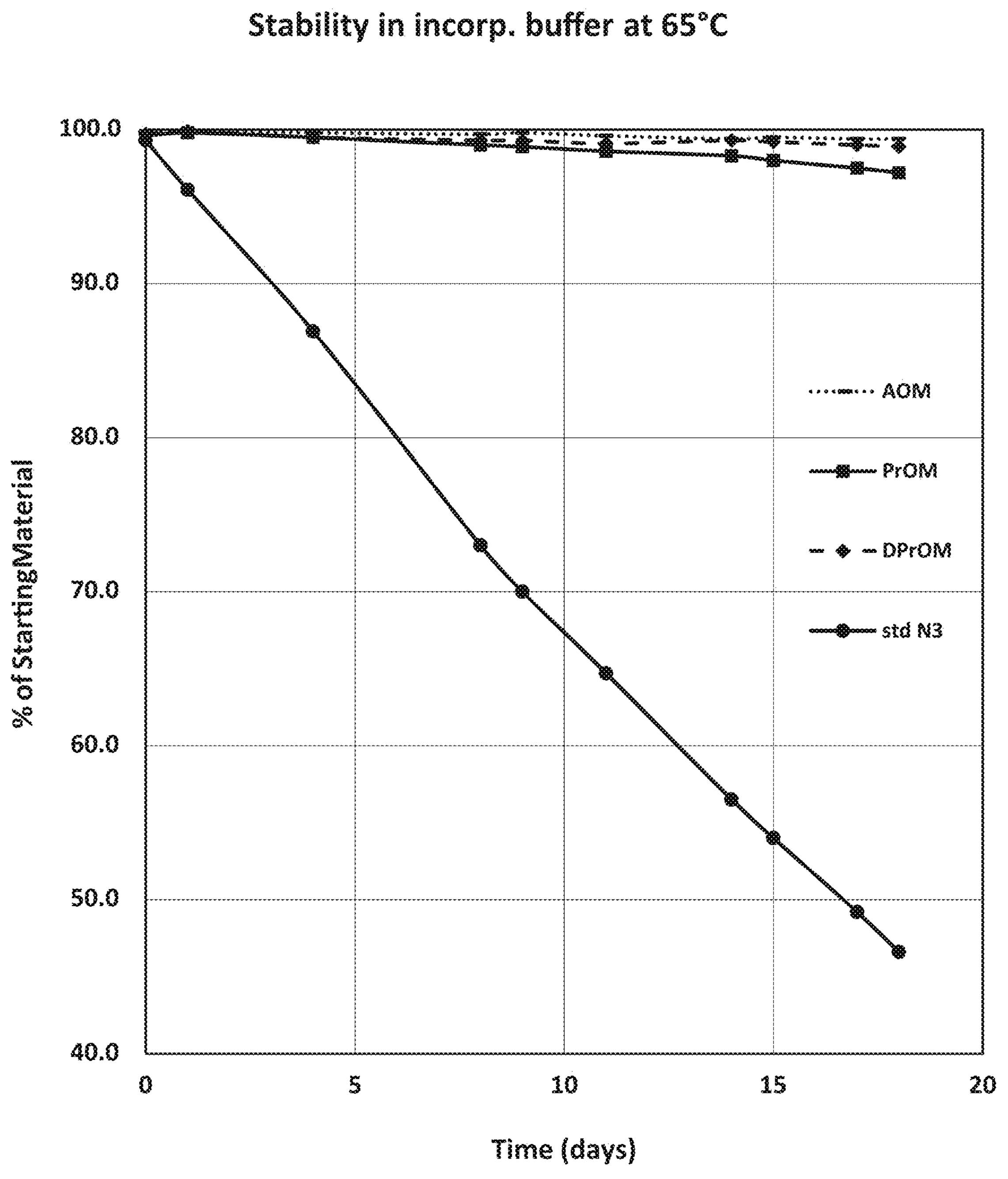
FIG. 1 is a line chart illustrating the stability of various 3' blocked nucleotides as a function of time in a buffer solution at 65° C.

Embodiments of the present disclosure relate to nucleosides and nucleotides with 3'-OH acetal or thiocarbamate blocking groups for sequencing applications, for example, sequencing-by-synthesis (SBS). These blocking groups offer better stability in solution compared to those known in the art. In particular, the 3'-OH blocking groups have improved stability during the synthesis of the fully functionalized nucleotides (ffNs) and also great stability in solution during formulation, storage and operation on the sequencing instruments. In addition, the 3'-OH blocking groups described herein may also achieve low pre-phasing, lower signal decay for improved data quality, which enables longer reads from the sequencing applications.

Some other embodiments of the present disclosure relate to methods of nucleic acid sequencing using nucleotide with 3' allyl blocking group. In particular, the sequencing method described herein involves the use of a Pd(0) catalyst formed from a Pd(II) complex and a water soluble tris(hydroxyalkyl)phosphine to cleave the 3' allyl blocking group after each cycle of the sequencing by synthesis. In some embodiments, the water-soluble phosphine is THPP. The method also involves the use of Pd(0) and/or Pd(II) scavengers. In further embodiments, the nucleotides used in the incorporation step of the sequencing method are labeled nucleotides where the detectable label is covalently attached to the nucleobase via a cleavable linker containing an allyl moiety. The 3' allyl blocking nucleotides can be used in both standard SBS setting in which the nucleotides are labeled, or in a post-incorporation labeling workflow in which the nucleotides are unlabeled.

Definitions

Unless defined otherwise, all technical and scientific terms used herein have the same meaning as is commonly understood by one of ordinary skill in the art. The use of the term "including" as well as other forms, such as "include", "includes," and "included," is not limiting. The use of the term "having" as well as other forms, such as "have", "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

As used herein, common organic abbreviations are defined as follows:

| | |
|---|---|
| ° C. | Temperature in degrees Centigrade |
| dATP | Deoxyadenosine triphosphate |
| dCTP | Deoxycytidine triphosphate |
| dGTP | Deoxyguanosine triphosphate |
| dTTP | Deoxythymidine triphosphate |
| ddNTP | Dideoxynucleotide triphosphate |
| ffN | Fully functionalized nucleotide |
| RT | Room temperature |
| SBS | Sequencing by Synthesis |
| SM | Starting material |

As used herein, the term "array" refers to a population of different probe molecules that are attached to one or more substrates such that the different probe molecules can be differentiated from each other according to relative location. An array can include different probe molecules that are each located at a different addressable location on a substrate. Alternatively, or additionally, an array can include separate substrates each bearing a different probe molecule, wherein the different probe molecules can be identified according to the locations of the substrates on a surface to which the substrates are attached or according to the locations of the substrates in a liquid. Exemplary arrays in which separate substrates are located on a surface include, without limitation, those including beads in wells as described, for example, in U.S. Pat. No. 6,355,431 B1, US 2002/0102578 and PCT Publication No. WO 00/63437. Exemplary formats that can be used in the invention to distinguish beads in a liquid array, for example, using a microfluidic device, such as a fluorescent activated cell sorter (FACS), are described, for example, in U.S. Pat. No. 6,524,793. Further examples of arrays that can be used in the invention include, without limitation, those described in U.S. Pat. Nos. 5,429,807; 5,436,327; 5,561,071; 5,583,211; 5,658,734; 5,837,858; 5,874,219; 5,919,523; 6,136,269; 6,287,768; 6,287,776; 6,288,220; 6,297,006; 6,291,193; 6,346,413; 6,416,949; 6,482,591; 6,514,751 and 6,610,482; and WO 93/17126; WO 95/11995; WO 95/35505; EP 742 287; and EP 799 897.

As used herein, the term "covalently attached" or "covalently bonded" refers to the forming of a chemical bonding that is characterized by the sharing of pairs of electrons between atoms. For example, a covalently attached polymer coating refers to a polymer coating that forms chemical bonds with a functionalized surface of a substrate, as compared to attachment to the surface via other means, for example, adhesion or electrostatic interaction. It will be appreciated that polymers that are attached covalently to a surface can also be bonded via means in addition to covalent attachment.

As used herein, any "R" group(s) represent substituents that can be attached to the indicated atom. An R group may be substituted or unsubstituted. If two "R" groups are described as "together with the atoms to which they are attached" forming a ring or ring system, it means that the collective unit of the atoms, intervening bonds and the two R groups are the recited ring. For example, when the following substructure is present:

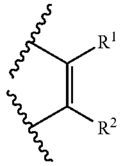

and $R^1$ and $R^2$ are defined as selected from the group consisting of hydrogen and alkyl, or $R^1$ and $R^2$ together with the atoms to which they are attached form an aryl or carbocyclyl, it is meant that $R^1$ and $R^2$ can be selected from hydrogen or alkyl, or alternatively, the substructure has structure:

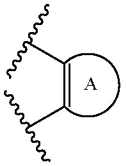

where A is an aryl ring or a carbocyclyl containing the depicted double bond.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as $-CH_2-$, $-CH_2CH_2-$, $-CH_2CH(CH_3)CH_2-$, and the like. Other radical naming conventions clearly indicate that the radical is a di-radical such as "alkylene" or "alkenylene."

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "$C_a$ to $C_b$" in which "a" and "b" are integers refer to the number of carbon atoms in an alkyl, alkenyl or alkynyl group, or the number of ring atoms of a cycloalkyl or aryl group. That is, the alkyl, the alkenyl, the alkynyl, the ring of the cycloalkyl, and ring of the aryl can contain from "a" to "b", inclusive, carbon atoms. For example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—; a $C_3$ to $C_4$ cycloalkyl group refers to all cycloalkyl groups having from 3 to 4 carbon atoms, that is, cyclopropyl and cyclobutyl. Similarly, a "4 to 6 membered heterocyclyl" group refers to all heterocyclyl groups with 4 to 6 total ring atoms, for example, azetidine, oxetane, oxazoline, pyrrolidine, piperidine, piperazine, morpholine, and the like. If no "a" and "b" are designated with regard to an alkyl, alkenyl, alkynyl, cycloalkyl, or aryl group, the broadest range described in these definitions is to be assumed. As used herein, the term "$C_1$-$C_6$" includes $C_1$, $C_2$, $C_3$, $C_4$, $C_5$ and $C_6$, and a range defined by any of the two numbers. For example, $C_1$-$C_6$ alkyl includes $C_1$, $C_2$, $C_3$, $C_4$, $C_5$ and $C_6$ alkyl, $C_2$-$C_6$ alkyl, $C_1$-$C_3$ alkyl, etc. Similarly, $C_2$-$C_6$ alkenyl includes $C_2$, $C_3$, $C_4$, $C_5$ and $C_6$ alkenyl, $C_2$-$C_5$ alkenyl, $C_3$-$C_4$ alkenyl, etc.; and $C_2$-$C_6$ alkynyl includes $C_2$, $C_3$, $C_4$, $C_5$ and $C_6$ alkynyl, $C_2$-$C_5$ alkynyl, $C_3$-$C_4$ alkynyl, etc. $C_3$-$C_8$ cycloalkyl each includes hydrocarbon ring containing 3, 4, 5, 6, 7 and 8 carbon atoms, or a range defined by any of the two numbers, such as $C_3$-$C_7$ cycloalkyl or $C_5$-$C_6$ cycloalkyl.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 6 carbon atoms. The alkyl group may be designated as "$C_1$-$C_4$alkyl" or similar designations. By way of example only, "$C_1$-$C_6$ alkyl" indicates that there are one to six carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_1$-$C_9$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 6 carbon atoms. The alkenyl group may be designated as "$C_2$-$C_6$ alkenyl" or similar designations. By way of example only, "$C_2$-$C_6$ alkenyl" indicates that there are two to six carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 6 carbon atoms. The alkynyl group may be designated as "$C_2$-$C_6$ alkynyl" or similar designations. By way of example only, "$C_2$-$C_6$ alkynyl" indicates that there are two to six carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atoms, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 6 carbon atoms. The heteroalkyl group may be designated as "$C_1$-$C_6$ heteroalkyl" or similar designations. The heteroalkyl group may contain one or more heteroatoms. By way of example only, "$C_4$-$C_6$ heteroalkyl" indicates that there are four to six carbon atoms in the heteroalkyl chain and additionally one or more heteroatoms in the backbone of the chain.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_6$-$C_{10}$ aryl," "$C_6$ or $C_{10}$ aryl," or similar designations. Examples of aryl groups include, but are not limited to, phenyl, naphthyl, azulenyl, and anthracenyl.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_1$-$C_6$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_1$-$C_6$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_3$-$C_6$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

As used herein, "cycloalkyl" means a fully saturated carbocyclyl ring or ring system. Examples include cyclopropyl, cyclobutyl, cyclopentyl, and cyclohexyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom (s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

An "O-carboxy" group refers to a "—OC(=O)R" group in which R is selected from hydrogen, $C_1$-$C_6$ alkyl, $C_2$-$C_6$ alkenyl, $C_2$-$C_6$ alkynyl, $C_3$-$C_7$ carbocyclyl, $C_6$-$C_{10}$ aryl, 5-10 membered heteroaryl, and 3-10 membered heterocyclyl, as defined herein.

A "C-carboxy" group refers to a "—C(=O)OR" group in which R is selected from the group consisting of hydrogen, $C_1$-$C_6$ alkyl, $C_2$-$C_6$ alkenyl, $C_2$-$C_6$ alkynyl, $C_3$-$C_7$ carbocyclyl, $C_6$-$C_{10}$ aryl, 5-10 membered heteroaryl, and 3-10 membered heterocyclyl, as defined herein. A non-limiting example includes carboxyl (i.e., —C(=O)OH).

A "sulfonyl" group refers to an "—$SO_2R$" group in which R is selected from hydrogen, $C_1$-$C_6$ alkyl, $C_2$-$C_6$ alkenyl, $C_2$-$C_6$ alkynyl, $C_3$-$C_7$ carbocyclyl, $C_6$-$C_{10}$ aryl, 5-10 membered heteroaryl, and 3-10 membered heterocyclyl, as defined herein.

A "sulfino" group refers to a "—S(=O)OH" group.

A "sulfo" group refers to a "—S(=O)$_2$OH" or "—$SO_3H$" group.

A "sulfonate" group refers to a "—$SO_3$—" group.

A "sulfate" group refers to "—$SO_4$" group.

A "S-sulfonamido" group refers to a "—$SO_2NR_AR_B$" group in which $R_A$ and $R_B$ are each independently selected from hydrogen, $C_1$-$C_6$ alkyl, $C_2$-$C_6$ alkenyl, $C_2$-$C_6$ alkynyl, $C_3$-$C_7$ carbocyclyl, $C_6$-$C_{10}$ aryl, 5-10 membered heteroaryl, and 3-10 membered heterocyclyl, as defined herein.

An "N-sulfonamido" group refers to a "—$N(R_A)SO_2R_B$" group in which $R_A$ and $R_b$ are each independently selected from hydrogen, $C_1$-$C_6$ alkyl, $C_2$-$C_6$ alkenyl, $C_2$-$C_6$ alkynyl, $C_3$-$C_7$ carbocyclyl, $C_6$-$C_{10}$ aryl, 5-10 membered heteroaryl, and 3-10 membered heterocyclyl, as defined herein.

A "C-amido" group refers to a "—C(=O)$NR_AR_B$" group in which $R_A$ and $R_B$ are each independently selected from hydrogen, $C_1$-$C_6$ alkyl, $C_2$-$C_6$ alkenyl, $C_2$-$C_6$ alkynyl, $C_3$-$C_7$ carbocyclyl, $C_6$-$C_{10}$ aryl, 5-10 membered heteroaryl, and 3-10 membered heterocyclyl, as defined herein.

An "N-amido" group refers to a "—$N(R_A)C(=O)R_B$" group in which $R_A$ and $R_B$ are each independently selected from hydrogen, $C_1$-$C_6$ alkyl, $C_2$-$C_6$ alkenyl, $C_2$-$C_6$ alkynyl, $C_3$-$C_7$ carbocyclyl, $C_6$-$C_{10}$ aryl, 5-10 membered heteroaryl, and 3-10 membered heterocyclyl, as defined herein.

An "amino" group refers to a "—$NR_AR_B$" group in which $R_A$ and $R_B$ are each independently selected from hydrogen, $C_1$-$C_6$ alkyl, $C_2$-$C_6$ alkenyl, $C_2$-$C_6$ alkynyl, $C_3$-$C_7$ carbocyclyl, $C_6$-$C_{10}$ aryl, 5-10 membered heteroaryl, and 3-10 membered heterocyclyl, as defined herein. A non-limiting example includes free amino (i.e., —$NH_2$).

An "aminoalkyl" group refers to an amino group connected via an alkylene group.

An "alkoxyalkyl" group refers to an alkoxy group connected via an alkylene group, such as a "$C_2$-$C_8$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$alkyl, $C_1$-$C_6$ alkoxy, $C_1$-$C_6$ haloalkyl, and $C_1$-$C_6$ haloalkoxy), halo, —CN, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, —$SO_3H$, sulfino, —$OSO_2C_{1-4}$alkyl, and oxo (=O). Wherever a group is described as "optionally substituted" that group can be substituted with the above substituents.

The term "hydroxy" as used herein refers to a —OH group.

The term "cyano" group as used herein refers to a "—CN" group.

The term "azido" as used herein refers to a —$N_3$ group.

As used herein, a "nucleotide" includes a nitrogen containing heterocyclic base, a sugar, and one or more phosphate groups. They are monomeric units of a nucleic acid sequence. In RNA, the sugar is a ribose, and in DNA a deoxyribose, i.e., a sugar lacking a hydroxyl group that is present in ribose. The nitrogen containing heterocyclic base can be purine or pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, a "nucleoside" is structurally similar to a nucleotide but is missing the phosphate moieties. An example of a nucleoside analogue would be one in which the label is linked to the base and there is no phosphate group attached to the sugar molecule. The term "nucleoside" is used herein in its ordinary sense as understood by those skilled in the art. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers.

The term "purine base" is used herein in its ordinary sense as understood by those skilled in the art and includes its tautomers. Similarly, the term "pyrimidine base" is used herein in its ordinary sense as understood by those skilled in the art and includes its tautomers. A non-limiting list of optionally substituted purine-bases includes purine, adenine, guanine, hypoxanthine, xanthine, alloxanthine, 7-alkylguanine (e.g., 7-methylguanine), theobromine, caffeine, uric acid and isoguanine. Examples of pyrimidine bases include, but are not limited to, cytosine, thymine, uracil, 5,6-dihydrouracil and 5-alkylcytosine (e.g., 5-methylcytosine).

As used herein, when an oligonucleotide or polynucleotide is described as "comprising" a nucleoside or nucleotide described herein, it means that the nucleoside or nucleotide described herein forms a covalent bond with the oligonucleotide or polynucleotide. Similarly, when a nucleoside or nucleotide is described as part of an oligonucleotide or polynucleotide, such as "incorporated into" an oligonucleotide or polynucleotide, it means that the nucleoside or nucleotide described herein forms a covalent bond with the oligonucleotide or polynucleotide. In some such embodiments, the covalent bond is formed between a 3' hydroxy group of the oligonucleotide or polynucleotide with the 5' phosphate group of a nucleotide described herein as a phosphodiester bond between the 3' carbon atom of the oligonucleotide or polynucleotide and the 5' carbon atom of the nucleotide.

As used herein, "derivative" or "analogue" means a synthetic nucleotide or nucleoside derivative having modified base moieties and/or modified sugar moieties. Such derivatives and analogs are discussed in, e.g., Scheit, *Nucleotide Analogs* (John Wiley & Son, 1980) and Uhlman et al., *Chemical Reviews* 90:543-584, 1990. Nucleotide analogs can also comprise modified phosphodiester linkages, including phosphorothioate, phosphorodithioate, alkyl-phosphonate, phosphoranilidate and phosphoramidate linkages. "Derivative", "analog" and "modified" as used herein, may be used interchangeably, and are encompassed by the terms "nucleotide" and "nucleoside" defined herein.

As used herein, the term "phosphate" is used in its ordinary sense as understood by those skilled in the art, and includes its protonated forms (for example,

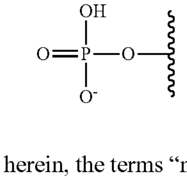 and 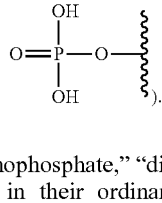).

As used herein, the terms "monophosphate," "diphosphate," and "triphosphate" are used in their ordinary sense as understood by those skilled in the art, and include protonated forms.

The terms "protecting group" and "protecting groups" as used herein refer to any atom or group of atoms that is added to a molecule in order to prevent existing groups in the molecule from undergoing unwanted chemical reactions. Sometimes, "protecting group" and "blocking group" can be used interchangeably.

As used herein, the prefixes "photo" or "photo-" mean relating to light or electromagnetic radiation. The term can encompass all or part of the electromagnetic spectrum including, but not limited to, one or more of the ranges commonly known as the radio, microwave, infrared, visible, ultraviolet, X-ray or gamma ray parts of the spectrum. The part of the spectrum can be one that is blocked by a metal region of a surface such as those metals set forth herein. Alternatively, or additionally, the part of the spectrum can be one that passes through an interstitial region of a surface such as a region made of glass, plastic, silica, or other material set forth herein. In particular embodiments, radiation can be used that is capable of passing through a metal. Alternatively, or additionally, radiation can be used that is masked by glass, plastic, silica, or other material set forth herein.

As used herein, the term "phasing" refers to a phenomenon in SBS that is caused by incomplete removal of the 3' terminators and fluorophores, and failure to complete the incorporation of a portion of DNA strands within clusters by polymerases at a given sequencing cycle. Pre-phasing is caused by the incorporation of nucleotides without effective 3' terminators, wherein the incorporation event goes 1 cycle ahead due to a termination failure. Phasing and pre-phasing cause the measured signal intensities for a specific cycle to consist of the signal from the current cycle as well as noise from the preceding and following cycles. As the number of cycles increases, the fraction of sequences per cluster affected by phasing and pre-phasing increases, hampering the identification of the correct base. Pre-phasing can be caused by the presence of a trace amount of unprotected or unblocked 3'-OH nucleotides during sequencing by synthesis (SBS). The unprotected 3'-OH nucleotides could be generated during the manufacturing processes or possibly during the storage and reagent handling processes. Accordingly, the discovery of nucleotide analogues which decrease the incidence of pre-phasing is surprising and provides a great advantage in SBS applications over existing nucleotide analogues. For example, the nucleotide analogues provided can result in faster SBS cycle time, lower phasing and pre-phasing values, and longer sequencing read lengths.

3' Acetal Blocking Groups

Some embodiments of the present disclosure relate to a nucleotide or nucleoside molecule comprising a ribose or deoxyribose having a removable 3'-OH protecting or blocking group forming a structure

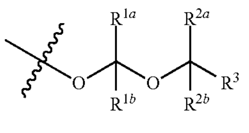

covalently attached to the 3'-carbon atom, wherein:

each $R^{1a}$ and $R^{1b}$ is independently H, $C_1$-$C_6$ alkyl, $C_1$-$C_6$ haloalkyl, $C_1$-$C_6$ alkoxy, $C_1$-$C_6$ haloalkoxy, cyano, halogen, optionally substituted phenyl, or optionally substituted aralkyl;

each $R^{2a}$ and $R^{2b}$ is independently H, $C_1$-$C_6$ alkyl, $C_1$-$C_6$ haloalkyl, cyano, or halogen;

alternatively $R^{1a}$ and $R^{2a}$ together with the atoms to which they are attached form an optionally substituted five to eight membered heterocyclyl group;

$R^3$ is H, optionally substituted $C_2$-$C_6$ alkenyl, optionally substituted $C_3$-$C_7$ cycloalkenyl, optionally substituted $C_2$-$C_6$ alkynyl, or optionally substituted ($C_1$-$C_6$ alkylene)$Si(R^4)_3$; and each $R^4$ is independently H, $C_1$-$C_6$ alkyl, or optionally substituted $C_6$-$C_{10}$ aryl; provided that when each $R^{1a}$, $R^{1b}$, $R^{2a}$ and $R^{2b}$ is H, then $R^3$ is not H.

Some further embodiments of the present disclosure relate to a compound having the structure of Formula (I):

(I)

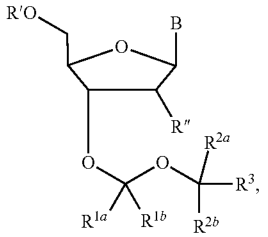

wherein R' is H, monophosphate, di-phosphate, tri-phosphate, thiophosphate, a phosphate ester analog, —O— attached to a reactive phosphorous containing group, or —O— protected by a protecting group; R" is H or OH; B is a nucleobase; each of $R^{1a}$, $R^{1b}$, $R^{2a}$, $R^{2b}$ and $R^3$ is defined above. In some further embodiment, B is

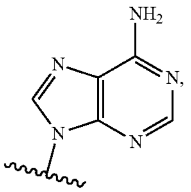

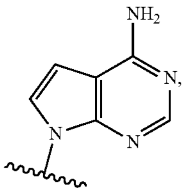

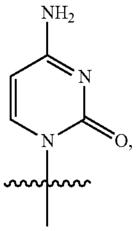

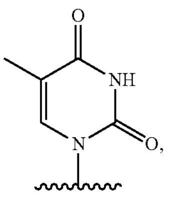

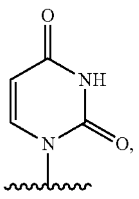

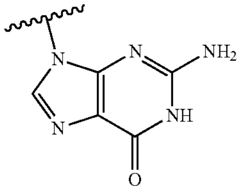

or

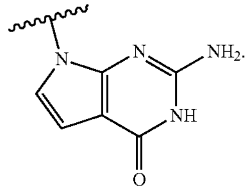

In some further embodiments, the nucleobase is covalently bounded to a detectable label (e.g., a fluorescent dye), optionally through a linker, for example, B is

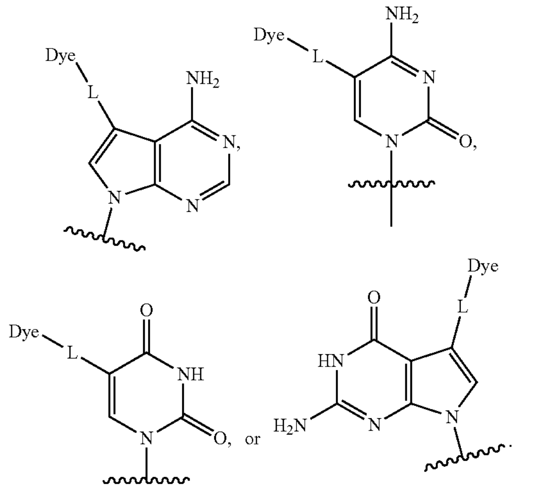

In some such embodiments, R' is triphosphate. In some such embodiment, R" is H.

In some embodiments of the acetal blocking group described herein, at least one of $R^{1a}$ and $R^{1b}$ is H. In some such embodiments, each $R^{1a}$ and $R^{1b}$ is H. In some other embodiments, at least one of $R^{1a}$ and $R^{1b}$ is $C_1$-$C_6$ alkyl, for example, methyl, ethyl, isopropyl or t-butyl. In some embodiments, each of $R^{2a}$ and $R^{2b}$ is independently H, halogen or $C_1$-$C_6$ alkyl. In some such embodiments, at least one of $R^{2a}$ and $R^{2b}$ is H or $C_1$-$C_6$ alkyl. In some such embodiment, each $R^{2a}$ and $R^{2b}$ is H. In some such embodiments, each $R^{2a}$ and $R^{2b}$ is $C_1$-$C_6$ alkyl, for example methyl, ethyl, isopropyl or t-butyl. In one embodiment, each $R^{2a}$ and $R^{2b}$ is methyl. In some such embodiments, each $R^{2a}$ and $R^{2b}$ is independently $C_1$-$C_6$ alkyl or halogen. In some such embodiments, $R^{2a}$ is H, and $R^{2b}$ is halogen or $C_1$-$C_6$ alkyl.

In some embodiments of the acetal blocking group described herein, $R^3$ is optionally substituted $C_2$-$C_6$ alkenyl. In some such embodiments, $R^3$ is $C_2$-$C_6$ alkenyl (for example, vinyl, propenyl) optionally substituted with one or more substituents independently selected from the group consisting of halogen, $C_1$-$C_6$ alkyl, $C_1$-$C_6$ haloalkyl, and combinations thereof. In some further embodiments, $R^3$ is

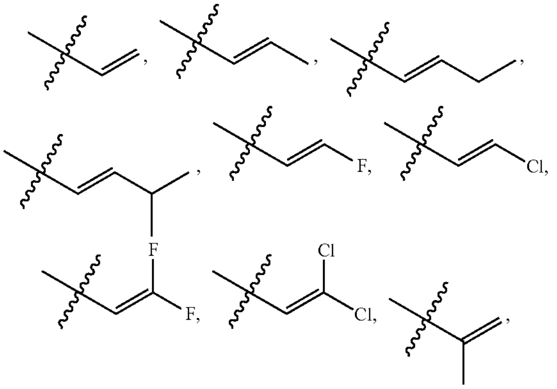

-continued

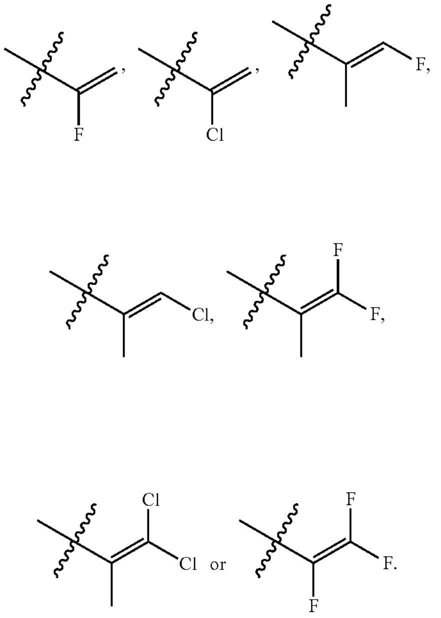

In some other embodiments, $R^3$ is optionally substituted $C_2$-$C_6$ alkynyl. In some such embodiments, $R^3$ is $C_2$-$C_6$ alkynyl (e.g., ethynyl, propynyl) optionally substituted with one or more substituents independently selected from the group consisting of halogen, $C_1$-$C_6$ alkyl, $C_1$-$C_6$ haloalkyl, and combinations thereof. In one embodiment, $R^3$ is optionally substituted ethynyl ( 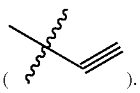 ).

In some other embodiments, $R^3$ is optionally substituted ($C_1$-$C_6$ alkylene)$Si(R^4)_3$. In some such embodiments, at least one of $R^4$ is $C_{1-4}$ alkyl. In some further embodiments, each one of $R^4$ is $C_1$-$C_4$ alkyl, for example, methyl, ethyl, isopropyl or t-butyl. In one embodiment, $R^3$ is $—(CH_2)—SiMe_3$. In some alternative embodiments, $R^3$ is $C_1$-$C_6$ alkyl.

In some alternative embodiments, $R^{1a}$ and $R^{2a}$ together with the atoms to which they are attached form a five to seven membered heterocyclyl. In some such embodiments, $R^{1a}$ and $R^{2a}$ together with the atoms to which they are attached form a six membered heterocyclyl. In some such embodiments, the six membered heterocyclyl group has the structure

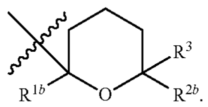

In some further embodiments, at least one of each $R^{1b}$, $R^{2b}$ and $R^3$ is H. In some other embodiments, at least one of each $R^{1b}$, $R^{2b}$ and $R^3$ is $C_1$-$C_6$ alkyl. In one embodiment, each $R^{1b}$, $R^{2b}$ and $R^3$ is H.

In some further embodiments, the compound of Formula (I) is also represented by Formula (Ia):

(Ia)

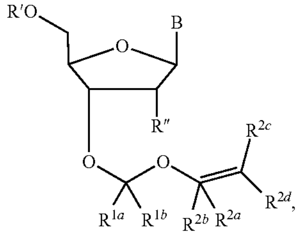

where each $R^{2c}$ and $R^{2d}$ is independently H, halogen (e.g., fluoro, chloro), $C_1$-$C_6$ alkyl (e.g., methyl, ethyl, or isopropyl), or $C_1$-$C_6$ haloalkyl (e.g., —$CHF_2$, —$CH_2F$, or —$CF_3$). In some such embodiments, one of $R^{1a}$ and $R^{1b}$ is H. In some such embodiments, each $R^{1a}$ and $R^{1b}$ is H. In some other embodiments, at least one of $R^{1a}$ and $R^{1b}$ is $C_1$-$C_6$ alkyl, for example, methyl, ethyl, isopropyl or t-butyl. In some embodiments, each of $R^{2a}$ and $R^{2b}$ is independently H, halogen or $C_1$-$C_6$ alkyl. In some such embodiment, each $R^{2a}$ and $R^{2b}$ is H. In some such embodiments, each of $R^{2c}$ and $R^{2d}$ is independently H, halogen or $C_1$-$C_6$ alkyl. In some such embodiments, each $R^{2c}$ and $R^{2d}$ is $C_1$-$C_6$ alkyl, for example methyl, ethyl, isopropyl or t-butyl. In one embodiment, each $R^{2c}$ and $R^{2d}$ is methyl. In some such embodiments, each $R^{2c}$ and $R^{2d}$ is independently halogen. In some such embodiments, $R^{2c}$ is H, and $R^{2d}$ is H, halogen (fluoro, chloro) or $C_1$-$C_6$ alkyl (e.g., methyl, ethyl, isopropyl or t-butyl). In further embodiments, each $R^{1a}$ and $R^{1b}$ is H; $R^{2a}$ is H; $R^{2b}$ is H, halogen or methyl; $R^{2c}$ is H; and $R^{2d}$ is H, halogen, methyl, ethyl, isopropyl or t-butyl.

Non-limiting embodiments of the blocking groups described herein including those having the structure selected from the group consisting of:

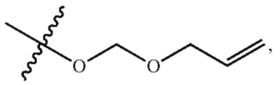

(AOM)

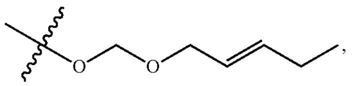

(eAOM)

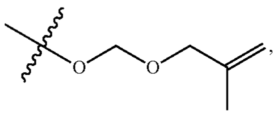

(iAOM)

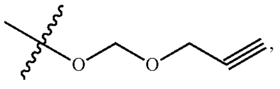

(PrOM)

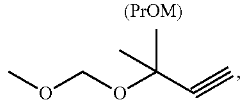

(DPrOM)

-continued

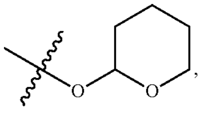

and (THP)

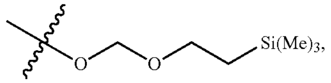

(SEM)

attached to the 3'-carbon of the ribose or deoxyribose.

3' Thiocarbamate Blocking Groups

Some additional embodiments of the present disclosure relate to a nucleoside or nucleotide comprising a ribose or deoxyribose having a removable 3'-OH blocking group forming a structure

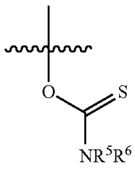

covalently attached to the 3'-carbon atom, wherein:

each of $R^5$ and $R^6$ is independently H, $C_1$-$C_6$ alkyl, $C_2$-$C_6$ alkenyl, $C_2$-$C_6$ alkynyl, $C_1$-$C_6$ haloalkyl, $C_2$-$C_8$ alkoxyalkyl, optionally substituted —$(CH_2)_m$-phenyl, optionally substituted —$(CH_2)_n$-(5 or 6 membered heteroaryl), optionally substituted —$(CH_2)_k$—$C_3$-$C_7$ carbocyclyl, or optionally substituted —$(CH_2)_p$-(3 to 7 membered heterocyclyl);

alternatively, $R^5$ and $R^6$ together with the atoms to which they are attached form an optionally substituted five to seven membered heterocyclyl;

each of —$(CH_2)_m$—, —$(CH_2)_n$—, —$(CH_2)_k$—, and —$(CH_2)_p$— is optionally substituted; and each of m, n, k, and p is independently 0, 1, 2, 3, or 4.

Some additional embodiments relate to a compound of Formula (II):

(II)

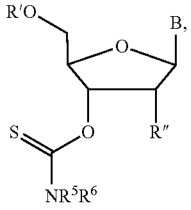

wherein R' is H, monophosphate, di-phosphate, tri-phosphate, thiophosphate, a phosphate ester analog, —O— attached to a reactive phosphorous containing group, or —O— protected by a protecting group; R" is H or OH; B is a nucleobase; each of $R^5$ and $R^6$ is defined above. In some further embodiment, B is

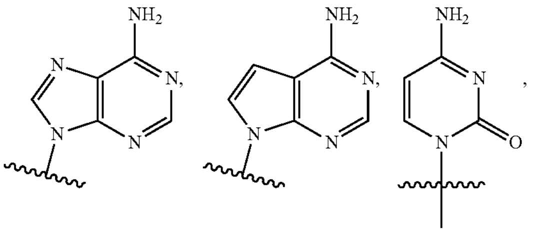

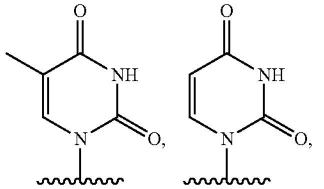

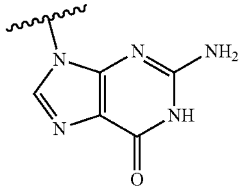

or

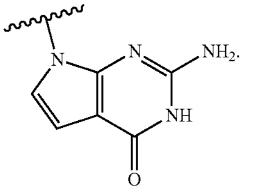

In some further embodiments, the nucleobase is covalently bounded to a detectable label (e.g., a fluorescent dye), optionally through a linker, for example, B is

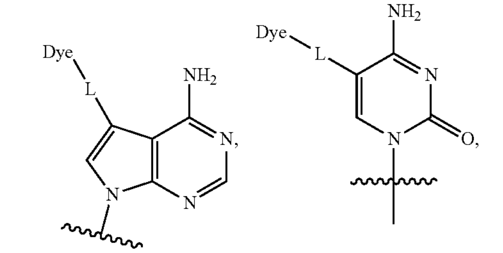

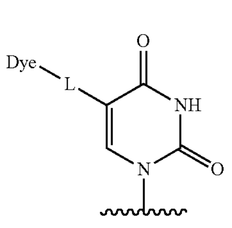

or

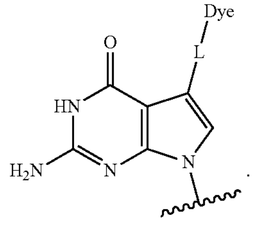

In some such embodiments, R' is triphosphate. In some such embodiment, R" is H.

In some embodiments of the thiocarbamate blocking group described herein, at least one of $R^5$ and $R^6$ is H. In some such embodiments, each $R^5$ and $R^6$ is H. In some such embodiments, $R^5$ is H and $R^6$ is $C_1$-$C_6$ alkyl, for example, methyl, ethyl, isopropyl or t-butyl. In some such embodiments, $R^5$ is H and $R^6$ is $C_2$-$C_6$ alkenyl (for example, vinyl or allyl) or $C_2$-$C_6$ alkynyl (for example, ethynyl or propynyl). In some such embodiments, $R^5$ is H and $R^2$ is optionally substituted $-(CH_2)_m$-phenyl, optionally substituted $-(CH_2)_n$-(5 or 6 membered heteroaryl), optionally substituted $-(CH_2)_k-C_3$-$C_7$ carbocyclyl, or optionally substituted $-(CH_2)_p$-(3 to 7 membered heterocyclyl). In some further embodiment, the $C_3$-$C_7$ carbocyclyl group may be a $C_3$-$C_7$ cycloalkyl or $C_3$-$C_7$ cycloalkenyl. The 3 to 7 membered heterocyclyl group may comprise zero or one double bond in the ring structure. In further embodiments, $R^5$ is H and $R^6$ is optionally substituted $-(CH_2)_m$-phenyl, optionally substituted $-(CH_2)_n$-6 membered heteroaryl, optionally substituted $-(CH_2)_k-C_5$ or $C_6$ carbocyclyl, or optionally substituted $-(CH_2)_p$-(5 or 6 membered heterocyclyl). In some embodiments, m, n, k, or p is 0. In other embodiments, m, n, k or p is 1 or 2. In some other embodiments, at least one of $R^5$ and $R^6$ is $C_1$-$C_6$ alkyl, for example, methyl, ethyl, isopropyl or t-butyl. In some further embodiments, both $R^5$ and $R^6$ are $C_1$-$C_6$ alkyl. In one embodiment, both $R^5$ and $R^6$ are methyl.

In some alternative embodiments, $R^5$ and $R^6$ together with the atoms to which they are attached form an optionally substituted five to seven membered heterocyclyl. In some such embodiments, $R^5$ and $R^6$ together with the atoms to which they are attached form an optionally substituted piperidinyl.

Non-limiting embodiments of the 3'-O-thiocarbamate blocking groups described herein including those having the structure selected from the group consisting of:

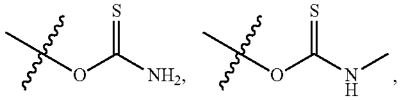

, and

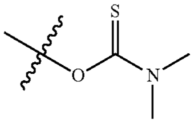

(DMTC)

covalently attached to the 3'-carbon of the ribose or deoxyribose.

Additional embodiments of the present disclosure relate to an oligonucleotide or a polynucleotide comprising a nucleoside or nucleotide described herein.

In any of the embodiments of the blocking groups described herein, when a group is described as "optionally substituted" it may be either unsubstituted or substituted.

In any embodiments of the nucleotides or nucleosides with the 3'hydroxy blocking group described herein, the nucleoside or nucleotide may be covalently attached to a detectable label (for example, a fluorophore), optionally via a linker. The linker may be cleavable or non-cleavable. In some such embodiments, the detectable label (e.g., fluorophore) is covalently attached to the nucleobase of the nucleoside or nucleotide via a cleavable linker. In some other embodiments, the detectable label (e.g., fluorophore) is covalently attached to the 3'oxygen of the nucleoside or nucleotide via a cleavable linker. In some further embodiments, such cleavable linker may comprise an azido moiety or a disulfide moiety, an acetal moiety, or a thiocarbamate moiety. In some embodiments, the 3' hydroxy blocking group and the cleavable linker (and the attached label) may be removed under the same or substantially same chemical reaction conditions, for example, the blocking group and the detectable label may be removed in a single chemical reaction. In other embodiments, the blocking group and the detectable labeled are removed in two separate steps.

In some embodiments, the nucleotides or nucleosides described herein comprises 2' deoxyribose. In some further aspect, the 2' deoxyribose contains one, two or three phosphate groups at the 5' position of the sugar ring. In some further aspect, the nucleotides described herein are nucleotide triphosphate.

In some embodiments, the 3' blocked nucleotides or nucleosides described herein provide superior stability in solution during storage, or reagent handling during sequencing applications, compared to the same nucleotides or nucleosides protected with a standard 3'-OH blocking group disclosed in the prior art, for example, the 3'-O-azidomethyl protecting group. For example, the acetal or thiocarbamate blocking groups disclosed herein may confer at least 5%, 10%, 20%, 30%, 40%, 50%, 60%, 70%, 80%, 90%, 100%, 200%, 300%, 400%, 500%, 600%, 700%, 800%, 900%, 1000%, 1500%, 2000%, 2500%, or 3000% improved stability compare to an azidomethyl protected 3'-OH at the same condition for the same period of time, thereby reducing the pre-phasing values and resulting in longer sequencing read lengths. In some embodiments, the stability is measured at ambient temperature or a temperature below ambient temperature (such as 4-10° C.). In other embodiments, the stability is measured at an elevated temperature, such as 40° C., 45° C., 50° C., 55° C., 60° C. or 65° C. In some such embodiments, the stability is measured in solution in a basic pH environment, e.g., at pH 9.0, 9.2, 9.4, 9.6, 9.8. or 10.0. In some such embodiments, the stability is measured with or without the presence of an enzyme, such as a polymerase (e.g., a DNA polymerase), a terminal deoxynucleotidyl transferase, or a reverse transcriptase.

In some embodiments, the 3' blocked nucleotides or nucleosides described herein provide superior deblocking rate in solution during the chemical cleavage step of the sequencing applications, compared to the same nucleotides or nucleosides protected with a standard 3'-OH blocking group disclosed in the prior art, for example, the 3'-O-azidomethyl protecting group. For example, the acetal or thiocarbamate blocking groups disclosed herein may confer at least 5%, 10%, 20%, 30%, 40%, 50%, 60%, 70%, 80%, 90%, 100%, 150%, 200%, 300%, 400%, 500%, 600%, 700%, 800%, 900%, 1000%, 1500%, or 2000% improved deblocking rate compare to an azidomethyl protected 3'-OH using the standard deblocking reagent (such as tris(hydroxypropyl)phosphine), thereby reducing the overall time for a sequencing cycle. In some embodiments, the deblocking rate is measured at ambient temperature or a temperature below ambient temperature (such as 4-10° C.). In other embodiments, the deblocking rate is measured at an elevated temperature, such as 40° C., 45° C., 50° C., 55° C., 60° C. or 65° C. In some such embodiments, the deblocking rate is measured in solution in a basic pH environment, e.g., at pH 9.0, 9.2, 9.4, 9.6, 9.8. or 10.0. In some such embodiments, the molar ratio of the deblocking reagent to substrate (i.e., 3' blocked nucleoside or nucleotide) is about 10:1, about 5:1, about 2:1 or about 1:1.

In some embodiments, a palladium deblocking reagent (e.g., Pd(0) is used to remove the 3' acetal blocking groups (e.g., AOM blocking group). Pd may forms a chelation complex with the two oxygen atoms of the AOM group, as well as the double bond of the allyl group, allowing the deblocking reagent in direct vicinity of the functionality to be removed and may result in accelerated deblocking rate.

Deprotection of the 3'-OH Blocking Groups

The 3'-acetal blocking groups described herein may be removed or cleaved under various chemical conditions. For acetal blocking groups

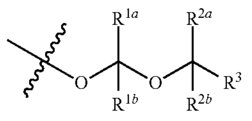

that contain a vinyl or alkenyl moiety, non-limiting cleaving condition includes a Pd(II) complex, such as $Pd(OAc)_2$ or allylPd(II) chloride dimer, in the presence of a phosphine ligand, for example tris(hydroxymethyl)phosphine (THMP), or tris(hydroxylpropyl)phosphine (THP or THPP). For those blocking groups containing an alkynyl group (e.g., an ethynyl), they may also be removed by a Pd(II) complex (e.g., $Pd(OAc)_2$ or allyl Pd(II) chloride dimer) in the presence of a phosphine ligand (e.g., THP or THMP).

Palladium Cleavage Reagents for Deblocking 3' Acetal Blocking Group

In some embodiments, the acetal blocking group described herein may be cleaved by a palladium catalyst. In some such embodiments, the Pd catalyst is water soluble. In some such embodiments, is a Pd(0) complex (e.g., Tris(3,3',3"-phosphinidynetris(benzenesulfonato)palladium(0) nonasodium salt nonahydrate). In some instances, the Pd(0) complex may be generated in situ from reduction of a Pd(II) complex by reagents such as alkenes, alcohols, amines, phosphines, or metal hydrides. Suitable palladium sources include $Na_2PdCl_4$, $Pd(CH_3CN)_2Cl_2$, $(PdCl(C_3H_5))_2$, $[Pd(C_3H_5)(THP)]Cl$, $[Pd(C_3H_5)(THP)_2]Cl$, $Pd(OAc)_2$, $Pd(Ph_3)_4$, $Pd(dba)_2$, $Pd(Acac)_2$, $PdCl_2(COD)$, and $Pd(TFA)_2$. In one such embodiment, the Pd(0) complex is generated in situ from $Na_2PdCl_4$. In another embodiment, the palladium source is allyl palladium(II) chloride dimer $[(PdCl(C_3H_5))_2]$. In some embodiments, the Pd(0) complex is generated in an aqueous solution by mixing a Pd(II) complex with a phosphine. Suitable phosphines include water soluble phosphines, such as tris(hydroxypropyl)phosphine (THP), tris(hydroxymethyl)phosphine (THMP), 1,3,5-triaza-7-phosphaadamantane (PTA), bis(p-sulfonatophenyl)phenylphosphine dihydrate potassium salt, tris(carboxyethyl)phosphine (TCEP), and triphenylphosphine-3,3',3"-trisulfonic acid trisodium salt.

In some embodiments, the Pd(0) is prepared by mixing a Pd(II) complex $[(PdCl(C_3H_5))_2]$ with THP in situ. The molar ratio of the Pd(II) complex and the THP may be about 1:2, 1:3, 1:4, 1:5, 1:6, 1:7, 1:8, 1:9, or 1:10. In some further embodiments, one or more reducing agents may be added, such as ascorbic acid or a salt thereof (e.g., sodium ascorbate). In some embodiments, the cleavage mixture may contain additional buffer reagents, such as a primary amine, a secondary amine, a tertiary amine, a carbonate salt, a phosphate salt, or a borate salt, or combinations thereof. In some further embodiments, the buffer reagent comprises ethanolamine (EA), tris(hydroxymethyl)aminomethane (Tris), glycine, sodium carbonate, sodium phosphate, sodium borate, 2-dimethyalaminomethanol (DMEA), 2-diethyalaminomethanol (DEEA), N,N,N',N'-tetramethylethylenediamine (TEMED), or N,N,N',N'-tetraethylethylenediamine (TEEDA), or combinations thereof. In one embodiment, the buffer reagent is DEEA. In another embodiment, the buffer reagent contains one or more inorganic salts such as a carbonate salt, a phosphate salt, or a borate salt, or combinations thereof. In one embodiment, the inorganic salt is a sodium salt.

Alternatively, alkynyl moiety containing blocking groups may also be cleaved in the presence of $(NH_4)_2MoS_4$. Other non-limiting cleaving condition for alkynyl moiety includes a Cu(II) complex with THPTA ligand (tris(3-hydroxypropyltriazolylmethyl)amine), and ascorbate. Non-limiting cleaving conditions for blocking groups containing a six-membered heterocycle (e.g., tetrahydropyran) include cyclodextrin or $Ln(OTf)_3$ (lanthanide triflate). Non-limiting cleaving condition for blocking groups containing an alkylsilane group (e.g., $—CH_2SiMe_3$) includes $LiBF_4$ (lithium tetrafluoroborate). Other acetal blocking groups such as $—O(CH_2)O—C_1$-$C_6$ alkyl may be removed by $LiBF_4$ or $Bi(OTf)_3$ (bismuth triflate). Non-limiting exemplary conditions for cleaving the described various blocking groups are illustrated in Scheme 1 below.

Scheme 1. Illustration of 3′-Deblocking Conditions

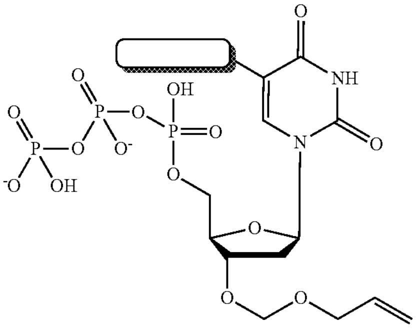

3′-AOM-ffT $Pd(OAc)_2$
THP

ROH

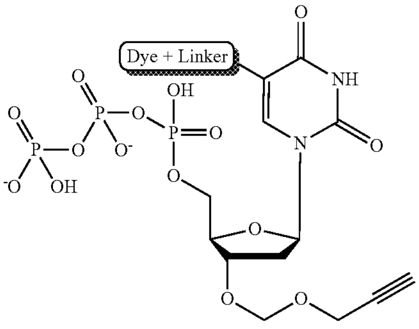

3′-PrOMT-ffT $Pd(OAc)_2$
THP
or
$(NH_4)_2MoS_4$

ROH

-continued

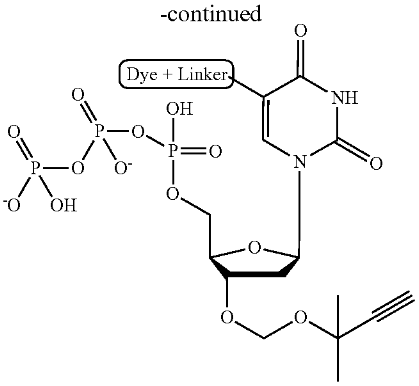

3′-DPrOM-ffT $Pd(OAc)_2$
THP
or
Cu (II), THPTA,
Ascorbate

ROH

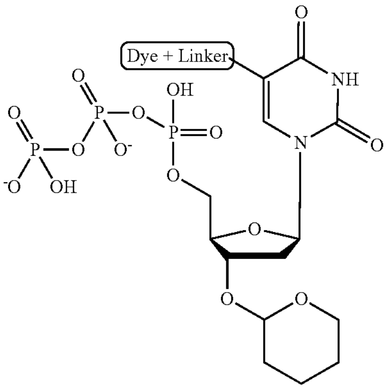

3′-THP-ffT

Cyclodextrine
or
$Ln(OTf)_3$

ROH

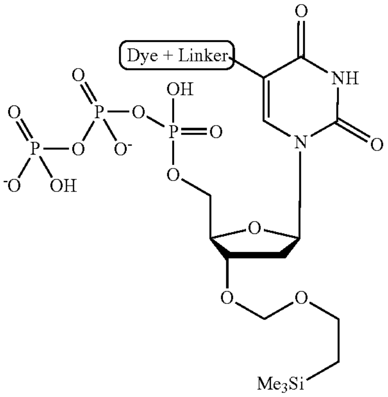

3′-SEM-ffT $LiBF_4$

ROH

-continued

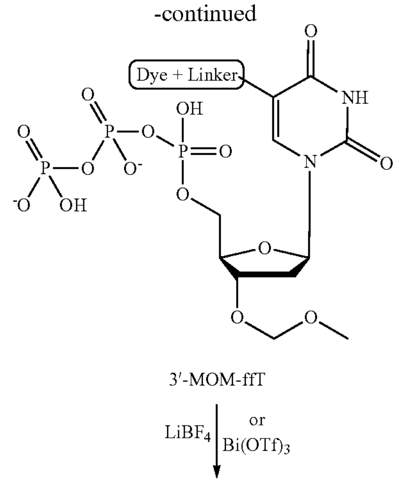

ROH

R is the unprotected labeled nucleotide triphosphaate with 3′ OH

The 3'-O-thiocarbamate blocking groups described herein may be removed or cleaved under various chemical conditions. Non-limiting exemplary conditions for cleaving the thiocarbamate blocking groups described herein include $NaIO_4$ and Oxone® (potassium peroxymonosulfate).

In addition, the azido group in —$CH_2N_3$ can be converted to an amino group by phosphine. Alternatively, the azido group in —$CH_2N_3$ may be converted to an amino group by contacting such molecules with the thiols, in particular water-soluble thiols such as dithiothreitol (DTT). In one embodiment, the phosphine is THP.

Labeled Nucleotides

According to an aspect of the disclosure, the described 3'-OH blocked nucleotide also comprises a detectable label and such nucleotide is called a labeled nucleotide. The label (e.g., a fluorescent dye) can be conjugated via an optional linker by a variety of means including hydrophobic attraction, ionic attraction, and covalent attachment. In some aspect, the dyes are conjugated to the substrate by covalent attachment. More particularly, the covalent attachment is by means of a linker group. In some instances, such labeled nucleotides are also referred to as “modified nucleotides.”

Labeled nucleosides and nucleotides are useful for labeling polynucleotides formed by enzymatic synthesis, such as, by way of non-limiting example, in PCR amplification, isothermal amplification, solid phase amplification, polynucleotide sequencing (e.g., solid phase sequencing), nick translation reactions and the like.

In some embodiments, the dye may be covalently attached to oligonucleotides or nucleotides via the nucleotide base. For example, the labeled nucleotide or oligonucleotide may have the label attached to the C5 position of a pyrimidine base or the C7 position of a 7-deaza purine base through a linker moiety.

Unless indicated otherwise, the reference to nucleotides is also intended to be applicable to nucleosides. The present application will also be further described with reference to DNA, although the description will also be applicable to RNA, PNA, and other nucleic acids, unless otherwise indicated.

Linkers

In some embodiments described herein, the purine or pyrimidine base of the nucleotide or nucleoside molecules described herein can be linked to a detectable label as described above. In some such embodiments, the linkers used are cleavable. The use of a cleavable linker ensures that the label can, if required, be removed after detection, avoiding any interfering signal with any labeled nucleotide or nucleoside incorporated subsequently. In some embodiments, the cleavable linker comprises an azido moiety, a —O—$C_2$-$C_6$ alkenyl moiety (e.g., —O-allyl), a disulfide moiety, an acetal moiety (same or similar to the 3'acetal blocking group described herein), or a thiocarbamate moiety (same or similar to the 3'acetal blocking group described herein).

In some other embodiments, the linkers used are non-cleavable. Since in each instance where a labeled nucleotide of the invention is incorporated, no nucleotides need to be subsequently incorporated and thus the label need not be removed from the nucleotide.

Cleavable linkers are known in the art, and conventional chemistry can be applied to attach a linker to a nucleotide base and a label. The linker can be cleaved by any suitable method, including exposure to acids, bases, nucleophiles, electrophiles, radicals, metals, reducing or oxidizing agents, light, temperature, enzymes etc. The linker as discussed herein may also be cleaved with the same catalyst used to cleave the 3'-O-blocking group bond. Suitable linkers can be adapted from standard chemical protecting groups, as disclosed in Greene & Wuts, Protective Groups in Organic Synthesis, John Wiley & Sons. Further suitable cleavable linkers used in solid-phase synthesis are disclosed in Guillier et al. (*Chem. Rev.* 100:2092-2157, 2000).

Where the detectable label is attached to the base, the linker can be attached at any position on the nucleotide base provided that Watson-Crick base pairing can still be carried out. In the context of purine bases, it is preferred if the linker is attached via the 7-position of the purine or the preferred deazapurine analogue, via an 8-modified purine, via an N-6 modified adenosine or an N-2 modified guanine. For pyrimidines, attachment is preferably via the 5-position on cytosine, thymidine or uracil and the N-4 position on cytosine.

In some embodiments, the linker can comprise a spacer unit. The length of the linker is unimportant provided that the label is held a sufficient distance from the nucleotide so as not to interfere with any interaction between the nucleotide and an enzyme, for example, a polymerase.

In some embodiments, the linker may consist of the similar functionality as the 3'-OH protecting group. This will make the deprotection and deprotecting process more efficient, as only a single treatment will be required to remove both the label and the protecting group.

Use of the term “cleavable linker” is not meant to imply that the whole linker is required to be removed. The cleavage site can be located at a position on the linker that ensures that part of the linker remains attached to the dye and/or substrate moiety after cleavage. Cleavable linkers may be, by way of non-limiting example, electrophilically cleavable linkers, nucleophilically cleavable linkers, photocleavable linkers, cleavable under reductive conditions (for example disulfide or azide containing linkers), oxidative conditions, cleavable via use of safety-catch linkers and cleavable by elimination mechanisms. The use of a cleavable linker to attach the dye compound to a substrate moiety ensures that the label can, if required, be removed after detection, avoiding any interfering signal in downstream steps.

Useful linker groups may be found in PCT Publication No. WO2004/018493 (herein incorporated by reference), examples of which include linkers that may be cleaved using water-soluble phosphines or water-soluble transition metal catalysts formed from a transition metal and at least partially water-soluble ligands, for example, a Pd(II) complex and THP. In aqueous solution the latter form at least partially water-soluble transition metal complexes. Such cleavable linkers can be used to connect bases of nucleotides to labels such as the dyes set forth herein.

Particular linkers include those disclosed in PCT Publication No. WO2004/018493 (herein incorporated by reference) such as those that include moieties of the formulae:

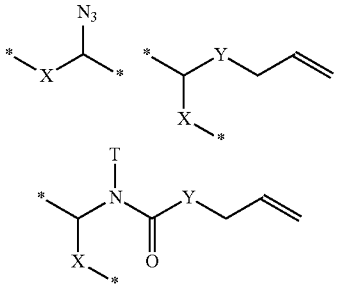

-continued

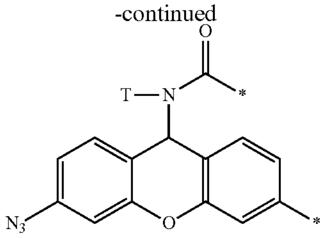

(wherein X is selected from the group comprising O, S, NH and NQ wherein Q is a $C_{1-10}$ substituted or unsubstituted alkyl group, Y is selected from the group comprising O, S, NH and N(allyl), T is hydrogen or a $C_1$-$C_{10}$ substituted or unsubstituted alkyl group and * indicates where the moiety is connected to the remainder of the nucleotide or nucleoside). In some aspect, the linkers connect the bases of nucleotides to labels such as, for example, the dye compounds described herein.

Additional examples of linkers include those disclosed in U.S. Publication No. 2016/0040225 (herein incorporated by reference), such as those include moieties of the formulae:

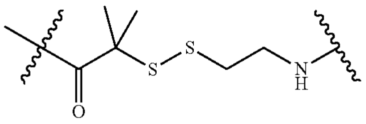

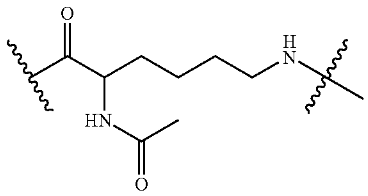

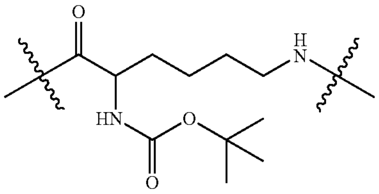

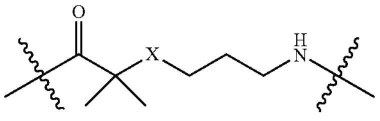

$X = CH_2$, O, S

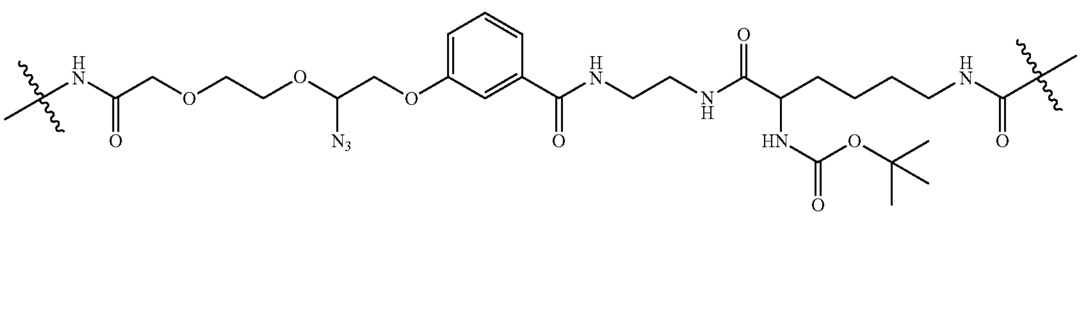

The linker moieties illustrated herein may comprise the whole or partial linker structure between the nucleotides/nucleosides and the labels.

Additional examples of linkers ("L") include moieties of the formula:

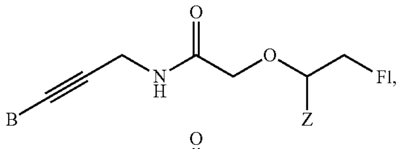

,

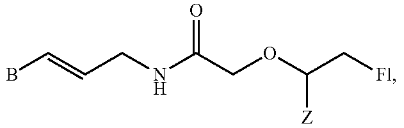

,

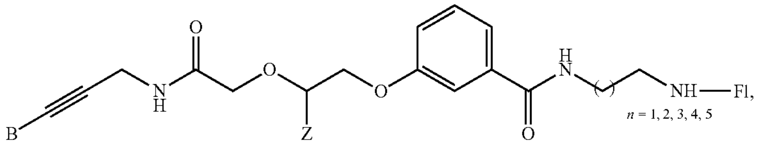

,

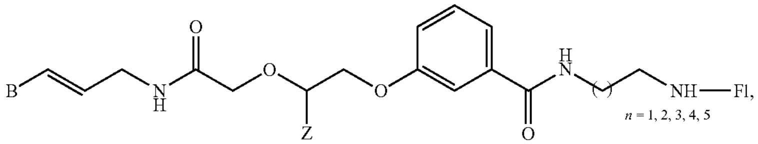

,

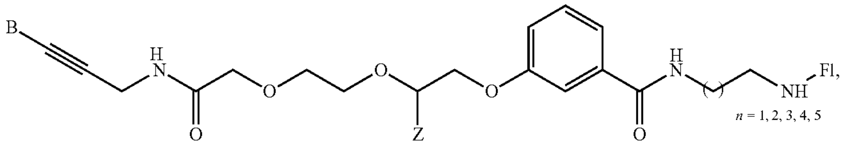

or

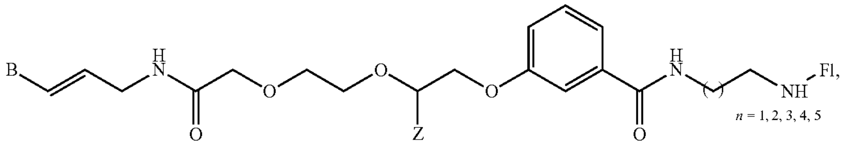

, wherein B is a nucleobase; Z is —$N_3$ (azido), —O—$C_1$-$C_6$ alkyl, —O—$C_2$-$C_6$ alkenyl, or —O—$C_2$-$C_6$ alkynyl; and Fl comprises a fluorescent label, which may contain additional linker structure. One of ordinary skill in the art understands that label is covalently bounded to the linker by reacting a functional group of the label (e.g., carboxyl) with a functional group of the linker (e.g., amino).

In particular embodiments, the length of the linker between a fluorescent dye (fluorophore) and a guanine base can be altered, for example, by introducing a polyethylene glycol spacer group, thereby increasing the fluorescence intensity compared to the same fluorophore attached to the guanine base through other linkages known in the art. Exemplary linkers and their properties are set forth in PCT Publication No. WO2007020457 (herein incorporated by reference). The design of linkers, and especially their increased length, can allow improvements in the brightness of fluorophores attached to the guanine bases of guanosine nucleotides when incorporated into polynucleotides such as DNA. Thus, when the dye is for use in any method of analysis which requires detection of a fluorescent dye label attached to a guanine-containing nucleotide, it is advantageous if the linker comprises a spacer group of formula $—((CH_2)_2O)_n—$, wherein n is an integer between 2 and 50, as described in WO 2007/020457.

Nucleosides and nucleotides may be labeled at sites on the sugar or nucleobase. As known in the art, a "nucleotide" consists of a nitrogenous base, a sugar, and one or more phosphate groups. In RNA, the sugar is ribose and in DNA is a deoxyribose, i.e., a sugar lacking a hydroxy group that is present in ribose. The nitrogenous base is a derivative of purine or pyrimidine. The purines are adenine (A) and guanine (G), and the pyrimidines are cytosine (C) and thymine (T) or in the context of RNA, uracil (U). The C-1 atom of deoxyribose is bonded to N-1 of a pyrimidine or N-9 of a purine. A nucleotide is also a phosphate ester of a nucleoside, with esterification occurring on the hydroxy group attached to the C-3 or C-5 of the sugar. Nucleotides are usually mono, di- or triphosphates.

A "nucleoside" is structurally similar to a nucleotide but is missing the phosphate moieties. An example of a nucleoside analog would be one in which the label is linked to the base and there is no phosphate group attached to the sugar molecule.

Although the base is usually referred to as a purine or pyrimidine, the skilled person will appreciate that derivatives and analogues are available which do not alter the capability of the nucleotide or nucleoside to undergo Watson-Crick base pairing. "Derivative" or "analogue" means a compound or molecule whose core structure is the same as, or closely resembles that of a parent compound but which has a chemical or physical modification, such as, for example, a different or additional side group, which allows the derivative nucleotide or nucleoside to be linked to another molecule. For example, the base may be a deazapurine. In particular embodiments, the derivatives should be capable of undergoing Watson-Crick pairing. "Derivative" and "analogue" also include, for example, a synthetic nucleotide or nucleoside derivative having modified base moieties and/or modified sugar moieties. Such derivatives and analogues are discussed in, for example, Scheit, *Nucleotide analogs* (John Wiley & Son, 1980) and Uhlman et al., *Chemical Reviews* 90:543-584, 1990. Nucleotide analogues can also comprise modified phosphodiester linkages including phosphorothioate, phosphorodithioate, alkyl-phosphonate, phosphoranilidate, phosphoramidate linkages and the like.

A dye may be attached to any position on the nucleotide base, for example, through a linker. In particular embodiments, Watson-Crick base pairing can still be carried out for the resulting analog. Particular nucleobase labeling sites include the C5 position of a pyrimidine base or the C7 position of a 7-deaza purine base. As described above a linker group may be used to covalently attach a dye to the nucleoside or nucleotide.

In particular embodiments the labeled nucleoside or nucleotide may be enzymatically incorporable and enzymatically extendable. Accordingly, a linker moiety may be of sufficient length to connect the nucleotide to the compound such that the compound does not significantly interfere with the overall binding and recognition of the nucleotide by a nucleic acid replication enzyme. Thus, the linker can also comprise a spacer unit. The spacer distances, for example, the nucleotide base from a cleavage site or label.

Nucleosides or nucleotides labeled with the dyes described herein may have the formula:

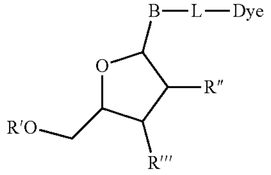

where Dye is a dye compound; B is a nucleobase, such as, for example uracil, thymine, cytosine, adenine, guanine and the like; L is an optional linker group which may or may not be present; R' can be H, monophosphate, diphosphate, triphosphate, thiophosphate, a phosphate ester analog, —O— attached to a reactive phosphorous containing group, or —O— protected by a blocking group; R''' can be H, OH, a phosphoramidite, or a 3'-OH blocking group described herein, and R'' is H or OH. Where R''' is phosphoramidite, R' is an acid-cleavable hydroxy protecting group which allows subsequent monomer coupling under automated synthesis conditions.

In a particular embodiment, the linker (between dye and nucleotide) and blocking group are both present and are separate moieties. In particular embodiments, the linker and blocking group are both cleavable under substantially similar conditions. Thus, deprotection and deblocking processes may be more efficient because only a single treatment will be required to remove both the dye compound and the blocking group. However, in some embodiments a linker and blocking group need not be cleavable under similar conditions, instead being individually cleavable under distinct conditions.

The disclosure also encompasses polynucleotides incorporating dye compounds. Such polynucleotides may be DNA or RNA comprised respectively of deoxyribonucleotides or ribonucleotides joined in phosphodiester linkage. Polynucleotides may comprise naturally occurring nucleotides, non-naturally occurring (or modified) nucleotides other than the labeled nucleotides described herein or any combination thereof, in combination with at least one modified nucleotide (e.g., labeled with a dye compound) as set forth herein. Polynucleotides according to the disclosure may also include non-natural backbone linkages and/or non-nucleotide chemical modifications. Chimeric structures comprised of mixtures of ribonucleotides and deoxyribonucleotides comprising at least one labeled nucleotide are also contemplated.

Non-limiting exemplary labeled nucleotides as described herein include:

A

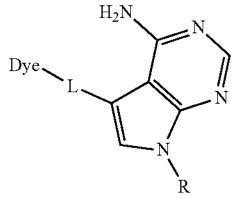

C

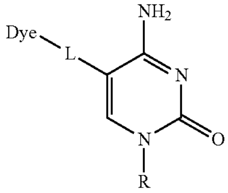

T

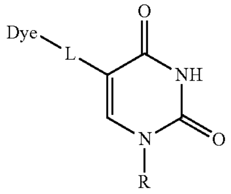

G

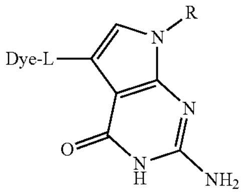

A

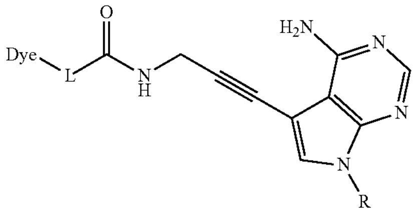

C

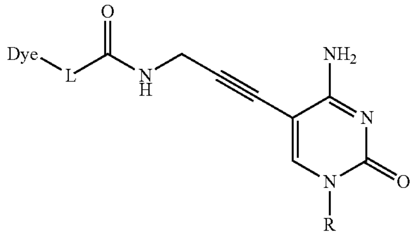

-continued
T
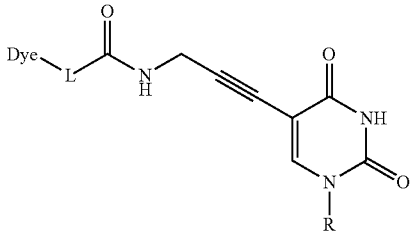
G
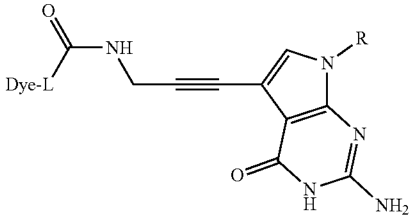
A
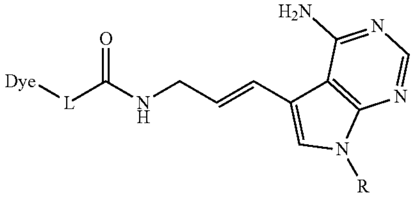
C
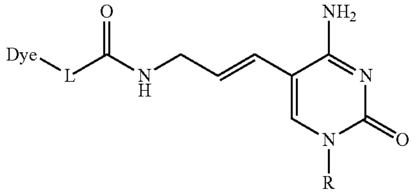
-continued
T
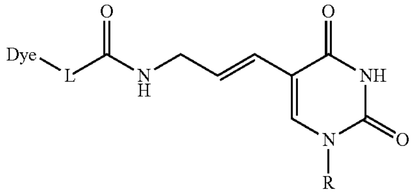
G
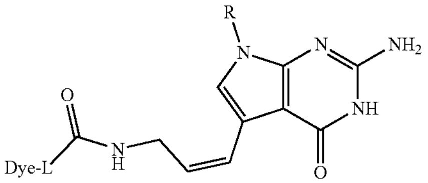
wherein L represents a linker and R represents a sugar residue as described above, or a sugar residue with the 5' position substituted with one, two or three phosphates.
In some embodiments, non-limiting exemplary fluorescent dye conjugates are shown below:
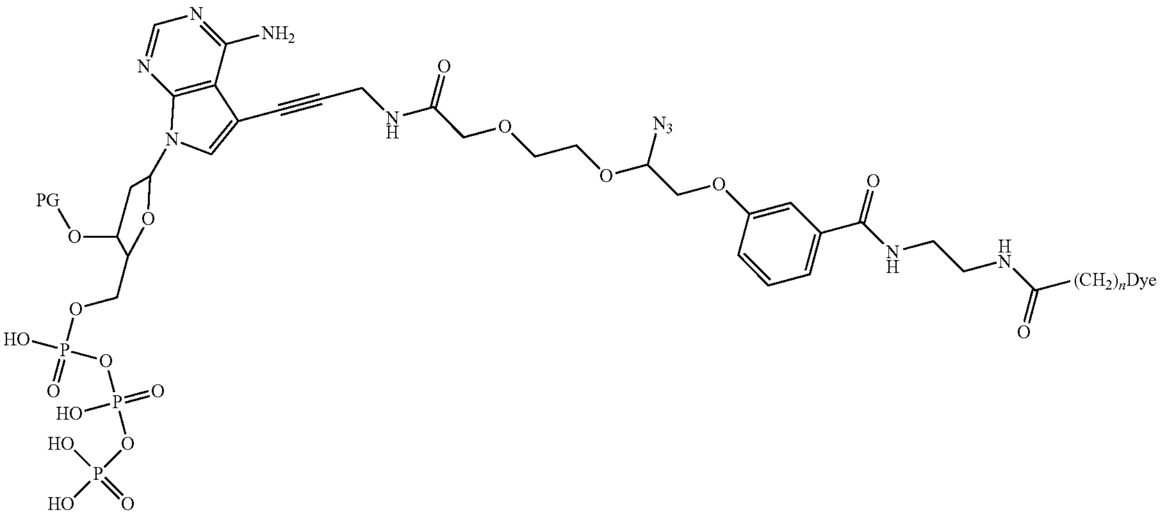
ffA-LN3-Dye -continued

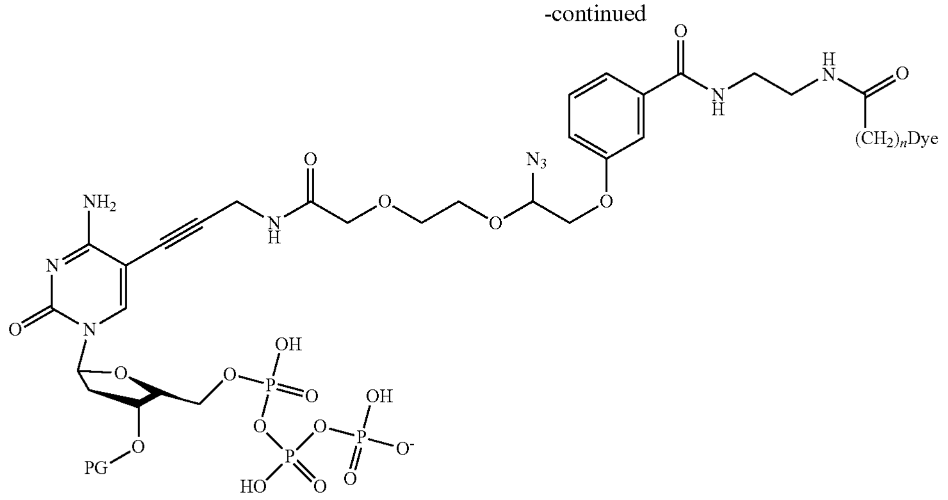

ffC-LN3-Dye wherein PG stands for the 3' hydroxy blocking groups described herein. In any embodiments of the labeled nucleotide described herein, the nucleotide is a nucleotide triphosphate.

Kits

The present disclosure also provides kits including one or more 3' blocked nucleosides and/or nucleotides described herein, for example, the 3' blocked nucleotide of Formula (I), (Ia), or (II). Such kits will generally include at least one 3' blocked nucleotide or nucleoside labeled with a dye together with at least one further component. The further component(s) may be one or more of the components identified in a method set forth herein or in the Examples section below. Some non-limiting examples of components that can be combined into a kit of the present disclosure are set forth below.

In a particular embodiment, a kit can include at least one labeled 3' blocked nucleotide or nucleoside together with labeled or unlabeled nucleotides or nucleosides. For example, nucleotides labeled with dyes may be supplied in combination with unlabeled or native nucleotides, and/or with fluorescently labeled nucleotides or any combination thereof. Combinations of nucleotides may be provided as separate individual components (e.g., one nucleotide type per vessel or tube) or as nucleotide mixtures (e.g., two or more nucleotides mixed in the same vessel or tube).

Where kits comprise a plurality, particularly two, or three, or more particularly four, 3' blocked nucleotides labeled with a dye compound, the different nucleotides may be labeled with different dye compounds, or one may be dark, with no dye compounds. Where the different nucleotides are labeled with different dye compounds, it is a feature of the kits that the dye compounds are spectrally distinguishable fluorescent dyes. As used herein, the term "spectrally distinguishable fluorescent dyes" refers to fluorescent dyes that emit fluorescent energy at wavelengths that can be distinguished by fluorescent detection equipment (for example, a commercial capillary-based DNA sequencing platform) when two or more such dyes are present in one sample. When two nucleotides labeled with fluorescent dye compounds are supplied in kit form, it is a feature of some embodiments that the spectrally distinguishable fluorescent dyes can be excited at the same wavelength, such as, for example by the same laser. When four 3' blocked nucleotides (A, C, T, and G) labeled with fluorescent dye compounds are supplied in kit form, it is a feature of some embodiments that two of the spectrally distinguishable fluorescent dyes can both be excited at one wavelength and the other two spectrally distinguishable dyes can both be excited at another wavelength. Particular excitation wavelengths are 488 nm and 532 nm.

In one embodiment, a kit includes a first 3' blocked nucleotide labeled with a first dye and a second nucleotide labeled with a second dye wherein the dyes have a difference in absorbance maximum of at least 10 nm, particularly 20 nm to 50 nm. More particularly, the two dye compounds have Stokes shifts of between 15-40 nm where "Stokes shift" is the distance between the peak absorption and peak emission wavelengths.

In an alternative embodiment, the kits of the disclosure may contain 3' blocked nucleotides where the same base is labeled with two or more different dyes. A first nucleotide (e.g., 3' blocked T nucleotide triphosphate or 3' blocked G nucleotide triphosphate) may be labeled with a first dye. A second nucleotide (e.g., 3' blocked C nucleotide triphosphate) may be labeled with a second spectrally distinct dye from the first dye, for example a "green" dye absorbing at less than 600 nm, and a "blue" dye absorbs at less than 500 nm, for example 400 nm to 500, in particular 450 nm to 460 nm). A third nucleotide (e.g., 3' blocked A nucleotide triphosphate) may be labeled as a mixture of the first and the second dyes, or a mixture of the first, the second and a third dyes, and the fourth nucleotide (e.g., 3' blocked G nucleotide triphosphate or 3' blocked T nucleotide triphosphate) may be 'dark' and contain no label. In one example, the nucleotides 1-4 may be labeled 'blue', 'green', 'blue/green', and dark. To simplify the instrumentation further, four nucleotides can be labeled with two dyes excited with a single laser, and thus the labeling of nucleotides 1-4 may be 'blue 1', 'blue 2', 'blue 1/blue 2', and dark.

In particular embodiments, the kits may contain four labeled 3' blocked nucleotides (e.g., A, C, T, G), where each type of nucleotide comprises the same 3' blocking group and a fluorescent label, and wherein each fluorescent label has a distinct fluorescence maximum and each of the fluorescent labels is distinguishable from the other three labels. The kits may be such that two or more of the fluorescent labels have a similar absorbance maximum but different Stokes shift. In some other embodiments, one type of the nucleotide is unlabeled.

Although kits are exemplified herein in regard to configurations having different nucleotides that are labeled with different dye compounds, it will be understood that kits can include 2, 3, 4 or more different nucleotides that have the same dye compound. In some embodiments, the kit also includes an enzyme and a buffer appropriate for the action of the enzyme. In some such embodiments, the enzyme is a polymerase, a terminal deoxynucleotidyl transferase, or a reverse transcriptase. In particular embodiments, the enzyme is a DNA polymerase, such as DNA polymerase 812 (Pol 812) or DNA polymerase 1901 (Pol 1901). The amino acid sequences of Pol 812 and Pol 1901 polymerases are described, for example, in U.S. patent application Ser. No. 16/670,876, filed Oct. 31, 2019, and Ser. No. 16/703,569, filed Dec. 4, 2019, both of which are incorporated by reference herein.

Other components to be included in such kits may include buffers and the like. The nucleotides of the present disclosure, and other any nucleotide components including mixtures of different nucleotides, may be provided in the kit in a concentrated form to be diluted prior to use. In such embodiments a suitable dilution buffer may also be included. Again, one or more of the components identified in a method set forth herein can be included in a kit of the present disclosure.

Methods of Sequencing

Labeled nucleotides or nucleosides according to the present disclosure may be used in any method of analysis such as method that include detection of a fluorescent label attached to a nucleotide or nucleoside, whether on its own or incorporated into or associated with a larger molecular structure or conjugate. In this context the term “incorporated into a polynucleotide” can mean that the 5' phosphate is joined in phosphodiester linkage to the 3'-OH group of a second (modified or unmodified) nucleotide, which may itself form part of a longer polynucleotide chain. The 3' end of a nucleotide set forth herein may or may not be joined in phosphodiester linkage to the 5' phosphate of a further (modified or unmodified) nucleotide. Thus, in one non-limiting embodiment, the disclosure provides a method of detecting a nucleotide incorporated into a polynucleotide which comprises: (a) incorporating at least one nucleotide of the disclosure into a polynucleotide and (b) detecting the nucleotide(s) incorporated into the polynucleotide by detecting the fluorescent signal from the dye compound attached to said nucleotide(s).

This method can include: a synthetic step (a) in which one or more nucleotides according to the disclosure are incorporated into a polynucleotide and a detection step (b) in which one or more nucleotide(s) incorporated into the polynucleotide are detected by detecting or quantitatively measuring their fluorescence.

Some embodiments of the present application are directed to methods of sequencing including: (a) incorporating at least one labeled nucleotide as described herein into a polynucleotide; and (b) detecting the labeled nucleotide(s) incorporated into the polynucleotide by detecting the fluorescent signal from the new fluorescent dye attached to said nucleotide(s).

Some embodiments of the present disclosure relate to a method for determining the sequence of a target single-stranded polynucleotide, comprising:

(a) incorporating a nucleotide comprising a 3'-OH blocking group and a detectable label as described herein into a copy polynucleotide strand complementary to at least a portion of the target polynucleotide strand;

(b) detecting the identity of the nucleotide incorporated into the copy polynucleotide strand; and (c) chemically removing the label and the 3'-OH blocking group from the nucleotide incorporated into the copy polynucleotide strand.

In some embodiments, the sequencing method further comprises (d) washing the chemically removed label and the 3' blocking group away from the copy polynucleotide strand. In some such embodiments, the 3' blocking group and the detectable label are removed prior to introducing the next complementary nucleotide. In some further embodiments, the 3' blocking group and the detectable label are removed in a single step of chemical reaction. In some embodiment, the washing step (d) also remove unincorporated nucleotides. In some further embodiments, a palladium scavenger is also used in the washing step after chemical cleavage of the label and the 3' blocking group.

In some embodiments, steps (a) to (d) are repeated until a sequence of the portion of the template polynucleotide strand is determined. In some such embodiments, steps (a) to (d) are repeated at least 50 times, at least 75 times, at least 100 times, at least 150 times, at least 200 times, at least 250 times, or at least 300 times.

In some embodiments, the label and the 3' blocking group are removed in two separate chemical reactions. In some such embodiments, removing the label from the nucleotide incorporated into the copy polynucleotide strand comprises contacting the copy strand including the incorporated nucleotide with a first cleavage solution. In some such embodiment, the first cleavage solution contains a phosphine, such as a trialkylphosphine. None-limiting examples of trialkylphosphines include tris(hydroxypropyl)phosphine (THP), tris-(2-carboxyethyl)phosphine (TCEP), tris(hydroxymethyl)phosphine (THMP), or tris(hydroxyethyl) phosphine (THEP). In one embodiment, the first cleavage solution contains THP. In some such embodiments, removing the 3' blocking group from the nucleotide incorporated into the copy polynucleotide strand comprises contacting the copy strand including the incorporated nucleotide with a second cleavage solution. In some such embodiments, the second cleavage solution contains a palladium (Pd) catalyst. In some further embodiments, the Pd catalyst is a Pd(0) catalyst. In some such embodiments, the Pd(0) is prepared by mixing a Pd(II) complex $[(PdCl(C_3H_5))_2]$ with THP in situ. The molar ratio of the Pd(II) complex and the THP may be about 1:2, 1:3, 1:4, 1:5, 1:6, 1:7, 1:8, 1:9, or 1:10. In one embodiment the molar ration of Pd:THP is 1:5. In some further embodiments, one or more reducing agents may be added, such as ascorbic acid or a salt thereof (e.g., sodium ascorbate). In some embodiments, the second cleavage solution may contain one or more buffer reagents, such as a primary amine, a secondary amine, a tertiary amine, a carbonate salt, a phosphate salt, or a borate salt, or combinations thereof. In some further embodiments, the buffer reagent comprises ethanolamine (EA), tris(hydroxymethyl) aminomethane (Tris), glycine, sodium carbonate, sodium phosphate, sodium borate, 2-dimethyalaminomethanol (DMEA), 2-diethyalaminomethanol (DEEA), N,N,N',N'-tetramethylethylenediamine(TEMED), or N,N,N',N'-tetraethylethylenediamine (TEEDA), or combinations thereof. In one embodiment, the buffer reagent is DEEA. In another embodiment, the buffer reagent contains one or more inorganic salts such as a carbonate salt, a phosphate salt, or a borate salt, or combinations thereof. In one embodiment, the inorganic salt is a sodium salt. In some other embodiments, the second cleavage solution contains $NaIO_4$ or Oxone®. In some further embodiments, the 3' blocked nucleotide contains a AOM group and the second cleavage solution contains a palladium (Pd) catalyst and one or more buffer reagents described herein (e.g., a tertiary amine such as DEEA) and have pH of about 9.0 to about 10.0 (e.g., 9.6 or 9.8).

In some alternative embodiments, the label and the 3'-OH blocking group are removed in a single chemical reaction. In some such embodiments, the label is attached to the nucleotide via a cleavage linker comprising the same moiety as the 3' blocking group, for example, both the linker and the 3' blocking group may comprise an acetal moiety

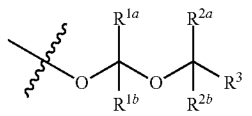

or a thiocarbamate moiety

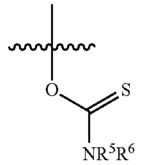

as described herein. In some such embodiment, the single chemical reaction is carried out in a cleavage solution containing a Pd catalyst described above.

In some further embodiments, the nucleotides used in the incorporation step (a) are fully functionalized A, C, T and G nucleotide triphosphate each contains a 3'blocking group described herein. In some such embodiments, the nucleotides herein provide superior stability in solution during sequencing runs, compared to the same nucleotides protected with a standard 3'-O-azidomethyl blocking group. For example, the acetal or thiocarbamate blocking groups disclosed herein may confer at least 5%, 10%, 20%, 30%, 40%, 50%, 60%, 70%, 80%, 90%, 100%, 200%, 300%, 400%, 500%, 600%, 700%, 800%, 900%, 1000%, 1500%, 2000%, 2500%, or 3000% improved stability compare to an azidomethyl protected 3'-OH at the same condition for the same period of time, thereby reducing the pre-phasing values and resulting in longer sequencing read lengths. In some embodiments, the stability is measured at ambient temperature or a temperature below ambient temperature (such as 4-10° C.). In other embodiments, the stability is measured at an elevated temperature, such as 40° C., 45° C., 50° C., 55° C., 60° C. or 65° C. In some such embodiments, the stability is measured in solution in a basic pH environment, e.g., at pH 9.0, 9.2, 9.4, 9.6, 9.8. or 10.0. In some further embodiments, the pre-phasing value with the 3' blocked nucleotide described herein is less than about 0.25, 0.24, 0.23, 0.22, 0.21, 0.20, 0.19, 0.18, 0.17, 0.16, 0.15, 0.14, 0.13, 0.12, 0.11, 0.10, 0.09, 0.08, 0.07, 0.06, or 0.05 after over 50, 100 or 150 cycles of SBS. In some further embodiments, the phasing value with the 3' blocked nucleotide is less than about 0.25, 0.24, 0.23, 0.22, 0.21, 0.20, 0.19, 0.18, 0.17, 0.16, 0.15, 0.14, 0.13, 0.12, 0.11, 0.10, 0.09, 0.08, 0.07, 0.06, or 0.05, after over 50, 100 or 150 cycles of SBS. In one embodiment, each ffN contains the 3'-AOM group.

In some embodiments, the 3' blocked nucleotides described herein provide superior deblocking rate in solution during the chemical cleavage step of the sequencing run, compared to the same nucleotides protected with a standard 3'-O-azidomethyl blocking group. For example, the acetal (e.g., AOM) or thiocarbamate blocking groups disclosed herein may confer at least 5%, 10%, 20%, 30%, 40%, 50%, 60%, 70%, 80%, 90%, 100%, 150%, 200%, 300%, 400%, 500%, 600%, 700%, 800%, 900%, 1000%, 1500%, or 2000% improved deblocking rate compare to an azidomethyl protected 3'-OH using the standard deblocking reagent (such as tris(hydroxypropyl)phosphine), thereby reducing the overall time for a sequencing cycle. In some embodiments, the deblocking time for each nucleotide is reduced by about 5%, 10%, 20%, 30%, 40%, 50%, or 60%. For example, the deblocking time for 3'-AOM and 3'-O-azidomethyl is about 4-5 seconds and about 9-10 seconds respectively under certain chemical reaction condition. In some embodiments, the half life ($t_{1/2}$) of AOM blocking group is at least 1, 2, 3, 4, 5, 6, 7, 8, 9 or 10 fold faster than azidomethyl blocking group. In some such embodiment, $t_{1/2}$ of AOM is about 1 minute while $t_{1/2}$ of azidomethyl is about 11 minutes. In some embodiments, the deblocking rate is measured at ambient temperature or a temperature below ambient temperature (such as 4-10° C.). In other embodiments, the deblocking rate is measured at an elevated temperature, such as 40° C., 45° C., 50° C., 55° C., 60° C. or 65° C. In some such embodiments, the deblocking rate is measured in solution in a basic pH environment, e.g., at pH 9.0, 9.2, 9.4, 9.6, 9.8. or 10.0. In some such embodiments, the molar ratio of the deblocking reagent to substrate (i.e., 3' blocked nucleoside or nucleotide) is about 10:1, about 5:1, about 2:1, about 1:1, about 1:2, about 1:5 or about 1:10. In one embodiment, each ffN contains the 3'-AOM group.

In any embodiments of the methods described herein, the labeled nucleotide is a nucleotide triphosphate. In any embodiments of the method described herein, the target polynucleotide strand is attached to a solid support, such as a flow cell.

In one embodiment, at least one nucleotide is incorporated into a polynucleotide in the synthetic step by the action of a polymerase enzyme. In some such embodiments, the polymerase may be DNA polymerase Pol 812 or Pol 1901. However, other methods of joining nucleotides to polynucleotides, such as, for example, chemical oligonucleotide synthesis or ligation of labeled oligonucleotides to unlabeled oligonucleotides, can be used. Therefore, the term "incorporating," when used in reference to a nucleotide and polynucleotide, can encompass polynucleotide synthesis by chemical methods as well as enzymatic methods.

In a specific embodiment, a synthetic step is carried out and may optionally comprise incubating a template polynucleotide strand with a reaction mixture comprising labeled 3' blocked nucleotides of the disclosure. A polymerase can also be provided under conditions which permit formation of a phosphodiester linkage between a free 3'-OH group on a polynucleotide strand annealed to the template polynucleotide strand and a 5' phosphate group on the nucleotide. Thus, a synthetic step can include formation of a polynucleotide strand as directed by complementary base-pairing of nucleotides to a template strand.

In all embodiments of the methods, the detection step may be carried out while the polynucleotide strand into which the labeled nucleotides are incorporated is annealed to a template strand, or after a denaturation step in which the two strands are separated. Further steps, for example chemical or enzymatic reaction steps or purification steps, may be included between the synthetic step and the detection step. In particular, the target strand incorporating the labeled nucleotide(s) may be isolated or purified and then processed further or used in a subsequent analysis. By way of example, target polynucleotides labeled with nucleotide(s) as described herein in a synthetic step may be subsequently used as labeled probes or primers. In other embodiments, the product of the synthetic step set forth herein may be subject to further reaction steps and, if desired, the product of these subsequent steps purified or isolated.

Suitable conditions for the synthetic step will be well known to those familiar with standard molecular biology techniques. In one embodiment, a synthetic step may be analogous to a standard primer extension reaction using nucleotide precursors, including nucleotides as described herein, to form an extended target strand complementary to the template strand in the presence of a suitable polymerase enzyme. In other embodiments, the synthetic step may itself form part of an amplification reaction producing a labeled double stranded amplification product comprised of annealed complementary strands derived from copying of the target and template polynucleotide strands. Other exemplary synthetic steps include nick translation, strand displacement polymerization, random primed DNA labeling, etc. A particularly useful polymerase enzyme for a synthetic step is one that is capable of catalyzing the incorporation of nucleotides as set forth herein. A variety of naturally occurring or modified polymerases can be used. By way of example, a thermostable polymerase can be used for a synthetic reaction that is carried out using thermocycling conditions, whereas a thermostable polymerase may not be desired for isothermal primer extension reactions. Suitable thermostable polymerases which are capable of incorporating the nucleotides according to the disclosure include those described in WO 2005/024010 or WO 06/120433, each of which is incorporated herein by reference. In synthetic reactions which are carried out at lower temperatures such as 37° C., polymerase enzymes need not necessarily be thermostable polymerases, therefore the choice of polymerase will depend on a number of factors such as reaction temperature, pH, strand-displacing activity and the like.

In specific non-limiting embodiments, the disclosure encompasses methods of nucleic acid sequencing, re-sequencing, whole genome sequencing, single nucleotide polymorphism scoring, any other application involving the detection of the labeled nucleotide or nucleoside set forth herein when incorporated into a polynucleotide. Any of a variety of other applications benefitting the use of polynucleotides labeled with the nucleotides comprising fluorescent dyes can use labeled nucleotides or nucleosides with dyes set forth herein.

In a particular embodiment, the disclosure provides use of labeled nucleotides according to the disclosure in a polynucleotide sequencing-by-synthesis (SBS) reaction. Sequencing-by-synthesis generally involves sequential addition of one or more nucleotides or oligonucleotides to a growing polynucleotide chain in the 5' to 3' direction using a polymerase or ligase in order to form an extended polynucleotide chain complementary to the template nucleic acid to be sequenced. The identity of the base present in one or more of the added nucleotide(s) can be determined in a detection or "imaging" step. The identity of the added base may be determined after each nucleotide incorporation step. The sequence of the template may then be inferred using conventional Watson-Crick base-pairing rules. The use of the labeled nucleotides set forth herein for determination of the identity of a single base may be useful, for example, in the scoring of single nucleotide polymorphisms, and such single base extension reactions are within the scope of this disclosure.

In an embodiment of the present disclosure, the sequence of a template polynucleotide is determined by detecting the incorporation of one or more 3' blocked nucleotides described herein into a nascent strand complementary to the template polynucleotide to be sequenced through the detection of fluorescent label(s) attached to the incorporated nucleotide(s). Sequencing of the template polynucleotide can be primed with a suitable primer (or prepared as a hairpin construct which will contain the primer as part of the hairpin), and the nascent chain is extended in a stepwise manner by addition of nucleotides to the 3' end of the primer in a polymerase-catalyzed reaction.

In particular embodiments, each of the different nucleotide triphosphates (A, T, G and C) may be labeled with a unique fluorophore and also comprises a blocking group at the 3' position to prevent uncontrolled polymerization. Alternatively, one of the four nucleotides may be unlabeled (dark). The polymerase enzyme incorporates a nucleotide into the nascent chain complementary to the template polynucleotide, and the blocking group prevents further incorporation of nucleotides. Any unincorporated nucleotides can be washed away and the fluorescent signal from each incorporated nucleotide can be "read" optically by suitable means, such as a charge-coupled device using laser excitation and suitable emission filters. The 3'-blocking group and fluorescent dye compounds can then be removed (deprotected) simultaneously or sequentially to expose the nascent chain for further nucleotide incorporation. Typically, the identity of the incorporated nucleotide will be determined after each incorporation step, but this is not strictly essential. Similarly, U.S. Pat. No. 5,302,509 (which is incorporated herein by reference) discloses a method to sequence polynucleotides immobilized on a solid support.

The method, as exemplified above, utilizes the incorporation of fluorescently labeled, 3'-blocked nucleotides A, G, C, and T into a growing strand complementary to the immobilized polynucleotide, in the presence of DNA polymerase. The polymerase incorporates a base complementary to the target polynucleotide but is prevented from further addition by the 3'-blocking group. The label of the incorporated nucleotide can then be determined, and the blocking group removed by chemical cleavage to allow further polymerization to occur. The nucleic acid template to be sequenced in a sequencing-by-synthesis reaction may be any polynucleotide that it is desired to sequence. The nucleic acid template for a sequencing reaction will typically comprise a double stranded region having a free 3'-OH group that serves as a primer or initiation point for the addition of further nucleotides in the sequencing reaction. The region of the template to be sequenced will overhang this free 3'-OH group on the complementary strand. The overhanging region of the template to be sequenced may be single stranded but can be double-stranded, provided that a "nick is present" on the strand complementary to the template strand to be sequenced to provide a free 3'-OH group for initiation of the sequencing reaction. In such embodiments, sequencing may proceed by strand displacement. In certain embodiments, a primer bearing the free 3'-OH group may be added as a separate component (e.g., a short oligonucleotide) that hybridizes to a single-stranded region of the template to be sequenced. Alternatively, the primer and the template strand to be sequenced may each form part of a partially self-complementary nucleic acid strand capable of forming an intra-molecular duplex, such as for example a hairpin loop structure. Hairpin polynucleotides and methods by which they may be attached to solid supports are disclosed in PCT Publication Nos. WO 01/57248 and WO 2005/047301, each of which is incorporated herein by reference. Nucleotides can be added successively to a growing primer, resulting in synthesis of a polynucleotide chain in the 5' to 3' direction. The nature of the base which has been added may be determined, particularly but not necessarily after each nucleotide addition, thus providing sequence information for the nucleic acid template. Thus, a nucleotide is incorporated into a nucleic acid strand (or polynucleotide) by joining of the nucleotide to the free 3'-OH group of the nucleic acid strand via formation of a phosphodiester linkage with the 5' phosphate group of the nucleotide.

The nucleic acid template to be sequenced may be DNA or RNA, or even a hybrid molecule comprised of deoxynucleotides and ribonucleotides. The nucleic acid template may comprise naturally occurring and/or non-naturally occurring nucleotides and natural or non-natural backbone linkages, provided that these do not prevent copying of the template in the sequencing reaction.

In certain embodiments, the nucleic acid template to be sequenced may be attached to a solid support via any suitable linkage method known in the art, for example via covalent attachment. In certain embodiments template polynucleotides may be attached directly to a solid support (e.g., a silica-based support). However, in other embodiments of the disclosure the surface of the solid support may be modified in some way so as to allow either direct covalent attachment of template polynucleotides, or to immobilize the template polynucleotides through a hydrogel or polyelectrolyte multilayer, which may itself be non-covalently attached to the solid support.

Sequencing Methods Utilizing Nucleotides with 3' Allyl Blocking Group

In addition to the method of sequencing using nucleotides with 3' acetal blocking group or 3' thiocarbamate blocking group, methods of sequencing using nucleotides with 3' allyl blocking group are also described herein.

Some embodiments of the present disclosure relate to a method of determining the sequence of a plurality of different target polynucleotides in parallel, the method comprising:

(a) contacting a solid support with a solution comprising sequencing primers under hybridization conditions, wherein:
   (i) the solid support comprises a plurality of different target polynucleotides; and
   (ii) the sequencing primers are complementary to at least a portion of the different target polynucleotides;

(b) contacting the solid support with an aqueous solution comprising DNA polymerase and nucleotides A, G, C and T or U (e.g., dATP, dCTP, dGTP and dTTP or dUTP) and under conditions suitable for DNA polymerase-mediated primer extension, wherein each nucleotide comprises a 2' deoxyribose moiety with a 3' unsubstituted or substituted allyl blocking group

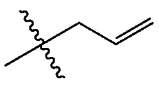 [SMILES: *CC=C]

attached to the 3' oxygen atom;

(c) imaging the solid support to determine the identity of incorporated nucleotides (e.g., by performing one or more fluorescent measurements of the extended copy polynucleotides);

(d) contacting the solid support with an aqueous deblocking solution comprising a palladium catalyst and tris (hydroxyalkyl)phosphine under conditions suitable to chemically remove 3' allyl blocking groups from incorporated nucleotides to expose a 3'-OH group for further nucleotide incorporation on the solid support;

(e) contacting said solid support with an aqueous wash solution; and (f) repeating steps (b)-(e) to determine target polynucleotide sequences. In some embodiments of the method described herein, the aqueous solution comprising DNA polymerase in step (b) further comprises a palladium scavenger. In further embodiments, the palladium scavenger in step (b) is a Pd(0) scavenger described herein. In some embodiments, the aqueous wash solution in step (e) further comprises a palladium scavenger. In some further embodiments, the palladium scavenger in step (e) is a Pd(II) scavenger described herein. In some further embodiments, the aqueous deblocking solution further comprises ascorbate, such as sodium ascorbate. In some embodiments, the solid support comprises at least 500,000, 1,000,000, 2,000,000, 3,000,000, 4,000,000, or 5,000,000 spatially distinguishable sites/cm$^2$ that comprise multiple copies of target polynucleotides.

In some embodiments of the method described herein, at least one type of nucleotide comprises a base attached to a detectable label via a cleavable linker. In some further embodiments, the cleavable linker comprises a moiety selected from the group consisting of:

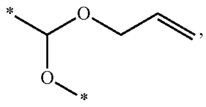
,
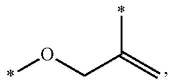
, and
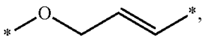
, and * indicates where the moiety is connected to the remainder of the nucleotide In some further embodiments, the cleavable linker is attached to the nucleobase via

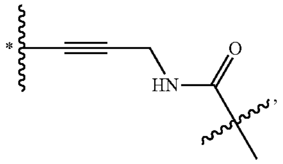
,
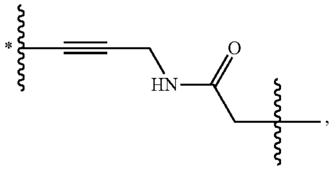
,
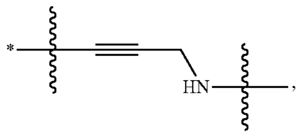
,

-continued

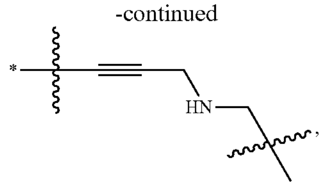

,

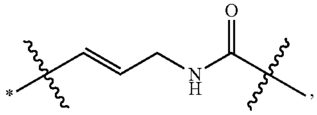

,

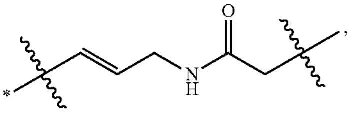

,

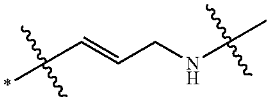

or

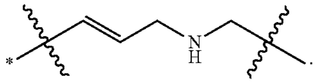

.

In some further embodiments, the detectable label is a fluorescent dye, and the cleavable linker is selected from the group consisting of:

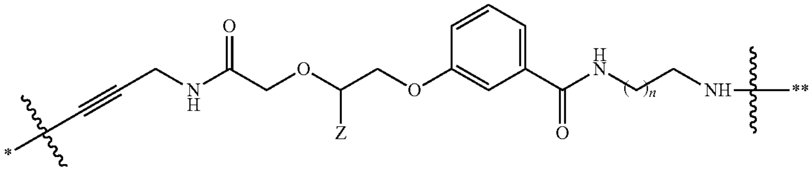

and

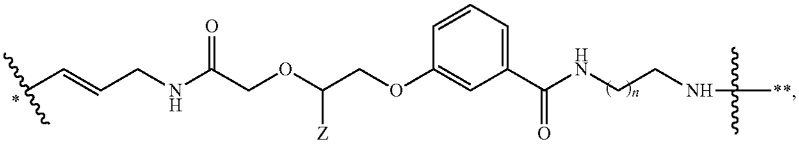

, wherein Z is —O—$CH_2$—CH═$CH_2$; n is an integer of 1, 2, 3, 4 or 5; * indicates the attachment point of the cleavable linker to the base; and ** indicates the attachment point of the cleavable linker to the detectable label. In further embodiments, when the nucleotide is T nucleotide, the cleavable linker is attached to the nucleobase via

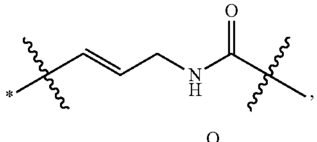

,

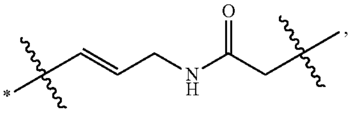

,

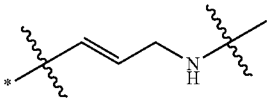

or

-continued

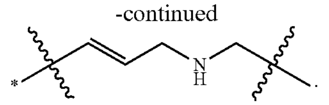

In some further embodiments, when the nucleotide is T nucleotide, the cleavable linker is

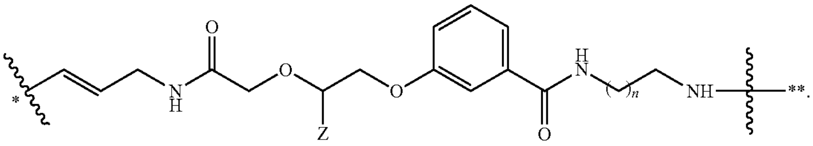

In some embodiments of the method described herein, at least three types of nucleotides comprise a nucleobase attached to a detectable label via a cleavable linker. In one embodiment, A, C, and T nucleotides each comprises a nucleobase attached to a detectable label via a cleavable linker described herein. In some further embodiments, the detectable label of each of the at least three types of nucleotides is distinguishable from the other detectable labels, and the cleavable linker is selected from the group consisting of:

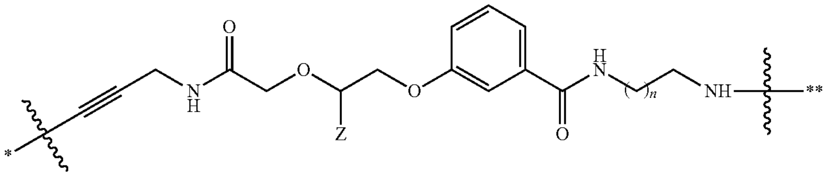

and

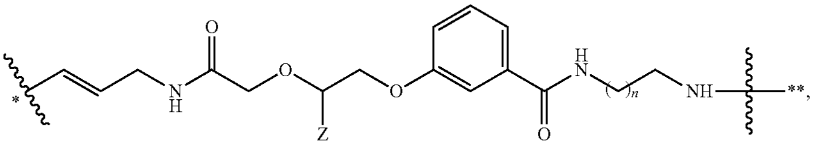

wherein Z is —O—$CH_2$—CH═$CH_2$; n is an integer of 1, 2, 3, 4 or 5; * indicates the attachment point of the cleavable linker to the base; and ** indicates the attachment point of the cleavable linker to the detectable label. In other embodiments, each of the four types of nucleotides is unlabeled.

Some other embodiments of the present disclosure relate to a method of determining the sequence of a plurality of different target polynucleotides in parallel, the method comprising:

(a) contacting a solid support with a solution comprising sequencing primers under hybridization conditions, wherein:

(i) the solid support comprises a plurality of different target polynucleotides; and (ii) the sequencing primers are complementary to at least a portion of the different target polynucleotides;

(b) contacting the solid support with an aqueous solution comprising DNA polymerase and nucleotides A, G, C, and T or U (e.g., dATP, dCTP, dGTP and dTTP or dUTP) under conditions suitable for DNA polymerase-mediated primer extension, wherein:

(i) each of at least three types of nucleotides independently comprises a base that is attached to a detectable label via a cleavable linker, and the cleavable linker comprises a moiety selected from the group consisting of:

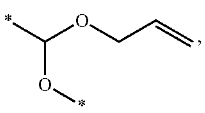, 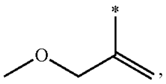, and 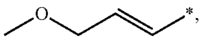, and * indicates where the moiety is connected to the remainder of the nucleotide;

(ii) each nucleotide comprises a 2' deoxyribose moiety with a 3' unsubstituted or substituted allyl group

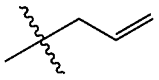 [SMILES: *CC=C]

attached to the 3' oxygen atom; and (iii) the DNA polymerase is an altered archaeal DNA polymerase;

(c) contacting the solid support with a solution comprising one or more radical scavengers and imaging the solid support to determine the identity of incorporated nucleotides (e.g., by performing one or more fluorescent measurements of the extended copy polynucleotides);

(d) contacting the solid support with an aqueous deblocking solution comprising a palladium catalyst and tris (hydroxyalkyl)phosphine under conditions suitable to chemically remove (i) 3' allyl blocking groups from incorporated nucleotides to expose a 3'-OH group for further nucleotide incorporation on the solid support, and (ii) detectable labels attached via cleavable linkers;

(e) contacting said solid support with an aqueous wash solution comprising a palladium scavenger; and (f) repeating steps (b)-(e) to determine target polynucleotide sequences. In some embodiments, the palladium scavenger in the aqueous wash solution of step (e) is a Pd(II) scavenger as described herein. In some further embodiments, the aqueous solution comprising DNA polymerase in step (b) further comprises a palladium scavenger. In some such embodiments, the palladium scavenger in step (b) is a Pd(0) scavenger described herein. In some embodiments, the solid support comprises at least 500,000, 1,000,000, 2,000,000, 3,000, 000, 4,000,000, or 5,000,000 spatially distinguishable sites/$cm^2$ that comprise multiple copies of target polynucleotides.

Some additional embodiments of the present disclosure relate to a method of determining the sequence of a plurality of different target polynucleotides in parallel, the method comprising:

(a) contacting a solid support with a solution comprising sequencing primers under hybridization conditions, wherein:

(i) the solid support comprises a plurality of different target polynucleotides; and (ii) the sequencing primers are complementary to at least a portion of the different target polynucleotides;

(b) contacting the solid support with an aqueous solution comprising DNA polymerase and nucleotides A, G, C, and T or U (e.g., dATP, dCTP, dGTP and dTTP or dUTP) under conditions suitable for DNA polymerase-mediated primer extension, wherein:

(i) at least one of the nucleotides comprise a base that is attached to a detectable label via a cleavable linker; and (ii) the nucleotides each comprises a 2' deoxyribose moiety with a 3' unsubstituted or substituted allyl blocking group

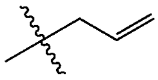

attached to the 3' oxygen atom;

(c) contacting the solid support with a solution comprising one or more radical scavengers and imaging the solid support to determine the identity of incorporated nucleotides (e.g., by performing one or more fluorescent measurements of the extended copy polynucleotides);

(d) contacting the solid support with an aqueous deblocking solution comprising a palladium catalyst and tris (hydroxyalkyl)phosphine under conditions suitable to chemically remove (i) 3' allyl groups from incorporated nucleotides to expose a 3'-OH group for further nucleotide incorporation on the solid support, and (ii) detectable labels attached via cleavable linkers;

(e) contacting said solid support with an aqueous wash solution; and (f) repeating steps (b)-(e) to determine target polynucleotide sequences. In some embodiments, the aqueous wash solution in step (e) further comprises a palladium scavenger. In some embodiments, the solid support comprises at least 500,000, 1,000,000, 2,000,000, 3,000,000, 4,000,000, or 5,000,000 spatially distinguishable sites/$cm^2$ that comprise multiple copies of target polynucleotides. In some such embodiments, the palladium scavenger in the aqueous wash solution of step (e) is a Pd(II) scavenger as described herein. In some further embodiments, the aqueous solution comprising DNA polymerase in step (b) further comprises a palladium scavenger. In some such embodiments, the palladium scavenger in step (b) is a Pd(0) scavenger described herein.

Post-Incorporation Labeling SBS Workflow

Another aspect of the present disclosure relates to an alternative sequencing by synthesis method in which at least one labeling reagent is introduced after the incorporation of unlabeled nucleotides. In particular, the disclosure relates to a method of determining the sequence of a plurality of different target polynucleotides in parallel, the method comprising:

(a) contacting a solid support with a solution comprising sequencing primers under hybridization conditions, wherein:

(i) the solid support comprises at least 5,000,000 spatially distinguishable sites/$cm^2$ that comprise multiple copies of target polynucleotides;

(ii) the solid support comprises a plurality of different target polynucleotides; and (iii) the sequencing primers are complementary to at least a portion of the different target polynucleotides;

(b) contacting the solid support with an aqueous incorporation mixture comprising DNA polymerase and one or more of four types of nucleotides A, G, C, and T or U under conditions suitable for DNA polymerase-mediated primer extension, wherein:

(i) the nucleotides each comprises a 2' deoxyribose moiety with a 3' allyl blocking group

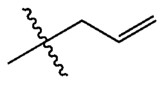 [SMILES: *CC=C]

attached to the 3' oxygen atom;

(ii) at least one type of nucleotide is unlabeled; and (iii) the first type of unlabeled nucleotides comprises a first functional moiety;

(c) contacting the extended copy polynucleotides with an aqueous labeling mixture comprising a first labeling reagent, wherein the first labeling reagent comprises one or more first detectable labels and a first binding moiety that is capable of specific binding to the first functional moiety of the first type of unlabeled nucleotide;

(d) imaging the solid support and performing one or more fluorescent measurements (i.e., to determine the identity of incorporated nucleotides);

(e) contacting the solid support with an aqueous deblocking solution comprising a palladium catalyst and tris (hydroxyalkyl)phosphine under conditions suitable to chemically remove (i) 3' allyl groups from incorporated nucleotides to expose a 3'-OH group for further nucleotide incorporation on the solid support;

(f) contacting said solid support with an aqueous wash solution; and (g) repeating steps (b)-(f) to determine target polynucleotide sequences. In some embodiments, at least two types of nucleotides are unlabeled.

In some embodiments, step (c) is performed under conditions where the first labeling reagent binds specifically to the incorporated unlabeled first type of nucleotides to provide labeled extended copy polynucleotides. In some embodiments, the first functional moiety of the first type of unlabeled nucleotide is bound to the first labeling reagent by covalent bonding, optionally via the cleavable linker as described herein. In some other embodiments, the first functional moiety of the first type of unlabeled nucleotide is bound to the first labeling reagent by noncovalent interaction, optionally via the cleavable linker as described herein.

In some embodiments, each of the four types of nucleotides in the aqueous incorporation mixture is unlabeled, the second type of unlabeled nucleotides comprises a second functional moiety, wherein the aqueous labeling mixture comprises a second labeling reagent, and the second labeling reagent comprises one or more second detectable labels and a second binding moiety that is capable of specific binding to the second functional moiety of the second type of unlabeled nucleotides. In some such embodiments, step (c) is performed under conditions where the first labeling reagent binds specifically to the incorporated unlabeled first type of nucleotides, and the second labeling reagent binds specifically to the incorporated unlabeled second type of nucleotides to provide labeled extended copy polynucleotides. In some such embodiments, the first functional moiety of the first type of unlabeled nucleotide is bound to the first labeling reagent by covalent bonding, optionally via a cleavable linker as described herein. In some other embodiments, the second functional moiety of the first type of unlabeled nucleotide is bound to the second labeling reagent by noncovalent interaction, optionally via the cleavable linker as described herein. In some such embodiments, the third type of unlabeled nucleotides comprises a third functional moiety, wherein the aqueous labeling mixture comprises a third labeling reagent, and the third labeling reagent comprises one or more third detectable labels and a third binding moiety that is capable of specific binding to the third functional moiety of the third type of unlabeled nucleotides. In some such embodiments, step (c) is performed under conditions where the first labeling reagent binds specifically to the incorporated unlabeled first type of nucleotides, the second labeling reagent binds specifically to the incorporated unlabeled second type of nucleotides, and the third labeling reagent binds specifically to the incorporated unlabeled third type of nucleotides to provide labeled extended copy polynucleotides. In some other embodiments, the third type of unlabeled nucleotide comprises a mixture of the third type of unlabeled nucleotides comprising the first functional moiety and the third type of unlabeled nucleotides comprising the second functional moiety, and wherein both the first labeling reagent and the second labeling reagent are capable of specific binding to the third type of unlabeled nucleotides.

In any embodiments of the post-incorporation labeling method described herein, the fourth type of unlabeled nucleotides is not capable of specific binding with any of the first, second, or third labeling reagent.

In some embodiments of the post-incorporation labeling method described herein, the T nucleotide has the structure:

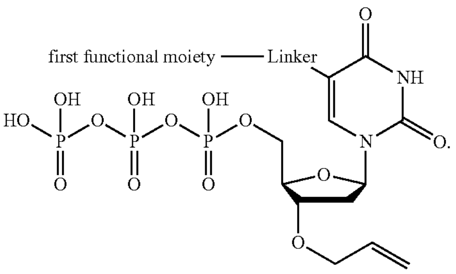

In some further embodiments, the T nucleotide has the structure:

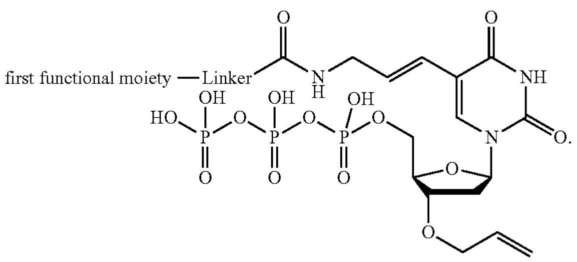

In further embodiments, the T nucleotide has the structure:

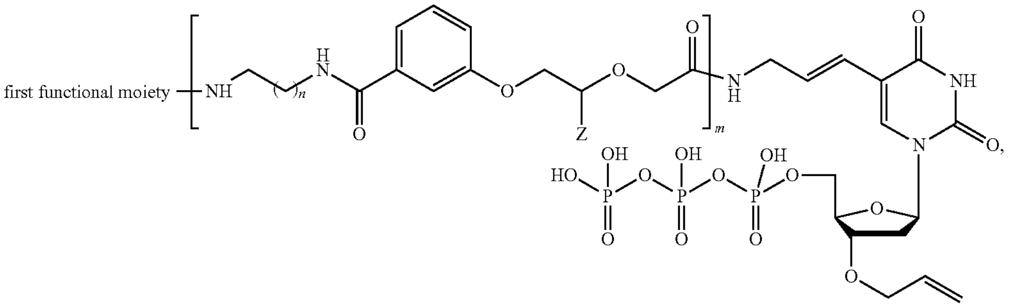

wherein Z is —O—$CH_2$—CH═$CH_2$, and each of m and n is independently an integer of 1, 2, 3, 4 or 5.

In some embodiments of the post-incorporation labeling method described herein, the C nucleotide has the structure:

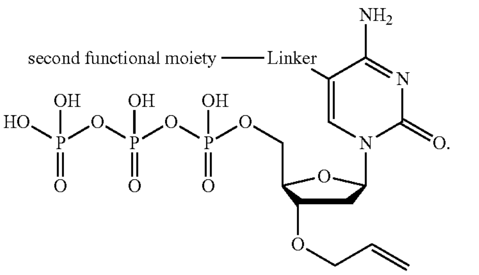

In some further embodiments, the C nucleotide has the structure:

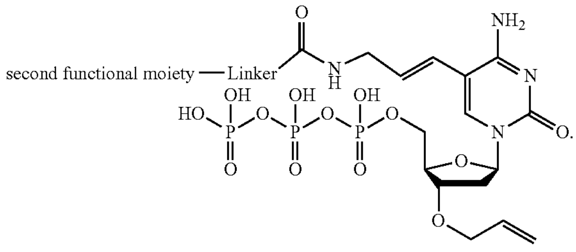

In further embodiments, the C nucleotide has the structure:

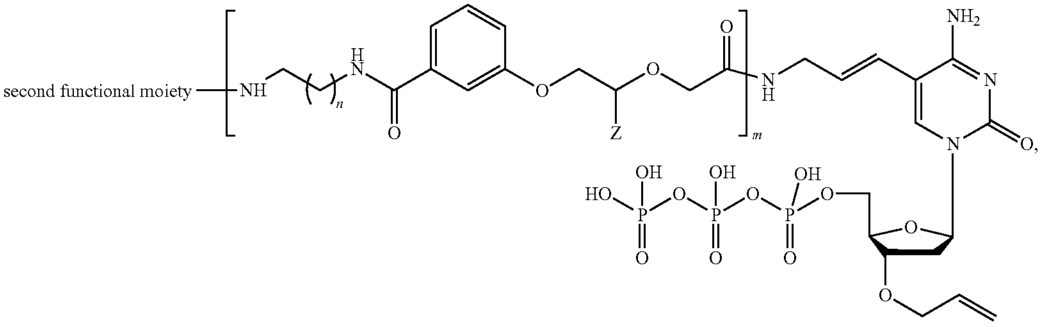

wherein Z is —O—$CH_2$—CH═$CH_2$, and each of m and n is independently an integer of 1, 2, 3, 4 or 5.

In some embodiments of the post-incorporation labeling method described herein, the A nucleotide has the structure:

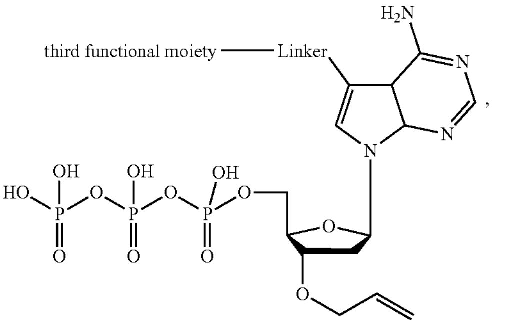

In some further embodiments, the A nucleotide has the structure:

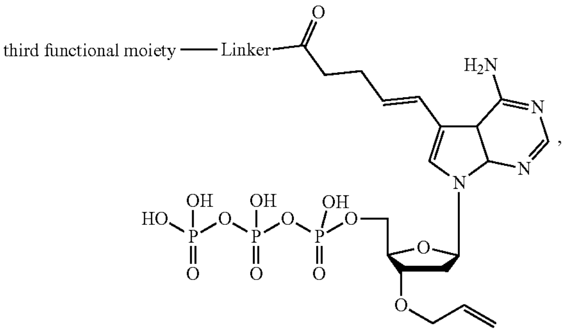

In further embodiments, the A nucleotide has the structure:

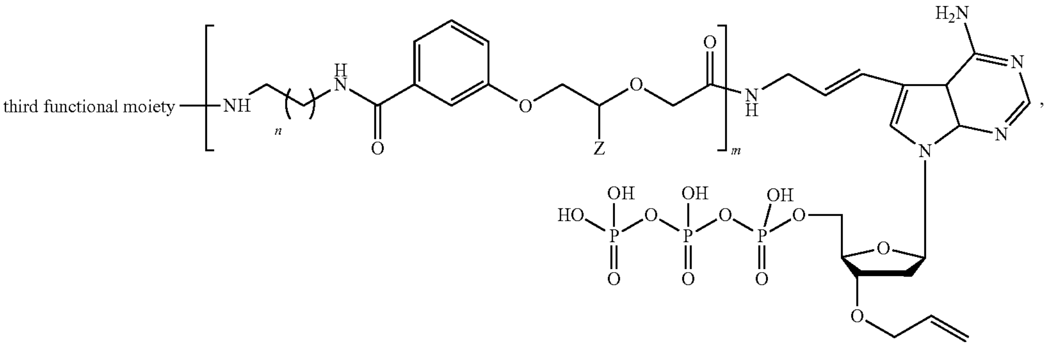

wherein Z is —O—$CH_2$—CH═$CH_2$, and each of m and n is independently an integer of 1, 2, 3, 4 or 5. In other embodiments, the A nucleotide has the structure:

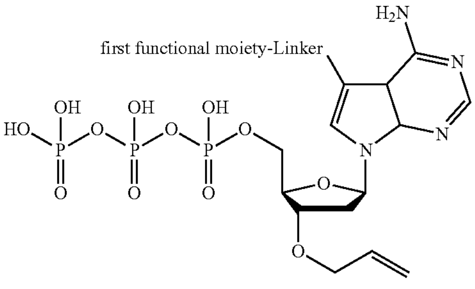
and
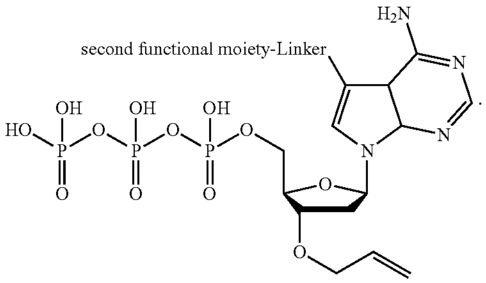
In further embodiments, the A nucleotide has the structure:
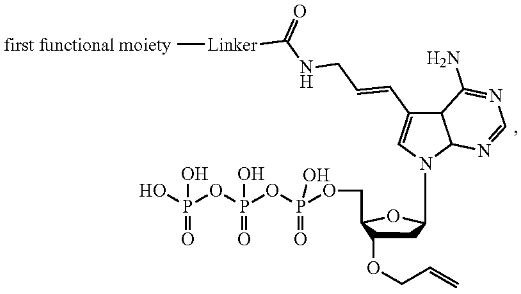
, and
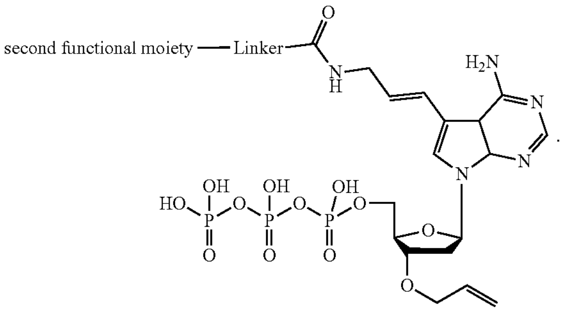
In further embodiments, the A nucleotide has the structure:
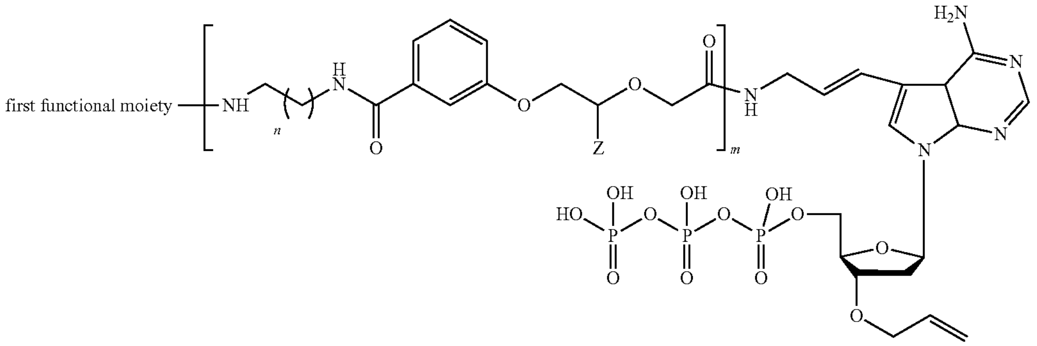
and -continued

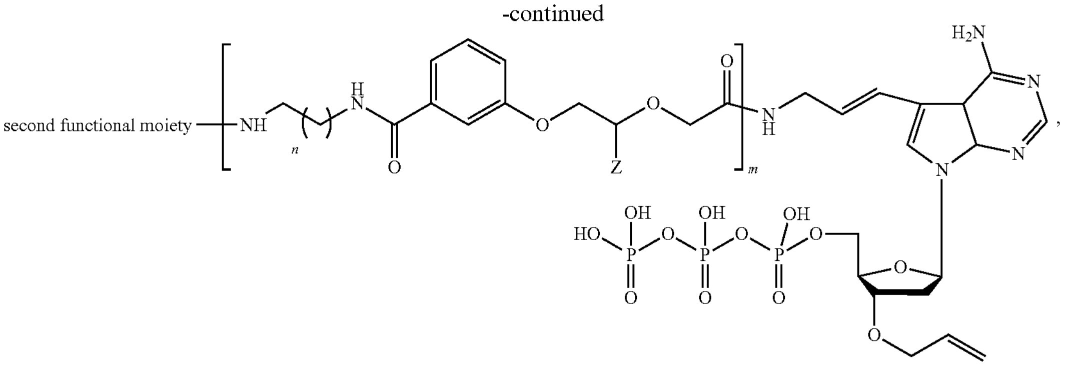

wherein Z is $-O-CH_2-CH{=}CH_2$, and each of m and n is independently an integer of 1, 2, 3, 4 or 5.

In some embodiments, the G nucleotide is unlabeled. In some further embodiments, G nucleotide has a structure selected from the group consisting of:

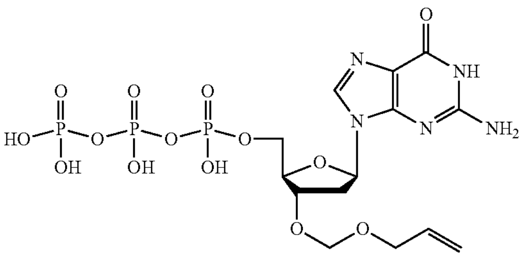

and

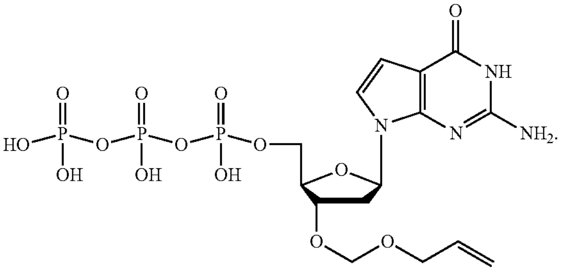

Additional examples of linkers are disclosed in U.S. Publication No. 2020/0216891 A1, which is incorporated by reference in its entirety:

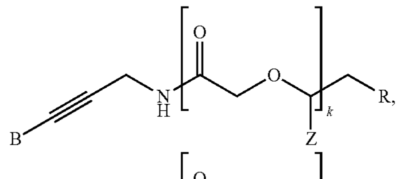

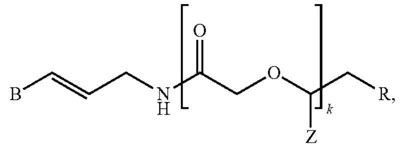

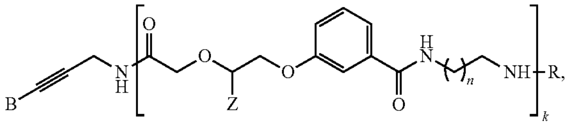

-continued

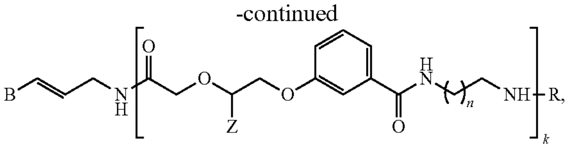

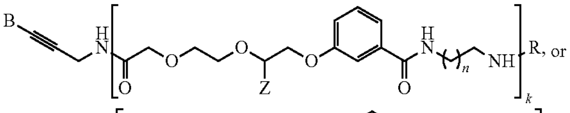

or

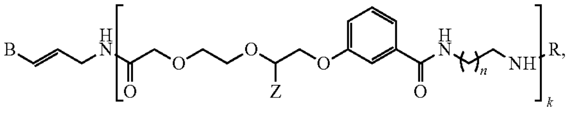

wherein B is a nucleobase; n is 1, 2, 3, 4, 5; k is 1; Z is $-N_3$ (azido), $-O-C_1$-$C_6$ alkyl, $-O-C_2$-$C_6$ alkenyl, or $-O-C_2$-$C_6$ alkynyl; and R comprises a detectable label or a binding moiety for post-incorporation labeling, which may contain additional linker and/or spacer structure. One of ordinary skill in the art understands that the detectable label or the binding moiety described herein is covalently bound to the linker by reacting a functional group of the binding moiety containing compound (e.g., carboxyl) with a functional group of the linker (e.g., amino) to form an amide bond. In one embodiment, the cleavable linker comprises

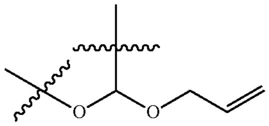 [SMILES: *OC(*)OCC=C]

("AOL" linker moiety) where Z is —O-allyl. For the purpose of the present disclosure, the nucleotide may contain multiple cleavable linkers repeating units (e.g., k is 1, 2, 3, 4 5, 6, 7, 8, 9 or 10).

In particular embodiments, the unlabeled nucleotide may be enzymatically incorporable and enzymatically extendable. Accordingly, a linker moiety may be of sufficient length to connect the nucleotide to the compound such that the compound does not significantly interfere with the overall binding and recognition of the nucleotide by a nucleic acid replication enzyme. Thus, the linker can also comprise a spacer unit, such as one or more PEG unit(s) $(-OCH_2CH_2-)_n$, where n is an integer of 1-20, for example 1, 2, 3, 4, 5, 6, 7, 8, 9, 10, 11, 12, 13, 14 or 15. The spacer distances, for example, the nucleotide base from a cleavage site or label.

In some embodiments of any of the methods described herein, said contacting the solid support with a deblocking solution (step (d) or step (e)) is performed for about 1 to 20 seconds, about 2 to 10 seconds, about 3 to 8 seconds, or about 4 to 5 seconds. For example, the contacting the solid support with a deblocking solution is performed for about 1, 2, 3, 4, 5, 6, 7, 8, 9, 10, 11, 12, 13, 14, 15, 16, 17, 18, 19 or 20 seconds, or a range defined by any two of the preceding values. In some further embodiments, said contacting the solid support with a deblocking solution is performed via continuous flow without pausing to incubate.

In some embodiments of any of the method described herein, the sequencing cycles (e.g., steps (b)-(e) of steps (b)-(f)) are repeated at least about 20 times, 30 times, or 50 times. In other embodiments, steps (b)-(e) or steps (b)-(f) are repeated at least about 100 times, 150 times, 200 times, 250 times, 300 times, 350 times, 400 times, 450 times or 500 times. In some embodiments, after about 50 repeated sequencing cycles the pre-phasing value is less than 0.18. In some embodiments, after about 50 repeated sequencing cycles the phasing value is less than 0.18. In further embodiments, after about 50 repeated sequencing cycles the pre-phasing or phasing value is less than 0.07. In some further embodiments, after about 100 repeated sequencing cycles the pre-phasing value is less than 0.10 and the phasing value is less than 0.10. In some further embodiments, after about 150 repeated sequencing cycles the pre-phasing value is less than 0.25 and the phasing value is less than 0.25. In some further embodiments, after about 150 repeated sequencing cycles the pre-phasing value is less than 0.2 and the phasing value is less than 0.2. In some further embodiments, after about 150 repeated sequencing cycles the pre-phasing value is less than 0.15 and the phasing value is less than 0.15. In some further embodiments, after about 150 repeated sequencing cycles the pre-phasing value is less than 0.1 and the phasing value is less than 0.1.

In some embodiments of any of the method described herein, the DNA polymerase is an altered family B archaeal DNA polymerase comprising a 3-amino acid region that is functionally equivalent or homologous to amino acids 408-410 in 9° N DNA polymerase, wherein the first amino acid of the 3-amino acid region is an amino acid selected from the group consisting of isoleucine (I), alanine (A), valine (V), and serine (S); the second amino acid of the 3-amino acid region is an amino acid selected from the group consisting of alanine (A) and glycine (G); and the third amino acid of the 3-amino acid region is an amino acid selected from the group consisting of alanine (A), isoleucine (I), valine (V), leucine (L), threonine (T), and proline (P).

Palladium Catalysts for Deblocking 3'Allyl Blocking Group

In any embodiments of any of the method described herein, the Pd catalyst used for removing or cleaving the 3' allyl blocking group described herein is water soluble. In some such embodiments, the Pd catalyst is the active Pd(0) form. In some instances, the Pd(0) catalyst may be generated in situ from reduction of a Pd complex or Pd precatalyst (e.g., a Pd(II) complex) by reagents such as alkenes, alcohols, amines, phosphines, or metal hydrides. Suitable Pd sources include $Pd(CH_3CN)_2Cl_2$, $[Pd(Allyl)Cl]_2$, [Pd(Allyl)(THPP)]Cl, $[Pd(Allyl)(THPP)_2]Cl$, $Na_2PdCl_4$, $K_2PdCl_4$, $Li_2PdCl_4$, $Pd(OAc)_2$, $Pd(PPh_3)_4$, $Pd(dba)_2$, $Pd(Acac)_2$, $PdCl_2(COD)$, $Pd(TFA)_2$, $Na_2PdBr_4$, $K_2PdBr_4$, $PdCl_2$, $PdBr_2$, and $Pd(NO_3)_2$. In one such embodiment, the Pd(0) complex is generated in situ from an organic or inorganic salt of palladate (II), for example, $Na_2PdCl_4$ or $K_2PdCl_4$. In another embodiment, the palladium source is allyl Pd(II) chloride dimer $[(Allyl)PdCl]_2$ or $[PdCl(C_3H_5)]_2$. In some embodiments, the Pd(0) catalyst is generated in an aqueous solution by mixing a Pd(II) complex with a water soluble phosphine, such as tris(hydroxyalkyl)phosphine. Suitable tris(hydroxyalkyl)phosphines include tris(hydroxypropyl)phosphine (THPP), tris(hydroxymethyl)phosphine (THMP), or tris(hydroxyethyl)phosphine (THEP), or combinations thereof. In one embodiment, the water soluble phosphine is THPP.

In some embodiments, the palladium catalyst is prepared by mixing $[(Allyl)PdCl]_2$ with THP in situ. The molar ratio of $[(Allyl)PdCl]_2$ and the THP may be about 1:1, 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, 1:9.5 or 1:10. In one embodiment, the molar ratio of $[(Allyl)PdCl]_2$ to THP is 1:10. In some other embodiment, the palladium catalyst is prepared by mixing a water soluble Pd reagent such as $Na_2PdCl_4$ or $K_2PdCl_4$ with THP in situ. The molar ratio of $Na_2PdCl_4$ or $K_2PdCl_4$ and THP may be about 1:1, 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, 1:9.5 or 1:10. In one embodiment, the molar ratio of $Na_2PdCl_4$ or $K_2PdCl_4$ to THP is about 1:3. In another embodiment, the molar ratio of $Na_2PdCl_4$ or $K_2PdCl_4$ to THP is about 1:3.5. In yet another embodiment, the molar ratio of $Na_2PdCl_4$ or $K_2PdCl_4$ to THP is about 1:2.5.

The Pd complex and the water soluble phosphine for use in the cleavage step of the method described herein may be in a composition or a mixture, also called cleavage mix. In some further embodiments, the cleavage mix may contain one or more reducing agents, such as ascorbic acid or a salt thereof (e.g., sodium ascorbate), or a boron-containing reducing agent. In some further embodiments, the cleavage mix may contain one or more buffer reagents, such as a primary amine, a secondary amine, a tertiary amine, a natural amino acid, a non-natural amino acid, a carbonate salt, a phosphate salt, or a borate salt, or combinations thereof. In some further embodiments, the buffer reagent comprises ethanolamine (EA), tris(hydroxymethyl)aminomethane (Tris), glycine, sodium carbonate, sodium phosphate, sodium borate, dimethylethanolamine (DMEA), diethylethanolamine (DEEA), N,N,N',N'-tetramethylethylenediamine(TMEDA), N,N,N',N'-tetraethylethylenediamine (TEEDA), or 2-piperidine ethanol (also known as (2-hydroxyethyl)piperidine, having the structure

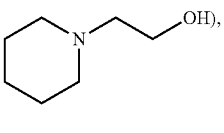

or combinations thereof. In one embodiment, the one or more buffer reagents comprise DEEA. In another embodiment, the one or more buffer reagents comprise (2-hydroxyethyl)piperidine. In another embodiment, the one or more buffer reagents contains one or more inorganic salts such as a carbonate salt, a phosphate salt, or a borate salt, or combinations thereof. In one embodiment, the inorganic salt is a sodium salt.

Reducing Agents

A reducing agent may be used to facilitate the formation of Pd(0) active species for a 3'deblocking reaction and/or cleavage of the linker in accordance with the present disclosure. In some embodiments, the reducing agent contains boron. For example, the reducing agent may be a borane, a borinic acid, a boronic acid, a boronic ester, or a borohydride. In some embodiments, the reducing agent is a borane or a boronic acid. Suitable boranes include diborane, triborane, tetraborane, pentaborane, hexaborane, heptaborane, octaborane, nonaborane, decaborane, borane tetrahydrofuran, borane dimethyl sulfide, catecholborane, dichlorophenylborane, borane diphenylphosphine complex, dicyclohexyliodoborane, bromodimethylborane, diethylmethoxyborane, dichloromethyldiisopropoxyborane, bromodimethylborane, and mono-bromoborane methyl sulfide. Suitable boranes include amino-boranes. Suitable amine-boranes include pyridine-boranes, N-based heteroaromatic-borane complexes, amminetrihydridoboron ($NH_3BH_3$), borane-ammonia complex, borane dimethylamine, borane tert-butylamine, borane trimethylamine, borane isopropylamine, dichloro(diisopropylamino)borane, and borazine. Suitable boronic acids include boric acid, 4-hydroxyphenylboronic acid, tetrahydroxidiboron ($B_2(OH)_4$), phenylboronic acid, 2-thienylboronic acid, methylboronic acid, cis-propenylboronic acid, and trans-propenylboronic acid. Suitable boronic esters include allylboronic acid pinacol ester, phenyl boronic acid trimethylene glycol ester, and diisopropoxymethylborane. Suitable borohydrides include sodium borohydride ($Na_2BH_4$), lithium borohydride, calcium borohydride, calcium borohydride bis(tetrahydrofuran), magnesium borohydride, potassium borohydride, potassium triethylborohydride, sodium triacetoxyborohydride, tetraethylammonium borohydride, and tetrabutylammonium borohydride. In some embodiments, the concentration of the reducing agent (such as boron-containing reducing agent) in the first aqueous solution (also called cleavage mixture) is about 0.1 mM, 0.2 mM, 0.3, mM, 0.4 mM, 0.5 mM, 0.6 mM, 0.7 mM, 0.8 mM, 0.9 mM, 1 mM, 1.5 mM, 2 mM, 2.5 mM, 3 mM, 3.5 mM, 4 mM, 4.5 mM, 5 mM, 5.5 mM, 6 mM, 6.5 mM, 7 mM, 7.5 mM, 8 mM, 8.5 mM, 9 mM, 9.5 mM, 10 mM, 12.5 mM, 15 mM, 17.5 mM, 20 mM, 22.5 mM, 25 mM, 37.5 mM, 30 mM, 35 mM, 40 mM, 45 mM, 50 mM, 55 mM, 60 mM, 65 mM, 70 mM, or 75 mM, or a range defined by any two of the preceding values.

In some embodiments, the cleavage condition for the 3' blocking group is the same as the condition for cleaving the cleavable linker of the nucleotide. For example, the nucleotide may comprise a linker moiety that is the same as the 3' blocking group. In other embodiments, the cleavage condition for the 3' blocking group is different from the condition for cleaving the cleavable linker of the nucleotide.

Palladium Scavengers

Pd(0) Scavengers

Certain aspects of the present disclosure relate to employing alternative palladium scavengers in several steps of sequencing by synthesis, where at least one palladium scavenger comprises one or more allyl moieties. For example, —O-allyl, —S-allyl, —NR-allyl, or —$N^+RR'$-allyl, or combinations thereof, wherein R is H, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_6$-$C_{10}$ aryl, unsubstituted or substituted 5 to 10 membered heteroaryl, unsubstituted or substituted $C_3$-$C_{10}$ carbocyclyl, or unsubstituted or substituted 5 to 10 membered heterocyclyl; and R' is H, unsubstituted $C_1$-$C_6$ alkyl or substituted $C_1$-$C_6$ alkyl.

The allyl containing Pd scavenger acts as a competitive substrate to consume any residual Pd(0) sticking on the nucleic acid (i.e., a Pd(0) scavenger). These palladium scavengers are described in WO/2022/243480, which is incorporated by reference in its entirety. The sequencing methods described herein substantially improve the sequencing metrics (e.g., reduce phasing and prephasing values) and may also reduce the sequencing time for each cycle by certain eliminating post-cleavage treatment step.

In some embodiments of any of the methods described herein, the Pd(0) scavenger comprises one or more allyl moieties is in the aqueous solution containing DNA polymerase and the nucleotides. In some instances, the aqueous solution in step (b) is also known as the incorporation mix (IMX). In some such embodiments, such palladium scavenger is compatible with the other sequencing reagents in the incorporation mix, which may also include a polymerase (such as DNA polymerase), in addition to the one or more different types of nucleotides. In some such embodiments, the polymerase is a DNA polymerase, such as a mutant of 9° N polymerase (e.g., those disclosed in WO 2005/024010, which is incorporated by reference), for example, Pol 812, Pol 1901, Pol 1558 or Pol 963. The amino acid sequences of Pol 812, Pol 1901, Pol 1558 or Pol 963 DNA polymerases are described, for example, in U.S. Patent Publication Nos. 2020/0131484 A1 and 2020/0181587 A1, both of which are incorporated by reference herein. In some embodiments, the incorporation mix further comprises one or more buffering agents. The buffering agents may comprise a primary amine, a secondary amine, a tertiary amine, a natural amino acid, or a non-natural amino acid, or combinations thereof. In further embodiments, the buffering agents comprise ethanolamine or glycine, or a combination thereof. In one embodiment, the buffer agent comprises or is glycine. In further embodiments, the palladium scavenger comprises one or more allyl moieties does not require a separate washing step prior to the next incorporation cycle. In further embodiments, the palladium scavenger in the incorporation mix is a Pd(0) scavenger described herein. In some embodiments, the Pd(0) scavenger is premixed with the DNA polymerase and/or the one or more of four types of nucleotides (e.g., dATP, dCTP, dGTP, and dTTP or dUTP). In other embodiments, the Pd(0) scavenger is stored separately form the DNA polymerase and/or the one or more of four types of nucleotides and is mixed with these components shortly before sequencing run starts.

In some embodiments of any of the methods described herein, the concentration of the Pd(0) scavenger comprising one or more allyl moieties in the aqueous solution containing the DNA polymerase and nucleotides (e.g., A, G, C, and T or U; or dATP, dCTP, dGTP, and dTTP or dUTP) is from about 0.1 mM to about 100 mM, from 0.2 mM to about 75 mM, from about 0.5 mM to about 50 mM, from about 1 mM to about 20 mM, or from about 2 mM to about 10 mM. In further embodiments, the concentration of the palladium scavenger (e.g., the Pd(0) scavenger) is about 0.1 mM, 0.2 mM, 0.3, mM, 0.4 mM, 0.5 mM, 0.6 mM, 0.7 mM, 0.8 mM, 0.9 mM, 1 mM, 1.5 mM, 2 mM, 2.5 mM, 3 mM, 3.5 mM, 4 mM, 4.5 mM, 5 mM, 5.5 mM, 6 mM, 6.5 mM, 7 mM, 7.5 mM, 8 mM, 8.5 mM, 9 mM, 9.5 mM, 10 mM, 12.5 mM, 15 mM, 17.5 mM or 20 mM, or a range defined by any two of the preceding values. In further embodiments, the concentration of such palladium scavenger is the concentration in the incorporation mix. In further embodiments, the pH of the incorporation mix is about 9.

In some other embodiments of any of the methods described herein, the Pd(0) scavenger comprises one or more allyl moieties is in a solution when performing one or more fluorescent measurements. In such embodiment, such palladium scavenger is compatible with the sequencing reagents of the scanning solution (also known as the scan mix). In further embodiments, the one or more palladium scavengers does not require a separate washing step prior to the next incorporation cycle. In further embodiments, the palladium scavenger in the scan solution is a Pd(O) scavenger described herein.

In other embodiments of the methods described herein, the Pd(0) scavenger comprises one or more allyl moieties is in the post cleavage wash solution of step (e) or step (f). In further embodiments, the palladium scavenger in the post cleavage wash solution is a Pd(0) scavenger described herein. In some such embodiment, the post cleavage wash solution does not comprise lipoic acid or 3,3'-dithiodipropionic acid (DDPA).

In still other embodiments of the method described herein, the Pd(0) scavenger comprises one or more allyl moieties may be present both in the incorporation mix of step (b) and the post cleavage wash solution of step (e) or step (f), or present in both the incorporation mix and the scan mix. In some such embodiment, the post cleavage wash solution does not comprise lipoic acid or DDPA.

Non-limiting examples of the Pd(0) scavenger comprising one or more —O-allyl or allyl moieties include the following:

(Compound A)

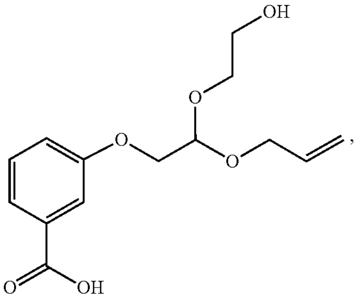

, (Compound B, N-Boc tyrosine(allyl)-OH)

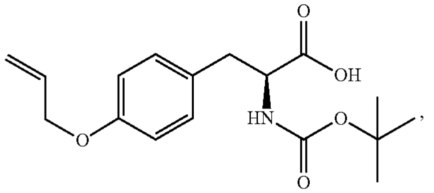

, (Compound C, allyl-β-D-gluocopyranoside)

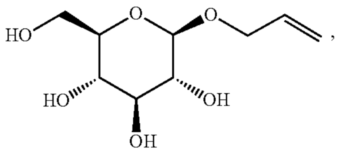

, (Compound D)

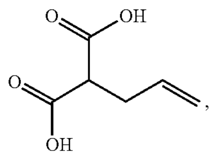

, (Compound E)

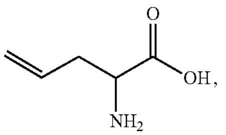

,

-continued (Compound F)

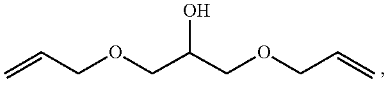

, (Compound G)

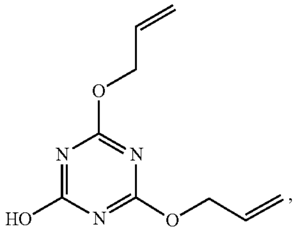

, (Compound H)

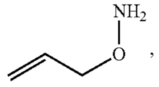

, (Compound I)

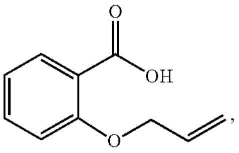

, (Compound J)

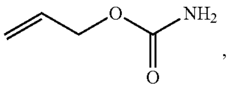

, (Compound K)

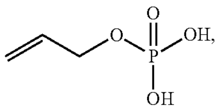

, (Compound L)

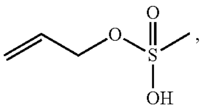

, (Compound M)

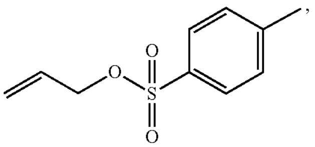

, and (Compound N)

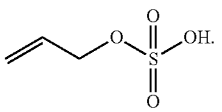

.

Non-limiting examples of the Pd(0) scavenger comprising one or more —S-allyl moieties include the following:

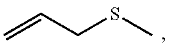

,

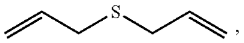

,

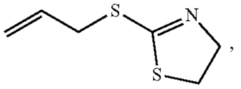

,

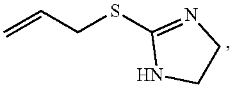

, and

-continued

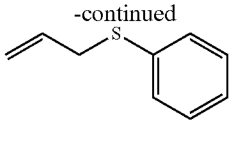,

Non-limiting examples of the Pd(0) scavenger comprising one or more —NR-allyl or —$N^+RR'$-allyl moieties include the following:

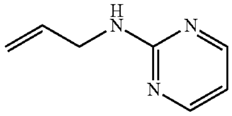,

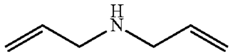,

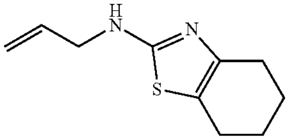,

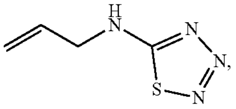

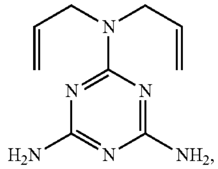

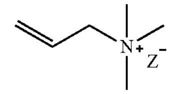

or

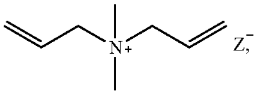

where $Z^-$ is an anion (e.g., a halide anion such as $F^-$ or $Cl^-$). In one embodiment, the palladium scavenger is

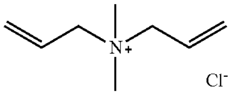.

(Compound O, diallyldimethylammonium chloride, also known as DADMAC)

Pd(II) Scavengers

In some embodiments of the methods described herein, the method may further use additional palladium scavenger(s), such as Pd(II) scavenger(s). In some such embodiments, the use of additional Pd(II) scavenger(s) may improve the phasing value of the sequencing metrics. For example, the Pd(II) scavenger(s) may comprise an isocyanoacetate (ICNA) salt, ethyl isocyanoacetate, methyl isocyanoacetate, cysteine (e.g., L-cysteine) or a salt thereof (e.g., N-acetyl-L-cysteine), potassium ethylxanthogenate, potassium isopropyl xanthate, glutathione, ethylenediaminetetraacetic acid (EDTA), iminodiacetic acid, nitrilodiacetic acid, trimercapto-S-triazine, dimethyldithiocarbamate, dithiothreitol, mercaptoethanol, allyl alcohol, propargyl alcohol, thiol, thiosulfate salt (e.g., sodium thiosulfate or potassium thiosulfate), tertiary amine and/or tertiary phosphine, or combinations thereof. In one embodiment, the method also includes the use of L-cysteine or a salt thereof. In another embodiment, the method also includes the use of a thiosulfate salt such as sodium thiosulfate ($Na_2S_2O_3$). In some such embodiments, the Pd(II) scavenger (e.g., L-cysteine or sodium thiosulfate) is in the aqueous solution containing the DNA polymerase and the nucleotides (i.e., incorporation mix). In other embodiments, the Pd(II) scavenger (e.g., L-cysteine or sodium thiosulfate) is in the post cleavage wash solution. In other embodiments, the Pd(II) scavenger (e.g., L-cysteine or sodium thiosulfate) may be both present in the incorporation mixture. In other embodiments, the Pd(II) scavenger (e.g., L-cysteine or sodium thiosulfate) may be present in the scan mixture (i.e., the solution in which one or more fluorescent measurements of the incorporated nucleotide are performed). In other embodiments, the Pd(II) scavenger may be present in one or more of incorporation mixture (i.e., the aqueous solution of step (b)), the scan mixture, or the post-cleavage wash solution (i.e., the aqueous solution of step (e)). In further embodiments, the concentration of the Pd(II) scavenger such as L-cysteine or sodium thiosulfate in the incorporation mixture or the post cleavage wash solution is from about 0.1 mM to about 100 mM, from 0.2 mM to about 75 mM, from about 0.5 mM to about 50 mM, from about 1 mM to about 20 mM, or from about 2 mM to about 10 mM. In further embodiments, the concentration of the Pd(II) scavenger such as L-cysteine or sodium thiosulfate is about 0.1 mM, 0.5 mM, 1 mM, 2 mM, 3 mM, 4 mM, 5 mM, 6 mM, 6.5 mM, 7 mM, 8 mM, 9 mM, 10 mM, 12.5 mM, 15 mM, 17.5 mM or 20 mM, or a range defined by any two of the preceding values. In further embodiments, the Pd(II) scavenger is in the post cleavage wash solution, and the concentration of the Pd(II) scavenger in the post cleavage wash solution is about 10 mM. In further embodiment, the post cleavage wash solution does not contain lipoic acid or DDPA. In other embodiments, the method does not include a post-cleavage wash step.

In some embodiments of the methods described herein, the target polynucleotide is immobilized to a surface of a substrate or a solid support. In some further embodiments, the surface comprises a plurality of immobilized target polynucleotides, for example, an array of different immobilized target polynucleotides. In some such embodiments, the substrate or solid support comprises glass, modified or functionalized glass, plastics, polysaccharides, nylon, nitrocellulose, resins, silica, silicon, modified silicon, carbon, metals, inorganic glasses, or optical fiber bundles, or combinations thereof. In some further embodiments, the substrate is a flowcell, a nanoparticle, or a bead (such as spherical silica beads, inorganic nanoparticles, magnetic nanoparticles, cadmium-based dots, and cadmium free dots, or a bead disclosed in U.S. Publication No. 2021/0187470 A1, which is incorporated by reference). In one embodiment, the substrate or solid support is a flowcell comprising patterned nanowells separated by interstitial regions, and wherein the immobilized target polynucleotides reside inside the patterned nanowells. In some embodiments, the substrate or solid support comprises at least 5,000,000 spatially distinguishable sites/$cm^2$ that comprise concatemers comprising said multiple copies of target polynucleotides. In some other embodiments, the substrate or solid support comprises at least 5,000,000 spatially distinguishable sites/$cm^2$ that comprise clusters of immobilized nucleic acid molecules comprising said multiple copies of target polynucleotides.

In some embodiments of any of the methods described herein, the method is performed on an automated sequencing instrument, and wherein the automated sequencing instrument comprises two light sources operating at different wavelengths (e.g., at about 450 nm to about 460 nm, and about 520 nm to about 540 nm, in particular at about 460 nm and about 532 nm). In other embodiments, the automated sequencing instrument comprises a single light source operating at one wavelength.

Cleavage Condition of the Cleavable Linker

In any embodiments of the sequencing methods described herein, the 3' blocking group and the cleavable linker (and the attached label) may be removable under the same or substantially same chemical reaction conditions, for example, the 3' blocking group and the detectable label may be removed in a single chemical reaction. In other embodiments, the 3' blocking group and the detectable labeled are removed in two separate steps.

The cleavable linker described herein may be removed or cleaved under various chemical conditions. Non-limiting cleaving condition includes a palladium catalyst, such as a Pd(II) complex (e.g., $Pd(OAc)_2$, allylPd(II) chloride dimer $[(Allyl)PdCl]_2$ or $Na_2PdCl_4$) in the presence of a water soluble phosphine ligand, for example tris(hydroxylpropyl) phosphine (THPP or THP), tris(hydroxymethyl)phosphine, and/or tris(2-carboxyethyl)phosphine (TCEP), with or without the presence of a reducing agent. In some embodiments, the 3' blocking group may be cleaved under the same or substantially the same cleavage condition as that for the cleavable linker.

Compatibility with Linearization

In order to maximize the throughput of nucleic acid sequencing reactions it is advantageous to be able to sequence multiple template molecules in parallel. Parallel processing of multiple templates can be achieved with the use of nucleic acid array technology. These arrays typically consist of a high-density matrix of polynucleotides immobilized onto a solid support material.

WO 98/44151 and WO 00/18957 both describe methods of nucleic acid amplification which allow amplification products to be immobilized on a solid support in order to form arrays comprised of clusters or “colonies” formed from a plurality of identical immobilized polynucleotide strands and a plurality of identical immobilized complementary strands. Arrays of this type are referred to herein as “clustered arrays.” The nucleic acid molecules present in DNA colonies on the clustered arrays prepared according to these methods can provide templates for sequencing reactions, for example as described in WO 98/44152. The products of solid-phase amplification reactions such as those described in WO 98/44151 and WO 00/18957 are so-called “bridged” structures formed by annealing of pairs of immobilized polynucleotide strands and immobilized complementary strands, both strands being attached to the solid support at the 5' end. In order to provide more suitable templates for nucleic acid sequencing, it is preferred to remove substantially all or at least a portion of one of the immobilized strands in the “bridged” structure in order to generate a template which is at least partially single-stranded. The portion of the template which is single-stranded will thus be available for hybridization to a sequencing primer. The process of removing all or a portion of one immobilized strand in a “bridged” double-stranded nucleic acid structure is referred to as “linearization.” There are various ways for linearization, including but not limited to enzymatic cleavage, photo-chemical cleavage, or chemical cleavage. Non-limiting examples of linearization methods are disclosed in PCT Publication No. WO 2007/010251, U.S. Patent Publication No. 2009/0088327, U.S. Patent Publication No. 2009/0118128, and U.S. Publication No. 2019/0352327, which are incorporated by reference in their entireties.

In some embodiments, the condition for the removal of the 3' blocking group and/or the cleavable linker is also compatible with the linearization processes, for example, a chemical linearization process which comprises the use of a Pd complex and a phosphine. In some embodiments, the Pd complex is a Pd(II) complex (e.g., $Pd(OAc)_2$, $[(Allyl)PdCl]_2$ or $Na_2PdCl_4$), which generates Pd(0) in situ in the presence of a water soluble phosphine described herein, without or without the presence of a reducing agent.

Embodiments and Alternatives of Sequencing-By-Synthesis

Alternatively, the sequencing methods described herein may also be carried out using unlabeled nucleotides and affinity reagents containing a fluorescent dye described herein. For example, one, two, three or each of the four different types of nucleotides (e.g., dATP, dCTP, dGTP and dTTP or dUTP) in the incorporation mixture of step (a) may be unlabeled. Each of the four types of nucleotides (e.g., dNTPs) has a 3' blocking group to ensure that only a single base can be added by a polymerase to the 3' end of the primer polynucleotide. After incorporation of an unlabeled nucleotide in step (b), the remaining unincorporated nucleotides are washed away. An affinity reagent is then introduced that specifically recognizes and binds to the incorporated dNTP to provide a labeled extension product comprising the incorporated dNTP. Uses of unlabeled nucleotides and affinity reagents in sequencing by synthesis have been disclosed in WO 2018/129214 and WO 2020/097607. A modified sequencing method of the present disclosure using unlabeled nucleotides may include the following steps:

(a') contacting a solid support with sequencing primers under hybridization conditions, wherein the solid support comprises a plurality of target polynucleotides immobilized thereon; and the sequencing primers are complementary to at least a portion of the target polynucleotides;

(b') contacting the solid support with an aqueous solution comprising DNA polymerase and one or more of four different types of nucleotides (A, G, C and T or U) under conditions suitable for DNA polymerase-mediated primer extension, wherein each of the nucleotides comprises a 3' blocking group as described herein (e.g., each nucleotide comprises a 2' deoxyribose moiety with a 3'AOM blocking group

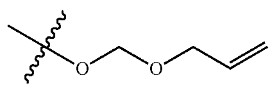 [SMILES: *OCOCC=C]

attached to the 3' carbon atom, or a 3' allyl blocking group

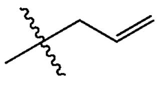 [SMILES: *CC=C]

attached to the 3' oxygen atom);

(c') contacting the extended copy polynucleotides with a set of affinity reagents under conditions wherein one affinity reagent binds specifically to the incorporated unlabeled nucleotides to provide labeled extended copy polynucleotides;

(d') imaging the solid support to determine the identity of the incorporated nucleotides (e.g., by performing one or more fluorescent measurements of the extended copy polynucleotides); and (e') contacting the solid support with an aqueous deblocking solution comprising a palladium catalyst and tris (hydroxyalkyl)phosphine under conditions suitable to chemically remove 3' blocking groups from incorporated nucleotides to expose a 3'-OH group for further nucleotide incorporation on the solid support; and repeating steps (b')-(e') to determine target polynucleotide sequences.

In some embodiments of the modified sequencing method described herein, the method further comprises removing the affinity reagents from the incorporated nucleotides. In still further embodiments, the 3' blocking group and the affinity reagent are removed in the same reaction. In some embodiments, the method further comprises a step (f') washing the solid support with a third aqueous wash solution. In further embodiments, steps (b') through (f') are repeated at least 50, 100, 150, 200, 250 or 300 cycles to determine the target polynucleotide sequences. In some embodiments, the set of affinity reagents may comprise a first affinity reagent that binds specifically to the first type of nucleotide, a second affinity reagent that binds specifically to the second type of nucleotide, and a third affinity reagent that binds specifically to the third type of nucleotide. In some further embodiments, each of the first, second and the third affinity reagents comprises a detectable labeled that is spectrally distinguishable. In some embodiments, the affinity reagents may include protein tags, antibodies (including but not limited to binding fragments of antibodies, single chain antibodies, bispecific antibodies, and the like), aptamers, knottins, affimers, or any other known agent that binds an incorporated nucleotide with a suitable specificity and affinity. In one embodiment, at least one affinity reagent is an antibody or a protein tag. In another embodiment, at least one of the first type, the second type, and the third type of affinity reagents is an antibody or a protein tag comprising one or more detectable labels (e.g., multiple copies of the same detectable label), wherein the detectable label is or comprises a bis-boron dye moiety described herein.

Some embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." *Science* 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurase, and the level of ATP generated is detected via luciferase-produced photons. The nucleic acids to be sequenced can be attached to features in an array and the array can be imaged to capture the chemiluminescent signals that are produced due to incorporation of a nucleotides at the features of the array. An image can be obtained after the array is treated with a particular nucleotide type (e.g., A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in WO 04/018497 and U.S. Pat. No. 7,057,026, the disclosures of which are incorporated herein by reference. This approach is being commercialized by Solexa (now Illumina, Inc.), and is also described in WO 91/06678 and WO 07/123,744, each of which is incorporated herein by reference. The availability of fluorescently-labeled terminators in which both the termination can be reversed, and the fluorescent label cleaved facilitates efficient cyclic reversible termination (CRT) sequencing. Polymerases can also be co-engineered to efficiently incorporate and extend from these modified nucleotides.

Preferably in reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially, and an image of the array can be obtained between each addition step. In such embodiments each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed, and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth below.

Some embodiments can utilize detection of four different nucleotides using fewer than four different labels. For example, SBS can be performed utilizing methods and systems described in the incorporated materials of U.S. Pub. No. 2013/0079232. As a first example, a pair of nucleotide types can be detected at the same wavelength but distinguished based on a difference in intensity for one member of the pair compared to the other, or based on a change to one member of the pair (e.g., via chemical modification, photo-chemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc.). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g. dATP having a label that is detected in the first channel when excited by a first excitation wavelength), a second nucleotide type that is detected in a second channel (e.g. dCTP having a label that is detected in the second channel when excited by a second excitation wavelength), a third nucleotide type that is detected in both the first and the second channel (e.g. dTTP having at least one label that is detected in both channels when excited by the first and/or second excitation wavelength) and a fourth nucleotide type that lacks a label that is not, or minimally, detected in either channel (e.g. dGTP having no label).

Further, as described in the incorporated materials of U.S. Pub. No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597, the disclosures of which are incorporated herein by reference in their entireties.

Some embodiments can utilize nanopore sequencing (Deamer, D. W. & Akeson, M. "Nanopores and nucleic acids: prospects for ultrarapid sequencing." *Trends Biotechnol.* 18, 147-151 (2000); Deamer, D. and D. Branton, "Characterization of nucleic acids by nanopore analysis," *Acc. Chem. Res.* 35:817-825 (2002); Li, J., M. Gershow, D. Stein, E. Brandin, and J. A. Golovchenko, "DNA molecules and configurations in a solid-state nanopore microscope," Nat. Mater. 2:611-615 (2003), the disclosures of which are incorporated herein by reference in their entireties). In such embodiments, the target nucleic acid passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores," *Clin. Chem.* 53, 1996-2001 (2007); Healy, K. "Nanopore-based single-molecule DNA analysis," *Nanomed.* 2, 459-481 (2007); Cockroft, S. L., Chu, J., Amorin, M. & Ghadiri, M. R. "A single-molecule nanopore device detects DNA polymerase activity with single-nucleotide resolution," *J. Am. Chem. Soc.* 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some other embodiments of sequencing method involve the use the 3' blocked nucleotide described herein in nanoball sequencing technique, such as those described in U.S. Pat. No. 9,222,132, the disclosure of which is incorporated by reference. Through the process of rolling circle amplification (RCA), a large number of discrete DNA nanoballs may be generated. The nanoball mixture is then distributed onto a patterned slide surface containing features that allow a single nanoball to associate with each location. In DNA nanoball generation, DNA is fragmented and ligated to the first of four adapter sequences. The template is amplified, circularized and cleaved with a type II endonuclease. A second set of adapters is added, followed by amplification, circularization and cleavage. This process is repeated for the remaining two adapters. The final product is a circular template with four adapters, each separated by a template sequence. Library molecules undergo a rolling circle amplification step, generating a large mass of concatemers called DNA nanoballs, which are then deposited on a flow cell. Goodwin et al., "Coming of age: ten years of next-generation sequencing technologies," Nat Rev Genet. 2016; 17(6): 333-51.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414, both of which are incorporated herein by reference, or nucleotide incorporations can be detected with zero-mode waveguides as described, for example, in U.S. Pat. No. 7,315,019, which is incorporated herein by reference, and using fluorescent nucleotide analogs and engineered polymerases as described, for example, in U.S. Pat. No. 7,405,281 and U.S. Pub. No. 2008/0108082, both of which are incorporated herein by reference. The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations," *Science* 299, 682-686 (2003); Lundquist, P. M. et al. "Parallel confocal detection of single molecules in real time," *Opt. Lett.* 33, 1026-1028 (2008); Korlach, J. et al. "Selective aluminum passivation for targeted immobilization of single DNA polymerase molecules in zero-mode waveguide nano structures," *Proc. Natl. Acad. Sci. USA* 105, 1176-1181 (2008), the disclosures of which are incorporated herein by reference in their entireties). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary) or sequencing methods and systems described in U.S. Pub. Nos. 2009/0026082; 2009/0127589; 2010/0137143; and 2010/0282617, all of which are incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

The methods set forth herein can use arrays having features at any of a variety of densities including, for example, at least about 10 features/$cm^2$, 100 features/$cm^2$, 500 features/$cm^2$, 1,000 features/$cm^2$, 5,000 features/$cm^2$, 10,000 features/$cm^2$, 50,000 features/$cm^2$, 100,000 features/$cm^2$, 1,000,000 features/$cm^2$, 5,000,000 features/$cm^2$, or higher.

An advantage of the methods set forth herein is that they provide for rapid and efficient detection of a plurality of target nucleic acid in parallel. Accordingly, the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system comprising components such as pumps, valves, reservoirs, fluidic lines and the like. A flow cell can be configured and/or used in an integrated system for detection of target nucleic acids. Exemplary flow cells are described, for example, in U.S. Pub. No. 2010/0111768 and U.S. patent application Ser. No. 13/273,666, each of which is incorporated herein by reference. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, CA) and devices described in U.S. patent application Ser. No. 13/273,666, which is incorporated herein by reference.

Arrays in which polynucleotides have been directly attached to silica-based supports are those for example disclosed in WO 00/06770 (incorporated herein by reference), wherein polynucleotides are immobilized on a glass support by reaction between a pendant epoxide group on the glass with an internal amino group on the polynucleotide. In addition, polynucleotides can be attached to a solid support by reaction of a sulfur-based nucleophile with the solid support, for example, as described in WO 2005/047301 (incorporated herein by reference). A still further example of solid-supported template polynucleotides is where the template polynucleotides are attached to hydrogel supported upon silica-based or other solid supports, for example, as described in WO 00/31148, WO 01/01143, WO 02/12566, WO 03/014392, U.S. Pat. No. 6,465,178 and WO 00/53812, each of which is incorporated herein by reference.

A particular surface to which template polynucleotides may be immobilized is a polyacrylamide hydrogel. Polyacrylamide hydrogels are described in the references cited above and in WO 2005/065814, which is incorporated herein by reference. Specific hydrogels that may be used include those described in WO 2005/065814 and U.S. Pub. No. 2014/0079923. In one embodiment, the hydrogel is PAZAM (poly(N-(5-azidoacetamidylpentyl) acrylamide-co-acrylamide)).

DNA template molecules can be attached to beads or microparticles, for example, as described in U.S. Pat. No. 6,172,218 (which is incorporated herein by reference). Attachment to beads or microparticles can be useful for sequencing applications. Bead libraries can be prepared where each bead contains different DNA sequences. Exemplary libraries and methods for their creation are described in *Nature,* 437, 376-380 (2005); *Science,* 309, 5741, 1728-1732 (2005), each of which is incorporated herein by reference. Sequencing of arrays of such beads using nucleotides set forth herein is within the scope of the disclosure.

Templates that are to be sequenced may form part of an "array" on a solid support, in which case the array may take any convenient form. Thus, the method of the disclosure is applicable to all types of high-density arrays, including single-molecule arrays, clustered arrays, and bead arrays. Labeled nucleotides of the present disclosure may be used for sequencing templates on essentially any type of array, including but not limited to those formed by immobilization of nucleic acid molecules on a solid support.

However, labeled nucleotides of the disclosure are particularly advantageous in the context of sequencing of clustered arrays. In clustered arrays, distinct regions on the array (often referred to as sites, or features) comprise multiple polynucleotide template molecules. Generally, the multiple polynucleotide molecules are not individually resolvable by optical means and are instead detected as an ensemble. Depending on how the array is formed, each site on the array may comprise multiple copies of one individual polynucleotide molecule (e.g., the site is homogenous for a particular single- or double-stranded nucleic acid species) or even multiple copies of a small number of different polynucleotide molecules (e.g., multiple copies of two different nucleic acid species). Clustered arrays of nucleic acid molecules may be produced using techniques generally known in the art. By way of example, WO 98/44151 and WO 00/18957, each of which is incorporated herein, describe methods of amplification of nucleic acids wherein both the template and amplification products remain immobilized on a solid support in order to form arrays comprised of clusters or "colonies" of immobilized nucleic acid molecules. The nucleic acid molecules present on the clustered arrays prepared according to these methods are suitable templates for sequencing using the nucleotides labeled with dye compounds of the disclosure.

The labeled nucleotides of the present disclosure are also useful in sequencing of templates on single molecule arrays. The term "single molecule array" ("SMA") as used herein refers to a population of polynucleotide molecules, distributed (or arrayed) over a solid support, wherein the spacing of any individual polynucleotide from all others of the population is such that it is possible to individually resolve the individual polynucleotide molecules. The target nucleic acid molecules immobilized onto the surface of the solid support can thus be capable of being resolved by optical means in some embodiments. This means that one or more distinct signals, each representing one polynucleotide, will occur within the resolvable area of the particular imaging device used.

Single molecule detection may be achieved wherein the spacing between adjacent polynucleotide molecules on an array is at least 100 nm, more particularly at least 250 nm, still more particularly at least 300 nm, even more particularly at least 350 nm. Thus, each molecule is individually resolvable and detectable as a single molecule fluorescent point, and fluorescence from said single molecule fluorescent point also exhibits single step photobleaching.

The terms "individually resolved" and "individual resolution" are used herein to specify that, when visualized, it is possible to distinguish one molecule on the array from its neighboring molecules. Separation between individual molecules on the array will be determined, in part, by the particular technique used to resolve the individual molecules. The general features of single molecule arrays will be understood by reference to published applications WO 00/06770 and WO 01/57248, each of which is incorporated herein by reference. Although one use of the nucleotides of the disclosure is in sequencing-by-synthesis reactions, the utility of the nucleotides is not limited to such methods. In fact, the nucleotides may be used advantageously in any sequencing methodology which requires detection of fluorescent labels attached to nucleotides incorporated into a polynucleotide.

In particular, the labeled nucleotides of the disclosure may be used in automated fluorescent sequencing protocols, particularly fluorescent dye-terminator cycle sequencing based on the chain termination sequencing method of Sanger and co-workers. Such methods generally use enzymes and cycle sequencing to incorporate fluorescently labeled dideoxynucleotides in a primer extension sequencing reaction. So-called Sanger sequencing methods, and related protocols (Sanger-type), utilize randomized chain termination with labeled dideoxynucleotides.

Thus, the present disclosure also encompasses labeled nucleotides which are dideoxynucleotides lacking hydroxy groups at both of the 3' and 2' positions, such dideoxynucleotides being suitable for use in Sanger type sequencing methods and the like.

Labeled nucleotides of the present disclosure incorporating 3' blocking groups, it will be recognized, may also be of utility in Sanger methods and related protocols since the same effect achieved by using dideoxy nucleotides may be achieved by using nucleotides having 3'-OH blocking groups: both prevent incorporation of subsequent nucleotides. Where nucleotides according to the present disclosure, and having a 3' blocking group are to be used in Sanger-type sequencing methods it will be appreciated that the dye compounds or detectable labels attached to the nucleotides need not be connected via cleavable linkers, since in each instance where a labeled nucleotide of the disclosure is incorporated; no nucleotides need to be subsequently incorporated and thus the label need not be removed from the nucleotide.

In any embodiments of the sequencing methods described herein, the nucleotide used in the sequencing application is a 3' blocked nucleotide described herein, for example, the nucleotide of Formula (I), (Ia), (II) or (III). In any embodiments, the 3' blocked nucleotide is a nucleotide triphosphate.

Nucleotides with 3' Allyl Blocking Group

Some embodiments of the present disclosure relate to a nucleotide molecule comprising a nucleobase, a ribose or deoxyribose moiety, and a 3' blocking group comprising an unsubstituted or substituted allyl moiety. In one embodiment, the 3' blocking group is an allyl group ($-CH_2CH{=}CH_2$), attached to the 3' oxygen atom of the deoxyribose moiety. In some embodiments, the nucleotide is unlabeled. In other embodiments, the nucleotide is a labeled nucleotide described herein. In some embodiments, wherein the bases for the A and G nucleotides are deazapurines (e.g., 7-deazapurine such as 7-deaza adenine or 7-deaza guanine). In some further embodiments, at least one type of nucleotide used in any of the sequencing method described herein has a structure selected from the group consisting of:

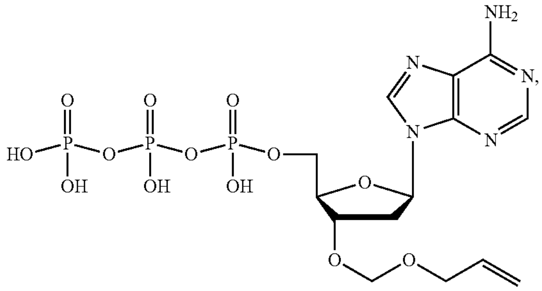
,

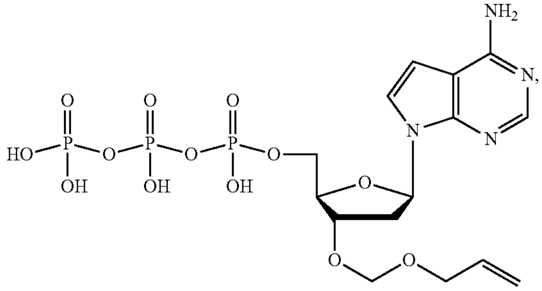
,

-continued

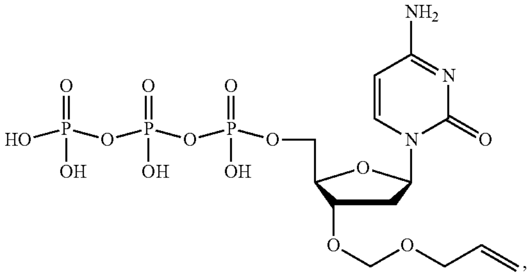
,

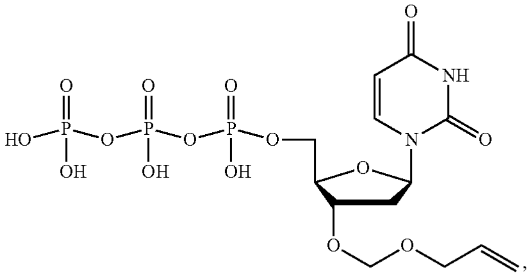
,

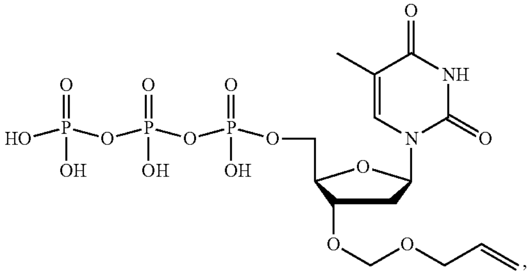
,

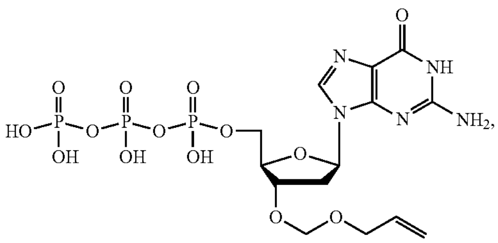
and

-continued

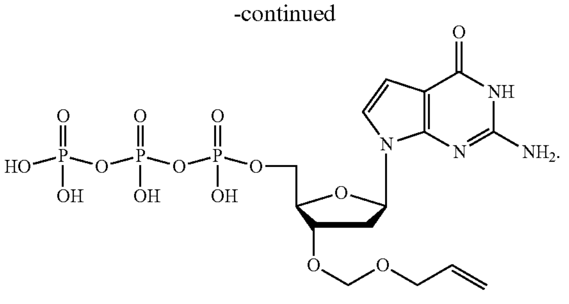

In further embodiments, at least one type of nucleotide has a structure selected from the group consisting of:

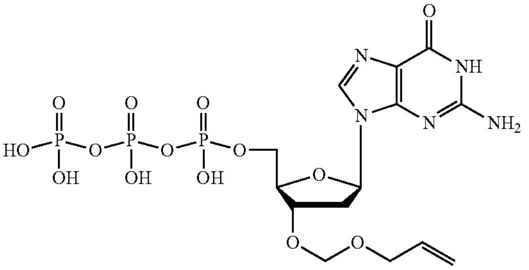
and

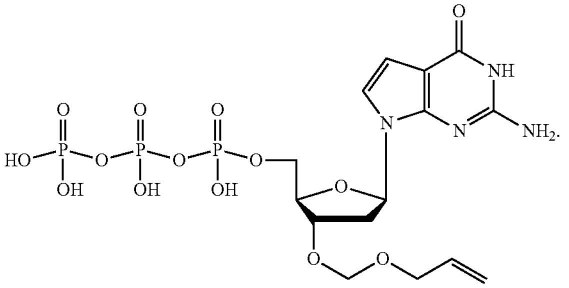

Labeled Nucleotides With 3'Allyl Blocking Group

In some embodiments, the 3' blocked nucleotide also comprises a detectable label and such nucleotide is called a labeled nucleotide or a fully functionalized nucleotide (ffN). The label (e.g., a fluorescent dye) is conjugated via a cleavable linker by a variety of means including hydrophobic attraction, ionic attraction, and covalent attachment. In some aspect, the dyes are conjugated to the nucleotide by covalent attachment via the cleavable linker. One of ordinary skill in the art understands that label may be covalently bounded to the linker by reacting a functional group of the label (e.g., carboxyl) with a functional group of the linker (e.g., amino). In some such embodiments, the cleavable linker may comprise a moiety that is the same as the 3' blocking group. As such, the cleavable linker and the 3' blocking group may be cleaved or removed under the same reaction condition. In some such embodiments, the cleavable linker may comprise an allyl moiety, more particularly comprises a moiety of the structure:

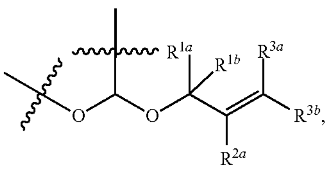
,

-continued

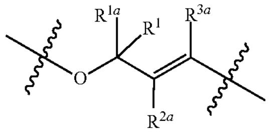

or

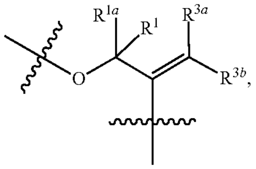

wherein each of $R^{1a}$, $R^{1b}$, $R^{2a}$, $R^{3a}$ and $R^{3b}$ is independently H, halogen, unsubstituted or substituted $C_1$-$C_6$ alkyl, or $C_1$-$C_6$ haloalkyl. In further embodiments, each of $R^{1a}$, $R^{1b}$, $R^{2a}$, $R^{3a}$ and $R^{3b}$ is H.

In some embodiments, the detectable label may be covalently attached to oligonucleotides or nucleotides via the nucleotide base. For example, the labeled nucleotide or oligonucleotide may have the label attached to the C5 position of a pyrimidine base or the C7 position of a 7-deaza purine base through a cleavable linker moiety.

Nucleotides may be labeled at sites on the sugar or nucleobase. As known in the art, a "nucleotide" consists of a nitrogenous base, a sugar, and one or more phosphate groups. In RNA, the sugar is ribose and in DNA is a deoxyribose, i.e., a sugar lacking a hydroxy group that is present in ribose. The nitrogenous base is a derivative of purine (e.g., deazapurine, 7-deazapurine) or pyrimidine. The purines are adenine (A) and guanine (G), and the pyrimidines are cytosine (C) and thymine (T) or in the context of RNA, uracil (U). The C-1 atom of deoxyribose is bonded to N-1 of a pyrimidine or N-9 of a purine. A nucleotide is also a phosphate ester of a nucleoside, with esterification occurring on the hydroxy group attached to the C-3 or C-5 of the sugar. Nucleotides are usually mono, di- or triphosphates.

Although the base is usually referred to as a purine or pyrimidine, the skilled person will appreciate that derivatives and analogues are available which do not alter the capability of the nucleotide or nucleoside to undergo Watson-Crick base pairing. "Derivative" or "analogue" means a compound or molecule whose core structure is the same as, or closely resembles that of a parent compound but which has a chemical or physical modification, such as, for example, a different or additional side group, which allows the derivative nucleotide or nucleoside to be linked to another molecule. For example, the base may be a deazapurine. In particular embodiments, the derivatives should be capable of undergoing Watson-Crick pairing. "Derivative" and "analogue" also include, for example, a synthetic nucleotide or nucleoside derivative having modified base moieties and/or modified sugar moieties. Such derivatives and analogues are discussed in, for example, Scheit, *Nucleotide analogs* (John Wiley & Son, 1980) and Uhlman et al., *Chemical Reviews* 90:543-584, 1990. Nucleotide analogues can also comprise modified phosphodiester linkages including phosphorothioate, phosphorodithioate, alkyl-phosphonate, phosphoranilidate, phosphoramidite linkages and the like.

In particular embodiments the labeled nucleotide may be enzymatically incorporable and enzymatically extendable. Accordingly, a linker moiety may be of sufficient length to connect the nucleotide to the compound such that the compound does not significantly interfere with the overall binding and recognition of the nucleotide by a nucleic acid replication enzyme. Thus, the linker can also comprise a spacer unit. The spacer distances, for example, the nucleotide base from a cleavage site or label.

The disclosure also encompasses polynucleotides incorporating a nucleotide described herein. Such polynucleotides may be DNA or RNA comprised respectively of deoxyribonucleotides or ribonucleotides joined in phosphodiester linkage. Polynucleotides may comprise naturally occurring nucleotides, non-naturally occurring (or modified) nucleotides other than the labeled nucleotides described herein or any combination thereof, in combination with at least one modified nucleotide (e.g., labeled with a dye compound) as set forth herein. Polynucleotides according to the disclosure may also include non-natural backbone linkages and/or non-nucleotide chemical modifications. Chimeric structures comprised of mixtures of ribonucleotides and deoxyribonucleotides comprising at least one labeled nucleotide are also contemplated.

In some embodiments, the labeled nucleotide described herein comprises or has the structure of Formula (III):

(III)

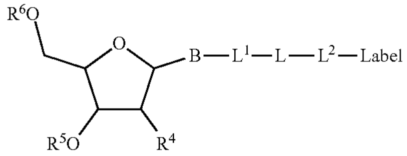

wherein B is the nucleobase;

$R^4$ is H or OH;

$R^5$ is an unsubstituted or substituted allyl group, such as

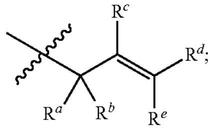

wherein each of $R^a$, $R^b$, $R^c$, $R^d$ and $R^e$ is independently H, halogen, unsubstituted or substituted $C_1$-$C_6$ alkyl, or $C_1$-$C_6$ haloalkyl;

$R^6$ is H, monophosphate, diphosphate, triphosphate, thiophosphate, a phosphate ester analog, a reactive phosphorous containing group, or a hydroxy protecting group;

L is an allyl moiety containing linker, such as

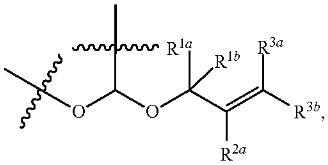

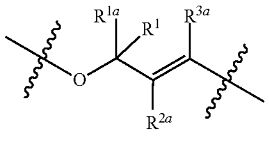

or

-continued

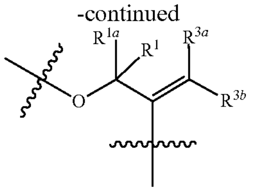

as described herein; and each of $L^1$ and $L^2$ is independently an optionally present linker moiety.

In some embodiments of the nucleotide of Formula (III) as described herein, each of $R^a$, $R^b$, $R^c$, $R^d$ and $R^e$ is H. In other embodiments, each of $R^a$ and $R^b$ is H and at least one of $R^c$, $R^d$ and $R^e$ is independently halogen (e.g., fluoro, chloro) or unsubstituted $C_1$-$C_6$ alkyl (e.g., methyl, ethyl, isopropyl, isobutyl, or t-butyl). For example, $R^c$ is unsubstituted $C_1$-$C_6$ alkyl and each of $R^d$ and $R^e$ is H. In another example, $R^c$ is H and one or both of $R^d$ and $R^e$ is halogen or unsubstituted $C_1$-$C_6$ alkyl. In some embodiments of the nucleotide described herein, each of $R^{1a}$, $R^{1b}$, $R^{2a}$, $R^{3a}$ and $R^{3b}$ is H. In other embodiments, at least one of $R^{1a}$, $R^{1b}$, $R^{2a}$, $R^{3a}$ and $R^{3b}$ is halogen (e.g., fluoro, chloro) or unsubstituted $C_1$-$C_6$ alkyl (e.g., methyl, ethyl, isopropyl, isobutyl, or t-butyl). In some such instances, each of $R^{1a}$ and $R^{1b}$ is H and at least one of $R^{2a}$, $R^{3a}$ and $R^{3b}$ is unsubstituted $C_1$-$C_6$ alkyl or halogen (for example, $R^{2a}$ is unsubstituted $C_1$-$C_6$ alkyl and each of $R^{3a}$ and $R^{3b}$ is H; or $R^{2a}$ is H and one or both of $R^{3a}$ and $R^{3b}$ is halogen or unsubstituted $C_1$-$C_6$ alkyl). In one embodiment, the cleavable linker or L comprises

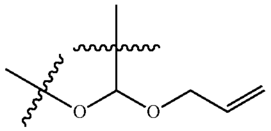 [SMILES: *OC(*)OCC=C]

("AOL" linker moiety).

In some embodiments of the nucleotide of Formula (III) as described herein, the nucleobase ("B" in Formula (I)) is purine (adenine or guanine), a deaza purine, or a pyrimidine (e.g., cytosine, thymine or uracil). In some further embodiments, the deaza purine is 7-deaza purine (e.g., 7-deaza adenine or 7-deaza guanine). Non-limiting examples of B comprises

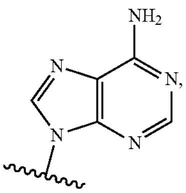,
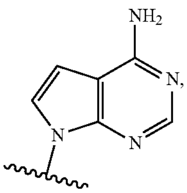,
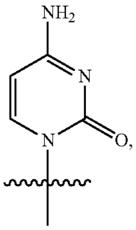,
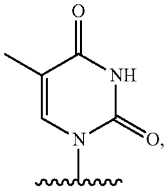,
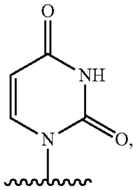,

-continued

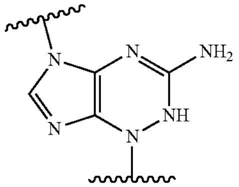
or
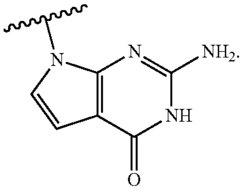.

or optionally substituted derivatives and analogs thereof. In some further embodiments, the labeled nucleobase comprises the structure

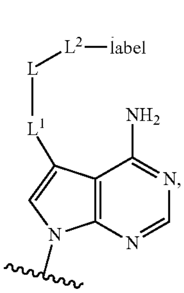,
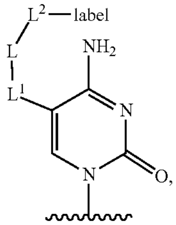,
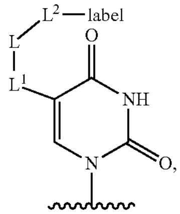, or
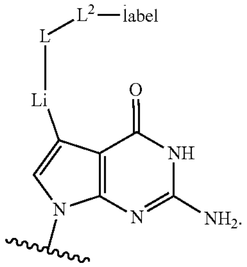.

In some embodiments of the nucleotide of Formula (III) as described herein, $L^1$ is present and $L^1$ comprises a moiety selected from the group consisting of a propargylamine, a propargylamide, an allylamine, an allylamide, and optionally substituted variants thereof. In some further embodiments, $L^1$ comprises

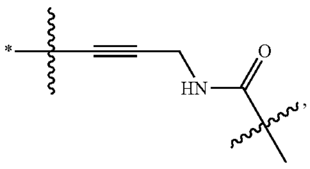,
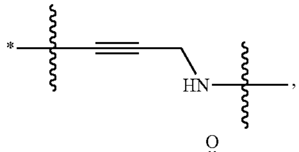,
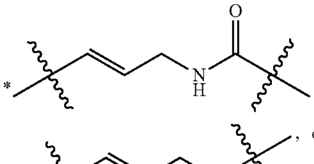, or
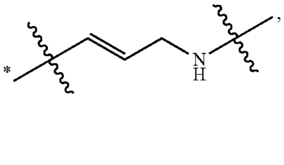, or

In some further embodiments, the asterisk * indicates the point of attachment of $L^1$ to the nucleobase (e.g., C5 position of a pyrimidine base or the C7 position of a 7-deaza purine base).

In further embodiments, when the nucleobase is T, $L^1$ comprises or

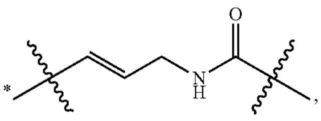

, or

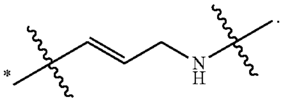

In some further embodiments of the nucleotide of Formula (III) as described herein, $L^2$ is present and $L^2$ comprises

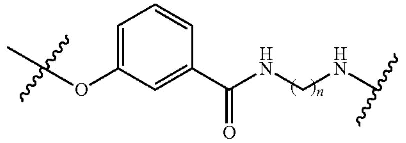

or

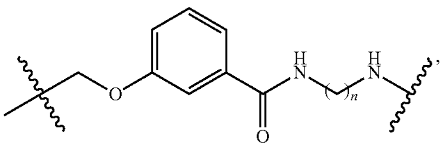

, wherein n is an integer of 1, 2, 3, 4, 5, 6, 7, 8, 9 or 10 and the phenyl moiety is optionally substituted. In some such embodiments, n is 5 and the phenyl moiety of $L^2$ is unsubstituted.

Additional non-limiting examples of a linker moiety may be incorporated into $L^1$ or $L^2$ include:

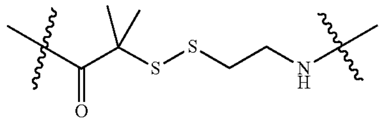

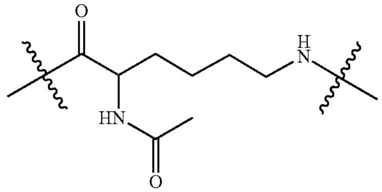

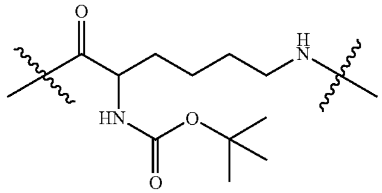

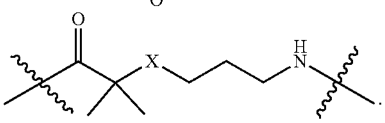

X = $CH_2$, O, S

Additional linker moieties are disclosed in WO 2004/018493 and U.S. Publication Nos. 2016/0040225 and 2021/0403500, which are herein incorporated by references.

Some further embodiments of T nucleotide described herein include:

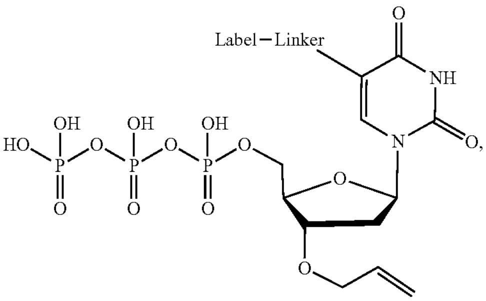

,

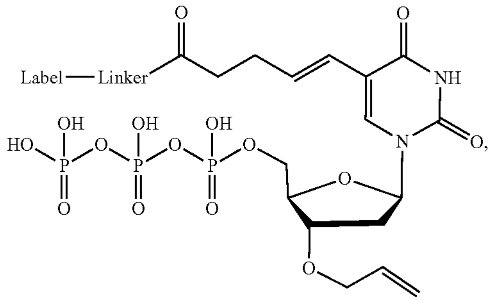

, or

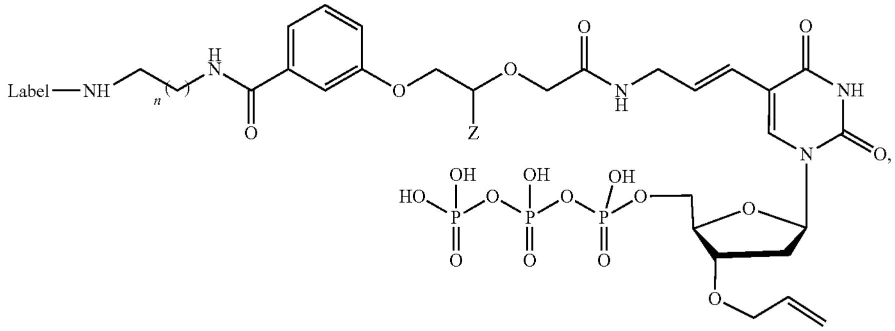

, wherein Z is —O—$CH_2$—CH═$CH_2$, and n is an integer of 1, 2, 3, 4 or 5.
Some further embodiments of the A nucleotide described herein include:
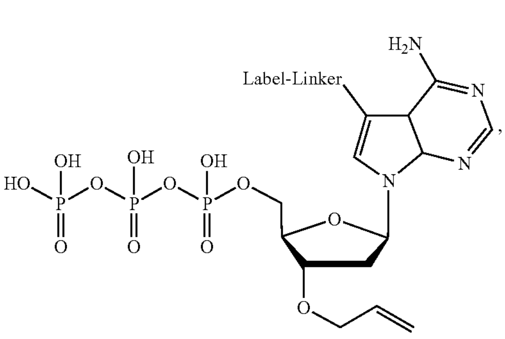
,
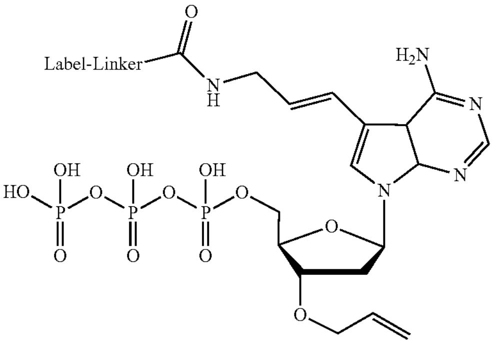
, or
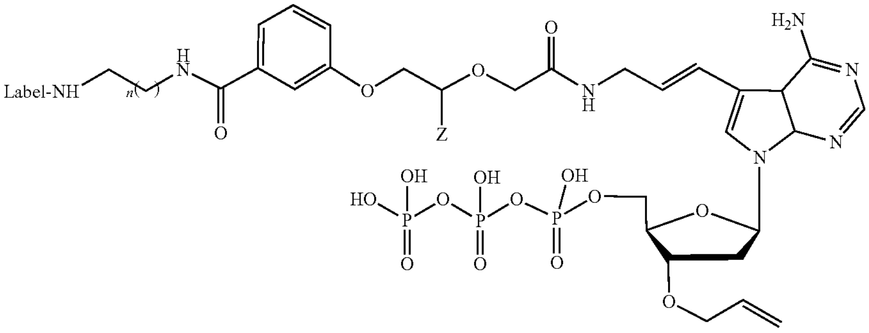
,
wherein Z is —O—$CH_2$—CH═$CH_2$, and n is an integer of 1, 2, 3, 4 or 5.
Some further embodiments of the C nucleotide described herein include:
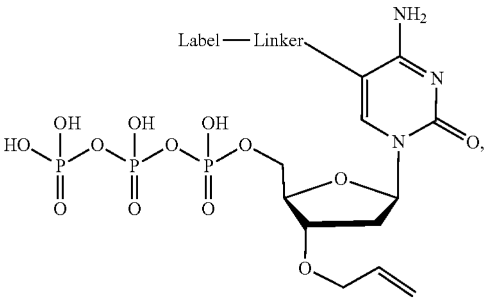
,
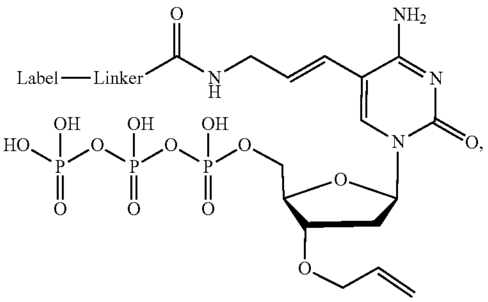
, or
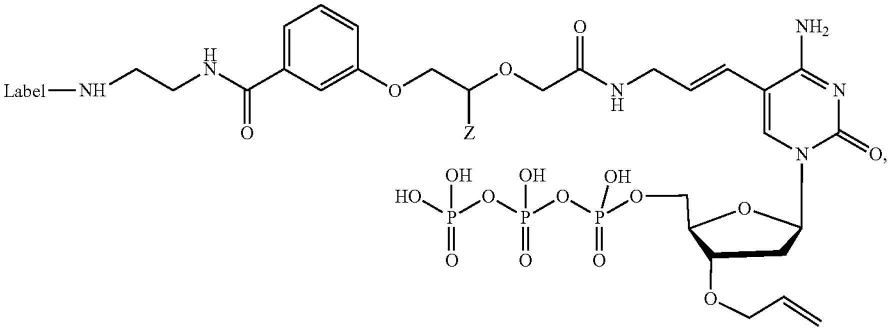
,
herein Z is —O—$CH_2$—CH═$CH_2$, and n is an integer of 1, 2, 3, 4 or 5.

Some further embodiments of the G nucleotide described herein include:
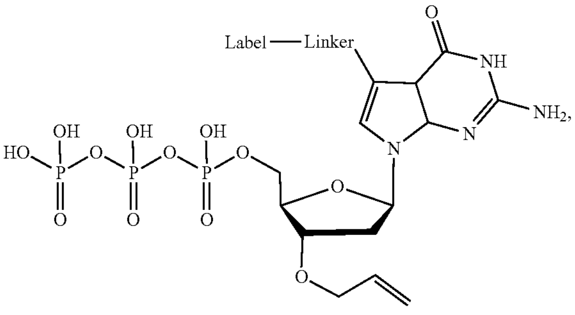
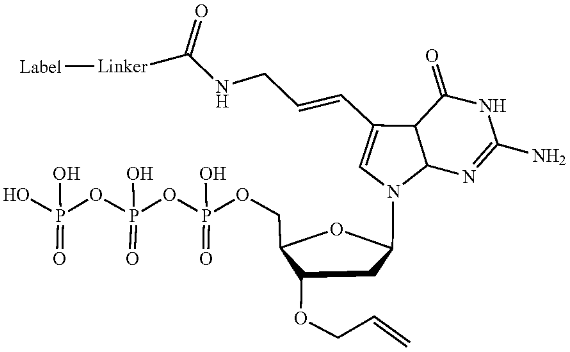
or
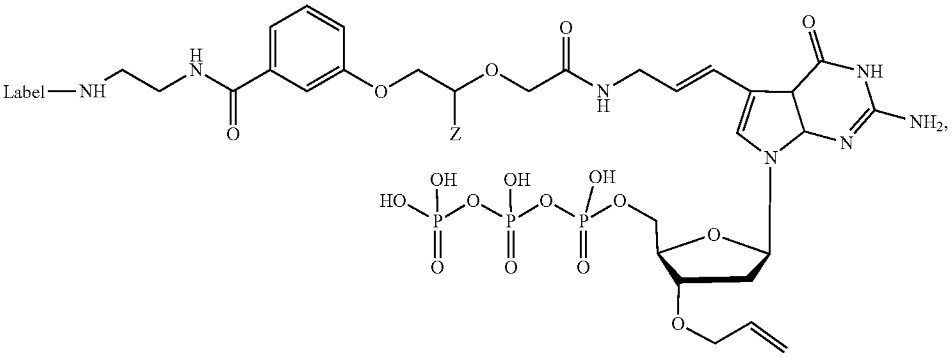
wherein Z is —O—$CH_2$—CH═$CH_2$, and n is an integer of 1, 2, 3, 4 or 5.

Non-limiting exemplary labeled nucleotides with 3' allyl blocking group as described herein include:
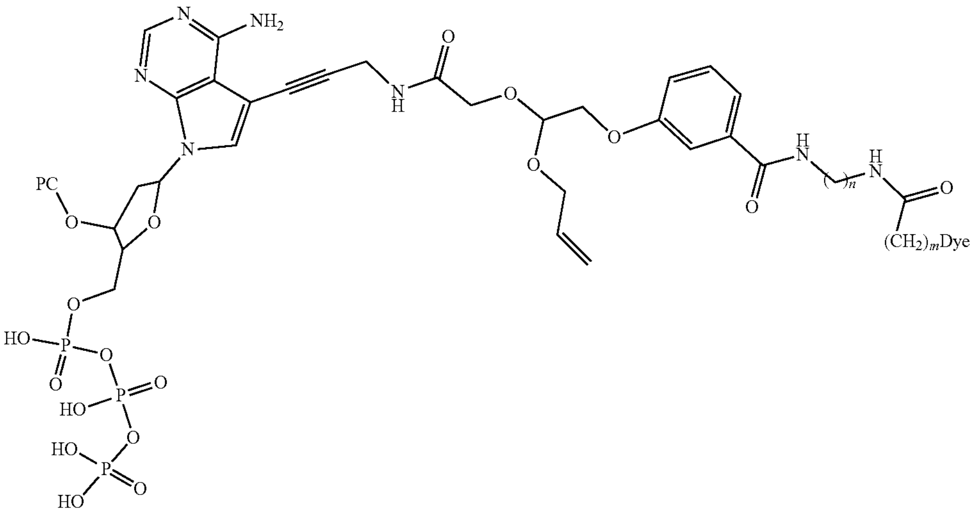
ffA-AOL-Dye
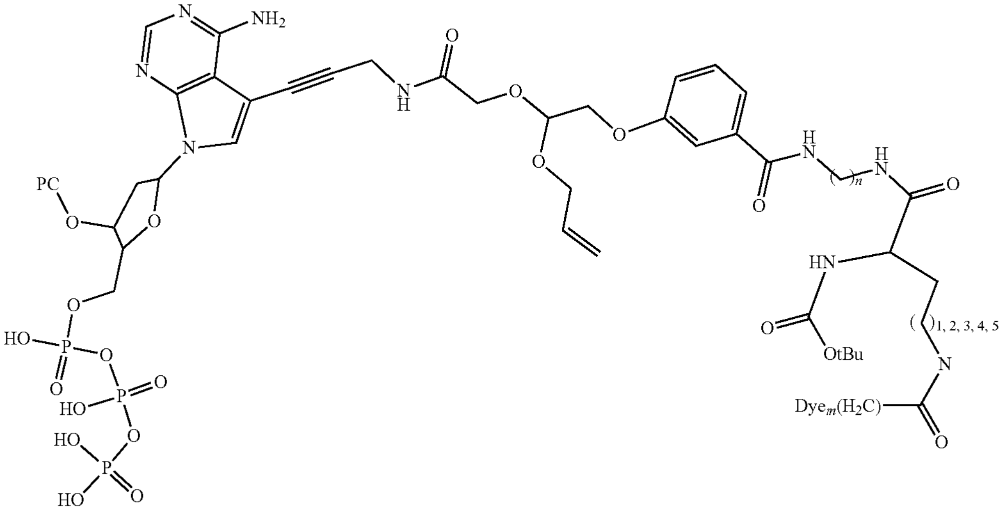
ffA-AOL-BL-Dye
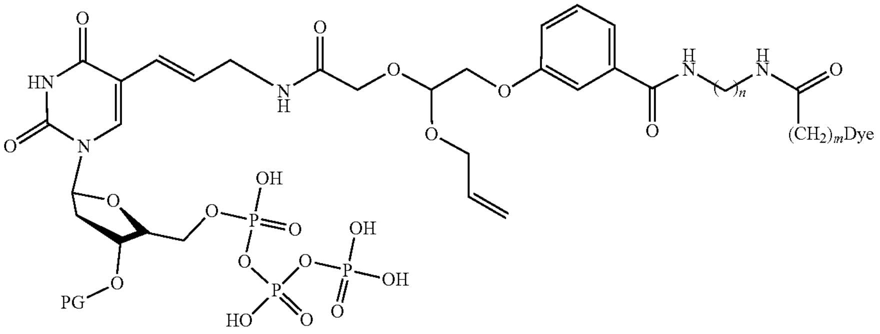
ffT-DB-AOL-Dye -continued
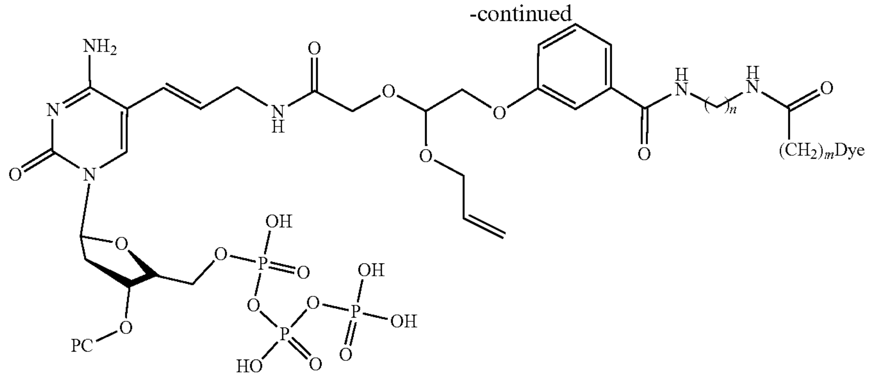
ffC-DB-AOL-Dye
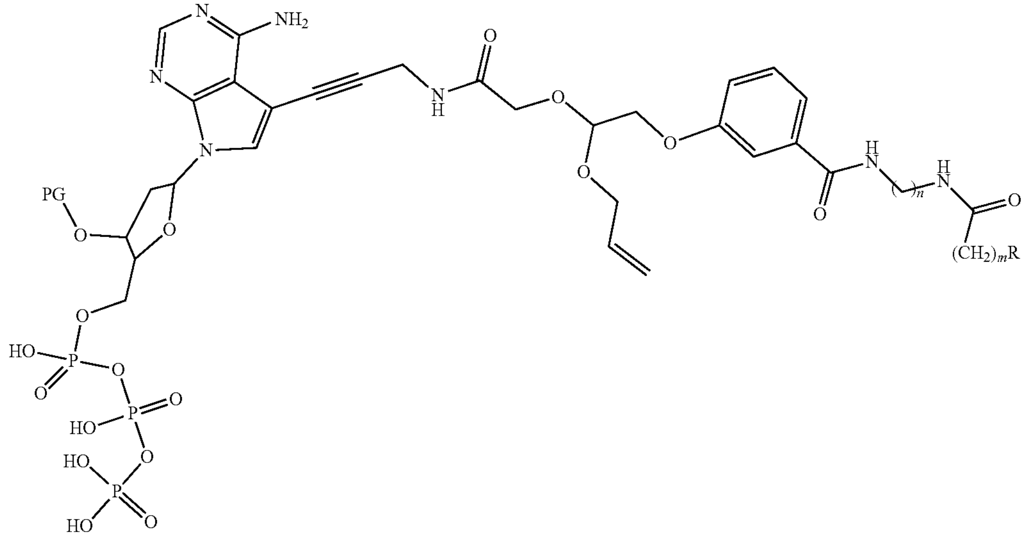
ffA-AOL-R
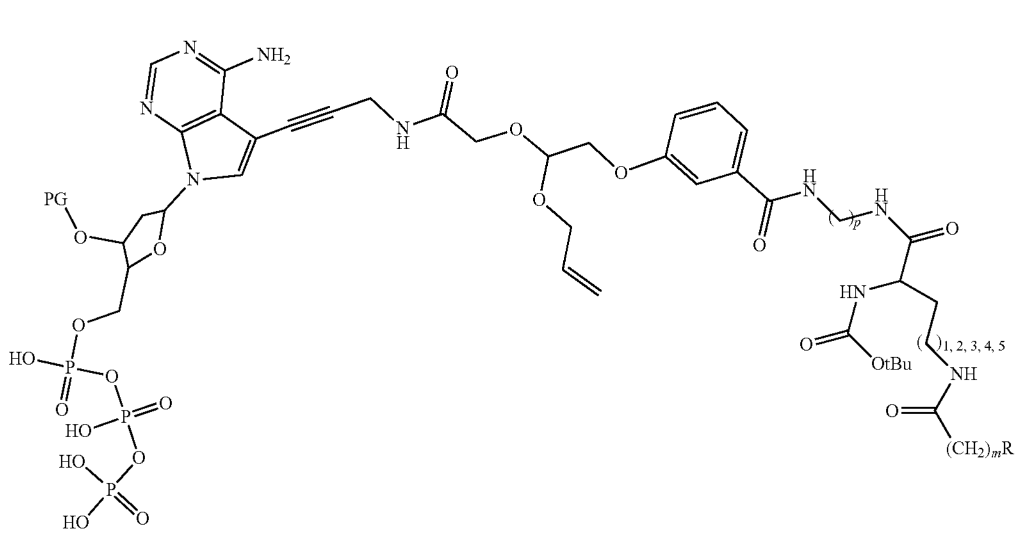
ffA-AOL-BL-R -continued

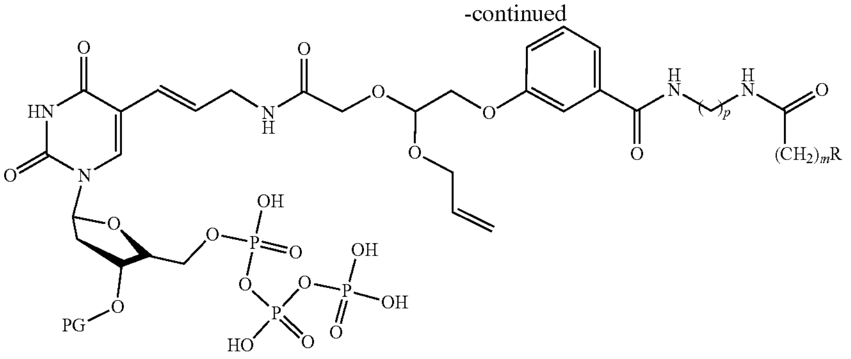

ffT-DB-AOL-R

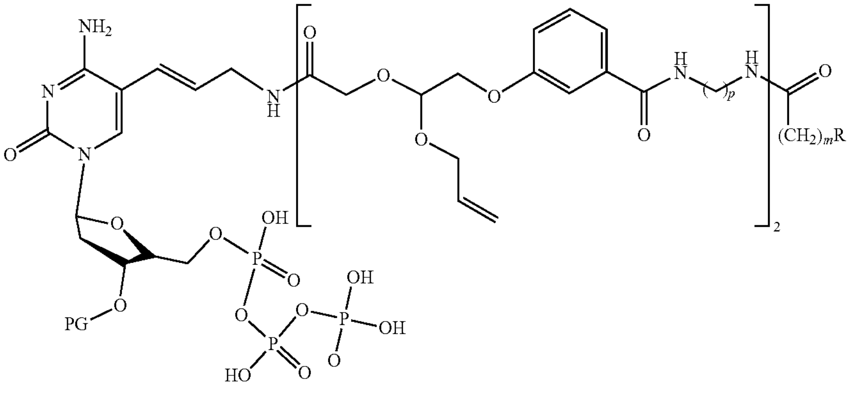

ffC-DB-AOL-AOL-R wherein PG stands for the 3' allyl blocking group described herein; n is an integer of 1, 2, 3, 4, 5, 6, 7, 8, 9, or 10; and m is 0, 1, 2, 3, 4, or 5. In one embodiment, n is 5.

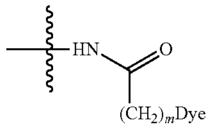

refers to the connection point of the Dye with the cleavable linker as a result of a reaction between an amino group of the linker moiety and the carboxyl group of the Dye. In one embodiment, p is 5.

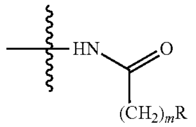

refers to the connection point of the first/second/third functional moiety with the cleavable linker as a result of a reaction between an amino group of the linker moiety and the carboxyl group of the first/second/third functional moiety. In further embodiments, the nucleotide may be attached to the first/second/third functional moiety via more than one of the same cleavable linkers (such as AOL-AOL). In addition, the linker may further include additional PEG spacers as described herein, for example, between R and $-(CH_2)_m-$.

Various fluorescent dyes may be used in the present disclosure as detectable labels, in particularly those dyes that may be excitation by a blue light (e.g., about 450 nm to about 460 nm) or a green light (e.g., about 520 nm to about 540 nm). These dyes may also be referred to as "blue dyes" and "green dyes" respectively. Examples of various type of blue dyes, including but not limited to coumarin dyes, chromenoquinoline dyes, and bisboron containing heterocycles are disclosed in U.S. Publication Nos. 2018/0094140, 2018/0201981, 2020/0277529, 2020/0277670, 2021/0188832, 2022/0033900, 2022/0195517, and 2022/0380389, and 2023/0313292, and U.S. Ser. No. 18/342,064, each of which is incorporated by reference in its entirety. Examples of green dyes including cyanine or polymethine dyes disclosed in International Publication Nos. WO2013/041117, WO2014/135221, WO 2016/189287, WO2017/051201 and WO2018/060482A1, each of which is incorporated by reference in its entirety.

In any embodiments of nucleotide described herein, the nucleotide comprises a 2' deoxyribose moiety (i.e., $R^4$ is Formula (III) is H). In some further respect, the 2' deoxyribose contains one, two or three phosphate groups at the 5' position of the sugar ring. In some further aspect, the nucleotides described herein are nucleotide triphosphate (i.e., —$OR^6$ in Formula (III) forms triphosphate).

Additional embodiments of the present disclosure relate to an oligonucleotide or a polynucleotide comprising a nucleoside or nucleotide described herein. In some such embodiments, the oligonucleotide or polynucleotide is hybridized to a template or target polynucleotide. In some such embodiments, the template polynucleotide is immobilized on a solid support.

Additional embodiments of the present disclosure relate to a solid support comprises an array of a plurality of immobilized template or target polynucleotides and at least a portion of such immobilized template or target polynucleotides is hybridized to an oligonucleotide or a polynucleotide comprising a nucleoside or nucleotide described herein.

Kits Containing Nucleotide with 3' Allyl Blocking Group

The present disclosure also provides kits including one or more 3' allyl blocked nucleosides and/or nucleotides described herein, for example, the 3' blocked nucleotide of Formula (III). Such kits will generally include at least one 3' blocked nucleotide or nucleoside labeled with a dye together with at least one further component. The further component (s) may be one or more of the components identified in a method set forth herein or in the Examples section below. Some non-limiting examples of components that can be combined into a kit of the present disclosure are set forth below.

Some additional embodiments of the present disclosure relate to a sequencing kit comprising:

(a) an incorporation mixture comprising DNA polymerase and nucleotides A, G, C, and T or U, wherein:
   (i) the nucleotides comprise a 2' deoxyribose moiety with a 3' unsubstituted or substituted allyl group as described herein (e.g.,

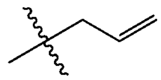

)

attached to the 3' carbon atom; and
   (ii) the DNA polymerase is an altered archaeal DNA polymerase;
(b) an aqueous deblocking solution comprising a palladium catalyst, tris(hydroxyalkyl)phosphine, and one or more buffer reagents that is suitable to chemically remove (i) 3' allyl groups from incorporated nucleotides to expose a 3'-OH group for further nucleotide incorporation on the solid support, and (ii) detectable labels attached via cleavable linkers; and
(c) an aqueous wash solution comprising a Pd(II) scavenger;

wherein said kit is configured for performing at least about 50, 100, 150, 200, 250, or 300 cycles of sequencing-by-synthesis.

In some further embodiment, the kit may comprise four types of labeled nucleotides of fully functionalized nucleotides described herein (A, C, T and G), where each type of nucleotide comprises the 3' allyl blocking group and the AOL linker moiety described herein. In further embodiments, G is unlabeled and does not comprise any cleavable linker. In still further embodiments, one or more the remaining three nucleotides (i.e., A, C and T) comprises an allylamine or allylamide linker moiety described herein. In one embodiment, the kit comprises unlabeled ffG, labeled ffA(s), labeled ffC, and labeled ffT (wherein ffT contains an allylamine or allylamide linker moiety between the nucleobase and the detectable label; also referred to as double bond or DB linker). In further embodiment, the kit comprises unlabeled ffG, labeled ffA(s), labeled ffC-DB, and labeled ffT-DB described herein. In some further embodiments, at least one type of the nucleotides comprises a base that is attached to a detectable label via a cleavable linker, and the cleavable linker is

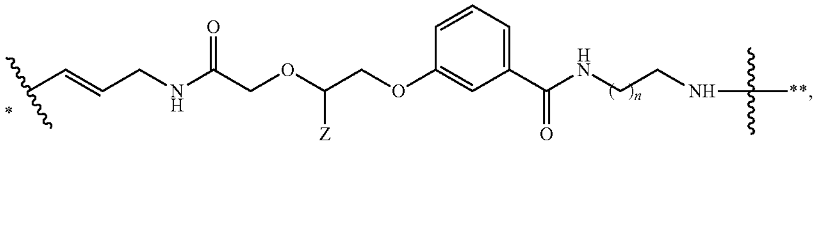

, wherein Z is —O—$CH_2$—CH═$CH_2$; n is an integer of 1, 2, 3, 4 or 5; * indicates the attachment point of the cleavable linker to the base; and ** indicates the attachment point of the cleavable linker to the detectable label. In further embodiments, the nucleobase of T nucleotide is attached to the detectable label via the cleavable linker. In some further embodiments, wherein each of at least three of the nucleotides independently comprises a base that is attached to a detectable label via a cleavable linker, and the cleavable linker is selected from the group consisting of:

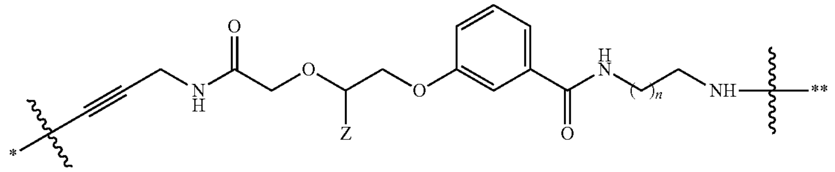

and

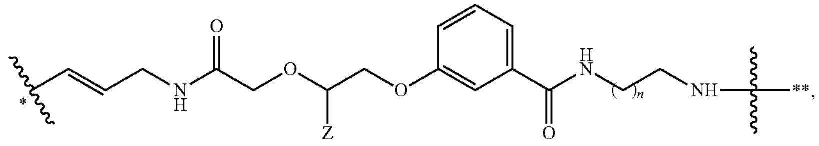

wherein Z is —O—$CH_2$—CH═$CH_2$; n is an integer of 1, 2, 3, 4 or 5; * indicates the attachment point of the cleavable linker to the base; and ** indicates the attachment point of the cleavable linker to the detectable label.

In other embodiments, one or more types of nucleotides A, G, C, and T or U are unlabeled, and wherein the first type of unlabeled nucleotides comprises a first functional moiety, and the kit further comprises a first labeling reagent, wherein the first labeling reagent comprises one or more first detectable labels and a first binding moiety that is capable of specific binding to the first functional moiety of the first type of unlabeled nucleotide. In some such embodiments, the first functional moiety of the first type of unlabeled nucleotide is bound to the first labeling reagent by either covalent bonding or noncovalent interaction via a cleavable linker described herein. In some embodiments, two or more types of nucleotides A, G, C, and T or U are unlabeled. In some further embodiments, each of the four types of nucleotides is unlabeled, and wherein the second type of unlabeled nucleotides comprises a second functional moiety, and the kit further comprises a second labeling reagent, wherein the second labeling reagent comprises one or more second detectable labels and a second binding moiety that is capable of specific binding to the second functional moiety of the second type of unlabeled nucleotide. In some such embodiments, the second functional moiety of the second type of unlabeled nucleotide is bound to the second labeling reagent by either covalent bonding or noncovalent interaction via a cleavable linker described herein. In some further embodiments, the third type of unlabeled nucleotides comprises a third functional moiety, and the kit further comprises a third labeling reagent, wherein the third labeling reagent comprises one or more third detectable labels and a third binding moiety that is capable of specific binding to the third functional moiety of the third type of unlabeled nucleotide. In some such embodiments, the third functional moiety of the third type of unlabeled nucleotide is bound to the third labeling reagent by either covalent bonding or noncovalent interaction via a cleavable linker described herein. In other embodiments, the third type of unlabeled nucleotides comprises a mixture of the third type of unlabeled nucleotides comprising the first functional moiety and the third type of unlabeled nucleotides comprising the second functional moiety, and wherein both the first labeling reagent and the second labeling reagent are capable of specific binding to the third type of unlabeled nucleotides. In some further embodiments, the fourth type of unlabeled nucleotides is not capable of specific binding with any of the first, second, or third labeling reagent. Post-incorporation labeling kits and methods have been described in U.S. Publication No. 2023/0383342 A1, which is incorporated by reference in its entirety. Non-limiting examples of noncovalent interaction between a functional moiety of the nucleotide and a binding moiety of the labeling reagent include but are not limited to avidin (e.g., streptavidin or neutravidin) and biotin; dinitrophenyl (DNP) moiety and anti-DNP antibody; digoxigenin (DIG) and anti-DIG antibody; 3-N-acetyl glucosamine (O-GlcNAc) and WGA (lectin); alkyl guanine moiety and SNAP-Tag®, alkyl chloride moiety and HaloTag®; 3-nitrotyrosine and anti-nitrotyrosine antibody; nickel or cobalt complex such as Ni-nitrilotriacetic acid (NTA) and His-Tag; zinc complex and oligo-aspartate protein. Non-limiting examples of covalent interaction between a functional moiety and a labeling reagent include but are not limited to a biorthogonal reaction selected from the group consisting of a [3+2]dipolar cycloaddition, a Diels-Alder cycloaddition, a [4+1] cycloaddition, a phosphine ligation, or condensation with 2-acylphenyl boronic acid. For example, one of the functional moiety and the binding moiety comprises or is norbornene, transcyclooctene (TCO), dibenzocyclooctyne (DBCO), or bicyclo[6.1.0]nonyne (BCN), and the other one of the functional moiety and the binding moiety comprises or is azido. In some other embodiments, one of the functional moiety and the binding moiety comprises or is TCO, and the other one of the functional moiety and the binding moiety comprises or is an optionally substituted 1,2,4,5-tetrazine moiety. The cleavable linker may comprise the structure

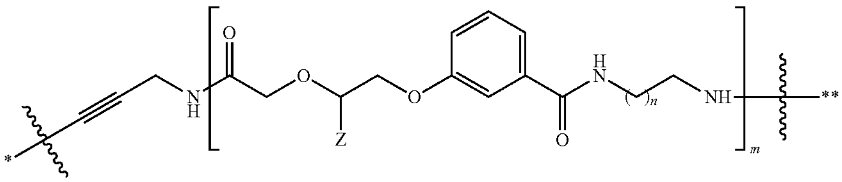

and

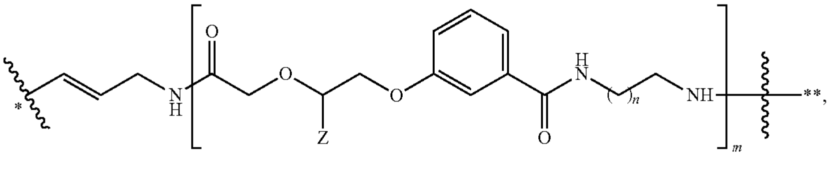

, wherein Z is —O—$CH_2$—CH═$CH_2$; each of m and n is independently an integer of 1, 2, 3, 4 or 5; * indicates the attachment point of the cleavable linker to the base; and ** indicates the attachment point of the cleavable linker to the first/second/third functional moiety of the unlabeled nucleotides. In some embodiments m is 2. In some further embodiments, n is 4.

In a particular embodiment, a kit can include at least one labeled 3' blocked nucleotide or nucleoside together with labeled or unlabeled nucleotides or nucleosides. For example, nucleotides labeled with dyes may be supplied in combination with unlabeled or native nucleotides, and/or with fluorescently labeled nucleotides or any combination thereof. Combinations of nucleotides may be provided as separate individual components (e.g., one nucleotide type per vessel or tube) or as nucleotide mixtures (e.g., two or more nucleotides mixed in the same vessel or tube).

Where kits comprise a plurality, particularly two, or three, or more particularly four, 3' blocked nucleotides labeled with a dye compound, the different nucleotides may be labeled with different dye compounds, or one may be dark, with no dye compounds. Where the different nucleotides are labeled with different dye compounds, it is a feature of the kits that the dye compounds are spectrally distinguishable fluorescent dyes. As used herein, the term "spectrally distinguishable fluorescent dyes" refers to fluorescent dyes that emit fluorescent energy at wavelengths that can be distinguished by fluorescent detection equipment (for example, a commercial capillary-based DNA sequencing platform) when two or more such dyes are present in one sample. When two nucleotides labeled with fluorescent dye compounds are supplied in kit form, it is a feature of some embodiments that the spectrally distinguishable fluorescent dyes can be excited at the same wavelength, such as, for example by the same laser. When four 3' blocked nucleotides (A, C, T, and G) labeled with fluorescent dye compounds are supplied in kit form, it is a feature of some embodiments that two of the spectrally distinguishable fluorescent dyes can both be excited at one wavelength and the other two spectrally distinguishable dyes can both be excited at another wavelength. Particular excitation wavelengths are 450 nm to 460 nm, or 520 nm to 532 nm.

In an alternative embodiment, the kits of the disclosure may contain 3' blocked nucleotides where the same base is labeled with two or more different dyes. A first nucleotide (e.g., 3' allyl blocked T nucleotide triphosphate or 3' blocked G nucleotide triphosphate) may be labeled with a first dye. A second nucleotide (e.g., 3' blocked C nucleotide triphosphate) may be labeled with a second spectrally distinct dye from the first dye, for example a "green" dye absorbing at less than 600 nm, and a "blue" dye absorbs at less than 500 nm, for example 400 nm to 500, in particular 450 nm to 460 nm). A third nucleotide (e.g., 3' blocked A nucleotide triphosphate) may be labeled as a mixture of the first and the second dyes, or a mixture of the first, the second and a third dyes, and the fourth nucleotide (e.g., 3' blocked G nucleotide triphosphate or 3' blocked T nucleotide triphosphate) may be 'dark' and contain no label. In one example, the nucleotides 1-4 may be labeled 'blue', 'green', 'blue/green', and dark. To simplify the instrumentation further, four nucleotides can be labeled with two dyes excited with a single laser, and thus the labeling of nucleotides 1-4 may be 'blue 1', 'blue 2', 'blue 1/blue 2', and dark.

In particular embodiments, the kits may contain four labeled 3' blocked nucleotides (e.g., A, C, T, G), where each type of nucleotide comprises the same 3' allyl blocking group and a fluorescent label, and wherein each fluorescent label has a distinct fluorescence maximum and each of the fluorescent labels is distinguishable from the other three labels. The kits may be such that two or more of the fluorescent labels have a similar absorbance maximum but different Stokes shift. In some other embodiments, one type of the nucleotide is unlabeled.

Although kits are exemplified herein in regard to configurations having different nucleotides that are labeled with different dye compounds, it will be understood that kits can include 2, 3, 4 or more different nucleotides that have the same dye compound. In some embodiments, the kit also includes an enzyme and a buffer appropriate for the action of the enzyme. In some such embodiments, the enzyme is a polymerase, a terminal deoxynucleotidyl transferase, or a reverse transcriptase. In particular embodiments, the enzyme is a DNA polymerase, such as DNA polymerase 812 (Pol 812) or DNA polymerase 1901 (Pol 1901). In some further embodiment, the kit may comprise an incorporation mix described herein. In further embodiments, the kit containing the incorporation mix described herein also comprises at least one Pd scavenger (e.g., the Pd(0) scavenger described herein that comprises one or more allyl moieties). In the Pd(0) scavenger comprises one or more allyl moieties each independently selected from the group consisting of —O-allyl, —S-allyl, —NR-allyl, and —$N^+$RR'-allyl, wherein R is H, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_6$-$C_{10}$ aryl, unsubstituted or substituted 5 to 10 membered heteroaryl, unsubstituted or substituted $C_3$-$C_{10}$ carbocyclyl, or unsubstituted or substituted 5 to 10 membered heterocyclyl; and R' is H, unsubstituted $C_1$-$C_6$ alkyl or substituted $C_1$-$C_6$ alkyl. In some such embodiments, the Pd(0) scavenger in the incorporation solution comprises one or more —O-allyl moieties as described herein in connection with the sequencing methods.

Other components to be included in such kits may include buffers and the like. The nucleotides of the present disclosure, and other any nucleotide components including mixtures of different nucleotides, may be provided in the kit in a concentrated form to be diluted prior to use. In such embodiments a suitable dilution buffer may also be included. For example, the incorporation mix kit may comprise one or more buffering agents selected from a primary amine, a secondary amine, a tertiary amine, a natural amino acid, or a non-natural amino acid, or combinations thereof. In further embodiments, the buffering agents in the incorporation mix comprise ethanolamine or glycine, or a combination thereof.

Again, one or more of the components identified in a method set forth herein can be included in a kit of the present disclosure. In some further embodiments, the kit may comprise a palladium catalyst described herein. In some embodiments, the Pd catalyst is generated by mixing a Pd(II) complex (i.e., a Pd pre-catalyst) with one or more water soluble phosphines described herein. In some such embodiments, the kit containing the Pd catalyst is the cleavage mix kit. In further embodiments, the cleavage mix kit may contain Pd(Allyl)Cl]$_2$ or $Na_2PdCl_4$ and a water soluble phosphine tris(hydroxyalkyl)phosphine such as THPP to generate the active Pd(0) species. The molar ratio of Pd(II) complex (e.g., Pd(Allyl)Cl]$_2$ or $Na_2PdCl_4$) to the water soluble phosphine (e.g., THP) may be about 1:1, 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, 1:9.5 or 1:10. In further embodiments, the cleavage mix kit may also contain one or more buffer reagents selected from the group consisting of a primary amine, a secondary amine, a tertiary amine, a carbonate salt, a phosphate salt, and a borate salt, and combinations thereof. Non-limiting example of the buffer reagents in the cleavage mix kit are selected from the group consisting of ethanolamine (EA), tris(hydroxymethyl)aminomethane (Tris), glycine, a carbonate salt, a phosphate salt, a borate salt, dimethylethanolamine (DMEA), diethylethanolamine (DEEA), N,N,N',N'-tetramethylethylenediamine (TEMED), and N,N,N',N'-tetraethylethylenediamine (TEEDA), 2-piperidine ethanol (also known as (2-hydroxyethyl)piperidine, having the structure)

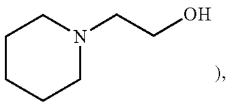
), and combinations thereof. In one embodiment, the cleavage mix kit contains DEEA. In other embodiment, the cleavage mix kit contains (2-hydroxyethyl)piperidine.

In some further embodiments, the kit may comprise one or more palladium scavengers (e.g., a Pd(II) scavenger described herein). In some such embodiments, the Pd(II) scavenger is in the post-cleavage washing buffer. In one embodiment, the post-cleavage washing buffer kit comprises L-cysteine or a salt thereof.

In any embodiments of the kits described herein, the Pd scavengers (e.g., the Pd(0) or Pd(II) scavengers described herein) are in separate containers/compartments from the Pd catalyst.

The present disclosure also provides for a cartridge for use with a sequencing apparatus, comprising a plurality of chambers, where one or more of the plurality of chambers is for use with the kit described herein. For example, the cartridge may contain two or more separate chambers, one chamber contains the aqueous cleavage mixture described herein, and another chamber contains the incorporation mixture described herein.

EXAMPLES

Additional embodiments are disclosed in further detail in the following examples, which are not in any way intended to limit the scope of the claims.

Example 1. Preparation of 3'-Acetal Blocked Nucleosides

In this example, various 3'-acetal protected T nucleoside were prepared according to Scheme 2.

Scheme 2.

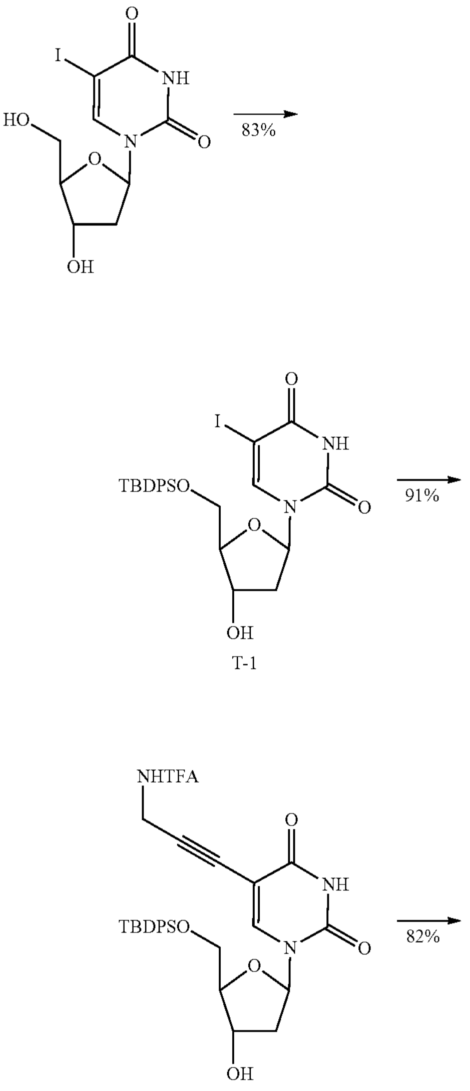

T-1

T-2

-continued

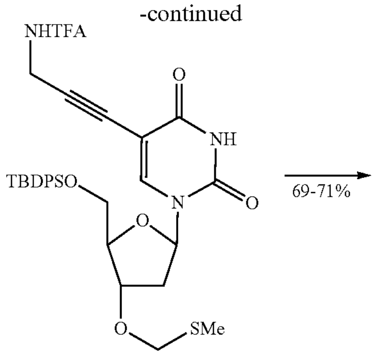

T-3

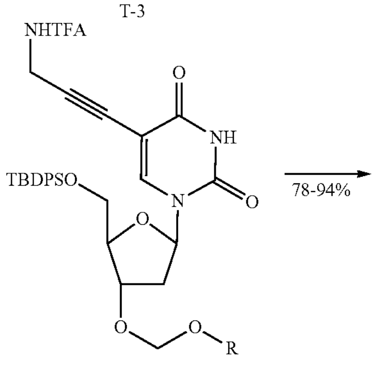

T-4

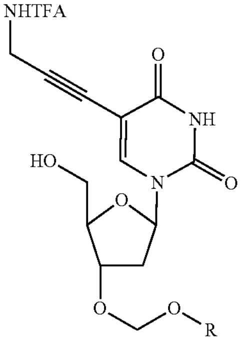

T-5

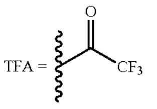

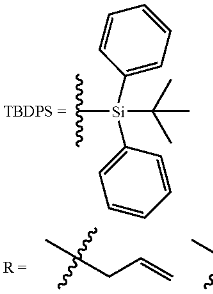

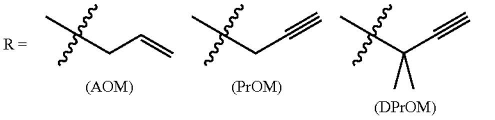

Preparation of T1: Into an oven-dried nitrogen-purged 100 mL flask was added 5-iodo-2'-deoxyuridine (5.0 g, 14.12 mmol). This was co-evaporated 3 times with 30 mL of pyridine then brought under Nitrogen. Anhydrous Pyridine (25 mL) was added and the reaction stirred at room temperature until a homogenous solution was obtained (~15 minutes). The mixture was cooled to 0° C. in an ice-water bath and tert-butyldiphenylsilyl chloride (4.04 mL, 15.5 mmol) was added slowly, dropwise with vigorous stirring (~1 hour). The reaction was maintained at 0° C. for 8 hours until all SM consumed by TLC. Saturated aqueous ammonium chloride solution (~15 mL) was added and the reaction allowed to warm to room temperature. The mixture was diluted with ethyl acetate (100 mL) and washed with saturated aqueous ammonium chloride (200 mL). The organic layer was separated, and the aqueous layer was extracted with ethyl acetate (4×50 mL). The organic layers were combined, dried ($MgSO_4$) and concentrated in vacuo to give ~8 g clear yellow oil after removal of residual solvent under high vacuum. The crude product T1 was purified by flash-column chromatography on silica as a white crystalline solid. Yield is 6.94 g (83%). LC-MS (Electrospray negative) 591.08 [M−H]

Preparation of T2: Into an oven-dried, nitrogen-purged, brown, 500 mL three-necked flask was added T1 (6.23 g, 10.5 mmol), copper (I) iodide (200 mg, 1.05 mmol) and bis(triphenylphosphine)palladium(II) dichloride (369 mg, 0.526 mmol) under nitrogen. The flask was protected from light and anhydrous degassed DMF (200 mL) added. To this solution was added 2,2,2-trifluoro-N-prop-2-ynyl-acetamide (4.74 g, 31.6 mmol), followed by degassed triethylamine (2.92 mL, 21.0 mmol). The reaction was stirred at room temperature under nitrogen for 6 hours when no further starting material was observed by TLC analysis. Volatiles were removed in vacuo (~15 mins) and DMF removed under high vacuum (~1 hour) to brown residue. This was dissolved in ethyl acetate (200 mL) and extracted with 0.1M EDTA in water (2×200 mL). The aqueous layers were combined and further extracted with ethyl acetate (200 mL). The organic phases were combined, dried ($MgSO_4$) and volatiles removed in vacuo (~30 min) and further dried under high vacuum (~1 hour) to give about 8 g of crude brown/yellow oil. The mixture was purified by flash-column chromatography on silica gel as an off-white solid. Yield: 6.0 g (85%). LC-MS (Electrospray negative) 614.19 [M−H].

Preparation of T3: To an oven dried nitrogen purged 100 mL flask containing starting nucleoside T2 (2.0 g, 3.25 mmol) under nitrogen was added anhydrous DMSO (6.9 ml, 97.5 mmol) in one portion at room temperature and stirred until a homogeneous solution was formed. Acetic acid (11.1 mL, 195 mmol) followed by acetic anhydride (15.1 mL, 162.09 mmol) were both added dropwise (~5 minutes each). The mixture was warmed to 50° C. and stirred until complete consumption of the starting nucleoside (~5 hours) by TLC (EtOAc/Petroleum ether 3:2). The reaction was then concentrated to half volume and cooled down with an ice bath to approximately 0.5° C. Work up commenced by slow addition of cold (~0.5° C.) $NaHCO_3$ (aq, sat.) (45 mL) and further stirring allowed until no more fizzing observed (~15 min). The solution was allowed to warm to room temperature, then the aqueous extracted into EtOAc (3×100 mL). Combined organic layers were dried over $MgSO_4$, filtered and the volatiles evaporated under reduced pressure and further by high vacuum. Crude product T3 was purified by flash chromatography on silica gel as an off-white solid. Yield: 1.79 g (82%). LC-MS (Electrospray negative) 674.20 $[M-H]^-$.

Preparation of T4: To a solution of the starting nucleoside T3 (1.79 g, 2.649 mmol) in anhydrous $CH_2Cl_2$ (50 mL) under $N_2$ was added cyclohexene (1.34 mL, 13.2 mmol). The mixture was cooled with an ice bath to 0° C. and distilled sulfuryl chloride (322 μL, 3.97 mmol) was slowly added dropwise (~20 min) under $N_2$. After stirring for 20 min at that temperature TLC (EtOAc:petroleum ether=3:2 v/v) indicated the full consumption of the starting nucleoside. The chloride intermediate was then quenched by direct, dropwise addition of freshly distilled the corresponding unsaturated alcohol (5 eq.) as shown in Scheme 3. The resulting solution was stirred at room temperature for 2 hours followed by evaporation of the volatiles under reduced pressure. The oily residue was partitioned between EtOAc: brine (3:2) (125 mL). The organic layer was separated and the aqueous was further extracted into EtOAc (2×50 mL). Combined organic extracts were dried over $MgSO_4$, filtered and the volatiles evaporated under reduced pressure. The oily residue was partitioned between EtOAc:brine (3:2) (125 mL). The organic layer was separated and the aqueous was further extracted into EtOAc (2×50 mL). Combined organic extracts were dried over $MgSO_4$, filtered and the volatiles evaporated under reduced pressure. The crude products T4 was purified by flash chromatography on silica gel to yield the final products as a yellow oil. Yield: 1.20 g (69%) for AOM; 1.29 g (71%) for PrOM; 1.34 g (71%) for DPrOM.

3'-AOM: Yellow oil. LC-MS (Electrospray negative) [M–H] 684.24.

3'-PrOM: Yellow oil. LC-MS (Electrospray negative) [M–H] 682.22.

3'-DPrOM: Yellow oil. LC-MS (Electrospray negative) [M–H] 710.25.

Scheme 3.

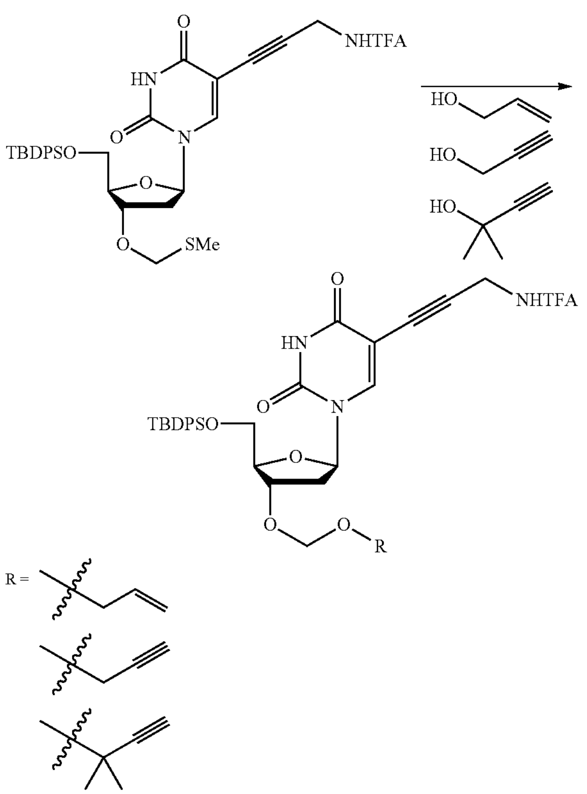

Preparation of T5: The starting material T4 (1.04 g, 1.516 mmol) in a 50 mL round bottom flask under nitrogen was added anhydrous THF (9 mL) at room temperature. Then TBAF (1.0 M in THF, 1.7 mL, 1.70 mmol) was added dropwise and the solution stirred until all SM consumed by TLC (~2 hours). The solution turned orange over the course of the reaction. Volatiles were removed in vacuo to give an orange residue which was dissolved in EtOAc (100 mL) and separated with $NaHCO_3$ (sat. aq) (60 mL). The two layers were separated, and the aqueous layer was extracted with EtOAc (60 mL). The organic layers were combined, dried ($MgSO_4$), filtered, and evaporated to give the crude product as a yellow oil. The crude product was purified by flash chromatography on silica gel to yield a clear yellow oil. Yield: 637 mg (94%) for AOM; 526 mg (78%) for PrOM; 617 mg (86%) for DPrOM.

3'-AOM: clear yellow oil. LC-MS (Electrospray negative) [M–H] 446.12.

3'-PrOM: Clear yellow oil (526 mg 78%). LC-MS (Electrospray negative): [M–H]444.10.

3'-DPrOM: Clear yellow oil (617 mg 86%). LC-MS (Electrospray negative): [M–H] 472.13.

In addition, two additional 3' blocked T nucleosides (3'-eAOM T and 3'-iAOM T) were prepared following the similar fashion as described above. 3'-iAOM T: LC-MS (ES): (negative ion) m/z 325.5 ($M–H^+$), (positive ion) 327.3 ($M+H^+$). 3'-eAOM T: LC-MS (ES): (positive ion) m/z 341.3 ($M+1H^+$).

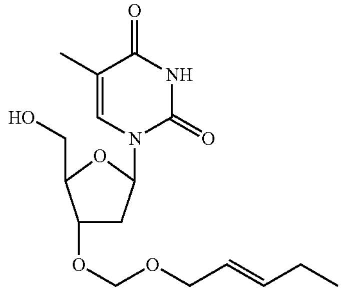

3'-eAOM T

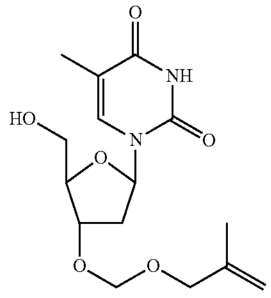

3'-iAOM T

Example 2. 3'-OH Blocking Group Stability Testing

In this example, the stability tests for 5'-mP 3'-AOM T nucleotide was performed side by side in an incorporation buffer solution with standard 5'-mP 3'-O-azidomethyl T nucleotide.

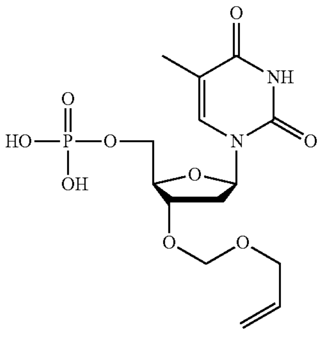

5′mP 3′-AOM T

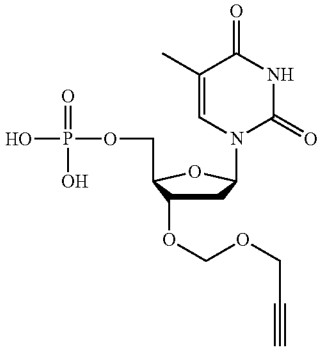

5′mP 3′-PrOM T

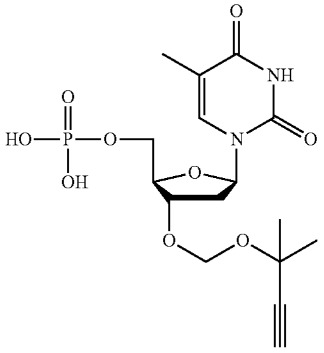

5′mP 3′-DPrOM T

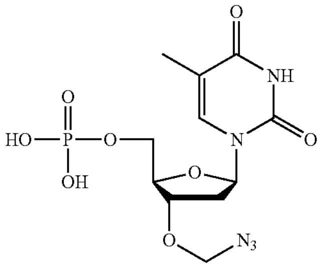

5′mP 3′-O-azidomethyl T

Formulation of the Buffer Solution 1 mL of 0.1 mM of each 5'-monophosphate 3'-protected T nucleotide in a solution of 100 mM ethanolamine buffer (pH 9.8), 100 mM NaCl, and 2.5 mM EDTA, was incubated at 65° C. in a heating block for 2 weeks. At set time points, 40 μL aliquots were taken and analyzed by HPLC to determine the percentage of blocked nucleotide remaining and the eventual formation of unblocked nucleotide.

The stability testing results relating to the 5'-monophosphate 3'-protected nucleotides with AOM, PrOM, DPrOM acetal protecting groups and the standard azidomethyl blocking group are illustrated in FIG. 1. It was observed that 3' blocked nucleotide monophosphate with AOM, PrOM and DPrOM blocking groups offered over 30-50 fold improvement in the reduction of the deblocking rate in the solution. This experiment mimics how the corresponding fully functionalized nucleotides (ffNs) would behave when stored in an incorporation mix on the cartridge of a sequencing device. The stability improvement offered by these acetal protecting groups would also lead to a lower pre-phasing rate in sequencing runs. Finally, it improves the shelf-life of the incorporation mix reagent.

Example 3. 3'-AOM Deblocking Testing

In this example, deblocking tests for 5'-mP 3'-AOM T and the standard 5'-mP 3'-O-azidomethyl T nucleotide were performed individually in a solution unique to each blocking group. Conditions were formulated to mimic Illumina's standard deblock reagent as closely as possible, and follow the same methodology. Concentrations of active deblock reagent, buffer, and nucleoside are kept the same across all tests, but the identity of each component was unique. In this way, the observed difference in rate between the individual deblocking chemistries cannot due to the differences in concentration of formulation.

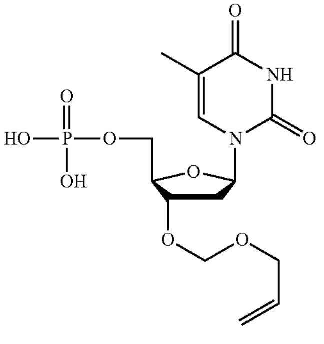

Deblock reagent:
Pd(II/0) + THP

5′mP 3′-AOM T

-continued

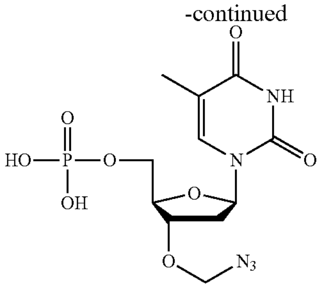

Deblock reagent: THP

5'mP 3'-O-azidomethyl T

Standard Azidomethyl Deblocking Condition

Nucleotide: 5'-monophosphate 3'-O-azidomethyl T. Active Deblock reagent: tris(hydroxypropyl)phosphine (THP) (1M in 18 mΩ water). (Optional) Additive: Sodium ascorbate (0.1 mM in 18 mΩ water) final conc.=1 mM. Buffer: Ethanolamine pH 9.8 (2M in 18 mΩ water). Quenching reagent: $H_2O_2$.

AOM Deblocking Condition

Nucleotide: 5'-monophosphate 3'-O-azidomethyl T. A stock solution of 3'-AOM T was diluted to 0.1 mM in a 100 mM ethanolamine buffer (pH 9.8), in a glass vial under nitrogen. A stock solution of sodium ascorbate additive was added to a final concentration of 0.1 mM and the solution stirred 5 minutes. To commence the assay, the deblock reagents (Pd/THP=1/5; sodium ascorbate; ethanolamine) were added, to a final concentration of 1 mM THP, to the stirring solution at room temperature. At specified time points, 40 μL aliquots were taken and quenched with 6 μL of a 1:3 mixture of EDTA/$H_2O_2$ (0.025:0.075 M). HPLC analysis was performed by measuring the area of the starting nucleoside peak, the 3'-OH peak, and any other nucleotide peaks that appear in the HPLC chromatogram. No other nucleotide-based side products were observed.

Figure 2A:
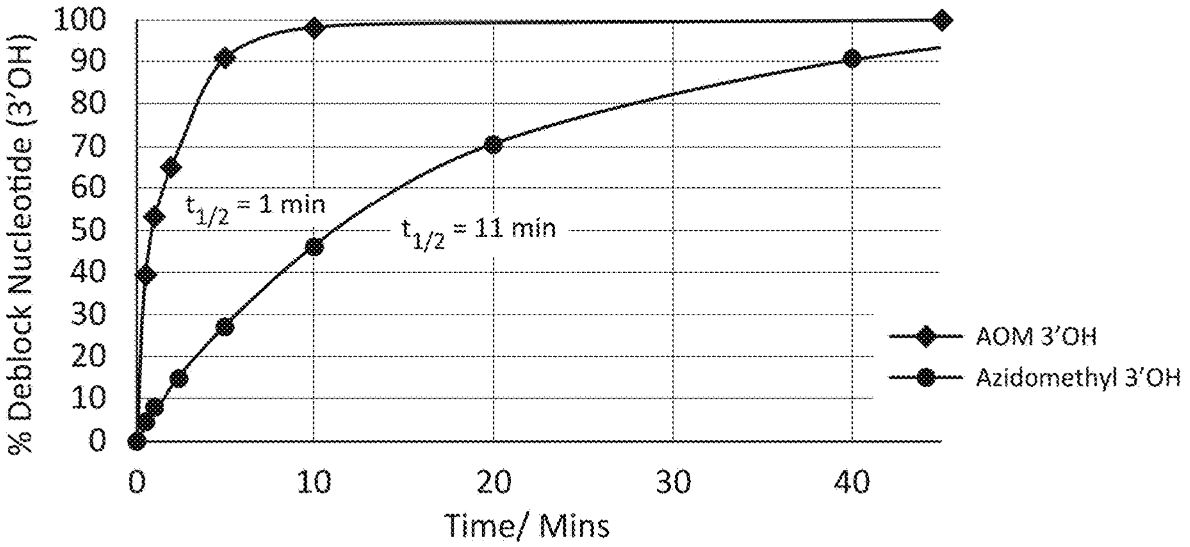
FIG. 2A is a line chart illustrating the percentage (%) of remaining nucleotide (starting material) as a function of time comparing the deblocking rate of nucleotide with 3'-AOM blocking group to nucleotide with the 3'-O-azidomethyl ($—CH_2N_3$) blocking group in solution.

The comparative result is shown in FIG. 2A. It was observed that AOM offered a 10-fold speed improvement in term of deblocking rate in solution compared to the standard azidomethyl blocking group. This experiment serves the purpose of mimicking how the corresponding ffNs would behave in sequencing during the deblocking step. The substantial improvement in the deblocking speed would allow for a flush-through deblocking step instead of the 10 to 20 second incubation time typically used in certain Illumina sequencing platforms. As a result, the deblocking rate will have a significant impact on sequencing by synthesis (SBS) cycle time.

Figure 2B:
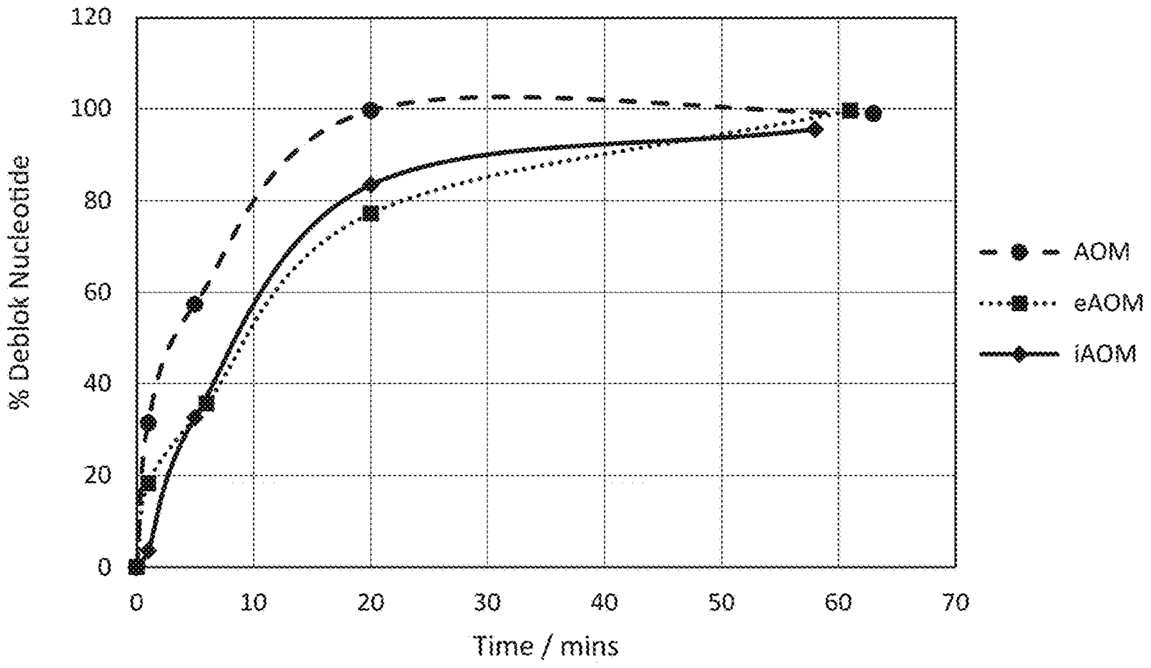
FIG. 2B is a line chart illustrating the percentage (%) of 3' deblocked nucleotides as a function of time comparing the deblocking rate of 3' blocked nucleotides with various acetal blocking groups in solution.

Similar experimental conditions were used for the deblocking assay for 3'-eAOM T and 3'-iAOM T. As a single alteration, Pd catalyst to substrate ratio was reduced to 5:1 in order to observe less distinct differences in the deblocking rate. 3'-AOM T was used as a reference and the results are illustrated in FIG. 2B. These results showed that the deblocking rate of eAOM and iAOM are 2 to 3 times slower than AOM at this specific concentration of the Pd catalyst deblocking reagent. It can be expected that the difference in deblocking rates among the substituted version and unsubstituted version of the AOM blocking groups would be smaller when Pd catalyst to substrate ratio is higher.

Example 4. Optimization of Palladium Cleavage Mix for Sequencing

The Pd/THP catalyst used in the deblocking reaction described in Example 2 is very air sensitive. When exposed to air, it showed a substantial loss of activity. In this example, an oxidation stress assay was developed to assess air sensitivity of different formulations of the palladium cleavage mix.

0.5 mL of Pd cleave mix were aliquoted in a 5 mL glass vial and left open to air for 3 hours at room temperature. The residual activity of the oxidized cleavage mix was assessed by measuring the cleavage of 3'-AOM T as follows. A stock solution of 3'-AOM T was diluted to 0.1 mM in 100 mM cleavage mix buffer. A stock solution of sodium ascorbate was added to a final concentration of 1 mM, followed by the oxidized cleavage mix to a final 1/20 dilution. After 1 hour, L of the solution were immediately quenched with 10 μL of a 1:1 mixture of EDTA/$H_2O_2$ (0.25:0.25 M) and analyzed by HPLC. In this experiment, various buffer reagents were screened, including: primary amines (such as ethanolamine, Tris and glycine); tertiary amines (such as 2-dimethyalaminomethanol ((DMEA), 2-diethyalaminomethanol (DEEA), N,N,N',N'-tetramethylethylenediamine (TEMED) or N,N,N',N'-tetraethylethylenediamine (TEEDA)); and various inorganic salts (such as a borate salt, an carbonate salt, a phosphate salt). It was observed that inorganic buffer reagents (such as sodium borate, sodium carbonate, sodium phosphate) offered the best air stability and the palladium complex retained high % activities. In addition, tertiary amines also substantially improved the stability of the Pd cleavage mix as compared to primary amines.

Based on these findings, two palladium cleavage mix were prepared. In a first example, a stock solution of 250 mM borate buffer aq. (pH 9.6, 20 mL) was diluted with water (14 mL) before addition of a stock solution of THP (1 M in 100 mM Tris, pH 9, 5 mL, 5.0 mmol) and of allylpalladium (II) chloride dimer (183 mg, 0.5 mmol). The mixture was vigorously stirred for a few minutes at room temperature before addition of 1 M sodium ascorbate aq. (0.5 mL, 0.5 mmol), 5 M NaCl aq. (10 mL) and 10% v/v Tween20 (0.5 mL). In a second example, a stock solution of 2 M DEEA buffer aq. (pH 9.6, 0.6 mL) was diluted with water (7.6 mL) before addition of a stock solution of THP (1 M in 100 mM Tris, pH 9, 1.2 mL, 1.2 mmol) and of solid allylpalladium (II) chloride dimer (43.9 mg, 0.12 mmol). The mixture was vigorously stirred for a few minutes at room temperature before addition of 1 M sodium ascorbate aq. (0.12 mL, 0.12 mmol), 5 M NaCl aq. (2.4 mL) and 10% v/v Tween20 (0.12 mL).

Example 5. Preparation of Fully Functionalized Nucleotides and Uses for Sequencing Application In this example, the preparation of various fully functionalized nucleotides (ffNs) with 3'-AOM blocking group are described in detail. These ffNs were also used in the sequencing by synthesis application on Illumina MiniSeq® platform.

Scheme 4. Synthesis of 3'-AOM-ffC-LN3-SO7181

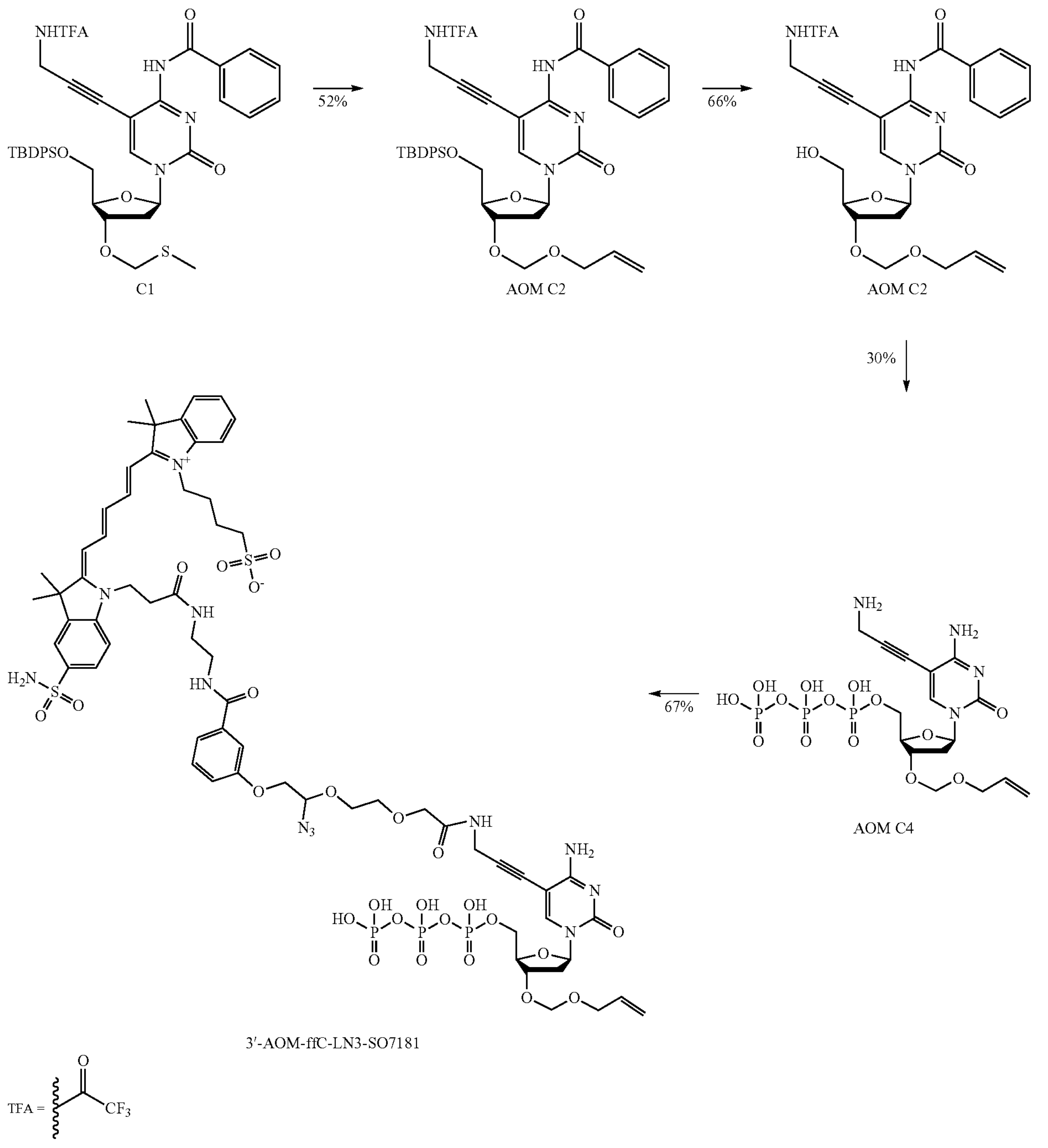

C1

AOM C2

AOM C2

AOM C4

3'-AOM-ffC-LN3-SO7181

TFA =

Synthesis of intermediate AOM $C_2$: Nucleoside C1 (0.5 g, 0.64 mmol) was dissolved in anhydrous DCM (12 mL) under $N_2$, and the mixture was cooled to 0° C. Cyclohexene (0.32 mL, 3.21 mmol) was added, followed by dropwise $SO_2Cl_2$ (1.0 M in DCM, 1.27 mL, 1.27 mmol). Additional cyclohexene (0.32 mL, 3.21 mmol) was added before quickly transferring the reaction to a rotary evaporator to remove all the volatiles under reduced pressure. The solid residue was additionally dried under high vacuum for 10 min before being dissolved in anhydrous DCM (5 mL) under $N_2$. The mixture was cooled to 0° C. and ice-cold allyl alcohol (5 mL) was added dropwise. The reaction was stirred at 0° C. for 2 h, before being quenched by addition of sat. $NaHCO_3$ aq. (50 mL) and DCM (30 mL). The two phases were separated, and the aqueous layer was extracted with EtOAc (2×50 mL). The organic layers were combined, dried over $MgSO_4$, filtered and the volatiles were evaporated under reduced pressure. The crude product was purified by flash chromatography on silica gel using a EtOAc/petroleum ether to give AOM C2 as a white solid (264 mg, 52% yield). LC-MS (Electrospray negative): [M–H] 787, [M+Cl] 823.

Synthesis of intermediate AOM C3: AOM C2 (246 mg, 0.31 mmol) was dissolved in anhydrous THF (9.5 mL) under $N_2$ and the mixture was cooled to 0° C. Acetic acid (0.054 mL, 0.94 mmol) was added, followed by dropwise TBAF (1.0 M in THF, 5 wt. % water, 0.99 mL, 0.94 mmol). The reaction was stirred at 0° C. for 5 h, before being diluted with EtOAc (20 mL) and then poured into 0.05 M HCl aq. (20 mL). The two layers were separated, and the aqueous layer was extracted with EtOAc (2×20 mL). The organic layers were combined, dried over $MgSO_4$, filtered and the volatiles were evaporated under reduced pressure. The crude product was purified by flash chromatography on silica gel using a DCM/EtOAc to give AOM C3 as a yellowish solid (114 mg, 66% yield). LC-MS (Electrospray negative): [M−H] 549, [M+$H_2$O—H] 567, [M+Cl] 585, (Electrospray positive): [M+H] 551, [M+$H_2$O+H] 569.

Synthesis of intermediate AOM C4: AOM C3 (0.114 g, 0.21 mmol), freshly activated 4 Å molecular sieves, proton sponge (0.066 g, 0.31 mmol) and a magnetic stirrer were placed under $N_2$ and anhydrous trimethyl phosphate (1.0 mL) was added. The reaction was cooled at −10° C. and freshly distilled $POCl_3$ (23 μL, 0.25 mmol) was added dropwise. The reaction was stirred at −10° C. for 1 hour. A solution of pyrophosphate as bis-tri-n-butylammonium salt (0.5 M in DMF, 1.7 mL, 0.85 mmol) and anhydrous tri-n-butyl amine (0.41 mL, 1.74 mmol) were premixed and added to the ice-cold activated nucleoside solution in one portion. The mixture was vigorously stirred for 5 minutes at room temperature. The reaction mixture was poured into a separate flask containing a vigorously stirred solution of 2 M TEAB aq. (~10 mL). The reaction flask was rinsed with a small amount of $H_2O$ and the washings added into the 2 M TEAB solution. The combined mixture was then stirred at room temperature for 4 hours, after which the solvent was evaporated under reduced pressure. The residue was dissolved in $NH_3$ aq. (35%, ~10 mL) and stirred at room temperature overnight. The reaction was concentrated under vacuum and purified by flash chromatography on DEAE-Sephadex. The product was further purified by preparative HPLC to give pure AOM C4 (62 μmol, 30% yield, determined by UV-Vis spectrometry, $\lambda_{max}$=294 nm, ε=8600 $M^{-1}$ $cm^{-1}$). LC-MS (Electrospray negative): [M−H] 589.

Synthesis of 3'-AOM-ffC-LN3-SO7181: LN3-SO7181 (0.0205 mmol) was dissolved in anhydrous DMA (4 mL) under $N_2$. N,N-diisopropylethylamine (28.6 μL, 0.164 mmol) was added, followed by TSTU (0.1 M in DMA, 234 μL, 0.0234 mmol). The reaction was stirred under $N_2$ at room temperature for 1 hour. In the meantime, an aqueous solution of AOM C4 (0.0101 mmol) was evaporated to dryness under reduced pressure, resuspended in 0.1 M TEAB aq. (400 μL) and added to the LN3-SO7181 solution. The reaction was stirred at RT for 17.5 hours and then quenched with 0.1M TEAB aq. (4 mL). The crude product was purified by flash chromatography on DEAE-Sephadex. The product was further purified by preparative HPLC to give pure 3'-AOM-ffC-LN3-SO7181 (6.81 μmol, 67% yield, determined by UV-Vis spectrometry, $\lambda_{max}$=644 nm, ε=200000 $M^{-1}$ $cm^{-1}$). LC-MS (Electrospray negative): [M−H] 1561, [M−2H] 781, [M−3H] 520.

Scheme 5. Synthesis of 3′-AOM-ffA

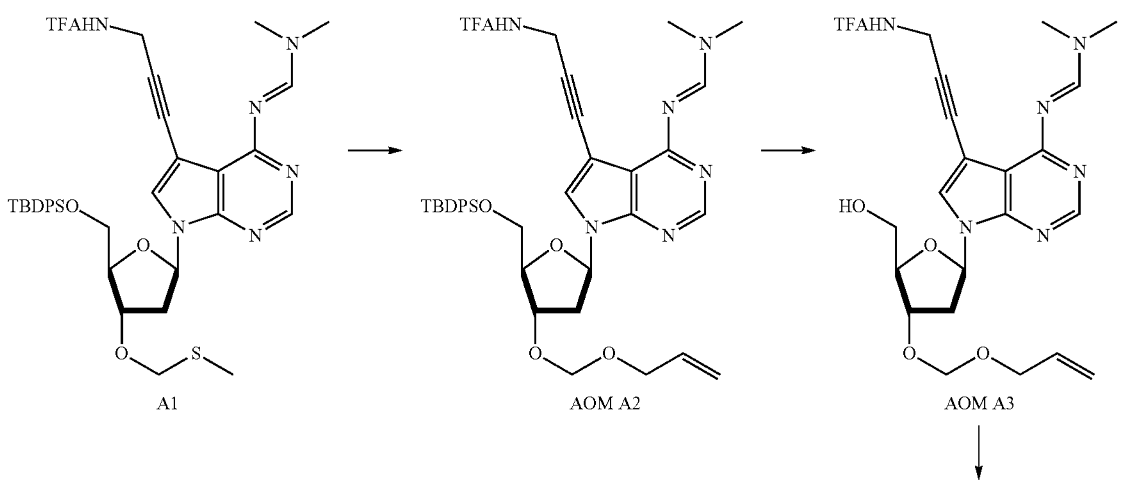

A1

AOM A2

AOM A3

-continued

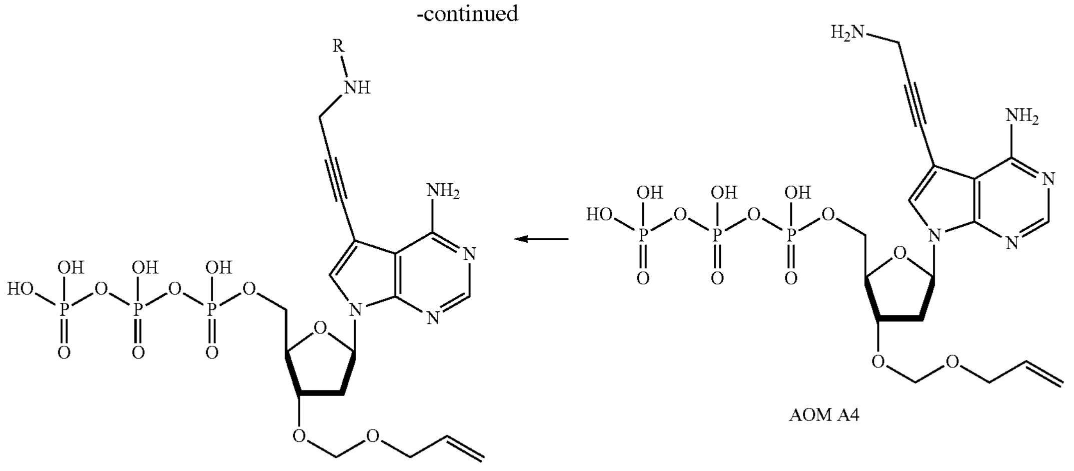

AOM A4

3'-AOM-ffA

R =

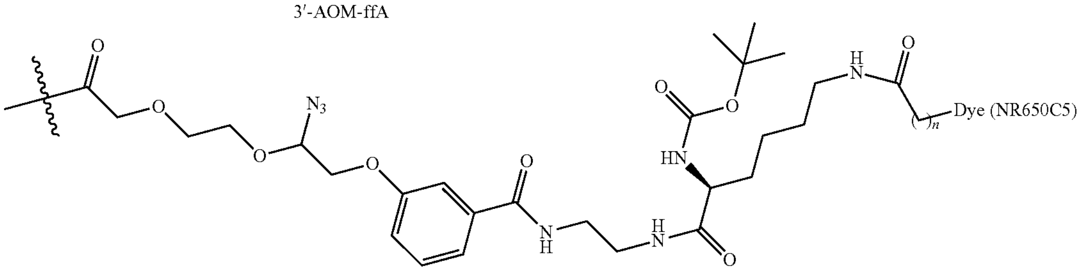

3'-AOM-ffA-LN3-BL-NR650C5

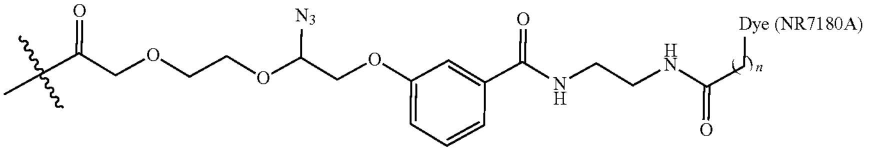

3'-AOM-ffA-LN3-NR7180A

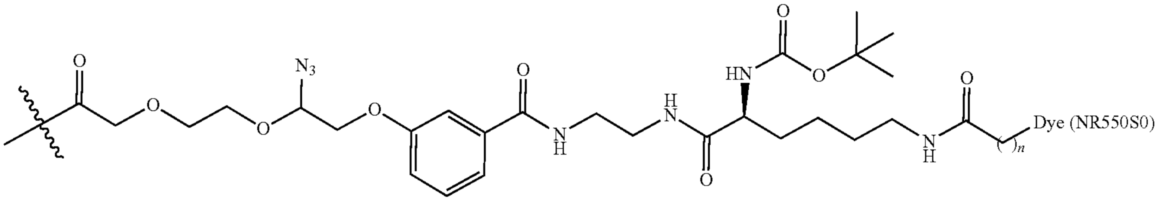

3'-AOM-ffA-LN3-BL-NR550S0

Synthesis of intermediate AOM A2: Nucleoside A1 (716 mg, 0.95 mmol) was dissolved in 10 mL of anhydrous dichloromethane under $N_2$ atmosphere, cyclohexene (481 μL, 4.75 mmol) was added and the solution was cooled to approximately −15° C. Sulfuryl chloride (distilled, 92 μL, 1.14 mmol) was added dropwise and the reaction was stirred for 20 minutes. After all the starting material had been consumed, an extra portion of cyclohexene was added (481 μL, 4.75 mmol) and the reaction was evaporated to dryness under reduced pressure. The residue was quickly purged with nitrogen, then allyl alcohol (5 mL, ~100 mmol) was added under stirring at 0° C. The reaction was stirred at 0° C. for 1 hour, then quenched with 50 mL of saturated aq. $NaHCO_3$. The mixture was extracted with 2× 100 mL of ethyl acetate. The pooled organic phases were washed with 100 mL of water and 100 mL of brine, then dried over $MgSO_4$, filtered and evaporated to dryness. The residue was purified by flash chromatography on silica gel using Petroleum ether/EtOAc. 60% yield (435 mg, 0.57 mmol). LC-MS (ES and CI): (positive ion) m/z 763 ($M+H^+$); (negative ion) m/z 761 ($M-H^+$).

Synthesis of intermediate AOM A3: Nucleoside AOM A2 (476 mg, 0.62 mmol) was dissolved in dry THF (5 mL) under $N_2$ atmosphere, then a solution of 1.0 M TBAF in THF (750 μL, 0.75 mmol) was added. The solution was stirred at room temperature for 1.5 hours. The solution was diluted with 50 mL of EtOAc, then washed with 100 mL of $NaH_2PO_4$ sat. (pH=3), and with 100 mL of brine. The organic phase was dried over $MgSO_4$, filtered and evaporated to dryness. The residue was purified by flash chromatography on silica gel using EtOAc/MeOH. 90% yield (292 mg, 0.55 mmol). LC-MS (ES and CI): (positive ion) m/z 525 ($M+H^+$); (negative ion) m/z 523 ($M-H^+$).

Synthesis of intermediate AOM A4: Nucleoside AOM A3 (285 mg, 0.544 mmol) was dried under reduced pressure over $P_2O_5$ for 18 hrs. Anhydrous triethyl phosphate (2 mL)

and some freshly activated 4 Å molecular sieves were added to it under nitrogen, then the reaction flask was cooled to 0° C. in an ice-bath. Freshly distilled $POCl_3$ (61 μL, 0.65 mmol) was added drop-wise followed by Proton Sponge® (175 mg, 0.816 mmol). After the addition, the reaction was further stirred at 0° C. for 15 minutes. Then, a 0.5 M solution of pyrophosphate as bis-tri-n-butylammonium salt (5.4 mL, 2.72 mmol) in anhydrous DMF was quickly added, followed immediately by tri-n-butyl amine (540 μL, 2.3 mmol). The reaction was kept in the ice-water bath for another 10 minutes, then quenched by pouring it into 1 M aqueous triethylammonium bicarbonate (TEAB, 20 mL) and stirred at room temperature for 4 hours. All the solvents were evaporated under reduced pressure. A 35% aqueous solution of ammonia (20 mL) was added to the above residue and the mixture was stirred at room temperature for at least 5 hours. The solvents were then evaporated under reduced pressure. The crude product was purified firstly by ion-exchange chromatography on DEAE-Sephadex A25 (100 g). The column was eluted with a gradient of aqueous triethylammonium bicarbonate. The fractions containing the triphosphate were pooled and the solvent was evaporated to dryness under reduced pressure. The crude material was further purified by preparative scale HPLC using a YMC-Pack-Pro C18 column, eluting with 0.1 M TEAB and acetonitrile. Compound AOM A4 was obtained as triethylammonium salt. 56% yield (306 μmol). LC-MS (ES and CI): (negative ion) m/z 612 ($M-H^+$); (positive ion) m/z 614 ($M+H^+$), 715 ($M+Et_3NH^+$).

General procedure for ffA synthesis: The dye-linker (0.020 mmol) was dissolved in 2 mL of anhydrous N,N'-dimethylacetamide (DMA). N,N-diisopropylethylamine (28.4 μL, 0.163 mmol) was added, followed by N,N,N',N'-tetramethyl-O—(N-succinimidyl)uronium tetrafluoroborate as 0.1 M solution in anhydrous DMA (TSTU, 232 μL, 0.023 mmol). The reaction was stirred under nitrogen at room temperature for 1 hour. In the meantime, an aqueous solution of the triphosphate AOM A4 (0.01 mmol) was evaporated to dryness under reduced pressure and resuspended in 200 μL of 0.1 M triethylammonium bicarbonate (TEAB) solution in water. The activated dye-linker solution was added to the triphosphate and the reaction was stirred at room temperature for 18 hours. The crude product was purified firstly by ion-exchange chromatography on DEAE-Sephadex A25 (25 g). The fractions containing the triphosphate were pooled and the solvent was evaporated to dryness under reduced pressure. The crude material was further purified by preparative scale RP-HPLC using a YMC-Pack-Pro C18 column. 3'-AOM-ffA-LN3-NR7180A: 38% yield (3.8 μmol). LC-MS (ES): (negative ion) m/z 1459 ($M-H^+$), 729 ($M-2H^+$), 486 ($M-3H^+$). 3'-AOM-ffA-LN3-BL-NR550S0: 37% yield (3.7 μmol). LC-MS (ES): (negative ion) m/z 1771 ($M-H^+$), 885 ($M-2H^+$), 589 ($M-3H^+$). 3'-AOM ffA-LN3-BL-NR650C5: 51% yield (51 μmol). LC-MS (ES): (negative ion) m/z 1917 ($M-H^+$), 958 ($M-2H^+$), 645 ($M-3H^+$).

Scheme 6. Synthesis of 3'-AOM-pppG

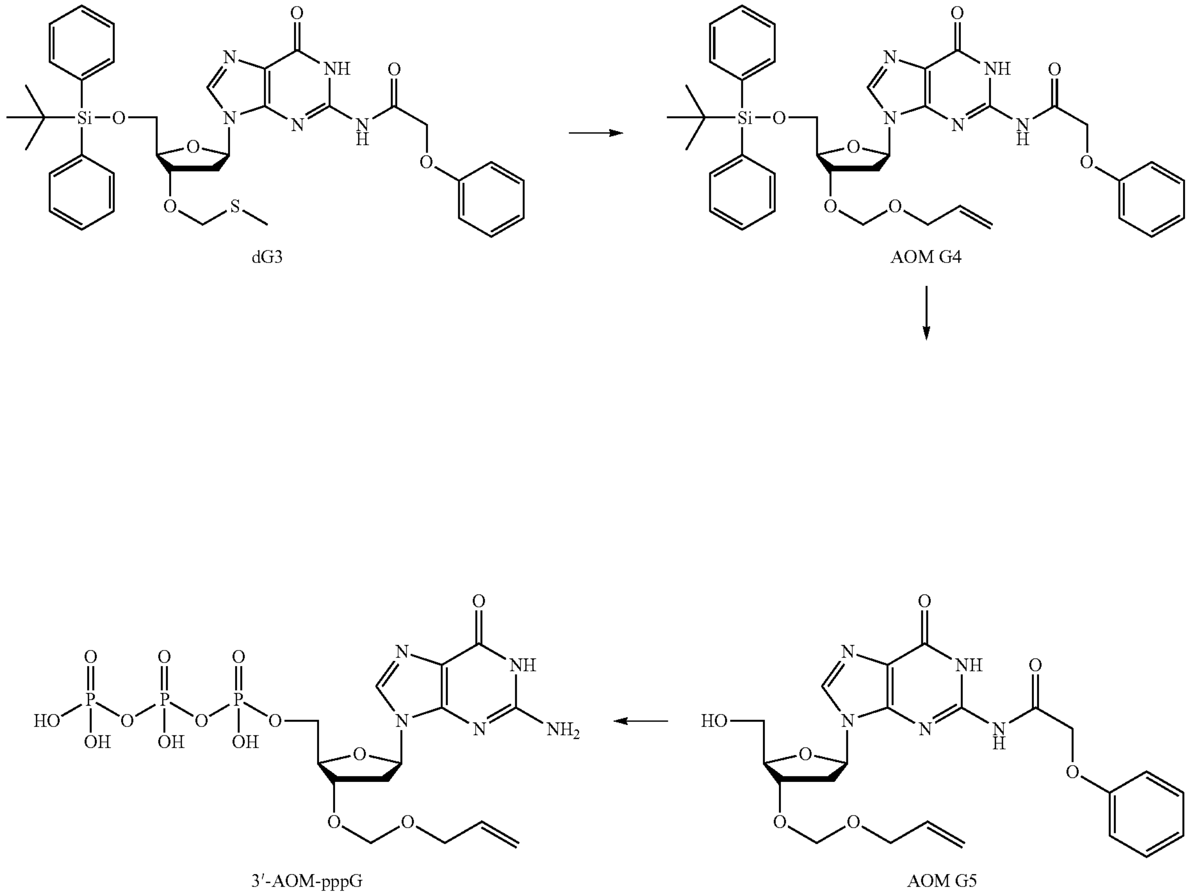

dG3 → AOM G4 → AOM G5 → 3'-AOM-pppG

Synthesis of intermediate AOM G4: Known nucleoside dG3 (100 mg, 0.143 mmol) was dissolved in 10 mL of anhydrous dichloromethane under $N_2$ atmosphere, Cyclohexene (72 μL, 0.714 mmol) was added and the solution cooled to −12° C. Sulfuryl chloride (distilled, (1M in DCM), 171 μL, 0.171 mmol) was added dropwise and the reaction was stirred for 10 min. An extra portion of cyclohexene (72 μL, 0.714 mmol) was added and the reaction stirred for 30 min at −12° C. The reaction was evaporated to dryness under reduced pressure, the residue was purged with nitrogen, and ice cold, neat allyl alcohol (distilled, 0.8 mL, 12 mmol) was added under stirring at −12° C. The reaction was stirred at −12° C. for 60 mins, then quenched with 2 mL of saturated aq. $NaHCO_3$. The mixture was separated with ethyl acetate (2 mL), the aqueous layer extracted with ethyl acetate. Combined organic phases were washed with 4 mL of water and 4 mL of brine, dried over $MgSO_4$, filtered and evaporated to crude oil. The residue was purified by flash chromatography on silica gel to give AOM G4 as a clear oil. 36% yield (50.9 mg, 0.072 mmol). LC-MS (ES and CI): (positive ion) m/z 710 $[M+H]^+$; (negative ion) m/z 708 $[M-H]^-$.

Synthesis of intermediate AOM G5: Nucleoside AOM-G4 (111 mg, 0.156 mmol) was dissolved in dry THF (5 mL) under $N_2$ atmosphere. Acetic acid (27 μL, 0.468 mmol) was added, followed by a solution of 1.0 M TBAF in THF (296 μL, 0.296 mmol). The solution was stirred at room temperature for 5 hours. The solution was diluted with 10 mL of EtOAc, washed with 10 mL of 0.05 M aq. HCl and organic separated. The aqueous phase was extracted with ethyl acetate. The combined organic phases were dried over $MgSO_4$, filtered and evaporated to dryness. The residue was purified by flash chromatography on silica gel to give AOM G5 as a white solid. 44% yield (32.4 mg, 0.068 mmol). LC-MS (ES and CI): (positive ion) m/z 472 $[M+H]^+$; (negative ion) m/z 470 $[M-H]^-$.

Synthesis of 3'-AOM-pppG: Nucleoside AOM-G5 (79 mg, 0.168 mmol) with freshly activated 4 Å molecular sieves were dried under reduced pressure over $P_2O_5$ for 18 hrs. Proton Sponge® (175 mg, 0.816 mmol) and anhydrous triethyl phosphate (0.8 mL) was added under nitrogen and stirred at room temperature for 1 hour. The reaction flask was cooled to 0° C. in an ice-bath, freshly distilled $POCl_3$ (19 μL, 0.202 mmol) was added drop-wise and the reaction was stirred at 0° C. for 15 minutes. Then, a 0.5 M solution of pyrophosphate as bis-tri-n-butylammonium salt (1.68 mL, 0.84 mmol) in anhydrous DMF was quickly added, followed immediately by tri-n-butyl amine (168 μL, 0.705 mmol). The reaction was removed from the ice/water bath and stirred vigorously for 5 minutes, then quenched by pouring it into 1 M aqueous triethylammonium bicarbonate (TEAB, 6 mL) and stirred at room temperature for 18 hours. All the solvents were evaporated under reduced pressure. The residue was dissolved in 35% aqueous ammonia solution (10 mL) and was stirred at room temperature for at least 5 hours. The solvents were then evaporated under reduced pressure and further co-evaporated with water. The crude product was purified firstly by ion-exchange chromatography on DEAE-Sephadex A25 (50 g). The column was eluted with a linear gradient of aqueous triethylammonium. The fractions containing the triphosphate were collected and the solvent was evaporated to dryness under reduced pressure. The crude material was further purified by preparative scale HPLC using a YMC-Pack-Pro C18 column. 3'-AOM-pppG was obtained as triethylammonium salt. 24% yield (39.7 μmol). LC-MS (ES and CI): (negative ion) m/z 576 $[M-H]^-$; (positive ion) m/z 578 $[M+H]^+$.

3'-AOM-ffT-LN3-NR550S0 was synthesized in a similar fashion as described in the preparation of the 3'-AOM ffA and ffC.

Scheme 7. 3'-AOM-ffT-LN3'-NR550S0
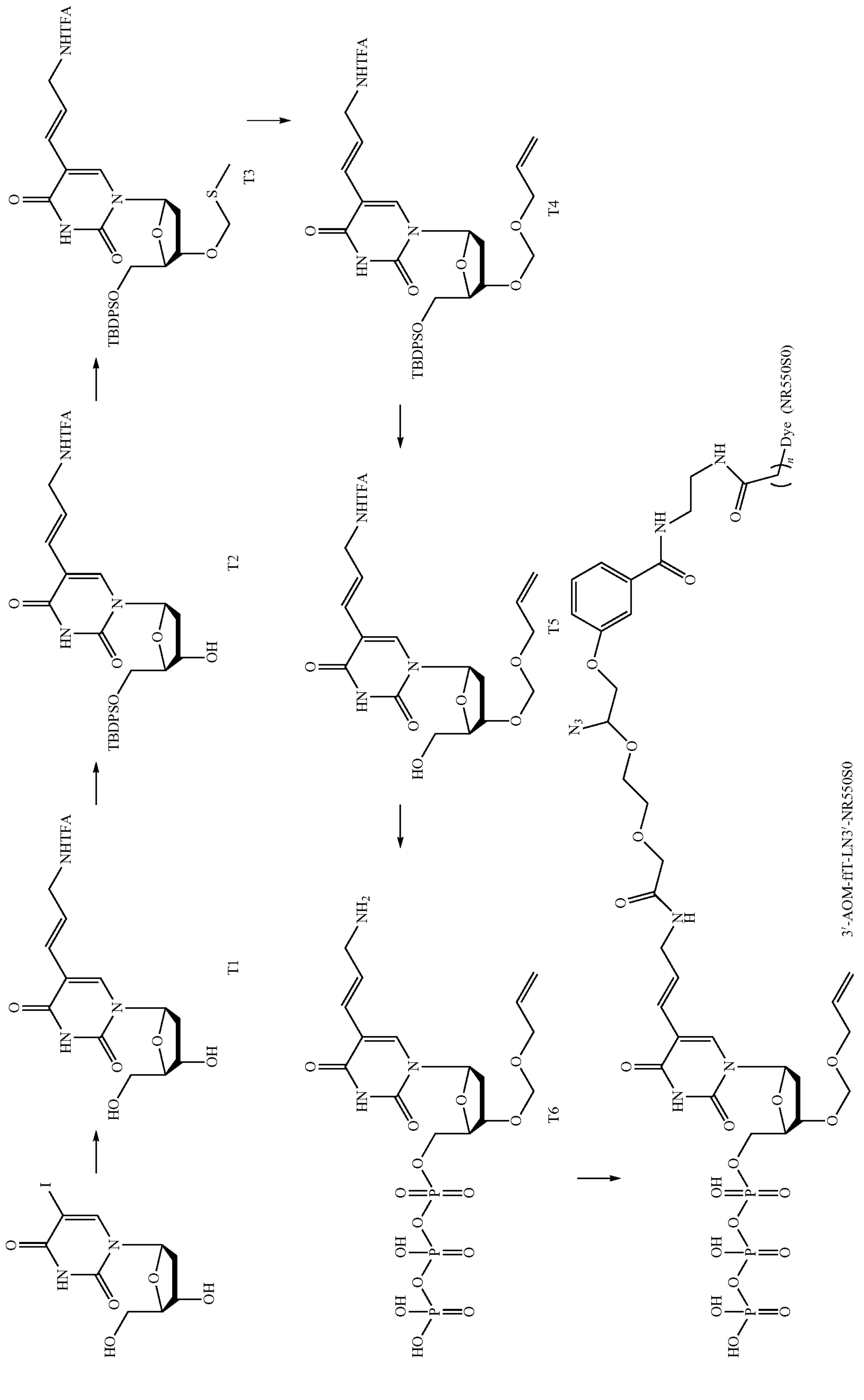
T1
T2
T3
T4
T5
T6
3'-AOM-ffT-LN3'-NR550S0

Synthesis of intermediate T1: 5-Iodo-2'-deoxyuridine (3 g, 8.4 mmol) and palladium (II) acetate (1.6 g, 7.14 mmol) were dissolved in dry degassed DMF, then N-allyltrifluoroacetamide (6.4 mL, 42 mmol) was added. The solution was placed under vacuum, then purged with nitrogen for 3 times, then degassed triethylamine (2.3 mL, 16.8 mmol) was added. The solution was heated to 80° C. for 2 hours. The black mixture was cooled down to room temperature then diluted with 50 mL of methanol. Approximately 0.5 g of activated charcoal was added, and the solution was filtered on Celite, then evaporated under reduced pressure to afford a brown thick oil. This crude was purified by chromatography on silica gel using a EtOAc/MeOH. Yield: (2.27 g, 5.99 mmol). LC-MS (ES and CI): (negative ion) m/z 378 ($M-H^+$).

Synthesis of intermediate T2: 5-[3-(2,2,2-trifluoroacetamido)-allyl]-2'-deoxyuridine (T1) (2.55 g, 6.72 mmol) was dissolved in dry DMF. Imidazole (1.37 g, 20.1 mmol) was added followed by 4-(dimethylamino)pyridine (410 mg, 3.36 mmol). The reaction was cooled to 0° C., then tert-butyl(chloro)diphenylsilane (1.92 mL, 7.39 mmol) was added slowly in 3 portions, 30 minutes apart. The reaction was stirred at 0° C. for 6 hours. The solvent was then evaporated, and the residue resuspended in 200 mL of EtOAc and washed with 2× 200 mL aq. saturated $NaHCO_3$ and 200 mL of water, then 100 mL of brine. The organic phase was dried over $MgSO_4$, filtered and evaporated to dryness. The crude was purified by flash chromatography on silica using a DCM/EtOAc. 68% yield (2.806 g, 4.54 mmol). LC-MS (ES and CI): (positive ion) m/z 618 ($M+H^+$); (negative ion) m/z 616 ($M-H^+$).

Synthesis of intermediate T3: 5'-O-(tert-butyldiphenylsilyl)-5-[3-(2,2,2-trifluoroacetamido)-allyl]-2'-deoxyuridine (T2) (2.8 g, 4.53 mmol) was dissolved in 10 mL of anhydrous DMSO (136 mmol), then glacial acetic acid (16 mL, 272 mmol) and acetic anhydride (16 mL, 158 mmol) were added. The reaction was heated to 50° C. for 6 hours then quenched with 200 mL of aq. saturated $NaHCO_3$. After the solution stopped bubbling, it was extracted with 2× 150 mL of EtOAc. The organic phases were pooled and washed with 2×200 mL of aq. saturated $NaHCO_3$, 200 mL of water and 100 mL of brine. The organic phase was dried over $MgSO_4$, filtered and evaporated to dryness. The crude was purified by flash chromatography on silica using a DCM/EtOAc. 77% yield (2.375 g, 3.51 mmol). LC-MS (ES and CI): (positive ion) m/z 678 ($M+H^+$); (negative ion) m/z 676 ($M-H^+$).

Synthesis of intermediate T4: 5'-O-(tert-butyldiphenylsilyl)-3'-O-methylthiomethyl-5-[3-(2,2,2-trifluoroacetamido)-allyl]-2'-deoxyuridine (T3) (310 mg, 0.45 mmol) was dissolved in 5 mL of anhydrous dichloromethane under $N_2$ atmosphere, cyclohexene (228 μL, 2.25 mmol) was added and the solution was cooled to approximately −15° C. Sulfuryl chloride (distilled, 55 μL, 0.675 mmol) was added dropwise and the reaction was stirred for 20 minutes. After all the starting material had been consumed, an extra portion of cyclohexene was added (228 μL, 2.25 mmol) and the reaction was evaporated to dryness under reduced pressure. The residue was quickly purged with nitrogen, then ice-cold allyl alcohol (2.5 mL) was added under stirring at 0° C. The reaction was stirred at 0° C. for 35 minutes, then quenched with 25 mL of saturated aq. $NaHCO_3$, then diluted further with 100 mL of saturated aq. $NaHCO_3$. The mixture was extracted with 2× 50 mL of ethyl acetate. The pooled organic phases were dried over $MgSO_4$, filtered and evaporated to dryness. The residue was purified by flash chromatography on silica gel using a DCM/EtOAc. 69% yield (214 mg, 0.311 mmol). LC-MS (ES and CI): (positive ion) m/z 688 ($M+H^+$); (negative ion) m/z 686 ($M-H^+$).

Synthesis of intermediate T5: 5'-O-(tert-butyldiphenylsilyl)-3'-O-allyloxymethyl-5-[3-(2,2,2-trifluoroacetamido)-allyl]-2'-deoxyuridine (T4) (210 mg, 0.305 mmol) was dissolved in dry THF (3 mL) under $N_2$ atmosphere. A solution of 1.0 M TBAF in THF (367 μL, 0.367 mmol) was added. The solution was stirred at room temperature for 3 hours. The solution was diluted with 50 mL of EtOAc, then washed with 50 mL of $NaH_2PO_4$ sat. (pH=3), and with 50 mL of water. The organic phase was dried over $MgSO_4$, filtered and evaporated to dryness. The residue was purified by flash chromatography on silica gel using DCM/EtOAc. 95% yield (130 mg, 0.289 mmol). LC-MS (ES and CI): (negative ion) m/z 448 ($M-H^+$), 484 ($M+Cl^-$).

Synthesis of intermediate T6: 3'-O-allyloxymethyl-5-[3-(2,2,2-trifluoroacetamido)-allyl]-2'-deoxyuridine (T5) (120 mg, 0.267 mmol) was dried under reduced pressure over $P_2O_5$ for 18 hrs. Anhydrous triethyl phosphate (1 mL) and some freshly activated 4 Å molecular sieves were added to it under nitrogen, then the reaction flask was cooled to 0° C. Freshly distilled $POCl_3$ (30 μL, 0.32 mmoles) was added drop-wise followed by Proton Sponge® (85 mg, 0.40 mmol). After the addition, the reaction was further stirred at 0° C. for 15 minutes. Then, a 0.5 M solution of pyrophosphate as bis-tri-n-butylammonium salt (2.7 mL, 1.33 mmol) in anhydrous DMF was quickly added, followed immediately by tri-n-butyl amine (270 μL, 1.2 mmol). The reaction was kept in the ice-water bath for another 10 minutes, then quenched by pouring it into 1 M aqueous triethylammonium bicarbonate (TEAB, 10 mL) and stirred at room temperature for 4 hours. All the solvents were evaporated under reduced pressure. A 35% aqueous solution of ammonia (10 mL) was added to the above residue and the mixture was stirred at room temperature for 18 hours. The solvents were then evaporated under reduced pressure, the residue resuspended in 10 mL of 0.1 M TEAB and filtered. The filtrate was purified firstly by ion-exchange chromatography on DEAE-Sephadex A25 (100 g). The column was eluted with aqueous triethylammonium bicarbonate (TEAB). The fractions containing the triphosphate were pooled and the solvent was evaporated to dryness under reduced pressure. The crude material was further purified by preparative scale HPLC using a YMC-Pack-Pro C18 column. Compound T6 was obtained as triethylammonium salt. 33% yield (89 μmol). LC-MS (ES and CI): (negative ion) m/z 592 ($M-H^+$), 295 ($M-2H^+$).

Synthesis of 3'-AOM-ffT-LN3'-NR550S0: The dried known compound LN3-NR550S0 (0.015 mmol) was dissolved in anhydrous DMA (2 mL) under $N_2$. N,N-diisopropylethylamine (17 μL, 0.1 mmol) was added, followed by TSTU (0.1 M in DMA, 180 μL, 0.018 mmol). The reaction was stirred under $N_2$ at room temperature for 1 hour. In the meantime, an aqueous solution of T6 (0.01 mmol) was evaporated to dryness under reduced pressure, resuspended in 0.1 M TEAB aq. (200 μL) and added to the LN3-NR550S0 solution. The reaction was stirred at RT for 18 hours and then quenched with 0.1M TEAB aq. (4 mL). The crude product was purified by flash chromatography on DEAE-Sephadex. The product was further purified by preparative HPLC to give pure 3'-AOM-ffT-LN3'-NR550S0. 67% yield (41 μmol, determined by UV-Vis spectrometry, $\lambda_{max}$=550 nm, ε=125000 $M^{-1}$ $cm^{-1}$). LC-MS (ES): (negative ion) m/z 1521 ($M-H^+$), 761 ($M-2H^+$), 507 ($M-3H^+$).

Sequencing-by-Synthesis Experiments

The ffNs were subsequently tested in sequencing using an Illumina MiniSeq® instrument. With the exception of a new incorporation mix including these ffNs, all standard commercial reagents were used. A standard 2×150 recipe was used. In addition to the standard sequencing-by-synthesis (SBS) protocols, a 5 seconds incubation in a solution of palladium cleavage mix (Pd:THP=1/5 in DEEA as described in Example 4) were added to unblock 3'-AOM.

In a first experiment, the following ffNs were used in the incorporation mix: 3'-AOM-ffT-LN3-NR550S, 3'-AOM-ffA-LN3-BL-NR550S, 3'-AOM-ffA-LN3-BL-NR650C5, 3'-AOM-ffA-LN3-NR7180A, 3'-AOM-ffC-LN3-SO7181, and 3'-AOM-pppG (dark G). and the sequencing result for Read 1 is summarized below.

| Read | % PF | Phasing | Pre-phasing | ER |
|---|---|---|---|---|
| 1 | 90.2% | 0.798 | 0.159 | 3.12 |

% PF: Percentage of cluster passing filter after 26 cycles

Figure 3A:
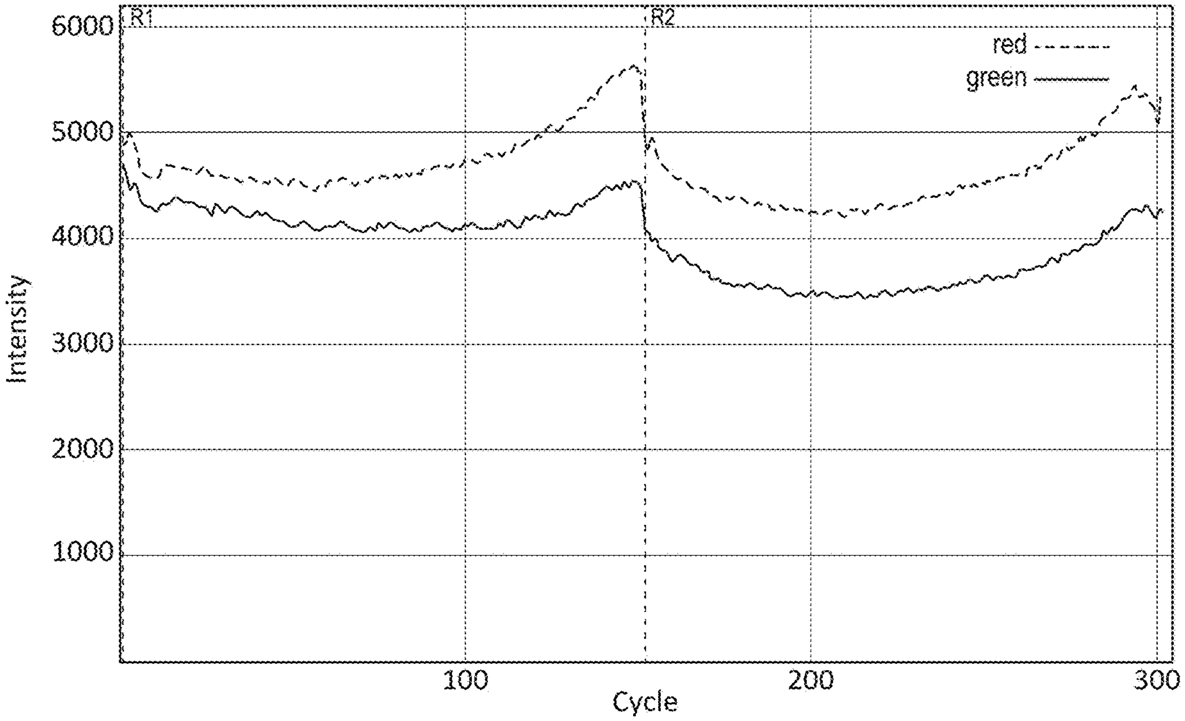
FIGS. 3A and 3B illustrate the sequencing results on Illumina MiniSeq® instrument using fully functionalized nucleotides (ffNs) with 3'-AOM blocking group in the incorporation mix.

In a second experiment, unlabeled 3'-AOM-pppT was synthesized similarly to the preparation of 3'-AOM-pppG described above (LC-MS (ES): (negative ion) m/z 551 ($M-H^+$)). It was used in presence of commercial green ffG-LN3-PEG12-ATTO532 (used on Illumina 4-channel systems) in sequencing and the same ffAs and ffC were used as those described in the first experiment above. The results are summarized below. There were significant improvements on phasing and pre-phasing values and no signal decay was observed (FIG. 3A). In addition, error rates for both Read 1 and Read 2 were also reduced.

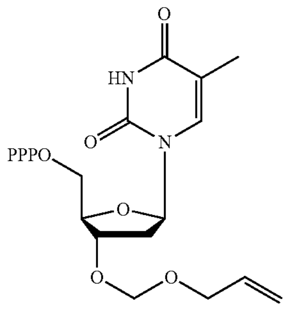

Dark 3'-AOM-pppT

| Read | Phasing | Pre-phasing | ER |
|---|---|---|---|
| 1 | 0.173 | 0.046 | 1.21 |
| 2 | 0.175 | 0.057 | 1.99 |

Figure 3B:
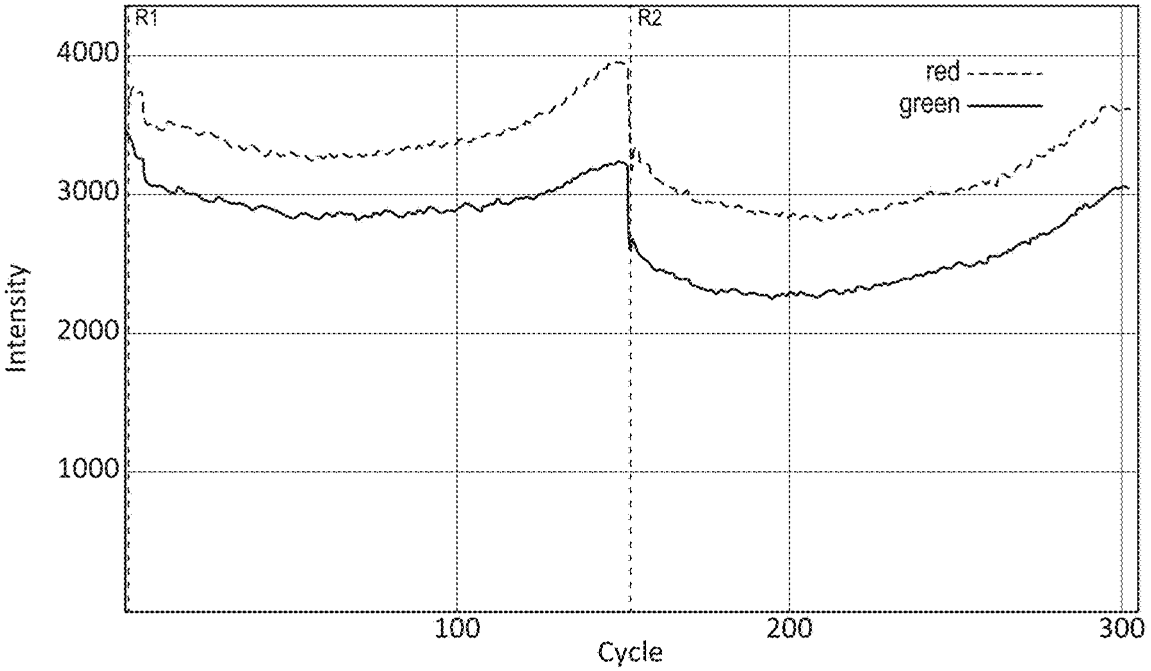
Figure 3C:
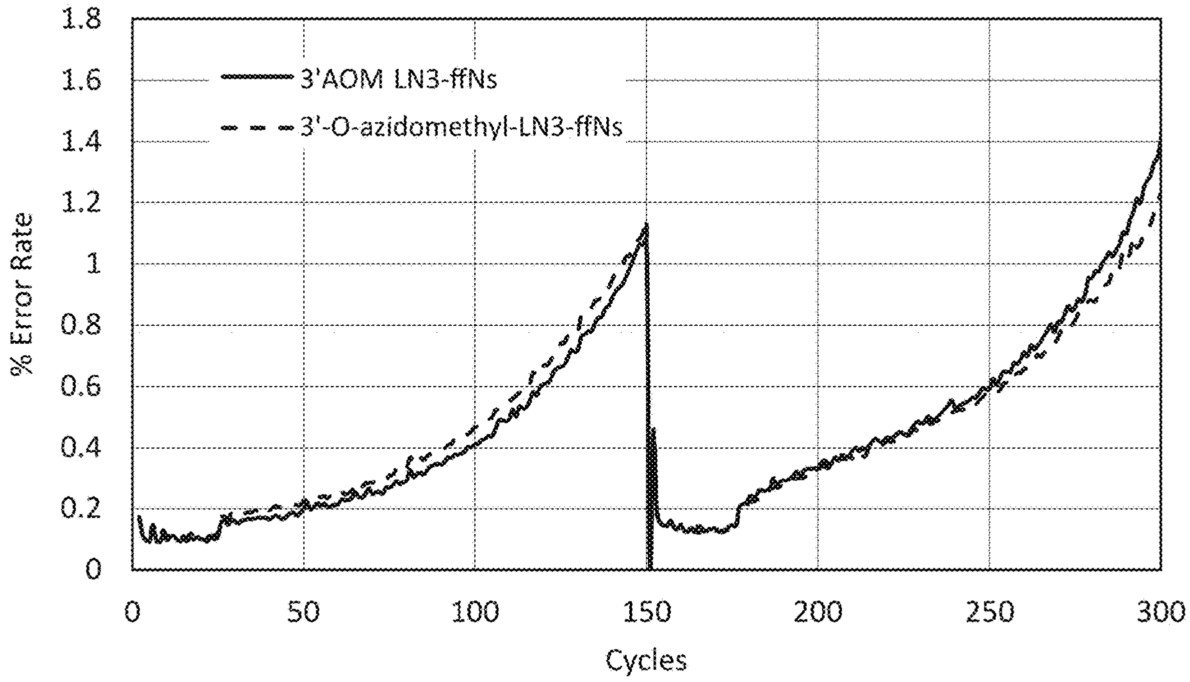
FIG. 3C illustrates the sequencing error rate using fully functionalized nucleotides (ffNs) with 3'-AOM blocking group in the incorporation mix as compared to the standard ffNs with 3'-O-azidometyl blocking group.

In another experiment, an incorporation mix containing 3'-AOM-ffT-LN3'-NR550S0, 3'-AOM-ffA-LN3-BL-NR550S0, 3'-AOM-ffA-LN3-BL-NR650C5, 3'-AOM-ffA-LN3-NR7180A, 3'-AOM-ffC-LN3-SO7181, and 3'-AOM-pppG (dark G) was used. Similar to previous runs, a 5 second incubation with a cleavage mixture containing a palladium catalyst (Pd/THP=1:10; 100 mM DEEA as described in Example 4) was added to the standard SBS cycle. Standard MiniSeq® DNA polymerase was used but at 2× incorporation time. No signal decay phenotype was observed (FIG. 3B). In addition, these sequencing results were compared to commercial MiniSeq® runs (average of 3; N=3) using ffNs with the standard azidomethyl blocking group. It was observed that the error rates were nearly identical (FIG. 3C). The sequencing results are summarized below.

| Read | Phasing | Pre-phasing | ER |
|---|---|---|---|
| 1 | 0.121 | 0.063 | 0.40 |
| 2 | 0.129 | 0.062 | 0.57 |

Figure 4A:
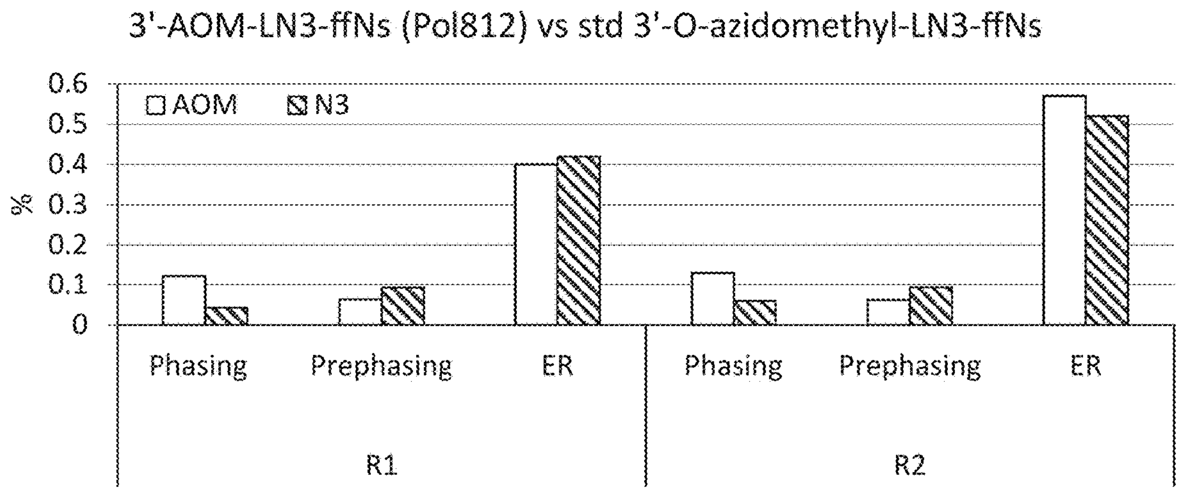
FIGS. 4A and 4B each illustrates comparison of the primary sequencing metrics including phasing, pre-phasing and error rate using fully functionalized nucleotides with 3'-AOM and 3'-O-azidomethyl blocking groups using two different DNA polymerases (Pol 812 and Pol 1901) respectively.

In addition, the primary sequencing metrics for the ffNs with 3'-AOM blocking groups were compared to those produced by the standard MiniSeq® commercial kit including DNA polymerase Pol 812 and the comparative results are demonstrated in FIG. 4A. Very low pre-phasing was observed due to the improved stability of the 3'-AOM-ffNs. However, phasing was still elevated even if 2× incorporation time was used.

Figure 4B:
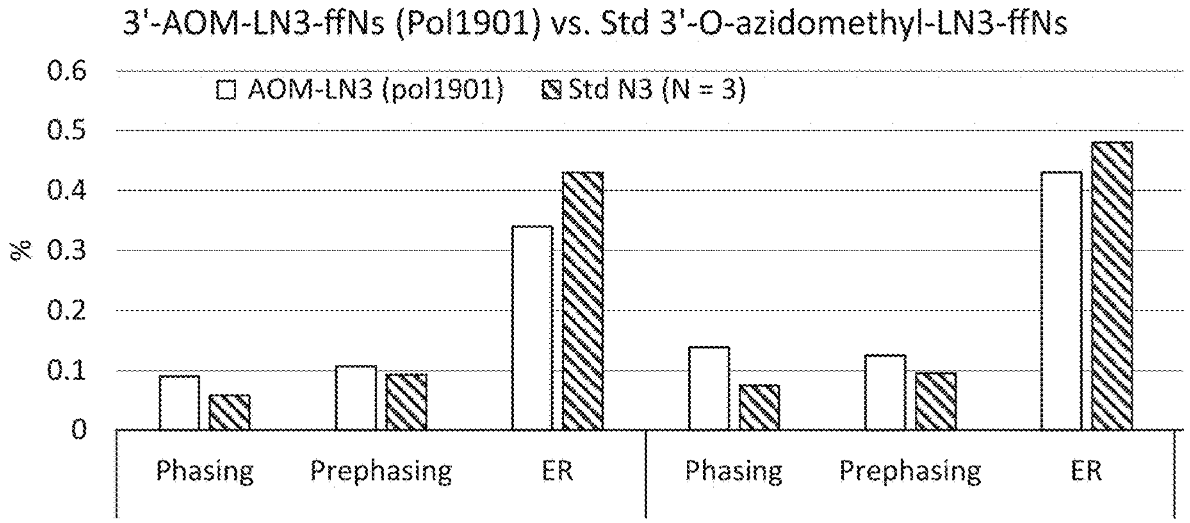

In yet another experiment, a different DNA polymerase (Pol 1901) was used instead of the DNA polymerase in the commercial MiniSeq® kits (Pol 812). Pol 1901 allowed for standard 1× incorporation time in sequencing instead of the 2× incorporation time described above. In addition, incubation in the Pd cleavage mixture was reduced by half compared to standard run. This allowed for a 10% time saving on the complete SBS chemistry cycle. The sequencing metrics were significantly improved and exceeded the values obtained from the standard commercial kits containing 3'-O-azidomethyl blocking group (FIG. 4B).

3' Blocking Group Stability Test in Sequencing

Figure 5:
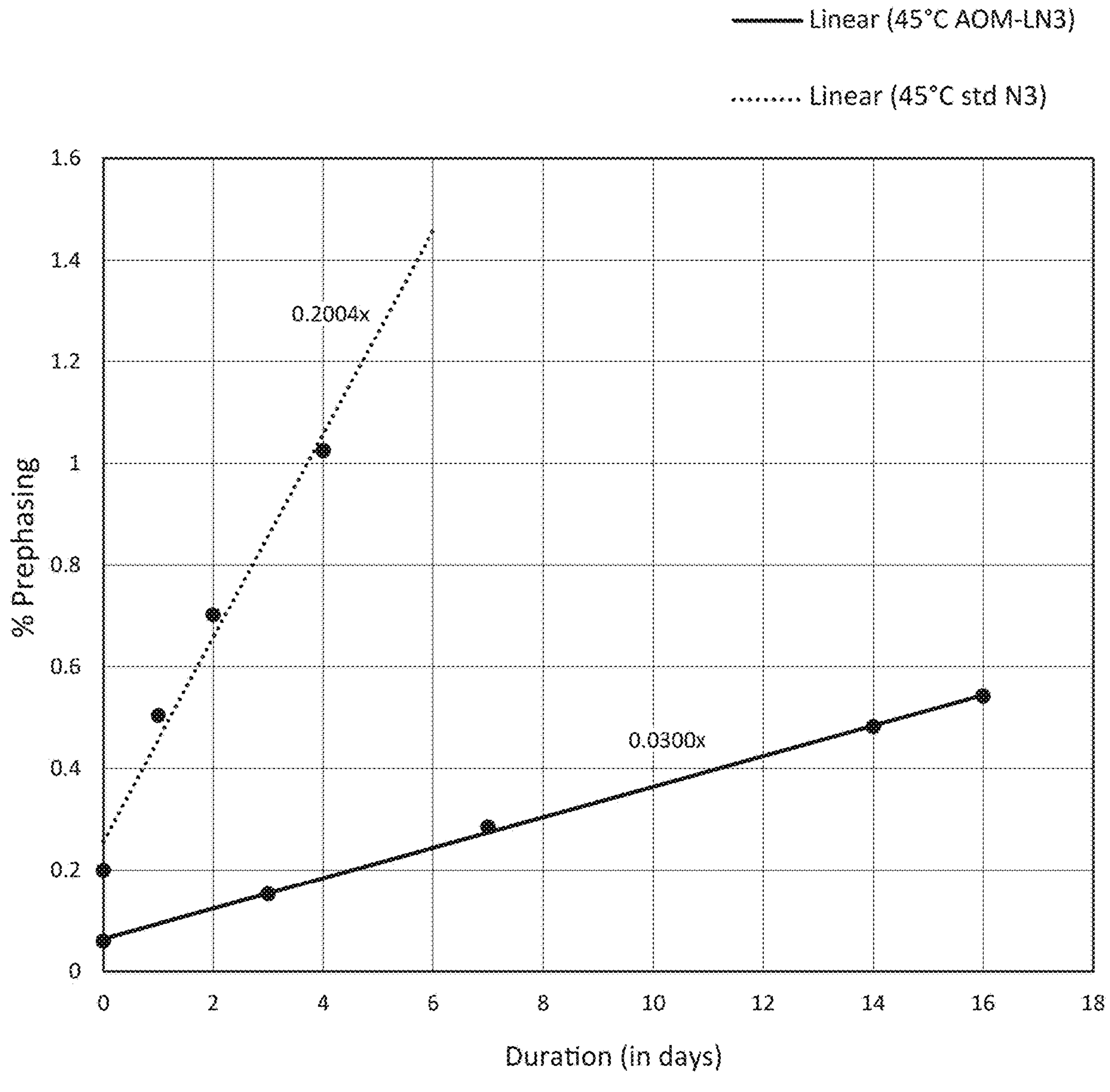
FIG. 5 is a line chart illustrating the sequencing stability of fully functionalized nucleotides with 3'-AOM or 3'-O-azidomethyl blocking groups as a function of time in a buffer solution at 45° C.

To demonstrate stability improvement of the ffNs with 3'-AOM, they were compared side by side with standard MiniSeq® ffNs with 3'-O-azidomethyl group. The two sets of ffNs were incubated at 45° C. for several days in standard incorporation mix formulations excluding only the DNA polymerase. For each time point, fresh polymerase was added to complete the incorporation mix directly prior loading on MiniSeq®. Sequencing conditions described previously were used. Pre-phasing % is a direct indicator of the percentage of 3'OH-ffNs present in the mix therefore directly correlates to the stability of the 3' block group. Pre-phasing values for both sets of ffNs were recorded and plotted (FIG. 5). At 45° C., it was observed that 3'-AOM containing ffNs appeared to be 6× more stable than standard ffNs with 3'-O-azidomethyl group. Sequencing metrics also confirmed the trend observed during the stability assay in solution—3'-AOM block was significantly more stable than 3'-O-azidomethyl group.

Example 6. Preparation of 3'-O-Thiocarbamate Blocked Nucleosides

In this example, various 3'-O-thiocarbamate protected T nucleoside were prepared according to Scheme 8.

Scheme 8. Synthesis of 3'-O-Dimethylthiocarbamate T Nucleoside

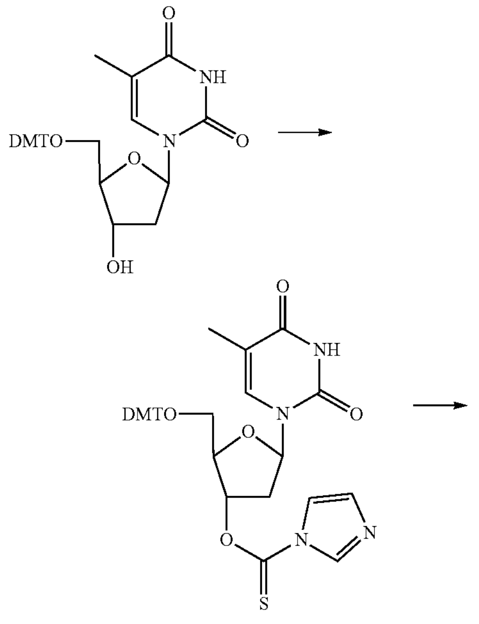

T-7

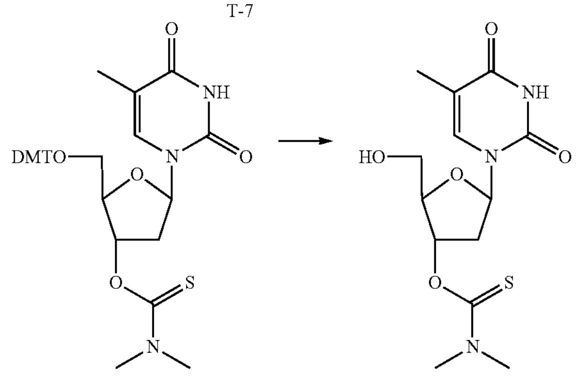

T-8

T-9

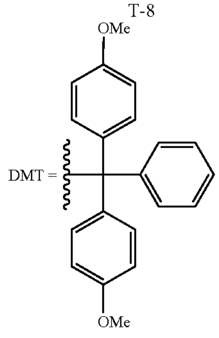

Preparation of T-7: Into an oven-dried nitrogen-purged 100 mL flask was added 5'-O-(4,4'-Dimethoxytrityl)thymidine (1.0 g, 1.836 mmol). This was co-evaporated with anhydrous DMF (3x20 mL) and brought under nitrogen. Anhydrous DCM (9.2 mL) and 4-dimethylaminopyridine (224 mg, 0.184 mmol) were added and stirred at room temperature until a homogeneous solution was formed. Then 1,1'-thiocarbonyldiimidazole (360 mg, 2.02 mmol) was added quickly over a stream of nitrogen, the reaction resealed and stirred at room temperature for 2 hours until all starting material was consumed. The reaction mixture is filtered through a pad of silica gel and the filter cake washed with EtOAc (10 mL). Volatiles were removed in vacuo and the crude residue used without further purification.

Preparation of T-8: Compound T-7 from the previous step was used immediately after drying in vacuo. The residue was brought under nitrogen in a 25 mL round bottomed flash and dimethylamine (2 M in THF, 7.3 mL, 14.6 mmol) was added and the reaction stirred for 2 hours until all starting material was consumed according to TLC. All volatiles were removed in vacuo to a form a clear crude residue, which was purified by flash-column chromatography on silica gel to afford T-8 as a white solid. Yield: 1.15 g (99%). LC-MS (Electrospray negative) 630.23 [M−H].

Preparation of T-9: Starting nucleoside T-8 (320 mg, 0.504 mmol) was dissolved in minimal acetonitrile in a 50 mL round bottomed flask in air. A solution of $AcOH/H_2O$ 5:1 (12.5 mL:2.5 mL) was added in one go and the reaction stirred at room temperature until all starting material was consumed (2-4 hours). Evaporation of all volatiles under vacuum and co-evaporating the residue in toluene (2x60 mL) provide crude product as an off white solid. The crude product was purified by flash column chromatography to afford T-9 as a white solid. Yield: 123 mg (74%). LC-MS (Electrospray negative) [M−H] 328.10.

Following similar synthetic procedure using the corresponding $MeNH_2$ or $NH_3$, nucleosides with two other thiocarbamate protecting groups were also prepared. The general reaction scheme is demonstrated below:

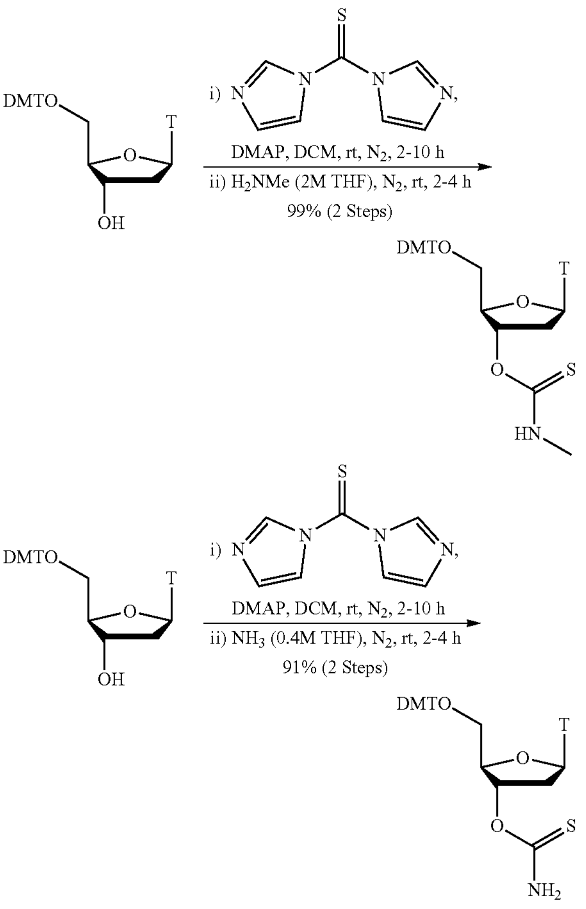

3'-O-Thiocarbamate Blocking Groups Stability Testing

The stability tests for 5'-mP 3'-DMTC T nucleotide was performed side by side in an incorporation buffer solution with standard 5'-mP 3'-O-azidomethyl T nucleotide.

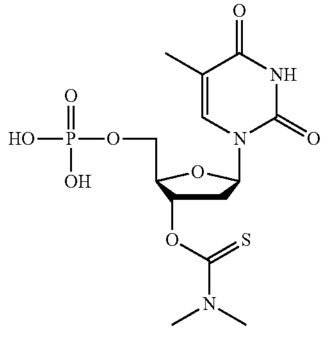

5′-mP 3′-DMTC T

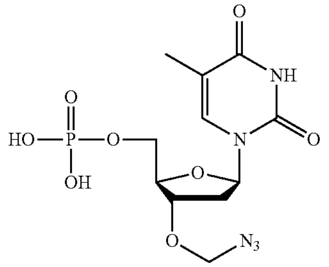

5′-mP 3′-O-azidomethyl T

For both 5'-mP 3'-DMTC T and 5'-mP 3'-O-azidomethyl T, the final solution volume was 1 mL and the final concentrations of the corresponding nucleotides were both 0.1 mM. Other components of the aqueous buffer solution include ethanolamine (EA), ethanolamine HCl, NaCl (100 mM), and EDTA (2.5 mM). The buffer solution has the following concentration: 0.5 M EA Buffer, 0.5 M NaCl, 0.01 M EDTA.

Stability Test Methodology

Figure 6:
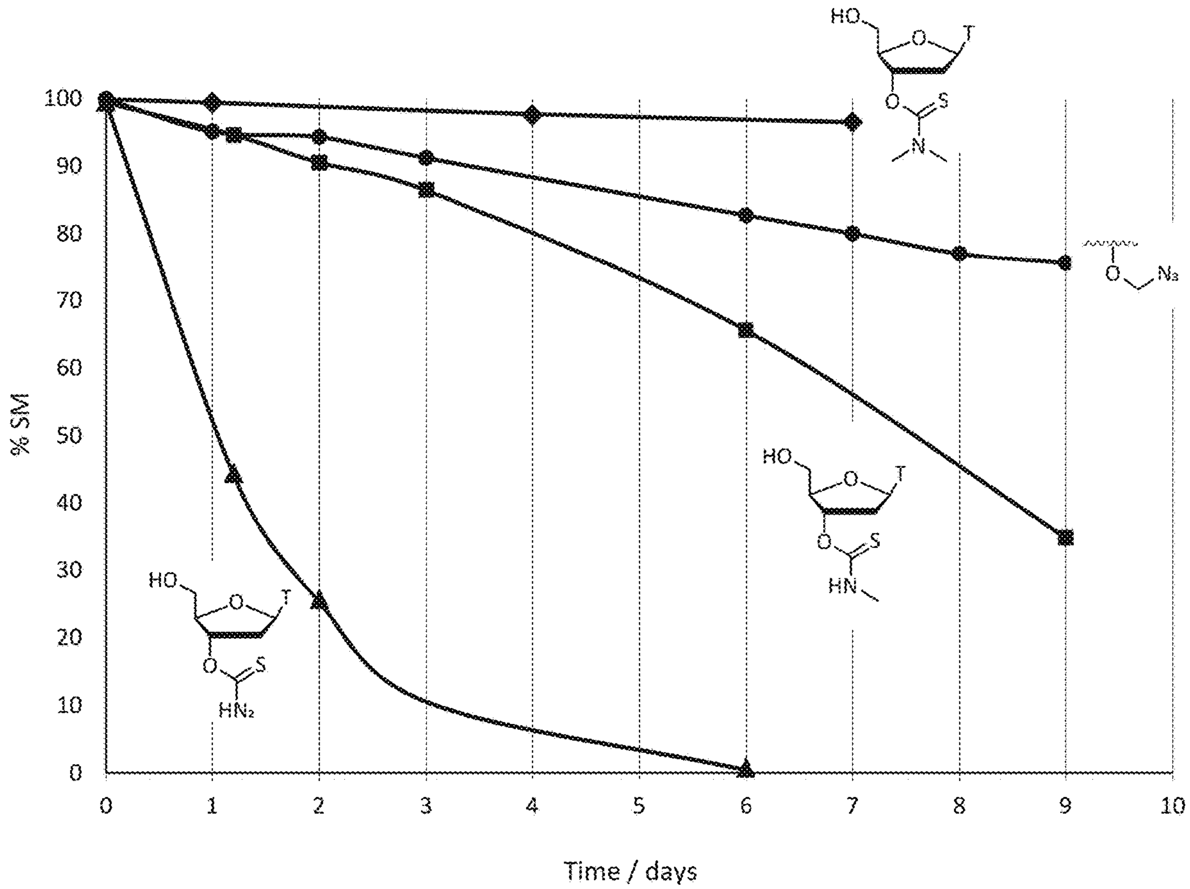
FIG. 6 is a line chart illustrating the stability of nucleosides with various 3' blocking groups as a function of time in a buffer solution at 65° C.

200 µL of 10× Buffer solution was added to a 1.7 mL polypropylene snap lock microtube and diluted with the correct volume of 18 mΩ water. The corresponding nucleoside was then added, the vial was sealed and mixed via inversion, gentle stirring or pumping with a micropipette. A 40 µL aliquot was taken and analyzed by HPLC to act as a starting (or t=0) value. The vials are then placed in a pre-heated heating mantle set to 65° C., covered with a thick layer of aluminum foil and left to heat for one month. 40 µL aliquots was taken periodically (week 1: once daily. Weeks 2-4: 1 every 2 days) and analyzed by HPLC to determine the percentage starting material and the percentage deblocked (3'-OH) nucleotide in the samples. HPLC analysis was performed by measuring the area of the stating nucleotide peak and the 3'OH peak. These values were used to calculate a percentage of deblocked nucleotide which was presented graphically and used to compare stability in an incorporation buffer between samples. FIG. 6 illustrates the comparative results of stability of three different thiocarbamate 3' blocking nucleotides to the nucleotide blocked with 3'-O-azidomethyl blocking group at 65° C. It was observed that while the nucleotide with 3'-O—C(═S)$NH_2$ or 3'-O—C(═S)$NHCH_3$ was less stable than the nucleotide protected with the standard 3'-O-azidomethyl group, the nucleotide with 3'-DMTC conferred improved stability during the 9-day testing period. As such, DMTC demonstrated superior stability over the standard azidomethyl blocking group.

Example 7. 3'-O-Thiocarbamate Blocking Group Deblocking Testing

In this example, deblocking or deblock tests for 5'-mP 3'-DMTC T and the standard 5'-mP 3'-O-azidomethyl T nucleotide were performed individually in a solution unique to each blocking group. Conditions were formulated to mimic Illumina's standard deblock reagent as closely as possible, and follow the same methodology. Concentrations of active deblock reagent, buffer, and nucleoside are kept the same across all tests, but the identity of each component was unique. In this way, the observed difference in rate between the individual deblocking chemistries cannot due to the differences in concentration of formulation.

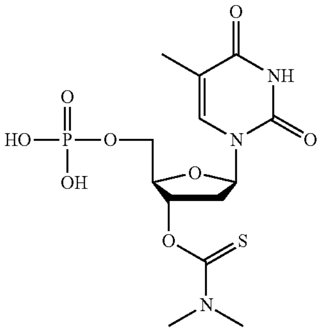

Deblock reagent: $NaIO_4$ or Oxone ®

5′mP 3′-DMTC T

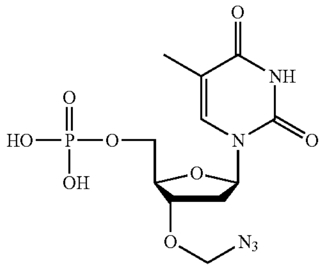

Deblock reagent: THP

5′mP 3′-O-azidomethyl T

Deblock Test General Methodology

Each reaction component was formulated individually as a concentrated stock in 18 mΩ water, stored appropriately, and aliquots combined in a specific order given below. Reaction was commenced by addition of the preformulated deblock reagent. Final Concentrations: nucleoside (0.1 mM), active deblock reagent (1 mM), additive (specific to deblock reagent), buffer (100 mM). Final Volume: 2000 µL.

In a 3 mL glass vial was added the preformulated buffer solution followed by preformulated additive solution. This was diluted with the correct volume of 18 mΩ water and stirred for 10 minutes. An aliquot of nucleotide solution was then added and stirred for 5 minutes. A 40 µL aliquot was then taken, quenching reagent added and analyzed by HPLC as a reference (or t=0 min) peak. The deblock reagent was then added in one go to the stirring solution and timing was commenced. At specified time points, 40 µL aliquots were taken and quenched immediately with an appropriate quenching reagent, then analyzed by HPLC to determine the amount of deblocked nucleotide that has occurred at these specified time points. Results were plotted graphically and are used to compare deblock efficiency and efficacy.

DMTC Deblocking

Nucleotide: 5'-mP 3'-DMTC T. Active deblock reagent: $NaIO_4$ (0.1M in 18 mΩ water) or Oxone® (0.1 M in 18 mΩ water). Additive: none. Buffer for $NaIO_4$: pH 6.75 phosphate buffer (1M in 18 mΩ water). Buffer for Oxone®: pH 8.65 phosphate buffer (1M in 18 mΩ water). Quenching reagent: sodium thiosulfate. The 3'-O-azidomethyl deblocking condition is the same as those described in Example 3.

Figure 7:
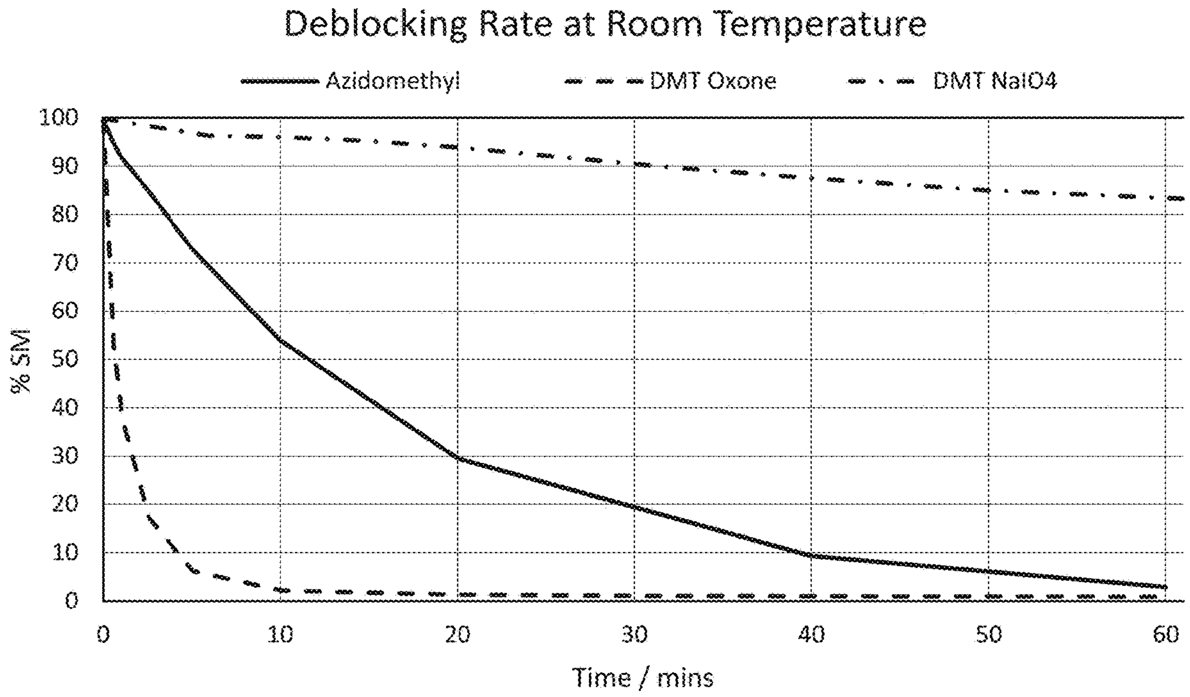
FIG. 7 is a line chart illustrating the percentage (%) of remaining 3' blocked nucleotide as a function of time, comparing the cleavage (deblocking) rate of a thiocarbamate 3' blocking group dimethylthiocarbamate (DMTC) under two different conditions (Oxone® or $NaIO_4$) to that of the 3'-O-azidomethyl ($3'-O—CH_2N_3$) blocking group.

HPLC analysis was performed by measuring the area of the stating nucleoside peak, the 3'-OH peak, and any other nucleotide peaks that appear in the HPLC chromatogram. These values were used to calculate a percentage of starting nucleotide and deblocked nucleotide which was presented graphically and used to compare deblock rate, efficiency and efficacy between samples. The comparative result is shown in FIG. 7. It was observed that deblocking of DMTC with $NaIO_4$ was not efficient. However, the % of starting material remaining was significantly less for the nucleotide with the DMTC blocking group when DMTC was cleaved with Oxone®. In summary, DMTC has demonstrated a superior deblocking rate (with Oxone®) over the deblocking rate of the standard azidomethyl blocking group.

Example 8. Pd Cleavage Solution Kinetic Study

Figure 8:
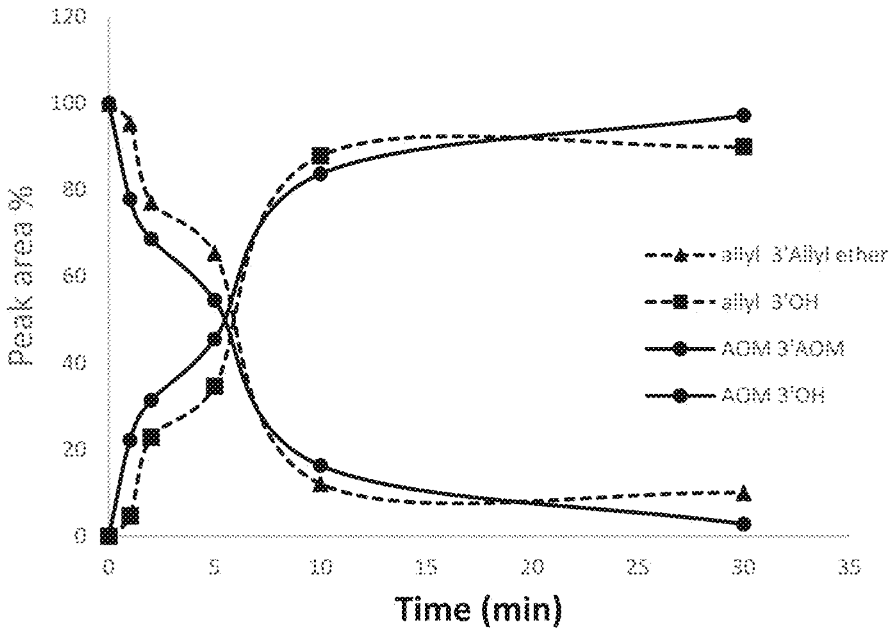
FIG. 8 is a line chart of percent peak area of nucleoside with 3' allyl blocking group in comparison to nucleoside with 3' AOM blocking group as a functional of time in a Pd cleavage solution kinetic assay.

In this example, the efficiency of a Pd(0) cleavage mixture generated in situ from a $Na_2PdCl_4$ and THPP in a molar ratio of 1:3.5, in a buffered solution containing (2-hydroxyethyl) piperidine at pH of about 9.8. T nucleosides with two different 3' blocking groups were used: 3'-O-Allyl-T-5'-OH and 3'-AOM-T-5'-OH. The study compared the effectiveness the Pd cleavage mixture in cleaving the 3' allyl blocking group and the 3'-AOM blocking group. As shown in FIG. 8, the Pd cleavage efficiency over the two blocking groups were very comparable, and the 3' blocking groups cleavage was nearly complete after 30 minutes.

Example 9. Syntheses of 3'-Allyl Blocked Fully Functionalized Nucleotides (ffNs)

Example of Synthesis of a 3'-allyl ffT

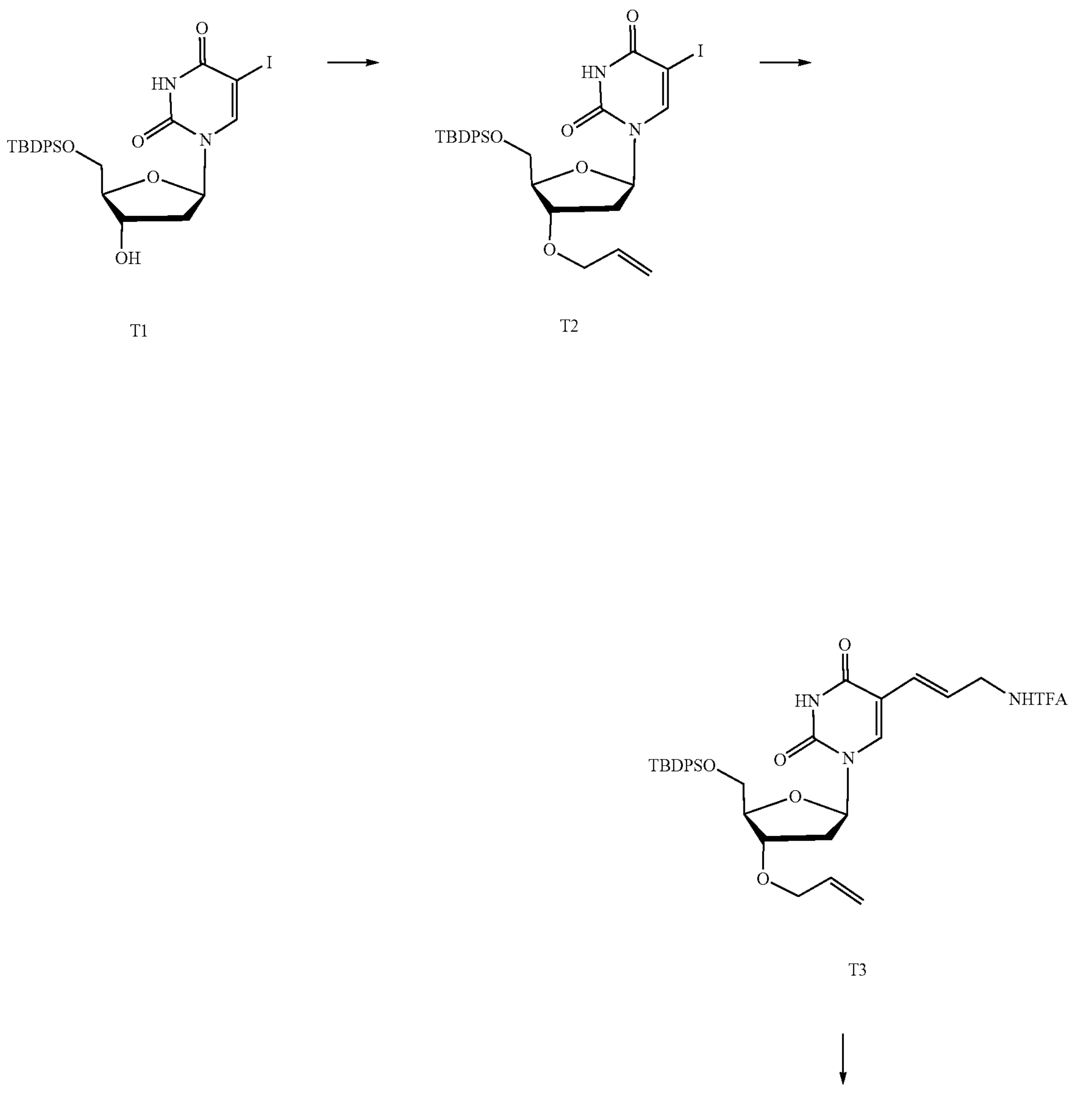

T1

T2

T3

-continued

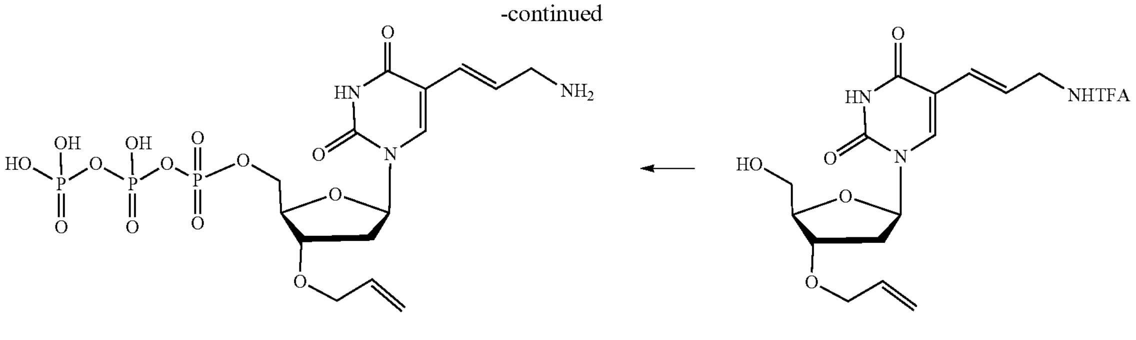

T5 T4

5'-O-(tert-butyldiphenylsilyl)-3'-O-allyl-5-iodo-2'-deoxyuridine (T2)

Sodium hydride (200 mg, 5 mmol) was suspended in 5 mL of anhydrous tetrahydrofuran in a flask under nitrogen. Then a solution of 5-Iodo-5'-TBDPS-2'-deoxyuridine T1 (1 g, 1.68 mmol) in 10 mL of anhydrous THF was added dropwise at 0° C. The reaction was then brought to room temperature and stirred for 30 minutes, then allyl bromide (430 μL, 5 mmol) was added dropwise at room temperature. The reaction was stirred overnight at room temperature, then quenched with 300 μL of acetic acid, diluted with 100 mL of water and extracted with 100 mL of ethyl acetate. The organic phase was washed with 100 mL of water, 100 mL of brine. The organic phase was dried over $MgSO_4$, filtered and evaporated to dryness. The residue was purified by flash chromatography on silica gel on a Biotage system (SNAP Sfar 25 g, gradient from 100% DCM to 75:25 to DCM/EtOAc). Yield: 724 mg (1.14 mmol), 68%. TLC (EtOAc/DCM 2:8): $R_f$ 0.7. $^1$H NMR (400 MHz, $d_6$-DMSO): δ (ppm) 11.76 (s, 1H, NH), 8.01 (s, 1H, C-6), 7.65 (ddd, J=7.9, 4.9, 1.7 Hz, 4H, Ph), 7.55-7.40 (m, 6H, Ph), 6.04 (dd, J=8.2, 5.9 Hz, 1H, 1'-CH), 5.87 (ddt, J=17.2, 10.5, 5.3 Hz, 1H, O—$CH_2$—CH═), 5.23 (dq, J=17.3, 1.8 Hz, 1H, CHH═), 5.15 (dq, J=10.4, 1.5 Hz, 1H, CHH═), 4.11 (dt, J=5.4, 2.4 Hz, 1H, 3'-CH), 4.06-4.00 (m, 1H, 4'-CH), 3.95 (tt, J=3.9, 1.5 Hz, 2H, $CH_2$ allyl), 3.85 (dd, J=11.3, 4.0 Hz, 1H, 5'-CHH), 3.73 (dd, J=11.3, 4.5 Hz, 1H, 5'-CHH), 2.36-2.27 (m, 1H, 2'-CHH), 2.22 (ddd, J=13.9, 8.3, 6.1 Hz, 1H, 2'-CHH), 1.03 (s, 9H, tBu). LC-MS (ES and CI): (positive ion) m/z 633 (M+H$^+$), 655 (M+Na$^+$); (negative ion) m/z 631 (M–H$^+$).

5'-O-(tert-butyldiphenylsilyl)-3'-O-allyl-5-[3-(2,2,2-trifluoroacetamido)-allyl]-2'-deoxyuridine (T3)

5'-O-(tert-butyldiphenylsilyl)-3'-O-allyl-5-iodo-2'-deoxyuridine (T2) (401 mg, 0.634 mmol), 2-Dicyclohexylphosphino-2',4',6'-triisopropylbiphenyl (24 mg, 0.05 mmol, XPhos), [3-(2,2,2-trifluoroacetamido)]-allylboronic acid pinacol ester (354 mg, 1.27 mmol) and allylpalladium (II) chloride dimer (9 mg, 0.025 mmol) were dissolved in 6 mL of anhydrous dimethylformamide and degassed by bubbling with nitrogen gas for 10 minutes. A solution of $Cs_2CO_3$ (412 mg, 1.27 mg) in 0.6 mL of water was then added and the reaction was heated to 45° C. After 1 hour the reaction was diluted with 100 mL of ethyl acetate and washed with 2× 100 mL of water and 100 mL of brine. The organic phase was dried over $MgSO_4$, filtered and evaporated to dryness. The residue was purified by flash chromatography on silica gel on a Biotage system (SNAP Sfar 25 g, gradient from 100% DCM to 7:3 to DCM/EtOAc). Yield: 282 mg (0.429 mmol), 68%. TLC (EtOAc/DCM 2:8): $R_f$ 0.5. $^1$H NMR (400 MHz, $d_6$-DMSO): δ (ppm) 11.52 (s, 1H, NH), 9.62 (t, J=5.7 Hz, 1H), 7.95 (s, 1H, C-6), 7.70-7.59 (m, 4H, Ph), 7.53-7.38 (m, 6H, Ph), 6.45 (dt, J=15.8, 6.3 Hz, 1H, Ar—CH═CH), 6.11 (t, J=7.1 Hz, 1H, 1'-CH), 5.99 (d, J=15.9 Hz, 1H, Ar—CH═, 5.89 (ddt, J=17.3, 10.6, 5.3 Hz, 1H, O—$CH_2$—CH═), 5.26 (dq, J=17.3, 1.8 Hz, 1H, CHH═), 5.16 (dq, J=10.4, 1.5 Hz, 1H, CHH═), 4.17 (dt, J=6.3, 3.3 Hz, 1H, 3'-CH), 4.08-3.94 (m, 3H, 4'-CH, O—$CH_2$-All), 3.88 (dd, J=11.1, 4.7 Hz, 1H, 5'-CHH), 3.77 (m, 3H, 5'-CHH, $CH_2$—NHTFA), 2.34-2.25 (m, 2H, 2'-$CH_2$), 1.01 (s, 9H, tBu). LC-MS (ES and CI): (positive ion) m/z 658 (M+H$^+$); (negative ion) m/z 656 (M–H$^+$).

3'-O-allyl-5-[3-(2,2,2-trifluoroacetamido)-allyl]-2'-deoxyuridine (T4)

5'-O-(tert-butyldiphenylsilyl)-3'-O-allyll-5-[3-(2,2,2-trifluoroacetamido)-allyl]-2'-deoxyuridine (T3) (470 mg, 0.743 mmol) was dissolved in dry THF (6 mL) under $N_2$ atmosphere, then a solution of 1.0 M TBAF in THF (390 μL, 0.89 mmol) was added. The solution was stirred at room temperature for 18 hours then TLC (EtOAC/DCM 1:1) showed completion. The solution was diluted with 100 mL of EtOAc, then washed with 50 mL of $NaH_2PO_4$ sat. (pH=3), and with 2× 50 mL of water. The organic phase was dried over $MgSO_4$, filtered and evaporated to dryness. The residue was purified by flash chromatography on silica gel on a Biotage system (SNAP Sfar 10 g, gradient from 100% DCM to 1:1 to DCM/EtOAc). Yield: 218 mg (520 mmol), 70%. TLC (EtOAc/DCM 1:1): $R_f$ 0.5. $^1$H NMR (400 MHz, $d_6$-DMSO): δ (ppm) 11.47 (s, 1H, NH), 9.68 (t, J=5.7 Hz, 1H, NHTFA), 8.03 (s, 1H, H-6), 6.47 (dt, J=15.9, 6.2 Hz, 1H, Ar—CH═CH), 6.21 (d, J=16.0 Hz, 1H, Ar—CH═), 6.12 (dd, J=7.9, 6.0 Hz, 1H, 1'-CH) 5.90 (ddt, J=17.3, 10.5, 5.3 Hz, 1H, O—$CH_2$—CH═), 5.28 (dq, J=17.3, 1.8 Hz, 1H, CHH═), 5.16 (m, 2H, CHH═, 5'-OH), 4.13 (dt, J=5.5, 2.6 Hz, 1H, 3'-CH), 4.03-3.94 (m, 3H, 4'-CH, O—$CH_2$-All), 3.88 (t, J=6.0 Hz, 2H, $CH_2$—NHTFA), 3.67-3.54 (m, 2H, 5'-$CH_2$), 2.28 (ddd, J=13.6, 6.0, 2.7 Hz, 1H, 2'-$CH_2$), 2.20 (ddd, J=13.7, 7.9, 5.8 Hz, 1H, 2'-$CH_2$). LC-MS (ES and CI): (positive ion) m/z 420 (M+H$^+$), 442 (M+Na$^+$); (negative ion) m/z 418 (M–H$^+$).

5'-O-triphosphate-3'-O-allyloxymethyl-5-(3-amino-allyl)-2'-deoxyuridine (T5)

3'-O-allyl-5-[3-(2,2,2-trifluoroacetamido)-allyl]-2'-deoxyuridine (T4) (210 mg, 0.501 mmol) was dried under reduced pressure over $P_2O_5$ for 18 hrs. Anhydrous triethyl phosphate (2 mL) and some freshly activated 4 Å molecular sieves were added to it under nitrogen, then the reaction flask was cooled to −15° C. in an ice/salt bath. Freshly distilled $POCl_3$ (56 µL, 0.601 mmoles) was added dropwise followed by Proton Sponge® (160 mg, 0.75 mmol). After the addition, the reaction was further stirred at 0° C. for 15 minutes. Then, pyrophosphate as bis-tri-n-butylammonium salt (1.3 g, 2.50 mmol) as 0.5 M solution in anhydrous DMF was quickly added, followed immediately by tri-n-butyl amine (537 µL, 2.25 mmol). The reaction was removed from the bath and stirred at room temperature for 10 minutes, then quenched into 1 M aqueous triethylammonium bicarbonate (TEAB, 20 mL) and further stirred at room temperature for 4 hours. Then the solution was extracted with 30 mL of ethyl acetate. The aqueous phase was evaporated under reduced pressure, then a 35% aqueous solution of ammonia (20 mL) was added to the residue and the mixture was stirred at room temperature for 4 hours. The solvents were then evaporated under reduced pressure, the residue resuspended in 10 mL of 0.1 M TEAB and filtered. The filtrate was purified firstly by ion-exchange chromatography on DEAE-Sephadex A25 (100 g). The column was eluted with a linear gradient of aqueous triethylammonium bicarbonate (TEAB, from 0.1 M to 0.8 M over 1 L). The fractions containing the triphosphate were pooled and the solvent was evaporated to dryness under reduced pressure. The crude material was further purified by preparative scale HPLC using a YMC-Pack-Pro C18 column, eluting with 0.1 M TEAB and acetonitrile. Compound T5 was obtained as triethylammonium salt. Yield: 195 µmol (39%). $^1H$ NMR (400 MHz, $D_2O$): δ (ppm) 8.15 (s, 1H, H-6), 6.50 (d, J=15.9 Hz, 1H, Ar—CH=), 6.38 (dt, J=16.0, 6.5 Hz, 1H, Ar—CH=CH—), 6.29 (dd, J=8.2, 5.9 Hz, 1H, 1'-CH), 5.91 (ddt, J=17.0, 10.3, 5.9 Hz, 1H O—$CH_2$—CH=), 5.30 (dq, J=17.3, 1.5 Hz, 1H, CHH=), 5.24-5.16 (m, 1H, CHH=), 4.41 (dt, J=5.9, 2.0 Hz, 1H, 3'-CH), 4.33 (m, 1H, 4'-CH), 4.22 (ddd, J=11.8, 4.1, 2.4 Hz, 1H, 5'-CHH), 4.15 (ddd, J=11.9, 6.2, 2.5 Hz, 1H, 5'-CHH), 4.07 (ddt, J=5.8, 2.3, 1.3 Hz, 2H, =CH—$CH_2$—0), 3.65 (dd, J=6.6, 1.1 Hz, 2H, $CH_2$—$NH_2$), 3.12 (q, J=7.3 Hz, $Et_3N^+$), 2.47 (ddd, J=14.3, 6.0, 2.1 Hz, 1H, 2'-CHH), 2.27 (ddd, J=14.2, 8.3, 5.8 Hz, 1H, 2'-CHH), 1.20 (t, J=7.3 Hz, $Et_3N^+$). LC-MS (ES and CI): (negative ion) m/z 562 (M−$H^+$).

Synthesis of ffT(DB)-3'All-AOL-NR550s0

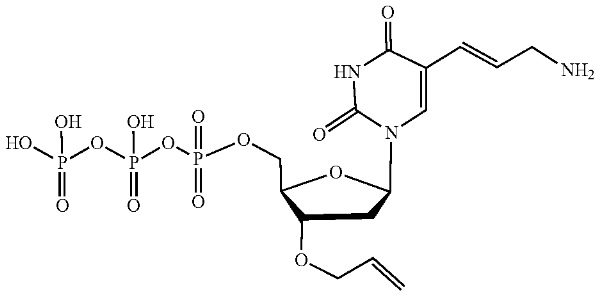

T5

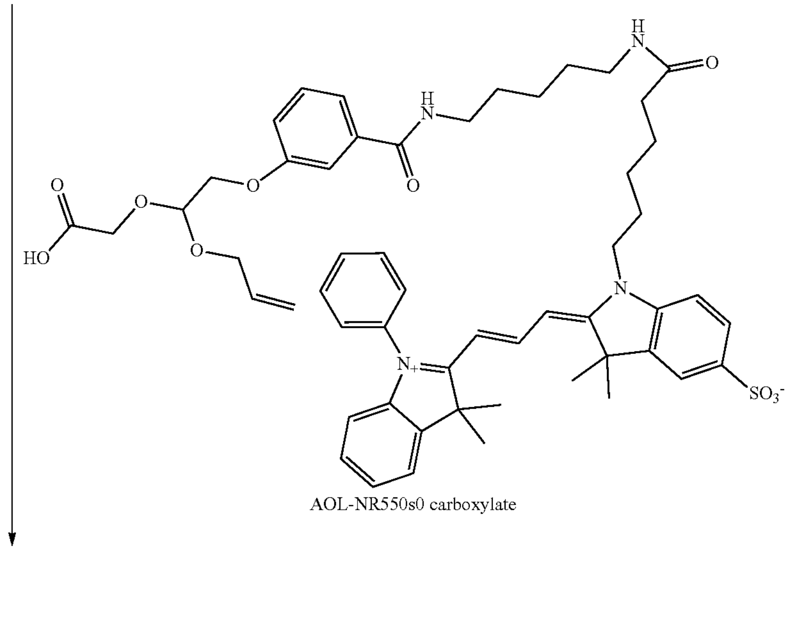

AOL-NR550s0 carboxylate

-continued

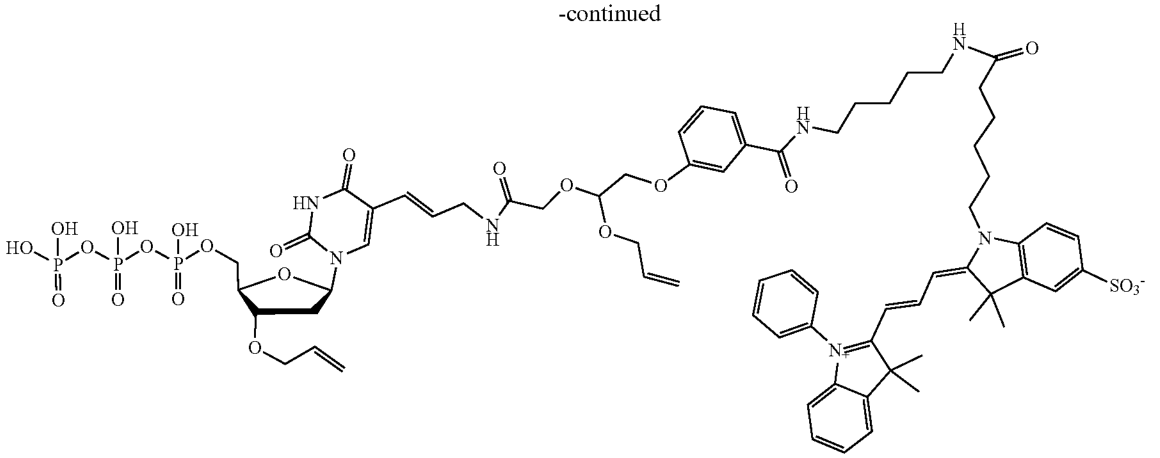

ffT(DB)-3'All-AOL-NR550s0

AOL-NR550s0 carboxylate (0.012 mmol) was coevaporated with 2×2 mL of anhydrous N,N'-dimethylformamide (DMF), then dissolved in 1.5 mL of anhydrous N,N'-dimethylacetamide (DMA). N,N-diisopropylethylamine (17 μL, 0.1 mmol) was added, followed by N,N,N',N'-tetramethyl-O—(N-succinimidyl)uronium tetrafluoroborate (TSTU, 140 μL of a 100 mM solution in DMF, 0.014 mmol). The reaction was stirred under nitrogen at room temperature for 1 hour. In the meantime, an aqueous solution of the triphosphate T5 (0.01 mmol) was evaporated to dryness under reduced pressure and resuspended in 150 μL of 0.1 M triethylammonium bicarbonate (TEAB) solution in water. The activated AOL-NR550s0 carboxylate solution was added to the triphosphate and the reaction was stirred at room temperature for 18 hours and monitored by RP-HPLC. The crude product was purified firstly by ion-exchange chromatography on DEAE-Sephadex A25 (25 g) eluting with a gradient from 0.1M TEAB/acetonitrile 8:2 to 1M TEAB/acetonitrile 8:2. The fractions containing the triphosphate were pooled and the solvent was evaporated to dryness under reduced pressure. The crude material was further purified by preparative scale RP-HPLC using a YMC-Pack-Pro C18 column, eluting with 0.1 M TEAB and acetonitrile. LC-MS (ES): (negative ion) m/z 1526 ($M-2H^{+}+Na^{+}$), 752 ($M-2H^{+}$). RP-HPLC (YMC-Packpro C18, 250×4.6 mm, gradient from 5% to 60% acetonitrile in 0.1 M TEAB, 20 minutes, flow rate 1 mL/min): $t_R$=18.3 min.

Synthesis of ffT(PA)-3'All-AOL-NR550s0

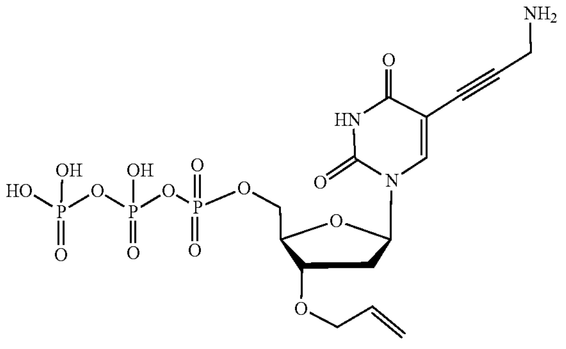

5'-O-triphosphate-3'-O-allyl-5-(3-aminopropargyl)-2'-deoxyuridine

-continued

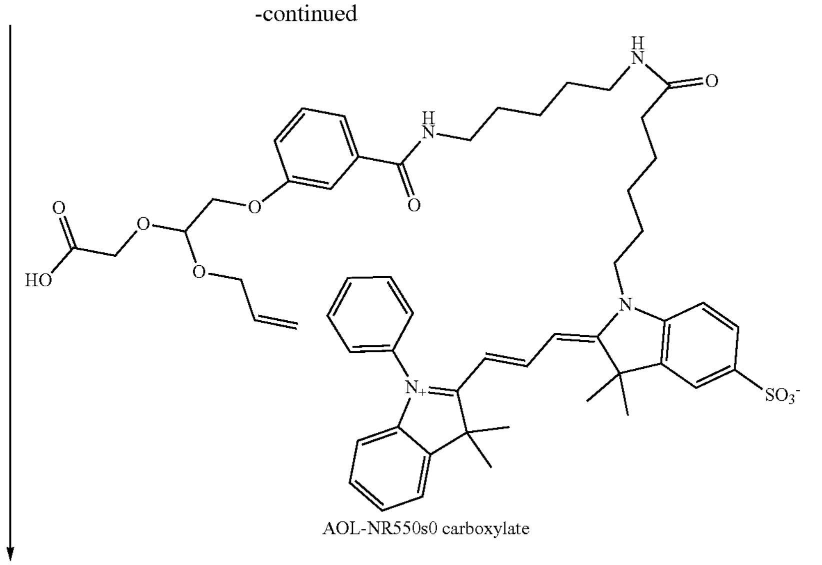

AOL-NR550s0 carboxylate

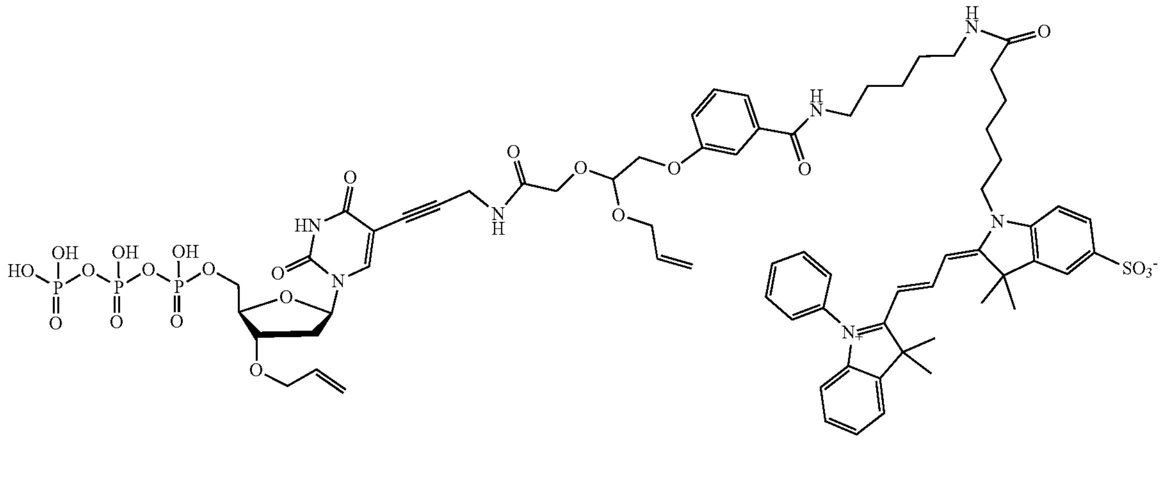

ffT(PA)-3′All-AOL-NR550s0

AOL-NR550s0 carboxylate (0.015 mmol) was coevaporated with 2× 2 mL of anhydrous N,N'-dimethylformamide (DMF), then dissolved in 2 mL of anhydrous N,N'-dimethylacetamide (DMA). N,N-diisopropylethylamine (17 μL, 0.1 mmol) was added, followed by N,N,N',N-tetramethyl-O—(N-succinimidyl)uronium tetrafluoroborate (TSTU, 180 μL of a 100 mM solution in DMF, 0.018 mmol). The reaction was stirred under nitrogen at room temperature for 1 hour. In the meantime, an aqueous solution of the 5'-O-triphosphate-3'-O-allyl-5-(3-aminopropargyl)-2'-deoxyuridine (0.01 mmol) was evaporated to dryness under reduced pressure and resuspended in 200 μL of 0.1 M triethylammonium bicarbonate (TEAB) solution in water. The activated Dye-linker solution was added to the triphosphate and the reaction was stirred at room temperature for 18 hours and monitored by RP-HPLC. The crude product was purified firstly by ion-exchange chromatography on DEAE-Sephadex A25 (25 g) eluting with a gradient from 0.1M TEAB/acetonitrile 8:2 to 1M TEAB/acetonitrile 8:2. The fractions containing the triphosphate were pooled and the solvent was evaporated to dryness under reduced pressure. The crude material was further purified by preparative scale RP-HPLC using a YMC-Pack-Pro C18 column, eluting with 0.1 M TEAB and acetonitrile. Yield: 65 μmol, (65%). LC-MS (ES): (negative ion) m/z 1502 (M–$H^+$), 750 (M–$2H^+$). RP-HPLC (YMC-Packpro C18, 250×4.6 mm, gradient from 5% to 60% acetonitrile in 0.1M TEAB, 20 minutes, flow rate 1 mL/min): $t_R$ 18.2 min.

Synthesis of ffT(DB)-3'All-(AOL)$_2$-LC-Biotin

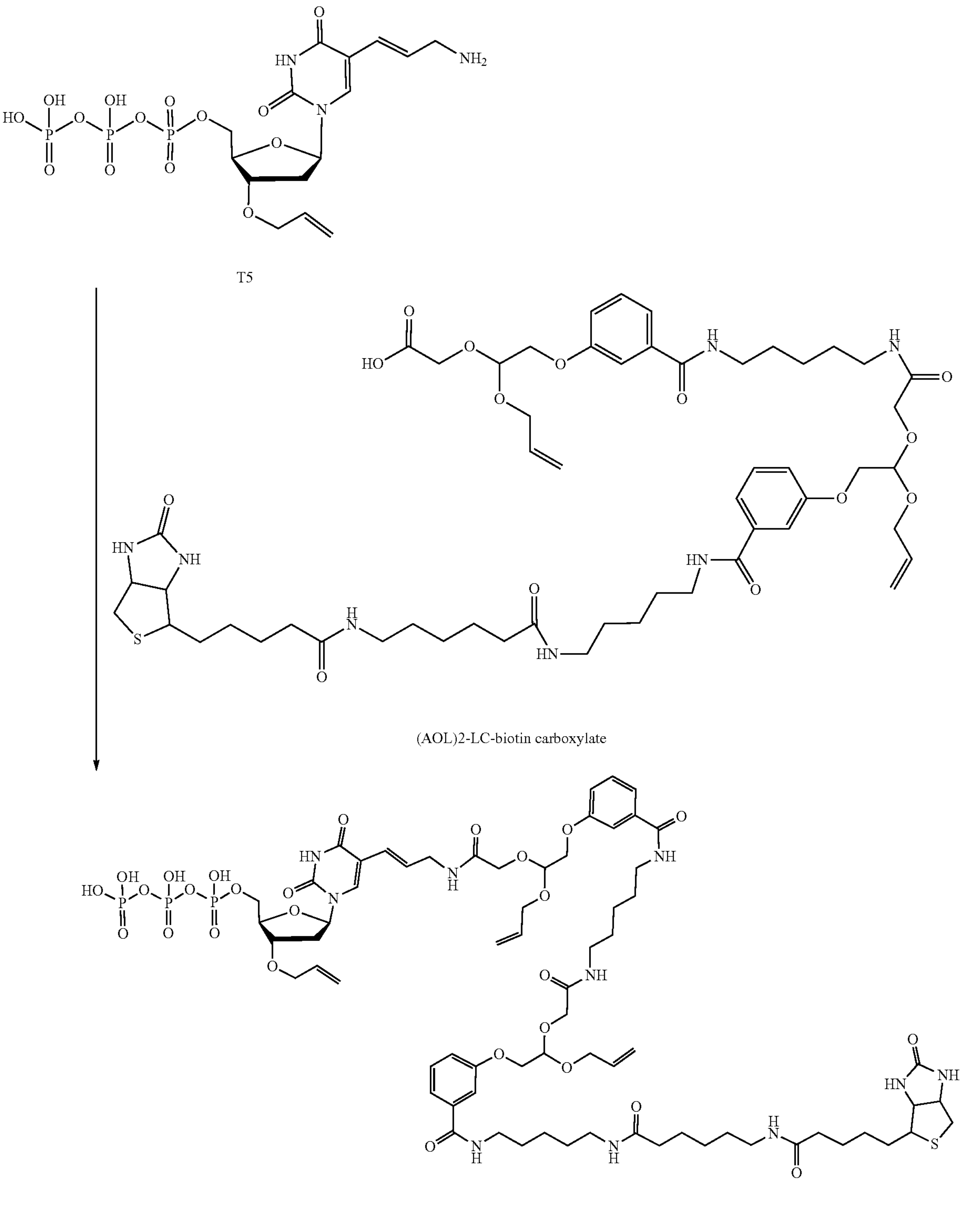

T5

(AOL)2-LC-biotin carboxylate ffT(DB-3'All-(AOL)2-LC-biotin (AOL)$_2$-LC-biotin carboxylate (0.01 mmol) was coevaporated with 2×2 mL of anhydrous N,N'-dimethylformamide (DMF), then dissolved in 1 mL of anhydrous N,N'-dimethylacetamide (DMA). N,N-diisopropylethylamine (8.7 μL, 0.05 mmol) was added, followed by N,N,N',N'-tetramethyl-O—(N-succinimidyl)uronium tetrafluoroborate (TSTU, 110 μL of a 100 mM solution in DMF, 0.011 mmol). The reaction was stirred under nitrogen at room temperature for 1 hour. In the meantime, an aqueous solution of the triphosphate T5 (0.005 mmol) was evaporated to dryness under reduced pressure and resuspended in 100 µL of 0.1 M triethylammonium bicarbonate (TEAB) solution in water. The activated (AOL)2-LC-biotin carboxylate solution was added to the triphosphate and the reaction was stirred at room temperature for 18 hours and monitored by RP-HPLC. The crude product was purified by preparative scale RP-HPLC using a YMC-Pack-Pro C18 column, eluting with 0.1 M TEAB and acetonitrile. LC-MS (ES): (negative ion) m/z 1625 ($M-H^+$), 812 ($M-2H^+$). RP-HPLC (YMC-Packpro C18, 250×4.6 mm, gradient from 5% to 50% acetonitrile in 0.1 M TEAB, 20 minutes, flow rate 1 mL/min): $t_R$ 17.9 min.

Example 10. 3'-Allyl Cleavage Study by Palladium Catalyst

Figure 9:
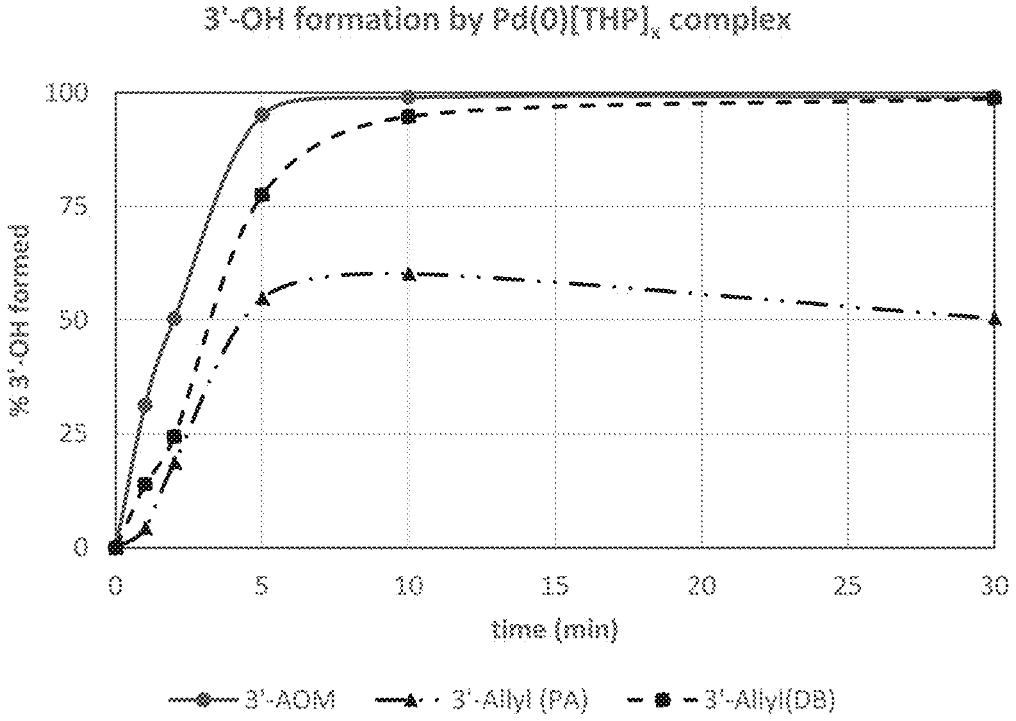
FIG. 9 is a line chart of percent 3'-OH nucleoside monophosphate formation as a functional of time in a Pd cleavage solution kinetic assay of three different 3' blocked nucleoside monophosphate.

The rate of 3'-allyl deprotection by palladium in solution was measured using the model compounds T6 and T7 and compared with the rate of deprotection of the 3'-AOM model compound A1. In a typical 400 µL reaction, to a 0.1 mM solution of substrate in 0.1 M DEEA buffer pH 9.8 was added a solution of Pd(0)[tris(3-hydroxypropyl)phosphine]$_x$ complex to a final palladium concentration of 1 mM. The reaction was incubated at room temperature in a closed tube and 20 µL aliquots of the reaction were taken at set time points, quenched immediately with 10 µL of 0.25 M $H_2O_2$/EDTA 1:1, then analyzed by UHPLC for the formation of the respective 3'-OH product. The formation of the 3'-OH product over time is shown in FIG. 9. The data shows that the rate of deprotection of compound T6 (3'-allyl (DB)), which contains the 3'-allyl blocking group and the double bond pendant arm is approximately 1.5 times slower compared to rate of deprotection of compound A1 (3'-AOM). With compound T7 (3'-allyl (PA)), however, incomplete deprotection was observed, even after 30 minutes of incubation. Several side-products were observed in the UHPLC traces generated from T7, indicating the triple bond pendant arm on thymidine is not inert to the palladium reagent used.

A1

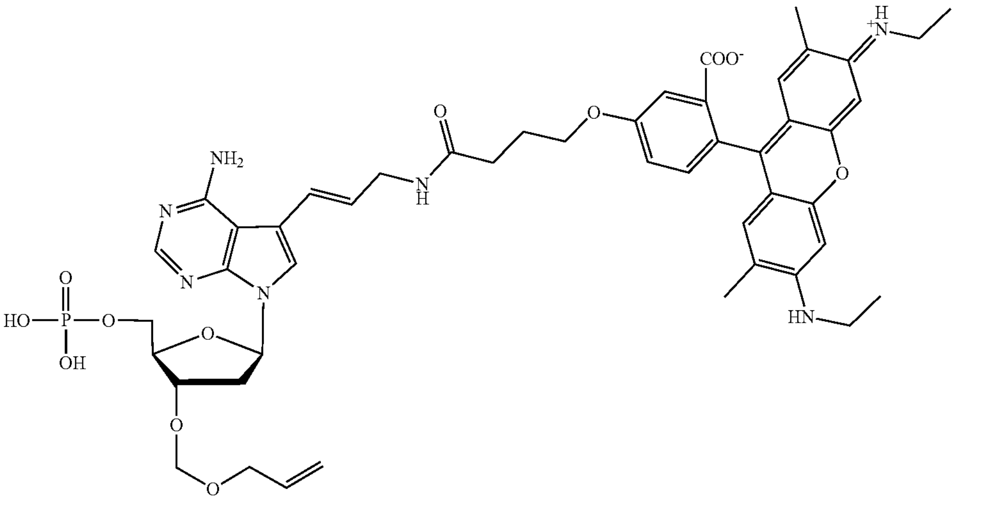

T6

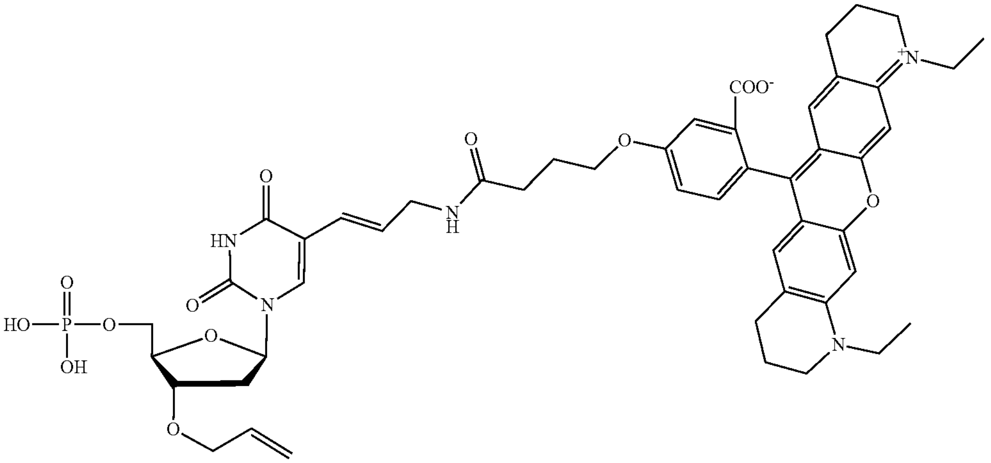

-continued

T7

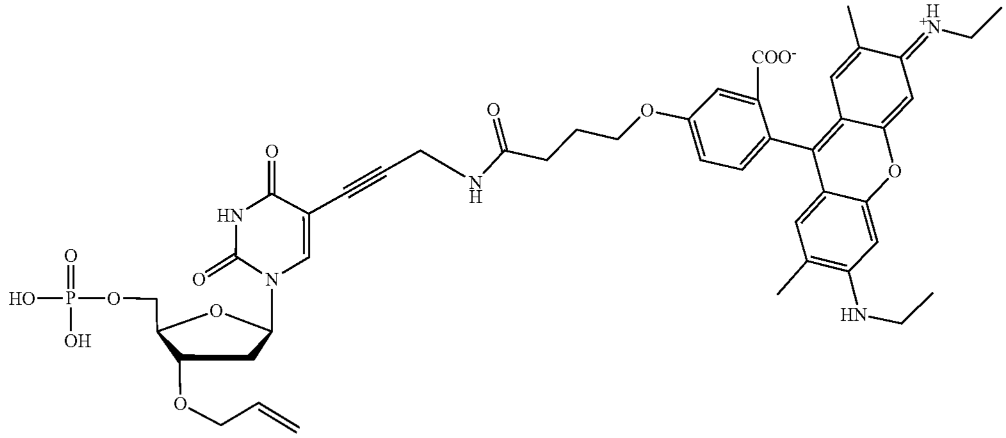

Example 11. Sequencing Experiments with ffT(PA)-3'All-AOL-NR550s0 and ffT(DB)-3'Allyl-AOL-NR550s0

Figure 10A:
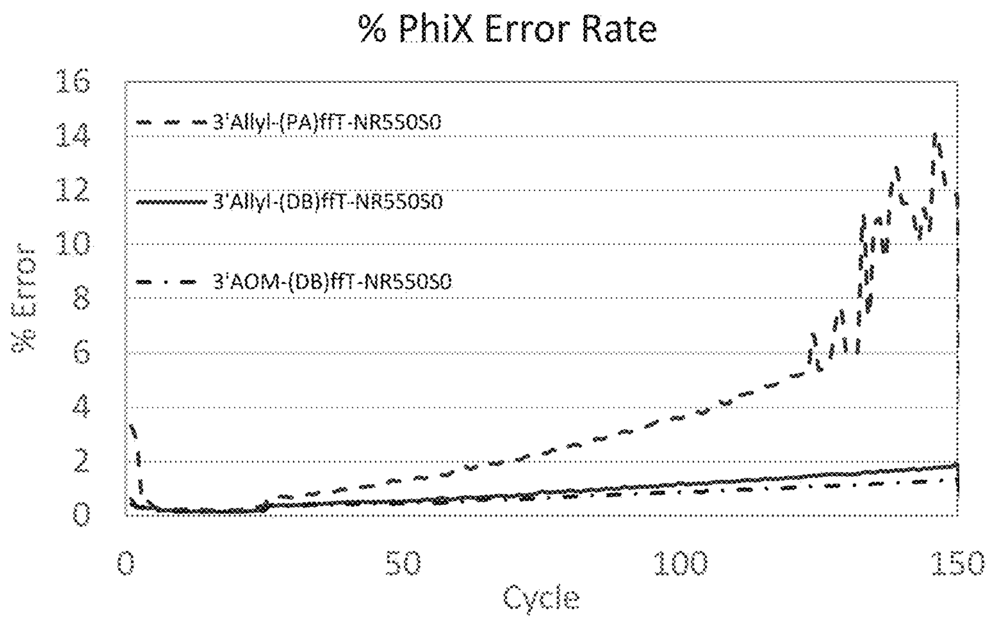
FIG. 10A is a line chart of percent error rate of standard sequence by synthesis runs on Illumina's iSeq100™ instrument, using three different fully functionalized T nucleotide (ffT) either having a 3' allyl blocking group or a 3' AOM blocking group.
Figure 10B:
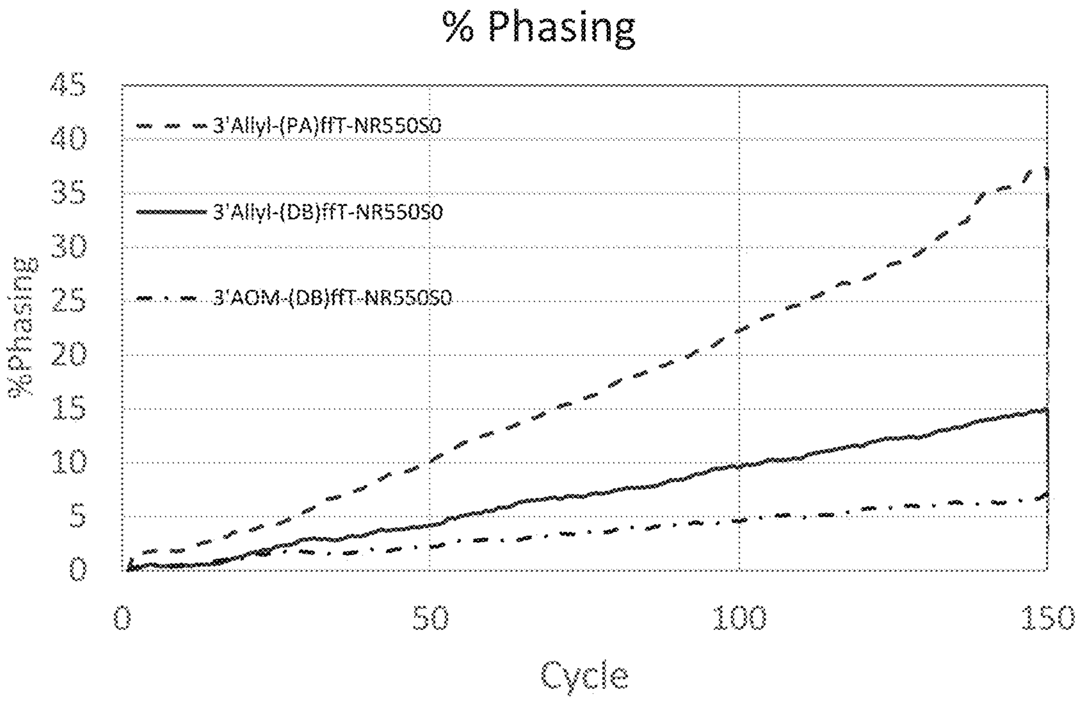
FIG. 10B is a line chart of percent phasing of standard sequence by synthesis runs on Illumina's iSeq100™ instrument, using three different fully functionalized T nucleotide (ffT) either having a 3' allyl blocking group or a 3' AOM blocking group.

The sequencing compatibility of the 3'-allyl fully functional T, ffT(PA)-3'-All-AOL-NR550s0 and ffT(DB)-3'All-AOL-NR550s0, was tested on an Illumina iSeq100™ using blue/green 2-excitation/1-emission chemistry and a corresponding set of dyes (blue ffC, dual blue/green ffA and dark ffG). In addition to the ffT, the following nucleotides were included in the incorporation mix: Dark G, ffA(DB)-AOM-AOL-chromenoquinoline dye A, ffC(DB)-AOM-AOL-coumarin dye B. The ffA, ffC and ffG used in the experiments each contained a 3'-AOM as the 3'blocking group. A Pd(0) $[THP]_x$ solution was used as cleavage reagent, and 10 mM sodium thiosulfate and lipoic acid were used as scavengers in the post-cleavage washes. A PhiX library was used as the template in individual single read 1×150 cycles experiments. The primary metrics of the sequencing experiments are shown in FIGS. 10A and 10B, as well as in Table 1, in comparison with a control experiment performed with a 3'-AOM ffT (ffT(DB)-3'AOM-AOL-NR550s0).

Chromenoquinoline dye A is disclosed in U.S. Publication No. 2022/0195517 A1 (incorporated by reference). Chromenoquinoline dye A has the structure moiety:

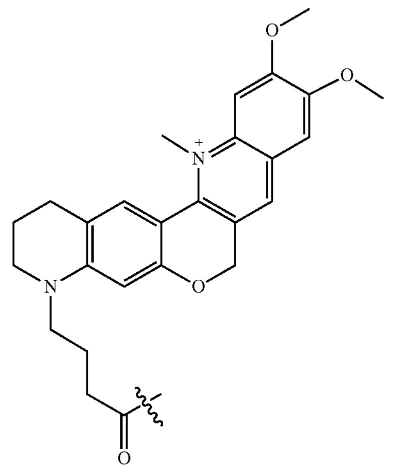

when conjugated with a nucleotide.

Coumarin dye B is disclosed in U.S. Publication No. 2018/0094140 A1 (incorporated by reference). Coumarin dye B has the structure moiety:

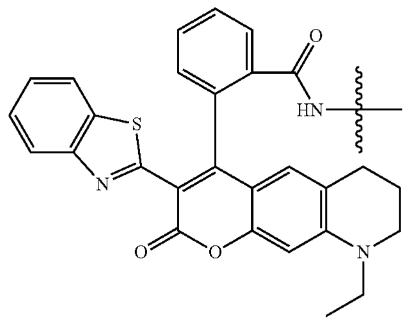 [SMILES: *NC(=O)c1ccccc1-c1c(-c2nc3ccccc3s2)c(=O)oc2cc3c(cc12)CCCN3CC]

when conjugated with a nucleotide.

The fluorescence intensity (in both green and blue channels) suffers a steeper decline when using ffT(PA)-3'All-AOL-NR550s0, while it is comparable between ffT(DB)-3'All-AOL-NR550s0 and ffT(DB)-3'AOM-AOL-NR550s0 experiments. Similar trends were observed in the % Q30. % PhiX error rate and phasing by cycle suffered a steeper increase with the compound ffF(PA)-3'All-AOL-NR550s0. The data suggests that the double bond pendant arm on T is essential for achieving high quality sequencing metrics with a palladium-based cleave mix.

TABLE 1

| ffT | Phasing | Prephasing | % PhiX Error (150 cycles) | % Q30 | % Q30 (last 10 cycles) |
|---|---|---|---|---|---|
| ffT(PA)-3'AII-AOL-NR550S0 | 0.21 | 0.11 | 3.5 | 78.9 | 57.3 |
| ffT(DB)-3'AII-AOL-NR550S0 | 0.11 | 0.11 | 0.9 | 88.8 | 85.8 |
| ffT(DB)-3'AOM-AOL-NR550S0 | 0.03 | 0.08 | 0.7 | 91.8 | 89.8 |

Example 12. Sequencing Experiments with ffT(DB)-3'All-$(AOL)_2$-Biotin

Figure 11A:
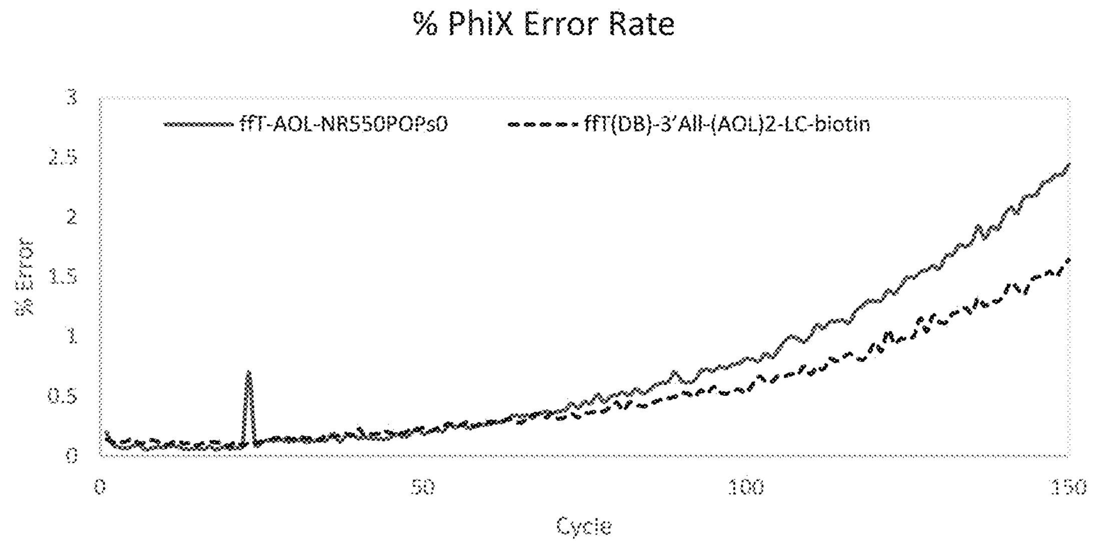
FIG. 11A is a line chart of percent error rate of sequence by synthesis runs on Illumina's Miseq® instrument in a post-incorporation labeling workflow, using two different fully functionalized T nucleotide (ffT) either having a 3' allyl blocking group or a 3' AOM blocking group.
Figure 11B:
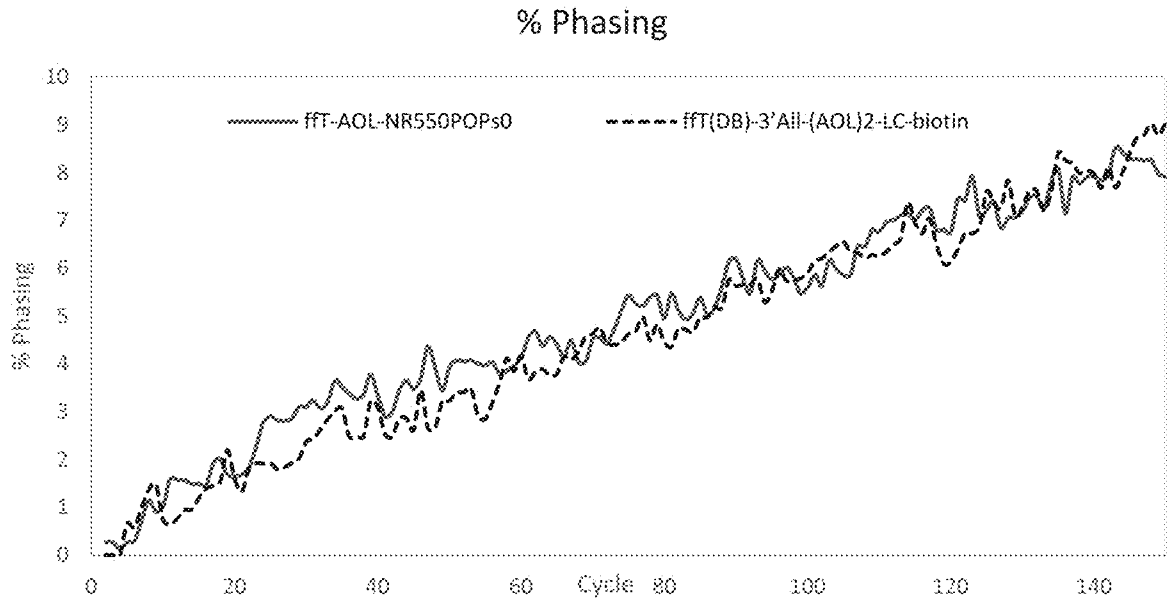
FIG. 11B is a line chart of percent phasing of sequence by synthesis runs on Illumina's Miseq® instrument in a post-incorporation labeling workflow, using two different fully functionalized T nucleotide (ffT) either having a 3' allyl blocking group or a 3' AOM blocking group.

The sequencing compatibility of a 3'-allyl fully functional T, ffT(DB)-3'All-$(AOL)_2$-LC-biotin in a post-incorporation labeling workflow was tested on a modified Illumina MiSeq® using blue/green 2-excitation/2-emission chemistry and a corresponding set of dyes (blue ffA, blue and green ffC and dark ffG). In addition to the ffT, the following nucleotides were included in the incorporation mix for the post-incorporation labeling workflow: Dark G, ffA(DB)-AOM-AOL-BL-coumarin dye C (blue dye), ffA(DB)-AOM-AOL-AF670POPO (a known green dye), ffC(DB)-AOM-AOL-coumarin dye C (blue dye), ffC(DB)-AOM-AOL-NR550s0. The ffA, ffC and ffG used in the experiments each contained a 3'-AOM as the 3'blocking group. An additional step was included after the incorporation step to label the DNA-incorporated ffT(DB)-3'All-(AOL)2-LC-biotin with multiple green fluorophore labeled streptavidin conjugate $(NR550C4)_6$-streptavidin. A Pd(0)$[THP]_x$ solution was used as cleavage reagent, and 10 mM sodium thiosulfate was included in the SBS wash buffer. A PhiX library was used as the template in individual single read 1×150 cycles experiments. The primary metrics of the sequencing experiments are shown in FIGS. 11A and 11B, as well as Table 2, in comparison with a control experiment performed with a 3'-AOM ffT (ffT(DB)-3'AOM-AOL-AF550POPOs0). For the control SBS experiments, the following ffT was used: ffT(DB)-AOM-AOL-AF550POPOs0 (green dye) and the remaining ffNs were the same as the post-incorporation labeling workflow.

Coumarin dye C has strong fluorescence and great stability. This dye is disclosed in U.S. Publication No. 2020/0277670 A1 (incorporated by reference), having the structure moiety

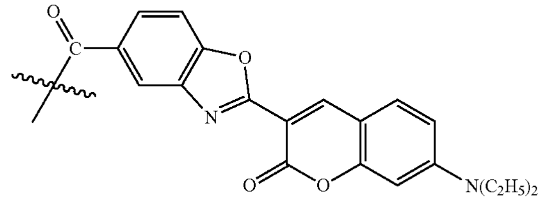

when conjugated with the ffA.

The fluorescence intensity (in both green and blue channels) and the signal decay are comparable between ffT(DB)-3'All-$(AOL)_2$-LC-Biotin labelled post-incorporation with a green dye-streptavidin conjugate and the standard ffT(DB)-3'AOM-AOL-AF550POPOs0. Similar trends were observed in the % Q30, % PhiX error rate and phasing metrics by cycle. The data suggests that 3'-allyl blocking group in combination the double bond pendant arm on T is compatible with a sequencing-by-synthesis workflow including a post-incorporation labelling step with a dye-labelled conjugate.

TABLE 2

| ffT | Phasing | Prephasing | % PhiX Error (150 cycles) | % Q30 | % Q30 (last 10 cycles) |
|---|---|---|---|---|---|
| ffT(DB)-3'AOM-AOL-AF550POPOS0 | 0.050 | 0.060 | 0.71 | 97.58 | 94.57 |
| ffT(DB)-3'AII(AOL)2-LC-Biotin | 0.054 | 0.052 | 0.53 | 97.45 | 93.38 |

What is claimed is:

1. A method of determining the sequence of a plurality of different target polynucleotides in parallel, the method comprising:

(a) contacting a solid support with a solution comprising sequencing primers under hybridization conditions, wherein:

(i) the solid support comprises at least 5,000,000 spatially distinguishable sites/$cm^2$ that comprise multiple copies of target polynucleotides;

(ii) the solid support comprises a plurality of different target polynucleotides; and (iii) the sequencing primers are complementary to at least a portion of the different target polynucleotides;

(b) contacting the solid support with an aqueous solution comprising DNA polymerase and nucleotides A, G, C, and T or U under conditions suitable for DNA polymerase-mediated primer extension, wherein:

(i) each of at least three types of nucleotides independently comprises a base that is attached to a detectable label via a cleavable linker, and the cleavable linker comprises a moiety selected from the group consisting of:

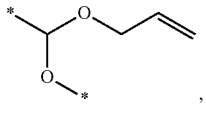
,
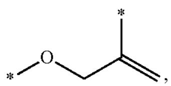
, and

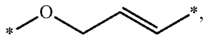

and * indicates where the moiety is connected to the remainder of the nucleotide;

(ii) each nucleotide comprises a 2' deoxyribose moiety with a 3' allyl group

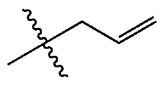 [SMILES: *CC=C]

attached to the 3' oxygen atom; and (iii) the DNA polymerase is an altered archaeal DNA polymerase;

(c) contacting the solid support with a solution comprising one or more radical scavengers and imaging the solid support to determine the identity of incorporated nucleotides;

(d) contacting the solid support with an aqueous deblocking solution comprising a palladium catalyst and tris (hydroxyalkyl)phosphine under conditions suitable to chemically remove (i) 3' allyl blocking groups from incorporated nucleotides to expose a 3'-OH group for further nucleotide incorporation on the solid support, and (ii) detectable labels attached via cleavable linkers;

(e) contacting said solid support with an aqueous wash solution comprising a palladium scavenger; and (f) repeating steps (b)-(e) to determine target polynucleotide sequences.

2. The method of claim 1, wherein the palladium scavenger in the aqueous wash solution of step (e) is a Pd(II) scavenger.

3. The method of claim 1, wherein the tris(hydroxyalkyl) phosphine is tris(hydroxypropyl) phosphine (THPP).

4. The method of claim 1, wherein the solid support comprises at least 5,000,000 spatially distinguishable sites/$cm^2$ that comprise concatemers comprising said multiple copies of target polynucleotides.

5. The method of claim 1, wherein the solid support comprises at least 5,000,000 spatially distinguishable sites/$cm^2$ that comprise clusters of immobilized nucleic acid molecules comprising said multiple copies of target polynucleotides.

6. The method of claim 1, wherein the T nucleotide has the structure:

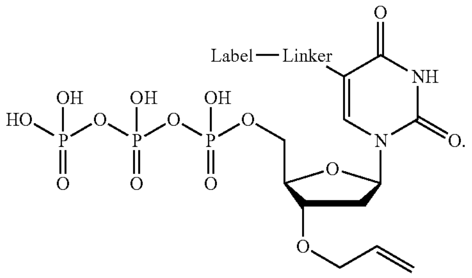

7. The method of claim 6, wherein the T nucleotide has the structure:

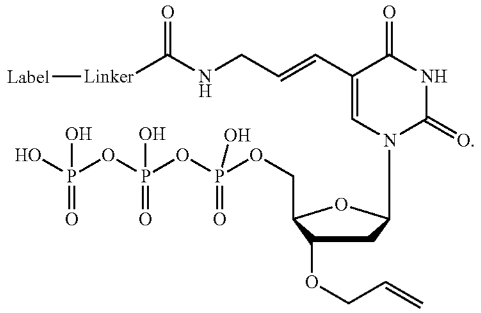

8. The method of claim 7, wherein the T nucleotide has the
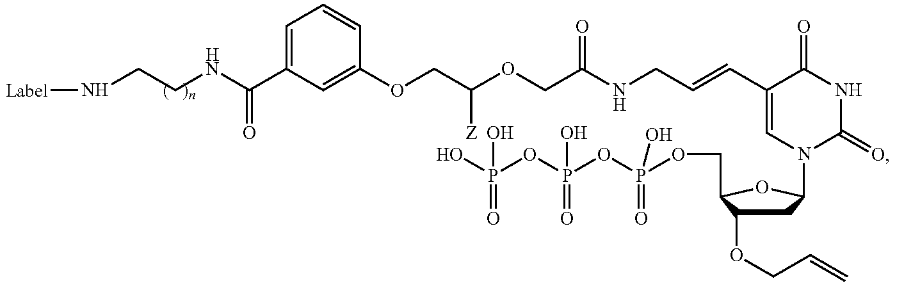
wherein
Z is $-O-CH_2-CH=CH_2$, and n is an integer of 1, 2, 3, 4 or 5.
9. The method of claim 1, wherein the A nucleotide has the structure:
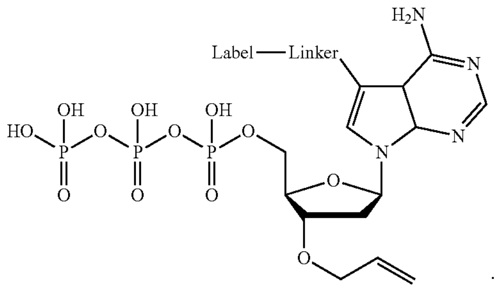
10. The method of claim 9, wherein the A nucleotide has the structure:
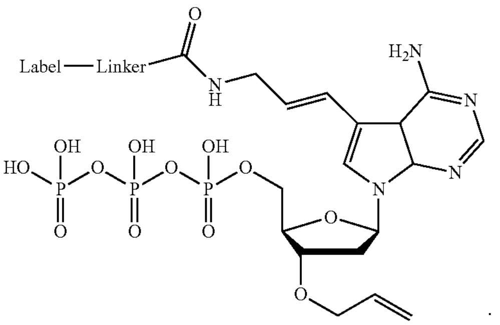
11. The method of claim 10, wherein the A nucleotide has the structure:
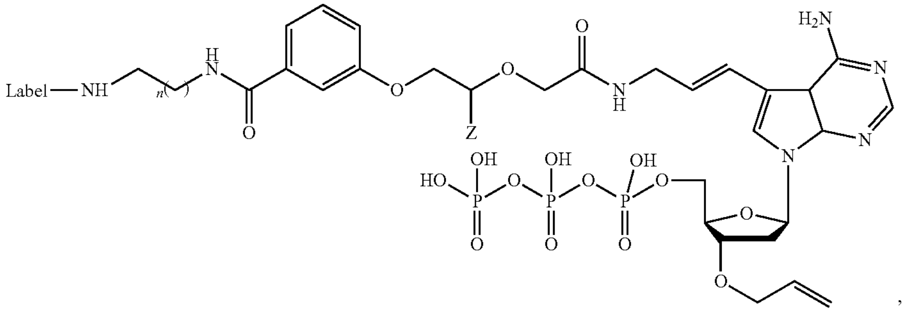

wherein
Z is —O—$CH_2$—CH═$CH_2$, and n is an integer of 1, 2, 3, 4 or 5.
12. The method of claim 1, wherein the C nucleotide has the structure:
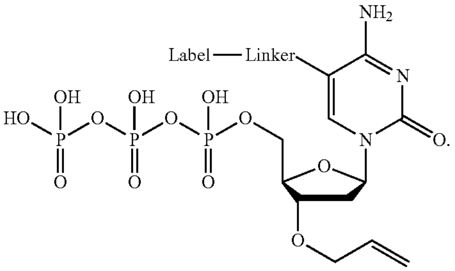
13. The method of claim 12, wherein the C nucleotide has the structure:
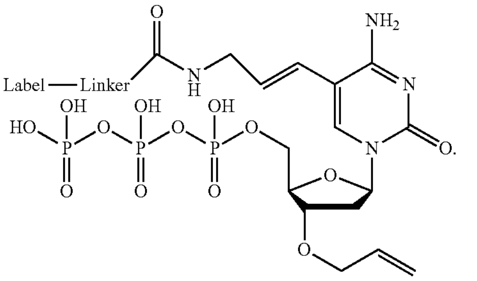
14. The method of claim 13, wherein the C nucleotide has the structure:
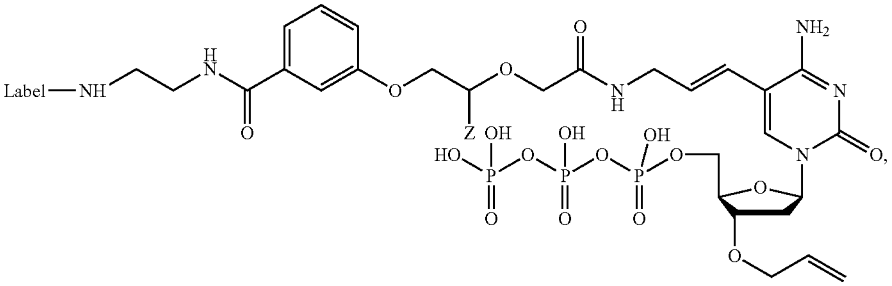

wherein

Z is —O—$CH_2$—CH═$CH_2$, and n is an integer of 1, 2, 3, 4 or 5.

15. The method of claim 1, wherein the G nucleotide has the structure:

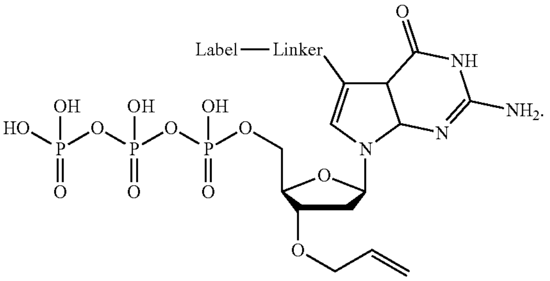

16. The method of claim 1, wherein at least one type of nucleotide has a structure selected from the group consisting of:

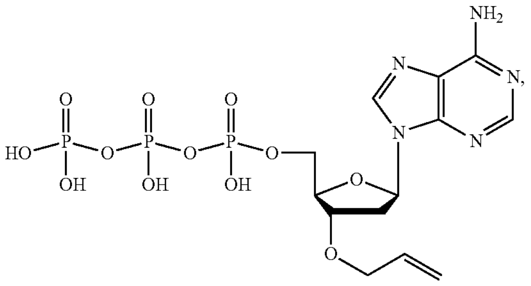

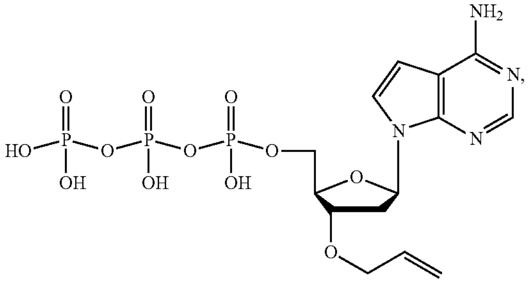

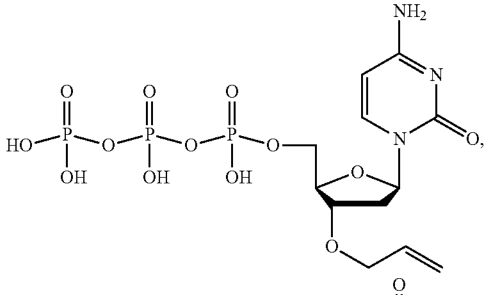

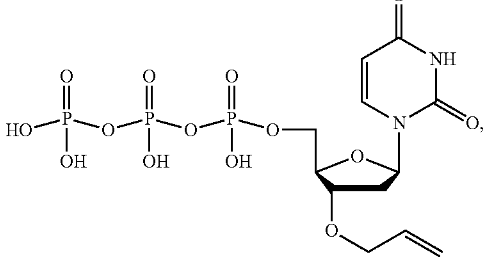

-continued

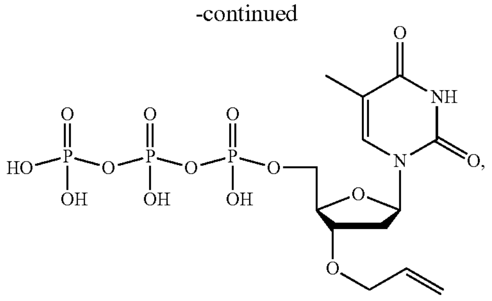

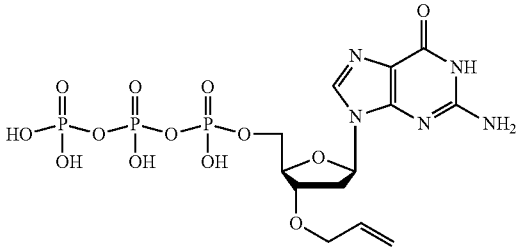

and

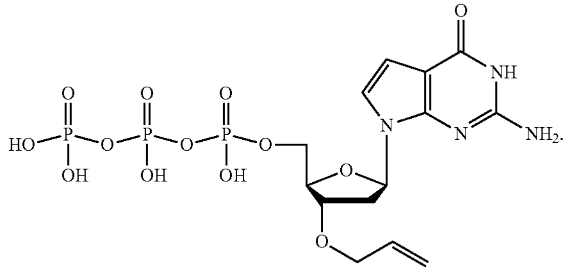

17. The method of claim 16, wherein at least one type of nucleotide has a structure selected from the group consisting of:

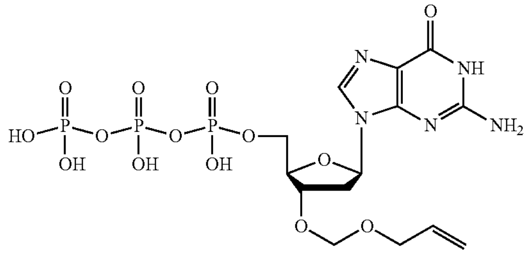

and

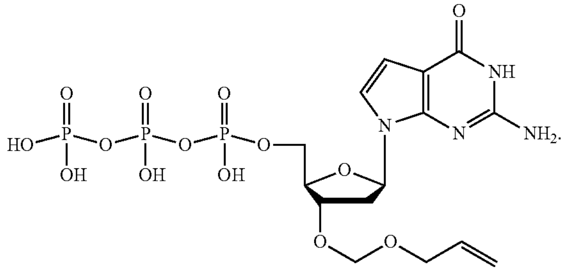

18. The method of claim 1, wherein sequencing cycles are repeated at least about 20 times, 30 times, 50 times, 100 times, 150 times, 200 times, 250 times, 300 times, 350 times, 400 times, 450 times or 500 times.

19. The method of claim 18, wherein after about 50 repeated sequencing cycles the pre-phasing value is less than 0.18.

20. The method of claim 19, wherein after about 50 repeated sequencing cycles the phasing value is less than 0.18.

21. The method of claim 18, wherein after about 100 repeated sequencing cycles the pre-phasing value is less than 0.10 and the phasing value is less than 0.10.

22. The method of claim 1, wherein the deblocking solution further comprises one or more buffer reagents selected from the group consisting of a primary amine, a secondary amine, a tertiary amine, a carbonate salt, a phosphate salt, and a borate salt, and combinations thereof.

23. The method of claim 1, wherein the DNA polymerase is an altered family B archaeal DNA polymerase comprising a 3-amino acid region that is functionally equivalent or homologous to amino acids 408-410 in 9° N DNA polymerase, wherein the first amino acid of the 3-amino acid region is an amino acid selected from the group consisting of isoleucine (I), alanine (A), valine (V), and serine(S); the second amino acid of the 3-amino acid region is an amino acid selected from the group consisting of alanine (A) and glycine (G); and the third amino acid of the 3-amino acid region is an amino acid selected from the group consisting of alanine (A), isoleucine (I), valine (V), leucine (L), threonine (T), and proline (P).

24. A sequencing kit comprising:

(a) an incorporation mixture comprising DNA polymerase and nucleotides A, G, C, and T or U, wherein:

(i) the nucleotides comprise a 2' deoxyribose moiety with a 3' allyl group

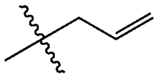 [SMILES: *CC=C]

attached to the 3' carbon atom;

(ii) the DNA polymerase is an altered archaeal DNA polymerase; and (iii) each of at least three types of nucleotides independently comprises a base that is attached to a detectable label via a cleavable linker, and the cleavable linker comprises a moiety selected from the group consisting of:

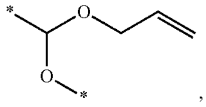
,
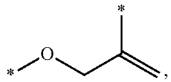
, and
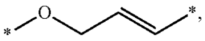
, and * indicates where the moiety is connected to the remainder of the nucleotide;

(b) an aqueous deblocking solution comprising a palladium catalyst, tris(hydroxyalkyl)phosphine, and one or more buffer reagents that is suitable to chemically remove (i) 3' allyl groups from incorporated nucleotides to expose a 3'—OH group for further nucleotide incorporation on the solid support, and (ii) detectable labels attached via cleavable linkers; and (c) an aqueous wash solution comprising a Pd(II) scavenger;

wherein said kit is configured for performing at least about 100 cycles of sequencing-by-synthesis.

* * * * *